US012559765B2

(12) United States Patent
Aharoni et al.

(10) Patent No.: US 12,559,765 B2
(45) Date of Patent: Feb. 24, 2026

(54) COMPOSITIONS AND METHODS FOR REGULATING GENE EXPRESSION FOR TARGETED MUTAGENESIS

(71) Applicant: YEDA RESEARCH AND DEVELOPMENT CO. LTD., Rehovot (IL)

(72) Inventors: Asaph Aharoni, Tel Aviv (IL); Samuel Bocobza, Rehovot (IL); Tal Dahan, Rehovot (IL); Avraham A. Levy, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 882 days.

(21) Appl. No.: 17/381,245

(22) Filed: Jul. 21, 2021

(65) Prior Publication Data

US 2021/0348179 A1     Nov. 11, 2021

Related U.S. Application Data

(63) Continuation of application No. 16/108,402, filed on Aug. 22, 2018, now Pat. No. 11,104,910, which is a continuation-in-part of application No. PCT/IL2017/051020, filed on Sep. 11, 2017.

(30) Foreign Application Priority Data

Sep. 11, 2016     (IL) .......................................... 247752

(51) Int. Cl.
*C12N 15/82* (2006.01)
*C12N 15/86* (2006.01)

(52) U.S. Cl.
CPC ..... *C12N 15/8216* (2013.01); *C12N 15/8222* (2013.01); *C12N 15/86* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 5,015,580 A | 5/1991 | Christou et al. | |
| 5,538,880 A | 7/1996 | Lundquist et al. | |
| 5,550,318 A | 8/1996 | Adams et al. | |
| 5,591,616 A | 1/1997 | Hiei et al. | |
| 5,635,055 A | 6/1997 | Sweet et al. | |
| 5,661,017 A | 8/1997 | Dunahay et al. | |
| 5,824,877 A | 10/1998 | Hinchee et al. | |
| 5,981,840 A | 11/1999 | Zhao et al. | |
| 6,160,208 A | 12/2000 | Lundquist et al. | |
| 6,384,301 B1 | 5/2002 | Martinell et al. | |
| 6,399,861 B1 | 6/2002 | Anderson et al. | |
| 6,403,865 B1 | 6/2002 | Koziel et al. | |
| 7,001,772 B2 | 2/2006 | Roessler et al. | |

| | | | |
|---|---|---|---|
| 8,802,925 B2 | 8/2014 | Luo et al. | |
| 11,104,910 B2 * | 8/2021 | Aharoni et al. ....... | C12N 15/62 |
| 2003/0028913 A1 | 2/2003 | Hein et al. | |
| 2003/0196219 A1 | 10/2003 | Zhang | |
| 2007/0079396 A1 | 4/2007 | Malvar et al. | |
| 2008/0194029 A1 | 8/2008 | Hegemann et al. | |
| 2008/0307541 A1 | 12/2008 | Hsieh | |
| 2009/0019562 A1 * | 1/2009 | Belknap et al. ... | C12N 15/8216 800/315 |
| 2010/0199371 A1 | 8/2010 | Castle et al. | |
| 2011/0113514 A1 | 5/2011 | Malvar et al. | |
| 2011/0209247 A1 | 8/2011 | Aharoni et al. | |
| 2013/0247451 A1 * | 9/2013 | Vanhercke et al. ....... | C11B 3/14 554/20 |
| 2014/0170753 A1 | 6/2014 | Zhang | |
| 2014/0179006 A1 | 6/2014 | Zhang | |
| 2014/0179770 A1 | 6/2014 | Zhang et al. | |
| 2014/0186843 A1 | 7/2014 | Zhang et al. | |
| 2014/0186919 A1 | 7/2014 | Zhang et al. | |
| 2014/0227230 A1 * | 8/2014 | Atarashi et al. ......... | C12Q 1/70 435/235.1 |
| 2014/0234972 A1 | 8/2014 | Zhang | |
| 2014/0248702 A1 | 9/2014 | Zhang et al. | |
| 2014/0273235 A1 * | 9/2014 | Voytas et al. ...... | C12N 15/8205 435/468 |
| 2014/0283166 A1 | 9/2014 | Kudithipudi et al. | |
| 2015/0067927 A1 * | 3/2015 | Kumar et al. ....... | C07K 14/415 800/320.2 |
| 2015/0082478 A1 | 3/2015 | Cigan et al. | |
| 2015/0184139 A1 | 7/2015 | Zhang et al. | |

(Continued)

FOREIGN PATENT DOCUMENTS

| | | |
|---|---|---|
| WO | WO/2003/104451 A2 | 12/2003 |
| WO | WO/2014/013056 A1 | 1/2014 |

(Continued)

OTHER PUBLICATIONS

Baltes et al. (2014) Plant Cell 26:151-63.*
Sun et al. (2021) KAH0652083.*
Mann et al. (2011) BMC Biotech 11 74.*
Baltes et al. (2014) Plant Cell 26(1):151-63.*
"*Beta vulgaris* subsp. *vulgaris* geraniol 8-hydroxylase-like (LOC104904803), mRNA", Dec. 10, 2014, URL: https://www.ncbi.nlm.nih.gov/protein/731359838.
Azeredo, H.M.C. "Betalains: properties, sources, applications, and stability—a review" 2009, International Journal of Food Science & Technology, vol. 44, pp. 2365-2376.

(Continued)

*Primary Examiner* — Russell T Boggs
(74) *Attorney, Agent, or Firm* — Mark S. Cohen; PEARL COHEN ZEDEK LATZER BARATZ LLP

(57) ABSTRACT

Disclosed herein are methods for gene targeting in a plant cell, as well as recombinant nucleic acid molecules used in these methods. Further disclosed are recombinant nucleic acid molecules comprising a target gene operably linked to a regulatory region of the UBQ10 gene.

18 Claims, 18 Drawing Sheets

Figure 1:
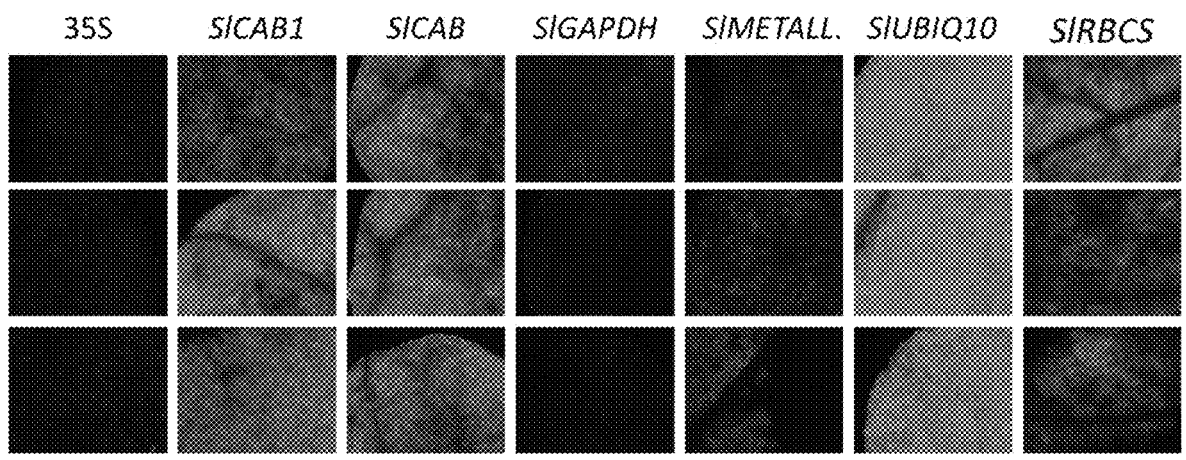

(5 of 18 Drawing Sheet(s) Filed in Color)

Specification includes a Sequence Listing.

(56) References Cited

U.S. PATENT DOCUMENTS

| | | | |
|---|---|---|---|
| 2015/0184182 A1* | 7/2015 | Kumar et al. | ..... C12N 15/8216 536/23.6 |
| 2015/0356239 A1 | 12/2015 | Zhang et al. | |
| 2016/0074535 A1 | 3/2016 | Ranganathan et al. | |
| 2016/0177304 A1 | 6/2016 | Collingwood et al. | |
| 2016/0208243 A1* | 7/2016 | Zhang et al. ........ | C12N 15/113 |
| 2016/0243251 A1 | 8/2016 | Blainey et al. | |
| 2016/0251648 A1 | 9/2016 | Wang et al. | |

FOREIGN PATENT DOCUMENTS

| | | | |
|---|---|---|---|
| WO | WO/2014/104878 A1 | | 7/2014 |
| WO | WO/2014/194190 A1 | | 12/2014 |
| WO | WO 2015 0026886 | * | 2/2015 |
| WO | WO/2015/048707 A2 | | 4/2015 |
| WO | WO/2015/131101 A1 | | 9/2015 |
| WO | WO/2016/033230 A1 | | 3/2016 |
| WO | WO/2017/034971 A1 | | 3/2017 |
| WO | WO/2017/222779 A1 | | 12/2017 |

OTHER PUBLICATIONS

Baltes N.J. et al., "DNA Replicons for Plant Genome Engineering" Jan. 2014, the Plant Cell, vol. 26, pp. 151-163.

Behera S. et al., "Analyses of Ca 2+ dynamics using a ubiquitin-10 promoter-driven Yellow Cameleon 3.6 indicator reveal reliable transgene expression and differences in cytoplasmic Ca 2+ responses in Arabidopis and rice (Oryza sativa) roots", New Phytologist, vol. 206, No. 2, Jan. 5, 2015, pp. 751-760.

Belhaj K. et al., "Plant genome editing made easy: targeted mutagenesis in model and crop plants using the CRISPR/Cas system", 2013, Plant Methods, 9:39.

Brockington, S.F., et al., "Lineage-specific gene radiations underlie the evolution of novel betalain pigmentation in Caryophyllales" 2015, New Phytol, vol. 207, Issue 4, pp. 1170-1180.

DeLoache et al. "An enzyme-coupled biosensor enables (S)-reticuline production in yeast from glucose", 2015, Nat Chem Biol., vol. 11, pp. 465-471.

Enfissi E.M. et al., "The regulation of carotenoid formation in tomato fruit" 2016, Plant J., vol. 89, pp. 774-788.

Gagandeep Jain et al., "Betalain induction by L-DOPA application confers photoprotection to saline-exposed leaves of Disphyma austral" 2015, New Phytologist, vol. 207, pp. 1075-1083.

Gandia-Herrero, F. et al. "Biosynthesis of betalains: yellow and violet plant pigments" 2013, Trends in Plant Science, vol. 18, pp. 334-343.

Gandia-Herrero, F. et al. "Characterization of recombinant Beta vulgaris 4,5-DOPA-extradiol-dioxygenase active in the biosynthesis of betalains" 2012, Planta, vol. 236, pp. 91-100.

Garbarino J.E. et al., "Expression of stress-responsive ubiquitin genes in potato tubers", Plant Molecular Biology, Springer, Dordrecht, NL, vol. 20, Jan. 1, 1992, pp. 235-244.

Grefen Ch et al, "A ubiquitin-10 promoter-based vector set for fluorescent protein tagging facilitates temporal stability and native protein distribution in transient and stable expression studies", 2010, the Plant Journal, vol. 64, pp. 355-365.

Hallmann A., "Algal Transgenic and Biotechnology" Apr. 2007, Transgenic Plant Journal, vol. 1(1), pp. 81-98.

Harris N.N. et al., "Betalain production is possible in anthocyanin-producing plant species given the presence of DOPA-dioxygenase and L-DOPA", BMC Plant Biology, Mar. 12, 2016, vol. 12, No. 1, pp. 1-12.

Hatlestad G. J. et al., "The beet R locus encodes a new cytochrome P450 required for red betalain production", Nature Genetics, Jun. 3, 2012, vol. 44, No. 7, pp. 816-820.

Heid et al., "Real Time Quantitative PCR", 1996 Genome Research, vol. 6, pp. 986-994.

Horsch R.B. et al., "Leaf disc transformation" 1988, Plant Molecular Biology Manual A5, pp. 1-9, Kluwer Academic Publishers, Dordrecht.

International Search Report dated Feb. 1, 2018 for PCT/IL2017/051020 of Sep. 11, 2017.

International Search Report dated Mar. 21, 2018 for PCT/IL2018/050040 of Jan. 11, 2018.

International Search Report dated Nov. 27, 2016 for PCT/IL2016/051010 of Sep. 11, 2016.

Isaacson T. et al., "Cloning of tangerine from Tomato Reveals a Carotenoid Isomerase Essential for the Production of -Carotene and Xanthophylls in Plants", 2002, Plant Cell vol. 14, pp. 333-342.

Killan et al., "High-efficiency homologous recombination in the oil-producing alga Nannochloropsis sp." PNAS 2011, 108(52), pp. 21265-21269.

Kyoungseon Min, et al., "Overview on the biotechnological production of L-DOPA" 2015, Appl Microbiol Biotechnol, vol. 99, pp. 575-584.

Meissner R. et al. "A new model system for tomato genetics", 1997, Plant J., vol. 12, pp. 1465-1472.

Misra Laxminarain et al., "Extraction of bioactive principles from Mucuna pruriens seeds" 2007, Indian Journal of Biochemistry & Biophysics, vol. 44, pp. 56-60.

Nakatsuka T. et al., "Genetic engineering of yellow betalain pigments beyond the species barrier", Scientific Reports, Jun. 13, 2013, vol. 3, pp. 1-7.

Podevin Nancy et al., "Site-directed nucleases: a paradigm shift in predictable, knowledge-base plant breeding", Apr. 17, 2013, Trends in Biotechnology, Elsevier Publications, Cambridge, GB, vol. 31, No. 6, pp. 375-383.

Potrykus I., "Gene Transfer to Plants: Assessment of Published Approaches and Results" 1991, Annual Review Plant Physiol, Plant Mol. Biol., vol. 42, pp. 205-225.

Qi et al., "Chapter 3: High efficient genome modification by designed zinc finger nuclease", Jan. 1, 2015, Advances in New Technology for Targeted Modification of Plant Genomes, Springer, pp. 39-53.

Radakovits et al., "Draft genome sequence and genetic transformation of the oleaginous alga Nannochloropsis gaditana", Feb. 21, 2012, Nat Commun., 3: 686.

Radakovits et al., "Genetic Engineering of Algae for Enhanced Biofuel Production Eukaryotic Cell", Apr. 2010, vol. 9(4), pp. 486-501.

Sarrion-Perdigones et al., "Design and construction of multigenic constructs for plant biotechnology using the GoldenBraid cloning strategy" 2014, Methods Mol. Biol., vol. 1116, pp. 133-151.

Sarrion-Perdigones et al., "GoldenBraid 2.0: A Comprehensive DNA Assembly Framework for Plant Synthetic Biology" 2013, Plant Physiology, vol. 162, pp. 1618-1631.

Sasaki, N., et.al., "Isolation and characterization of cDNAs encoding an enzyme with glucosyltransferase activity for cyclo-DOPA from four o'clocks and feather cockscombs" 2005, Plant and Cell Physiology, vol. 46, pp. 666-670.

Sekiguchi, H. et.al., "In Vitro Synthesis of Betaxanthins Using Recombinant DOPA 4,5-Dioxygenase and Evaluation of Their Radical Scavenging Activities" 2010, Journal of Agricultural and Food Chemistry, vol. 58, pp. 12504-12509.

Shdema Filler Hayut et al., "Targeted recombination between homologous chromosomes for precise breeding in tomato", May 26, 2017, Nature Communications, vol. 8, p. 15605.

Shimamoto K. et al., "Fertile transgenic rice plants regenerated from transformed protoplasts" Mar. 16, 1989, Nature, vol. 338, pp. 274-276.

Simon Shiml et al., "The CRISPR/Cas system can be used as nuclease for in planta gene targeting and as paired nickases for directed mutagenesis in Arabidopsis resulting in heritable progeny", Nov. 11, 2014, the Plant Journal, vol. 80, No. 6, pp. 1139-1150.

Solomon, E.I., et al., "Multicopper oxidases and oxygenases" 1996, Chemical Reviews, vol. 96, pp. 2563-2605.

Sunnadeniya R. et al., "Tyrosine Hydroxylation in Betalain Pigment Biosynthesis is Performed by Cytochrome P450 Enzymes in Beets (Beta vulgaris)" Feb. 18, 2016, PloS One, 11(2).

Trenchard Isis J., et al., "De novo production of the key branch point benzylisoquinoline alkaloid reticuline in yeast" 2015, Elsevier Metabolic Engineering, vol. 31, pp. 74-83.

(56) References Cited

OTHER PUBLICATIONS

Weissbach and Weissbach, "Methods for Plant Molecular Biology" (Eds.), Chapters 23 and 24 pp. 355-401, 1988 Academic Press, Inc., San Diego, California, article by Potrykus I. et al., "Protoplasts: Isolation, Culture, Plant Regeneration".

XP002775476, "Cloning vector PNIGEL16, complete sequence.", retrieved from Database EMBL [Online], Apr. 7, 2009.

Zhang, Y. et al., "Anthocyanins Double the Shelf Life of Tomatoes by Delaying Overripening and Reducing Susceptibility to Gray Mold." 2013, Current Biology, vol. 23, pp. 1094-1100.

Kumar, M. et al. (2022). Optimization of T-DNA configuration with UBIQUITIN10 promoters and tRNA-sgRNA complexes promotes highly efficient genome editing in allotetraploid tobacco. *Plant Cell Reports*, 1-20.

* cited by examiner

35S     SICAB1     SICAB     SIGAPDH     SIMETALL.     SIUBIQ10     SIRBCS

SIUBIQ10     StUBIQ10     AtUBIQ10 long     AtUBIQ10 short

COMPOSITIONS AND METHODS FOR REGULATING GENE EXPRESSION FOR TARGETED MUTAGENESIS

CROSS REFERENCE TO RELATED APPLICATIONS

This application is a Continuation Application of U.S. application Ser. No. 16/108,402 filed on Aug. 22, 2018, and published as US 2019/0048330-A1 on Feb. 14, 2019, which filed as a Continuation-in-Part Application of International Application No. PCT/IL2017/051020 filed Sep. 11, 2017, and published as WO 2018/047183 on Mar. 15, 2018, which claims priority of Israel Patent Application No. 247752, filed Sep. 11, 2016. Each of the above listed documents is hereby incorporated by reference in its entirety.

SEQUENCE LISTING STATEMENT

The instant application contains a Sequence Listing which has been submitted electronically in ASCII format and is hereby incorporated by reference in its entirety. Said ASCII copy, created on Feb. 26, 2019, is named P-80446-US1-SQL-26FEB19-ST25.txt and is 144,347 bytes in size.

FIELD OF DISCLOSURE

Disclosed herein are compositions and methods for regulating gene expression for gene targeting in eukaryotes, including plants and algae. Specifically, disclosed herein are recombinant nucleic acid molecules having the adjacent regions of POLYUBIQUITIN10 gene and uses thereof for enhancing the expression of a gene. Also disclosed here are methods for gene targeting in a plant cell, via homologous or non-homologous DNA repair and recombinant nucleic acid molecules used in these methods. The recombinant nucleic acid molecules comprise a viral replicon comprising a donor nucleic acid sequence and a nucleic acid comprising a nuclease system operably linked to a regulatory region of the UBQ10 gene.

BACKGROUND

The recently developed CRISPR-CAS system allows performing targeted gene modifications in most organisms. In plants, this technology can be used to knock-out specific genes to improve commercial traits. The limitation of this technology is its relatively low efficiency. To ensure highest efficiency, the (CAS9 gene must be expressed at high levels in a stable manner. This is usually achieved by using the obvious cauliflower mosaic virus (CaMV) 35S promoter. This promoter is a viral promoter and is widely used in the field of plant sciences in both dicots and monocots. However, this promoter is often subjected to silencing by the plant machinery, which results in the low expression of the adjacent gene, and is even inactive in certain cell types, such as pollen. Surprisingly, this promoter is still the promoter of choice used during research in the plant science field.

Recently, the CRISPR-CAS system was developed and allows the mutagenesis of any given genes. To this end, one must express the CAS9 gene together with a guide RNA (gRNA) that can recognize the desired target. As a consequence, CAS9 cleaves the genomic DNA, and the DNA repair machinery restores the chromosome, typically inserting or deleting a few nucleotides. This causes a frame shift at the target site and prevents correct gene expression.

Expression of the CAS9 gene under a low-efficiency promoter results in low mutagenesis success. Consequently, in order to obtain the desired homozygous mutant, one has to first screen for the mutation, select the mutant plants, and further cross the mutant plants several times. Due to the long-life cycle of most plants species (several months at least), this procedure may take several months or years depending on the zygosity of the plant species of interest.

A recent work reported on gene targeting in tomato plants in the absence of mutant plants selection. The reported rates of targeted mutations were low, and only 1 plant had germinally transmitted mutations (Yu et al. 2017, Sci. Rep., 1-18). Other works in rice showed very low rates of germinally transmitted gene mutations using Cas9 and Cpf1.

Several approaches have been developed throughout the years to increase the frequency of homologous recombination between a genomic target and an extrachromosomal homologous donor. These include the expression of genes involved in homologous recombination (HR) that can increase rates of gene targeting (GT), the use of single stranded donor DNA, and the use of viral vectors albeit with limited success.

Inducing a DSB in a certain genomic region was shown to increase the rate of repair by HR with an *Agrobacterium*-delivered T-DNA vector. The increase was of 2-3 orders of magnitudes, but the GT rate remained very low, in the $10^{-2}$-$10^{-3}$ range. This might be due to the competition with the more efficient non-homologous end-joining (NHEJ) repair pathway or due to low DNA DSB efficiency. Gene replacement can also be achieved via NHEJ through DSB-mediated excision of the targeted locus and insertion of the new donor DNA into the empty site. An improvement of the DSB-induced GT, called In planta GT approach, consists in the coordinated induction of a DSB in the genomic target and excision of the donor repair template from the plant DNA where it had been previously introduced.

Viral vectors are another approach that has been used for genetic manipulation of plants and for GT. Plant RNA viruses like the potato virus X (PVX) and the tobacco rattle virus (TRV) are commonly used for gene silencing and were also used for delivering ZFN nucleases or the CRISPR guide RNA (gRNA). Similarly, the Cabbage Leaf Curl virus was used for gRNA delivery in *Nicotiana Benthamiana*. These viruses spread efficiently in the plant yet the addition of an exogenous sequence to their genome is very limited due to size constraints of the viral particles, thus delivering the sequence of large proteins like Cas9 is not feasible.

Plant viruses from the geminivirus family have a DNA genome that replicates by a rolling circle replication (RCR) mechanism. Their genes can be transcribed within the plant nucleus, generating the proteins necessary for the RCR and for encapsidation to form virions. The ability of the virus to move from cell-to-cell (systemic infection) can be lost through insertion of DNA fragments whose length prevents encapsidation. For example, the maize streak virus (MSV) have shown to tolerate insertions in their genome and deliver DNA fragments to the plant, yet their systemic movement was damaged.

An engineered geminiviral replicon, which can undergo RCR but is not infective, was recently developed to deliver large sequences such as sequence specific nucleases (SSNs) and DNA repair templates, based on the bean yellow dwarf virus (BeYDV). This system was used in tomato to replace an endogenous promoter upstream of the ANTI gene with the cauliflower mosaic virus 35S promoter, which promotes constitutive anthocyanin synthesis serving as a marker for GT as early as in the stage of the calli formation. The BeYDV replicon was also used for generating targeted mutations and gene targeting in potato and cassava, and two different geminiviruses, the wheat dwarf virus (WDV) and the tomato leaf curl virus (ToLCV) were used for GT in hexaploid wheat, with WDV used for GT in rice.

Overall, the efficiency of GT achieved by the methods described above was relatively low or had to rely on markers, such as resistance (glyphosate), GFP, RFP, ANTI etc. This is not amenable to agricultural and research applications, where there is a need of a routine method with no addition of exogenous selectable or reporter markers. However, only a highly efficient GT would allow breeding transgenic plants without the need of selection markers.

Therefore, there is an unmet need for, and it would be highly advantageous to have means and methods for highly efficient GT in a plant.

SUMMARY OF THE DISCLOSURE

In one aspect, disclosed herein is a method for gene targeting in a plant cell, the method comprising: (a) introducing into said plant cell a first nucleic acid comprising a viral replicon comprising a donor nucleic acid sequence, said donor sequence targeted to a plant endogenous DNA sequence; and (b) introducing into said same plant cell a second nucleic acid comprising a nuclease system, wherein said nuclease system is targeted to said plant endogenous DNA sequence, and wherein at least one component of said nuclease system is expressed under a UBQ10 regulatory sequence; wherein homologous recombination occurs between the donor sequence and said plant endogenous DNA sequence.

In a related aspect, the viral replicon is selected from a group comprising: a geminiviral replicon, a bean yellow dwarf virus (BeYDV) replicon, a cabbage leaf curl virus (CalCuV) replicon, a tomato leaf curl virus (ToLCV) replicon, a wheat dwarf virus (WDV) replicon, or any combination thereof. In a related aspect, the donor sequence comprises a gene, a mutated gene, a part of a gene, a regulatory sequence, a mutated regulatory sequence, a sequence upstream of a gene, a sequence downstream of a gene, an exon sequence, an intron sequence, or any combination thereof.

In a related aspect, the nuclease system is selected from a group comprising: a nickase, a zinc finger nuclease (ZFN) system, a transcription activator-like effector nuclease (TALEN) system, a meganuclease, or a clustered regularly interspaced short palindromic repeats (CRISPR)/CRISPR associated proteins (Cas) nuclease. In a related aspect, the CRISPR/Cas nuclease system comprises a CRISPR-associated endonuclease (Cas) and a gRNA molecule, wherein said gRNA molecule binds within said plant endogenous DNA sequence.

In a related aspect, the Cas enzyme is selected from the group comprising Cas1, Cas1B, Cas2, Cas3, Cas4, Cas5, Cas6, Cas7, Cas8, Cas9, Cas10, C2cl, CasX, NgAgo, Cpf1, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4, or homologs thereof, or modified versions thereof. In a related aspect, the Cas is operably linked to said UBQ10 regulatory sequence.

In a related aspect, the single expression vector comprises said first nucleic acid and said second nucleic acid. In a related aspect, the UBQ10 regulatory sequence is selected from a group comprising: *Solanum lycopersicum, Solanum tuberosum*, or *Arabidopsis thaliana* UBQ10 regulatory sequence. In a related aspect, the *Solanum lycopersicum* UBQ10 regulatory sequence comprises *Solanum lycopersicum* UBQ10 promoter and terminator regions. In a related aspect, the gene targeting comprises gene editing, gene replacement, or a combination of both.

In one aspect, disclosed herein is a recombinant nucleic acid molecule comprising a first nucleotide sequence encoding a nuclease system, wherein said nuclease system is targeted to a plant endogenous DNA sequence, and wherein at least one component of said nuclease system is operably linked to a UBQ10 regulatory sequence.

In a related aspect, the recombinant nucleic acid molecule further comprises a second nucleotide sequence encoding a viral replicon comprising a donor nucleic acid sequence targeted to said plant endogenous DNA sequence.

In one aspect, disclosed herein is a method for producing a transgenic plant seed, the method comprising: (a) introducing into at least one cell of a plant a first nucleic acid comprising a viral replicon comprising a donor nucleic acid sequence, said donor sequence targeted to a plant endogenous DNA sequence; and (b) introducing into the cell of (a) a second nucleic acid comprising a nuclease system, wherein said nuclease system is targeted to said plant endogenous DNA sequence, and wherein at least one component of said nuclease system is expressed under a UBQ10 regulatory sequence; (c) generating a transgenic plant from said at least one cell; and (d) growing said transgenic plant to obtain a seed; wherein homologous recombination occurs between the donor sequence and said plant endogenous DNA sequence; thereby producing a transgenic seed of a plant, wherein any plant produced from said seed comprises said donor nucleic acid sequence.

BRIEF DESCRIPTIONS OF THE DRAWINGS

The patent or patent application file contains at least one drawing executed in color. Copies of this patent or patent application publication with color drawing(s) will be provided by the Office upon request and payment of the necessary fee.

FIG. 1. RFP fluorescence observed in *N. benthamiana* leaves 7 days post inoculation, with *Agrobacterium* containing a plasmid that harbor the RFP gene under the control of various promoters and terminators. 35S: cauliflower mosaic virus (CaMV)—control; SlCAB1: CHLOROPHYLL A-B BINDING PROTEIN (Solyc02g071010)—SlCAB1 promoter region (SEQ ID NO: 8)/SlTHI4 terminator region (SEQ ID NO: 21); SlCAB: CHLOROPHYLL A-B BINDING PROTEIN (Solyc03g005760)—SlCAB promoter region (SEQ ID NO: 11)/SlTHI4 terminator region (SEQ ID NO: 21); SlGAPDH: GLYCERALDEHYDE3-PHOSPHATE DEHYDROGENASE (Solyc04g009030)—SlGAPDH promoter region (SEQ ID NO: 14)/SlTHI4 terminator region (SEQ ID NO: 21), SlMETALL: TYPE 2 METALLOTHIONEIN (Solyc09g010800)—SlMETALL promoter region (SEQ ID NO: 17)/SlTHI4 terminator region (SEQ ID NO: 21); SlUBQ10: POLYUBIQUITIN10 (Solyc07g064130)—SlUBQ10 promoter region (SEQ ID NO: 23)/SlUBQ10 terminator region (SEQ ID NO: 27); SlRBCS: RIBULOSE BISPHOSPHATE CARBOXYLASE SMALL CHAIN (Solyc03g034220)—SlRBCS promoter region (SEQ ID NO: 31)/SlTHI4 terminator region SEQ ID NO: 21).

Figure 2:
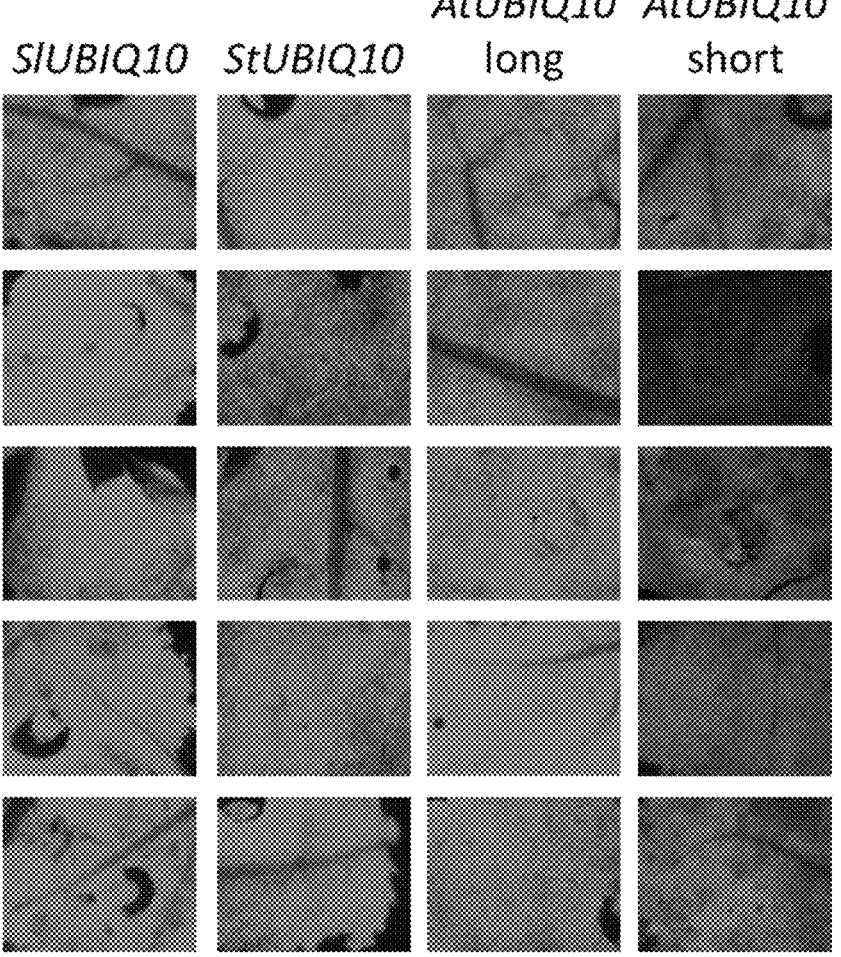

FIG. 2. RFP fluorescence observed in *N. benthamiana* leaves 7 days post inoculation, with *Agrobacterium* containing a plasmid that harbor the RFP gene under the control of various promoters and terminators. SlUBQ10: POLYUBIQ-UITIN10 of tomato (Solyc07g064130-StUBQ10 promoter region (SEQ ID NO: 23)/SlUBQ10 terminator region (SEQ ID NO: 27); StUBQ10: POLYUBIQUITIN10 of potato (Sotub07g026130-StUBQ10 promoter region (SEQ ID NO: 34)/StUBQ10 terminator region (SEQ ID NO: 38)); AtUBQ10: POLYUBIQUITIN10 of *Arabidopsis* (AT4G05320-AtUBQ10 long promoter region (SEQ ID NO: 41)/AtUBQ10 long terminator region (SEQ ID NO: 45) and AtUBQ10 short promoter region (SEQ ID NO: 48)/ AtUBQ10 short terminator region (SEQ ID NO: 45).

Figure 3:
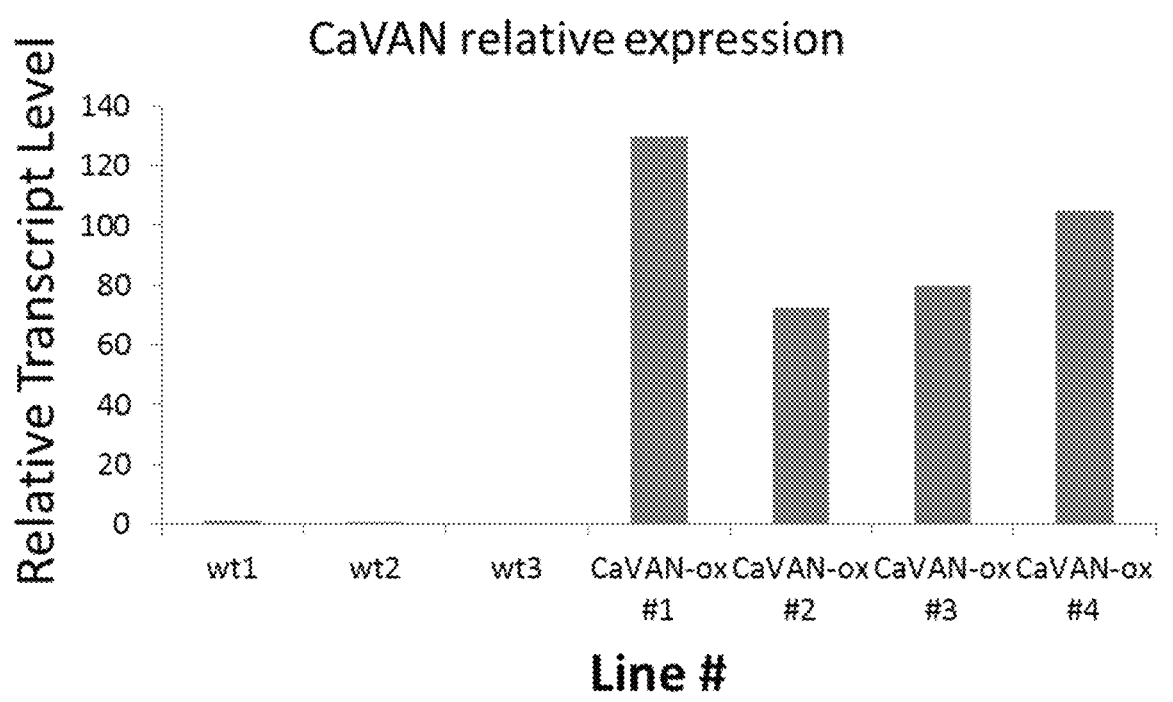

FIG. 3. Relative expression level of the VAN/LIN SYN-THASE gene of *Capsicum* annum (CaVAN) in transgenic tomatoes obtained in Example 3. (wt—wild type plant; Lines 1, 2, 3, and 4 tomatoes transformed using the CaVAN expression vector wherein CaVAN gene expression is under the control of the SlPOLYUBIQUITIN10 cassette (SlUBQ10 promoter region (SEQ ID NO: 23)/SlUBQ10 terminator region (SEQ ID NO: 27) CaVAN-ox—CaVAN-overexpression).

Figure 4A:
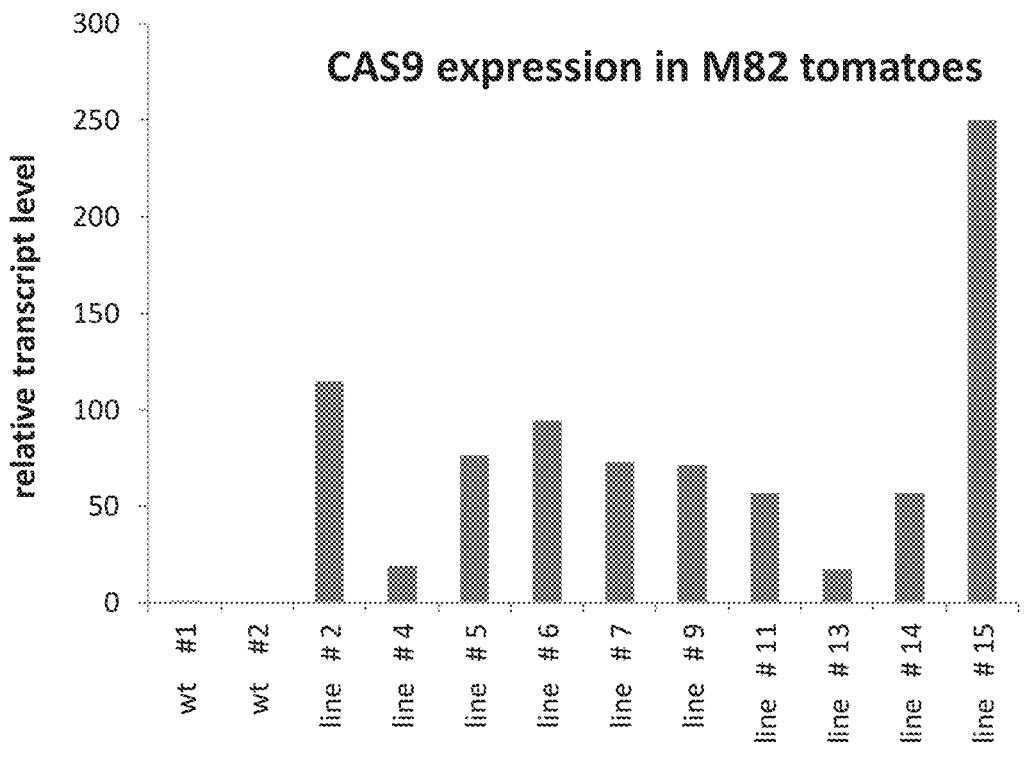
Figure 4B:
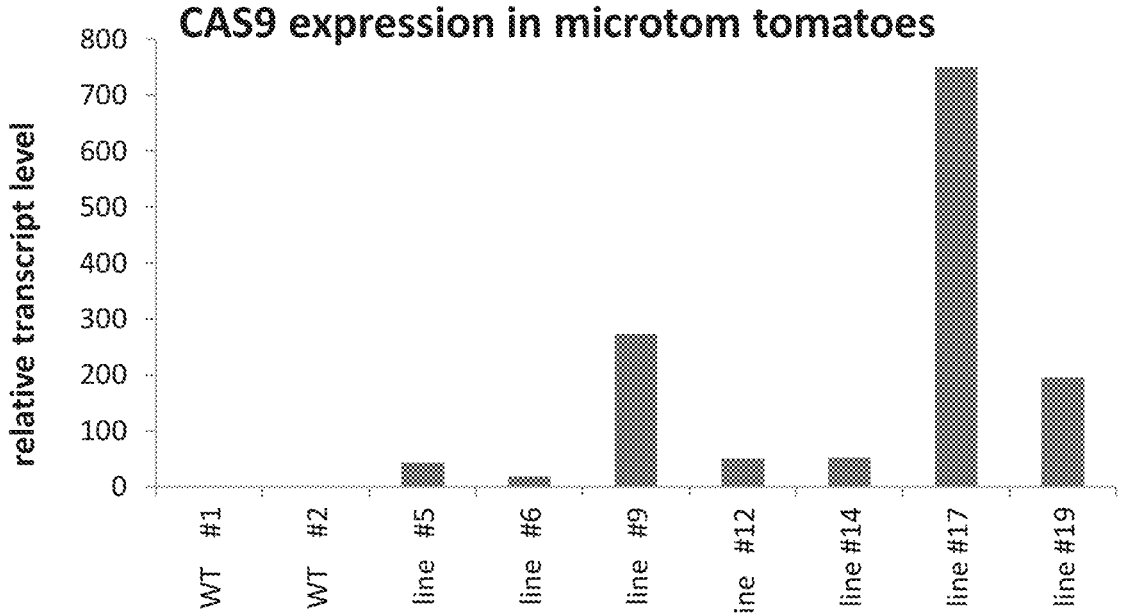

FIGS. 4A-4B. Relative expression level of the CAS9 gene in transgenic tomatoes obtained in Example 2, measured by (qRT-PCR). FIG. 4A shows CAS9 expression in M82 tomatoes. wt—wild-type plant. Lines 4, 5, 6, 7, 9, 11, 13, 14, and 15—M82 tomatoes transformed with the CAS9 expression vector wherein CAS9 gene expression is under the control of the SlPOLYUBIQUITIN10 cassette (SlUBQ10 promoter region (SEQ ID NO: 23)/SlUBQ10 terminator region (SEQ ID NO: 27)). FIG. 4B shows CAS9 expression in microtom tomatoes. wt—wild-type plant (CAS9 gene was expressed in a SlUBIQUITIN10 cassette). Lines 5, 6, 9, 12, 14, 17, and 19—microtom tomatoes transformed with the CAS9 expression vector wherein CAS9 gene expression is under the control of the SlPOLYUBIQUITIN10 cassette (SlUBQ10 promoter region (SEQ ID NO: 23)/SlUBQ10 terminator region (SEQ ID NO: 27)).

Figure 5A:
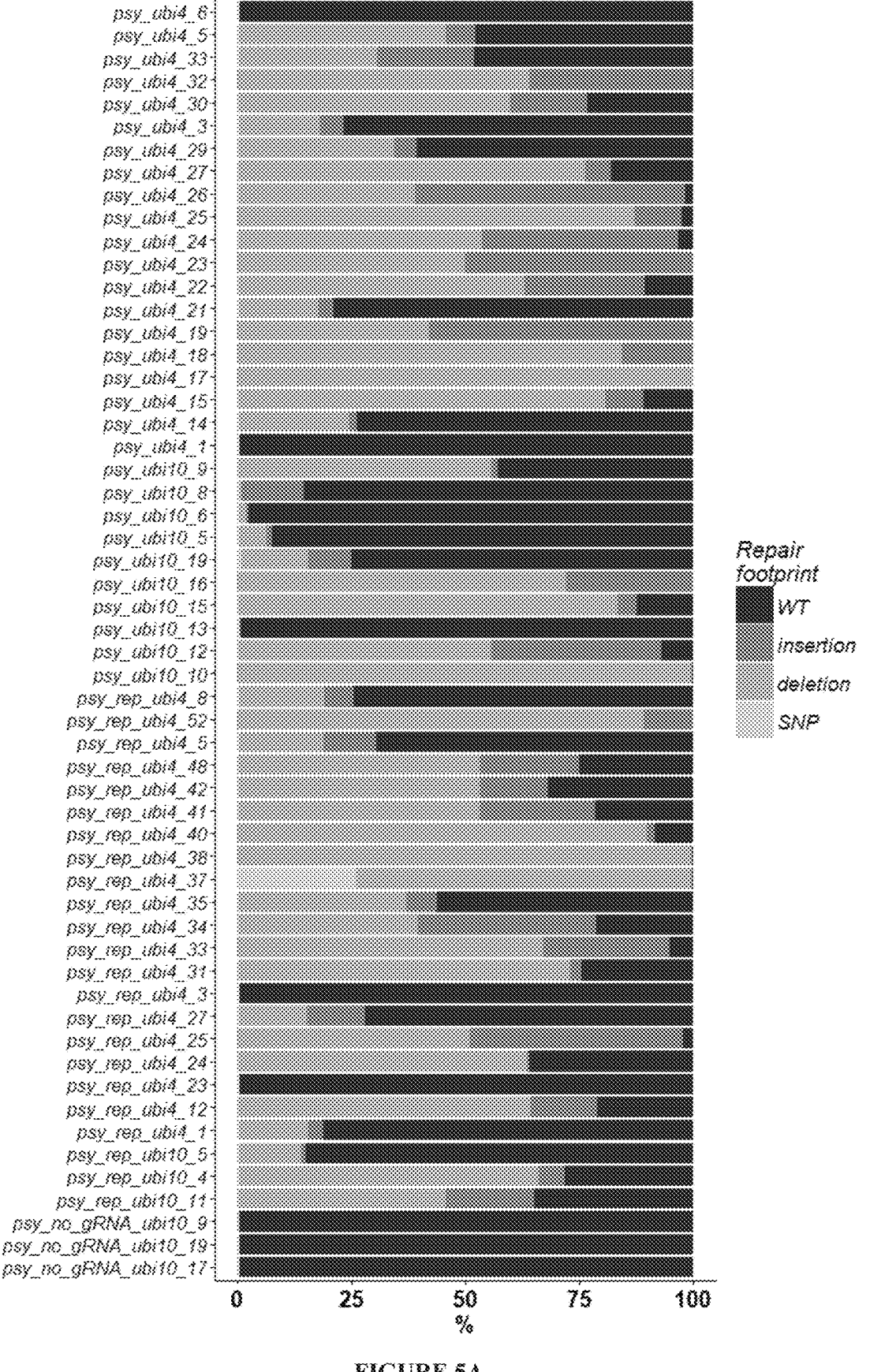
Figure 5B:
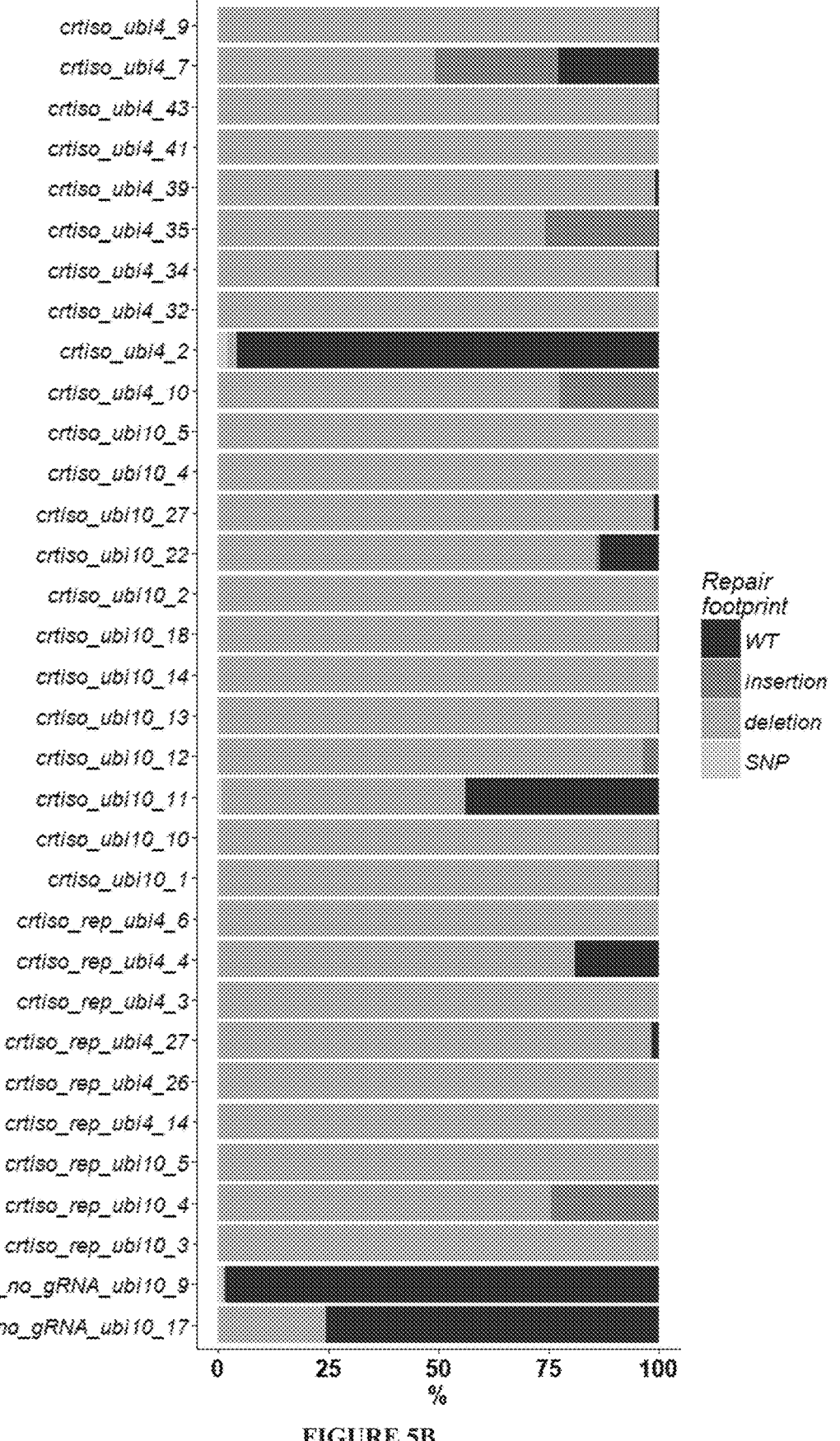

FIGS. 5A and 5B. Frequency of indels present in the plants of Table 3 at the target site of PSY1 gene (FIG. 5A) and CRTiso gene (FIG. 5B) (gRNA—guide RNA; psy—PSY1 gene; ubi10-SlPOLYUBIQUITIN10 cassette (SlUBQ10 promoter region (SEQ ID NO: 23)/SlUBQ10 terminator region (SEQ ID NO: 27)); #—identifies the different tomato lines; rep—BeYDV Replicon; ubi4-PcU-BIQUITIN4-2 promoter; crtiso—CRTiso gene).

Figures 6, 7:
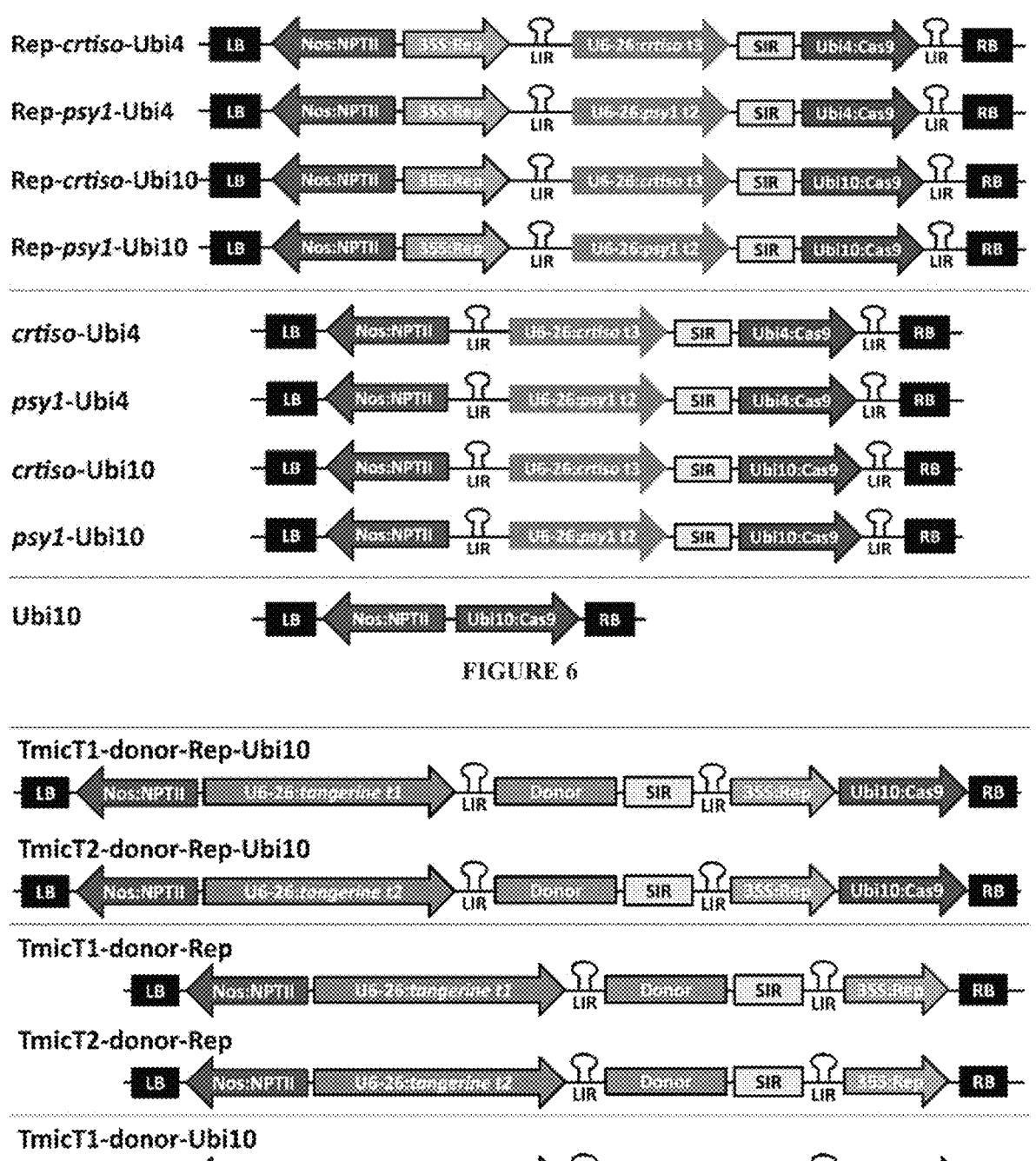

FIG. 6. Constructs used for gene targeting optimization. Two different constitutive promoters for the expression of the Cas9 endonuclease were used, PcUbiquitin4-2 (Ubi4) and SlUbiquitin10 (Ubi10), with two different gRNAs, expressed under the U6-26 promoter, targeting either CRTISO or PSY1 genes. Each combination was tested with or without the Rep proteins expressed under the 35S promoter. The kanamycin resistance gene is indicated by the arrow "Nos:NPTH". The geminiviral large intergenic regions (LIRs, stem loop structure) flanking the gRNA, the geminiviral short intergenic region (SIR, orange box) and the Cas9 to create a replicon that contains the CRISPR/Cas9 components. The T-DNA left and right borders (LB and RB) are shown as black boxes. Construct Ubi10, expressing only Cas9 and kanamycin resistance was used as negative control.

FIG. 7. Gene targeting constructs. The gene targeting construct ("TmicT1-donor-Rep-Ubi10" or "TmicT2-donor-Rep-Ubi10") contains the CRISPR/Cas9 system and the Rep protein on the T-DNA outside the geminiviral replicon (defined by the LIR sequences) and the donor repair template is within the replicon. Two different gRNAs that were examined, target 1 ("T1") and target 2 ("T2") both specific to the deleted allele and not affecting the repaired allele. Control constructs have either the geminiviral replicon and gRNA with no Cas9 endonuclease ("TmicT1-donor-Rep", "TmicT2-donor-Rep") or only the CRISPR/Cas9 system and the geminiviral intergenic regions containing the donor repair template with no Rep proteins ("TmicT1-donor-Ubi10", "TmicT2-donor-Ubi10"). Other controls have only the gRNA and the intergenic regions containing the donor repair template but with no Cas9 and Rep ("TmicT1-donor", "TmicT2-donor"), or with only the Cas9 and Rep ("Rep-Ubi10"), or only Rep ("Rep") or only Cas9 ("Ubi10").

Figure 8:
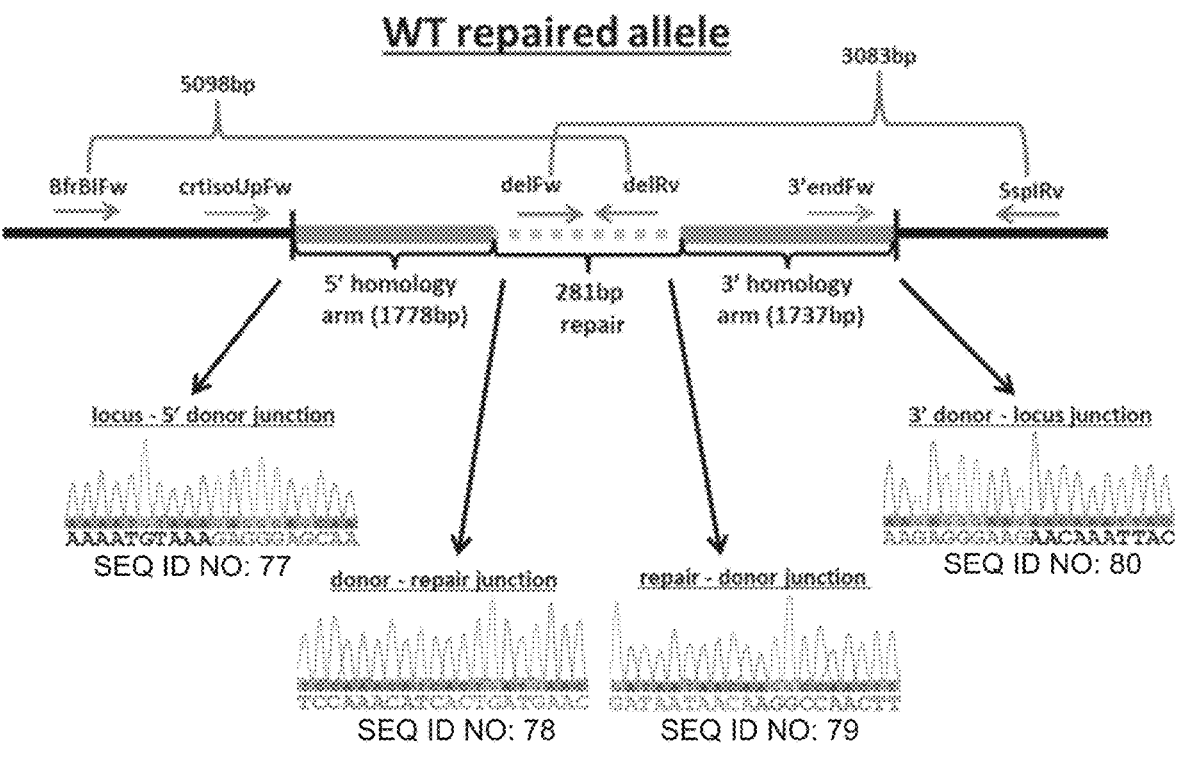

FIG. 8. Primers used for long range PCR and Sanger sequencing of gene targeting integration sites. Sanger sequencing using primers crtisoUpFw and delRv to verify the junction between the CRTISO locus and the 5' homology arm (HA) of the donor repair template, and the junction between the 5' HA of the donor and the 281 bp repair sequence, respectively. Primers delFw and 3'endFw were used to verify the junction between the 281 bp repair sequence and the 3' HA of the donor, and the junction between the donor 3' HA and the CRTISO locus. Sequencing results obtained had the expected sequences for all junctions. Embodiments of junction nucleotide sequences shown in the figure include locus 5' donor junction (SEQ ID NO: 77), donor-repair junction (SEQ ID NO: 78), repair—donor junction (SEQ ID NO: 79), and a 3' donor—locus junction (SEQ ID NO: 80).

Figure 9:
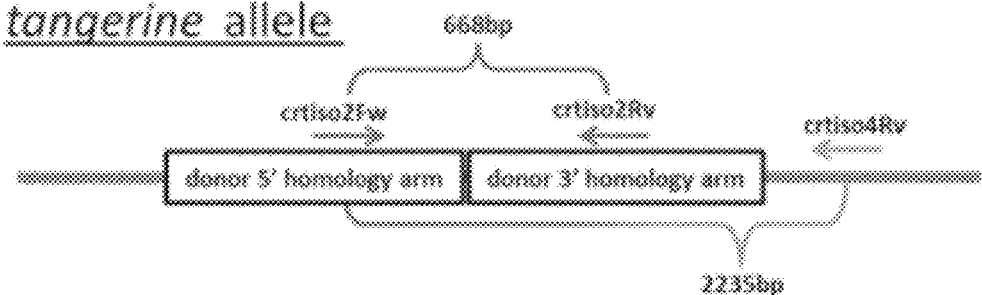
Figure 9:
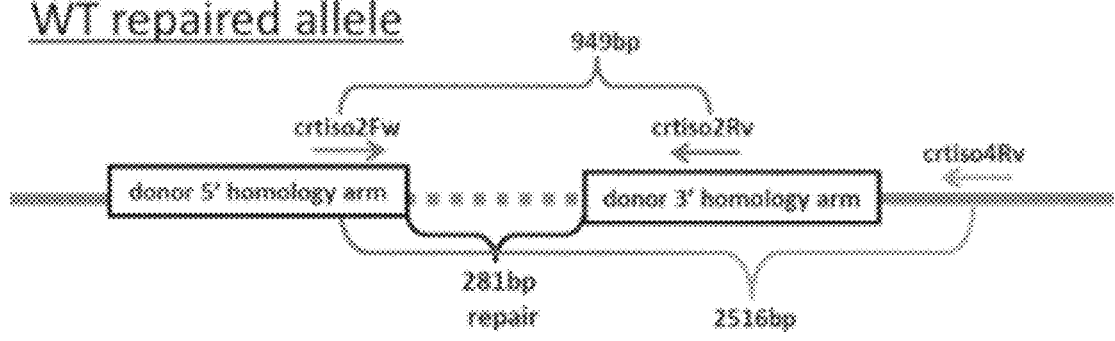

FIG. 9. Primers used for detection of $T_0$ gene targeting plants zygosity. A scheme of the tangerine and WT repaired alleles with the position of the primers used for the screen. Primers crtiso2Fw and crtiso2Rv were used to check heterozygosity by differentiating a tangerine (668 bp) or WT (either if the donor repair template or a repaired allele, 949 bp) allele fragments, together with primers crtiso2Fw and crtiso4Rv that amplify a repair allele (2516 bp) and tangerine allele (2235 bp).

Figure 10A:
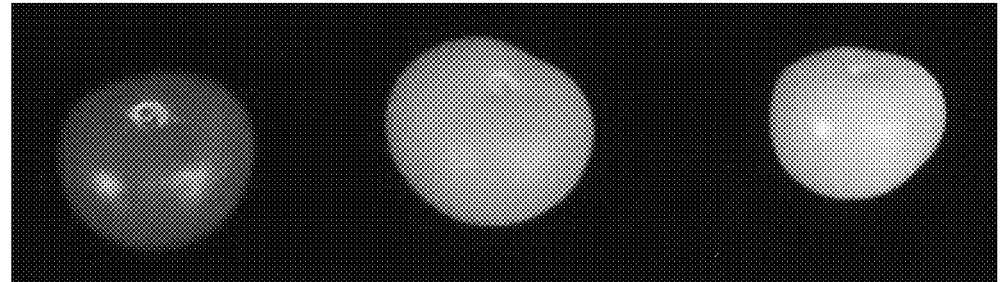
Figure 10B:
Figure 10C:

FIGS. 10A-10C. Gene targeting in Micro-Tom. Phenotypes of crtiso and psy1 mutants. FIG. 10A shows mutants with distinctive phenotypes in comparison to WT, from right to left: psy1 mutant yellow ripe fruit, crtiso mutant orange ripe fruit and WT red ripe fruit. FIG. 10B crtiso mutant plant (right) exhibiting late greening of the young leaves phenotype, two days after moving from tissue culture to soil, as compared to psy1 mutant plant with green young leaves phenotype (left). FIG. 10C WT yellow flower (right) in comparison to inflorescence of crtiso mutant plant with white petals and orange anthers (left).

Figure 11A:
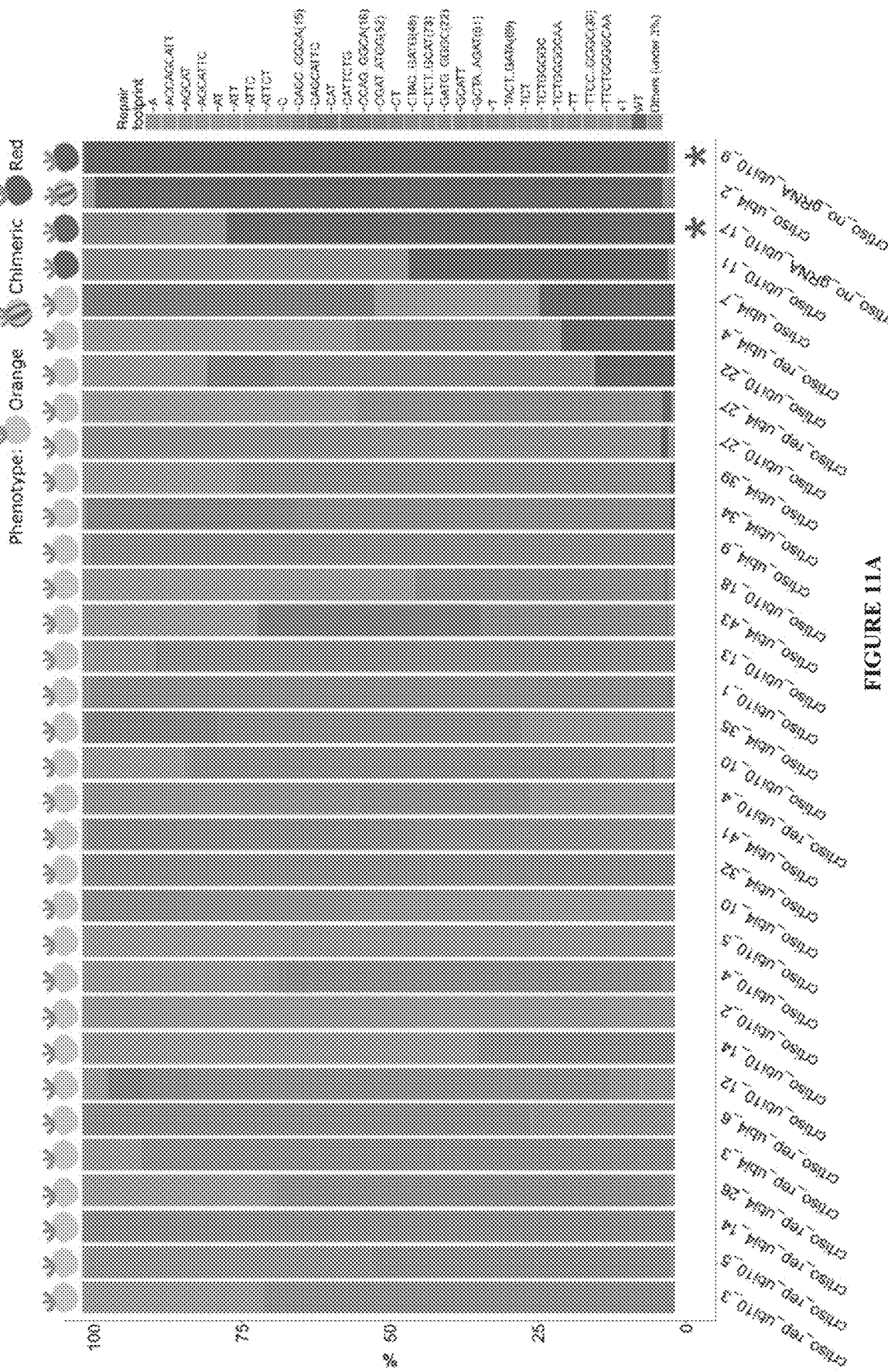
Figure 11B:
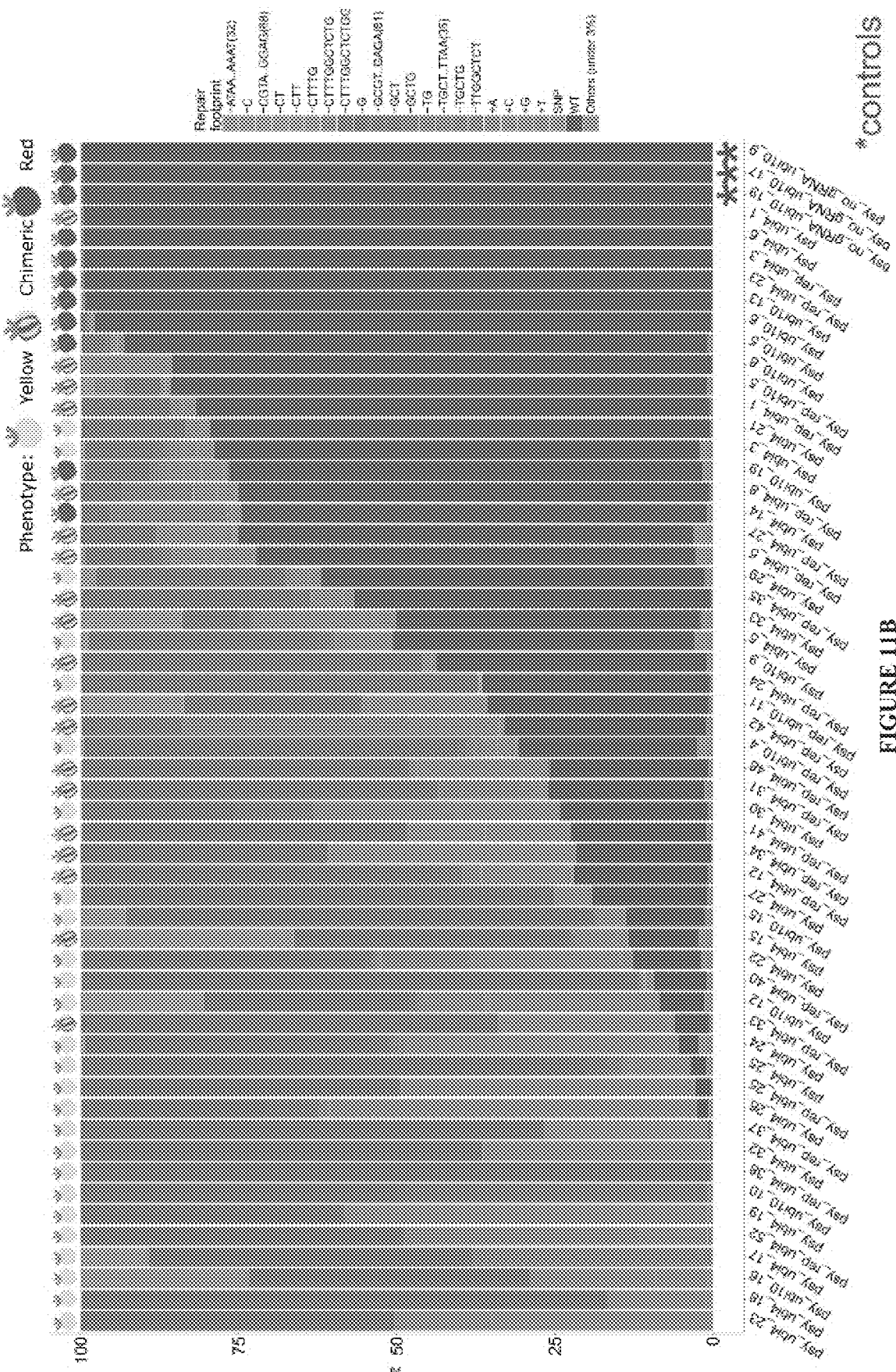

FIGS. 11A-11B. Targeted mutagenesis in Micro-Tom. Sequence footprints of CRTISO and PSY) genes. FIG. 11A shows sequence footprints in CRTISO as a result of non-homologous end-joining repair, and their frequencies in individual plants. Each column represents a different $T_0$ plant where the CRTISO gene has been targeted using different constructs, except for two plants with Ubi10:Cas9 and no gRNA (9 and 17, marked with asterisks) which served as a negative control. The color-code for the sequence of the indel footprints is shown on the right. The frequency of each footprint, determined from the frequency of Illumina reads, is shown on the X axis; footprints represented under 3% of the reads are grouped in "Others". Fruit color phenotypes are represented right to the barplot of each plant. CRTISO target: gcgatgctaccagcattctgGGG.

FIG. 11B shows sequence footprints in PSY1 as a result of non-homologous end-joining repair, and their frequencies in individual plants. Each column represents a different $T_0$ plant where the PSY1 gene has been targeted using different constructs, except for three plants with Ubi10:Cas9 and no gRNA (9, 17 and 19, marked with asterisks) which served as a negative control. The color-code for the sequence of the indel footprints is shown on the right. The frequency of each footprint, determined from the frequency of Illumina reads, is shown on the X axis; footprints represented under 3% of the reads are grouped in "Others". Fruit color phenotypes are represented right to the barplot of each plant. PSY1 target: gagcgtatataatgctgcttTGG.

Figure 12:
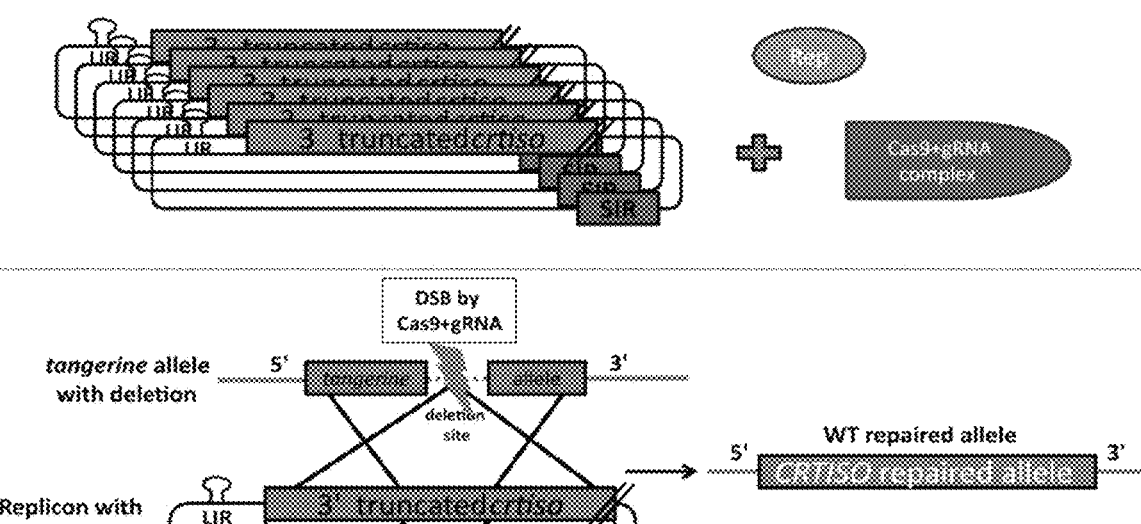

FIG. 12 shows the gene targeting strategy used for the experiments. Plants are transformed with a construct comprising Cas9 under the expression of the SlUbiquitin10 (Ubi10) promoter, a gRNA (U6-26:tangerine t1 or t2), the Rep protein, and a donor sequence comprising a truncated CRTISO WT coding region that deleted in the tangerine mutant.

Figure 13:
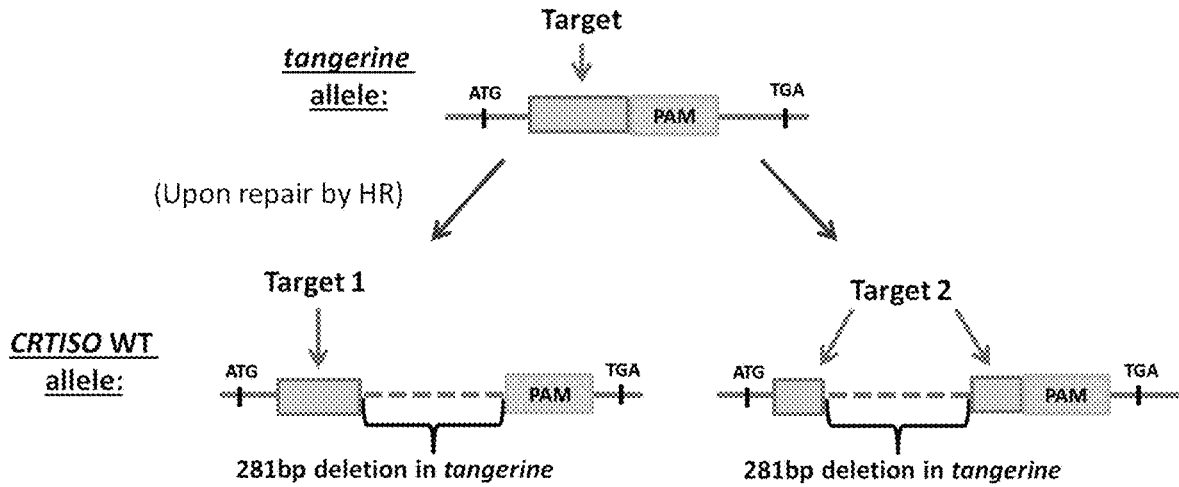

FIG. 13 shows the design of CRISPR gRNAs tangerine. CRISPR gRNAs were designed to match target sequences (yellow boxes) in the tangerine allele that are destroyed upon insertion of repair sequence. Target 1 ("T1", left) was designed so that it is destroyed upon repair of the gene by homologous recombination, as the CRISPR mandatory PAM sequence (light blue box) separates from the target sequence. Target 2 ("T2", right) is destroyed because the deletion is in the middle of the target, and insertion of the 281 bp upon repair splits it.

Figure 14:
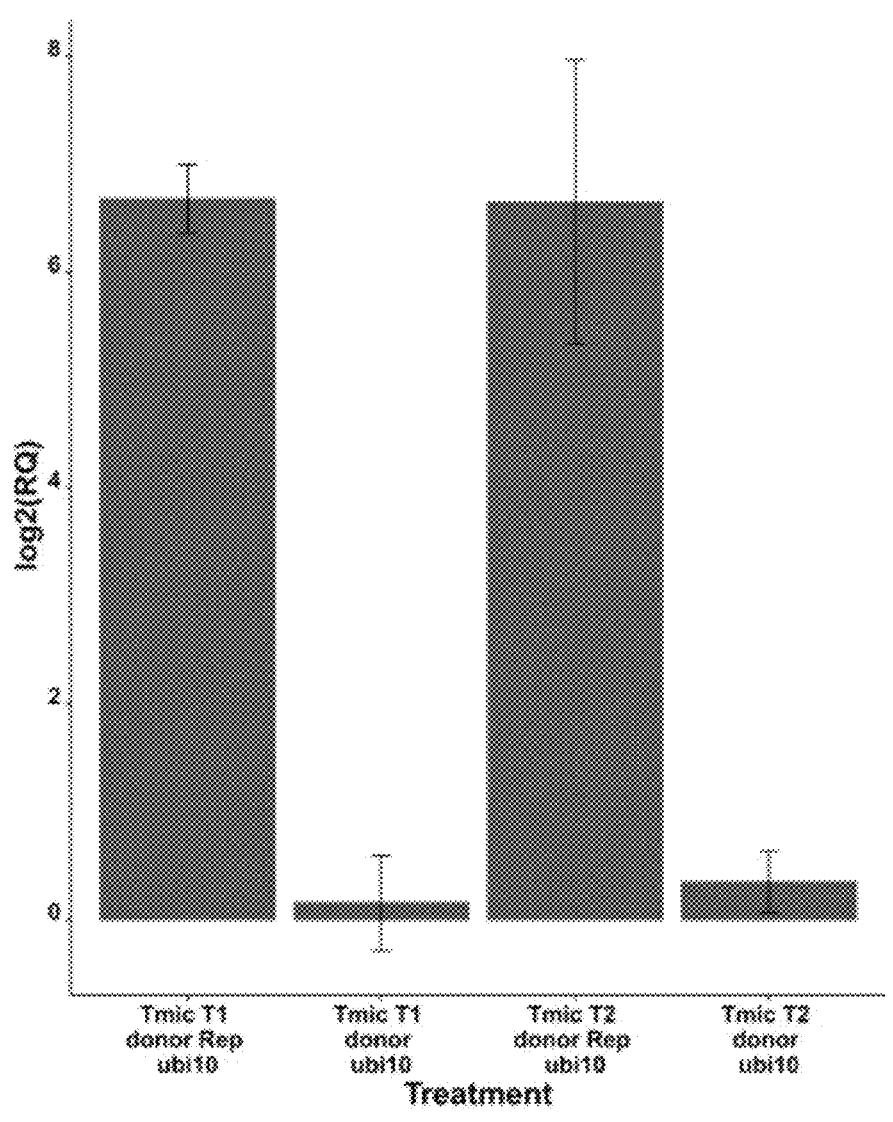

FIG. 14 shows relative quantification (RQ) of replicons in plants transfected with Constructs with or without Rep. Three biological replicates of plants from 4 different gene targeting constructs described in FIG. 2. Results indicate up to ~90 fold increase in copy number. Bars represent the standard error of biological replicates.

Figure 15A:
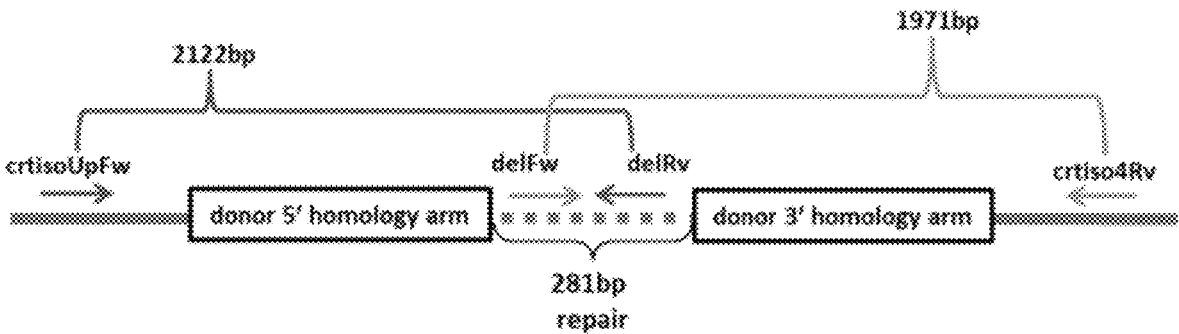
Figure 15B:
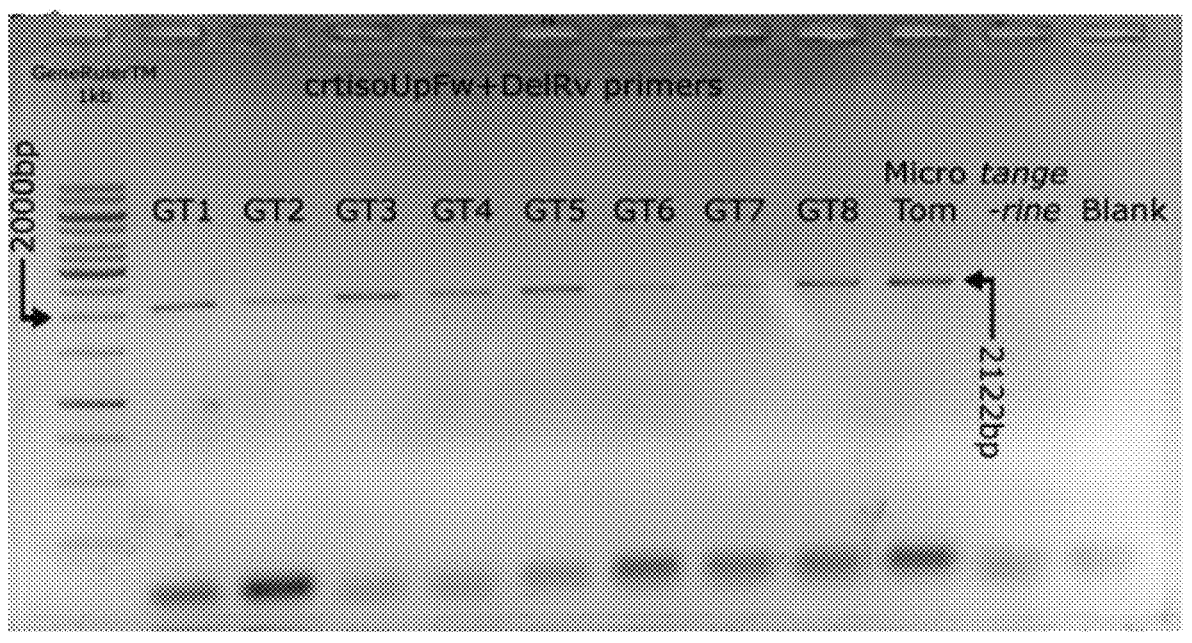
Figure 15C:
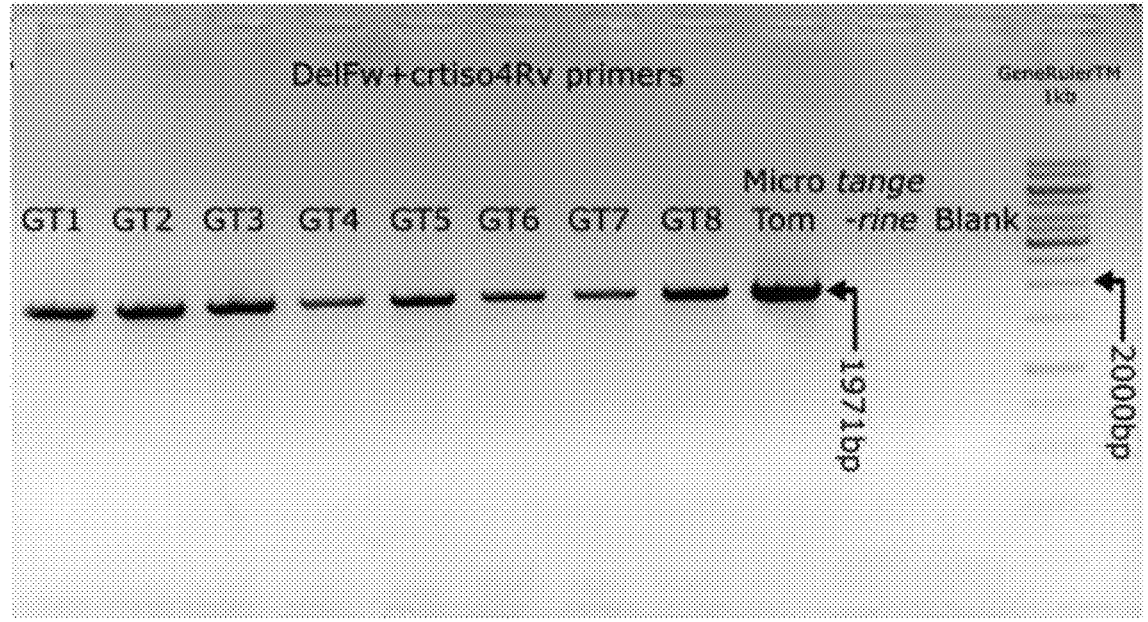

FIGS. 15A-15C show the validation of gene targeting with the TmicT2-donor-Rep-Ubi10 construct. FIG. 15A shows a scheme of the repaired WT allele with the position of the primers used for the analysis of integration events. FIGS. 15B and 15C show an EtBr-stained agarose gels of the PCR product using crtisoUpFw and delRv primers (2122 bp) (FIG. 15B) and using delFw and crtiso4R primers (1971 bp) (FIG. 15C).

Figure 16A:
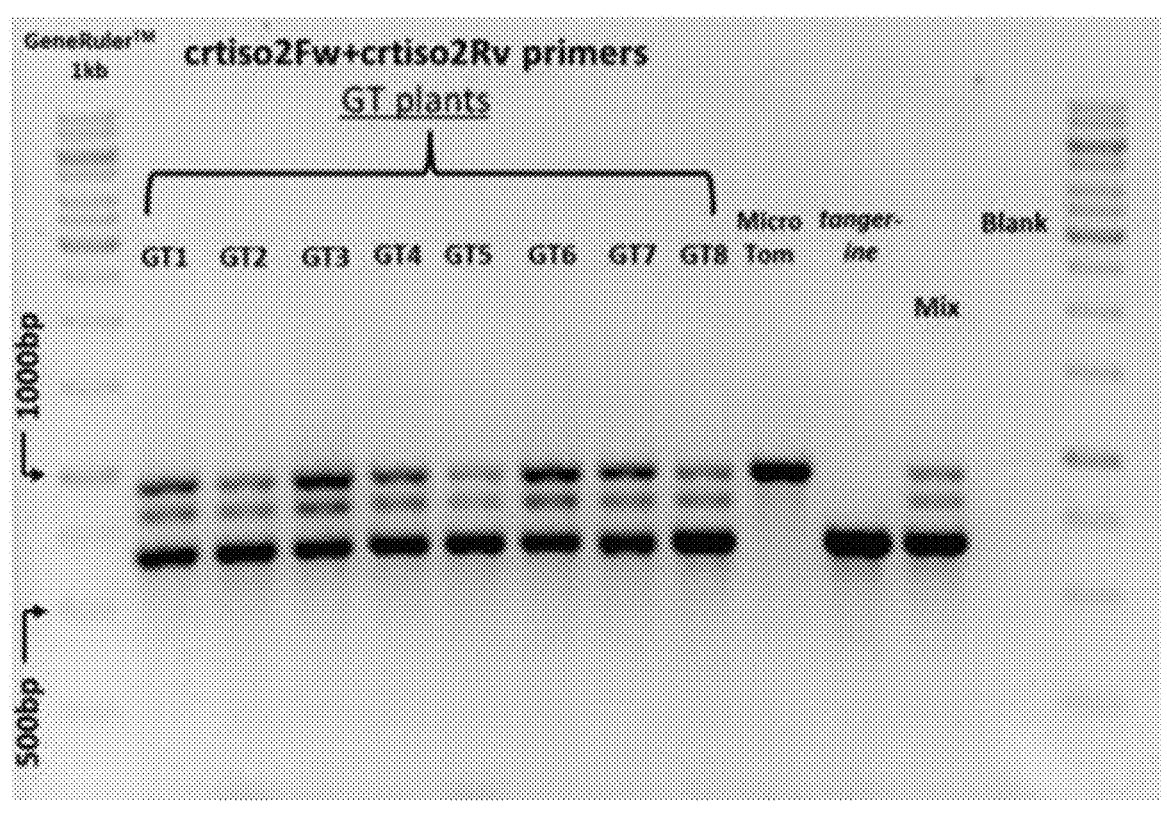
Figure 16B:
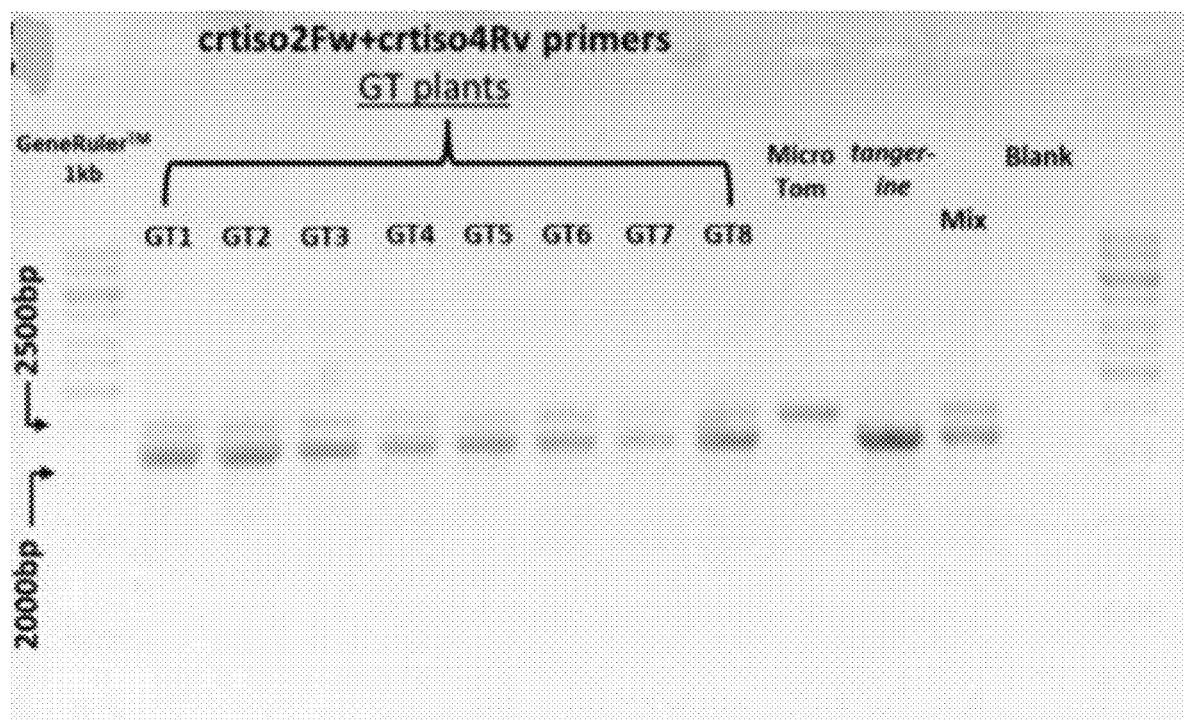

FIGS. 16A and 16B show the detection of zygosity in $T_0$ plants with gene targeting phenotype. FIGS. 16A and 16B show electrophoresis in an EtBr agarose gel of PCR products obtained by amplification from both sides of the deletion with primers crtiso2Fw and crtiso2Rv (FIG. 16A) and primers crtiso2Fw and crtiso4Rv (FIG. 16B).

Figure 17A:
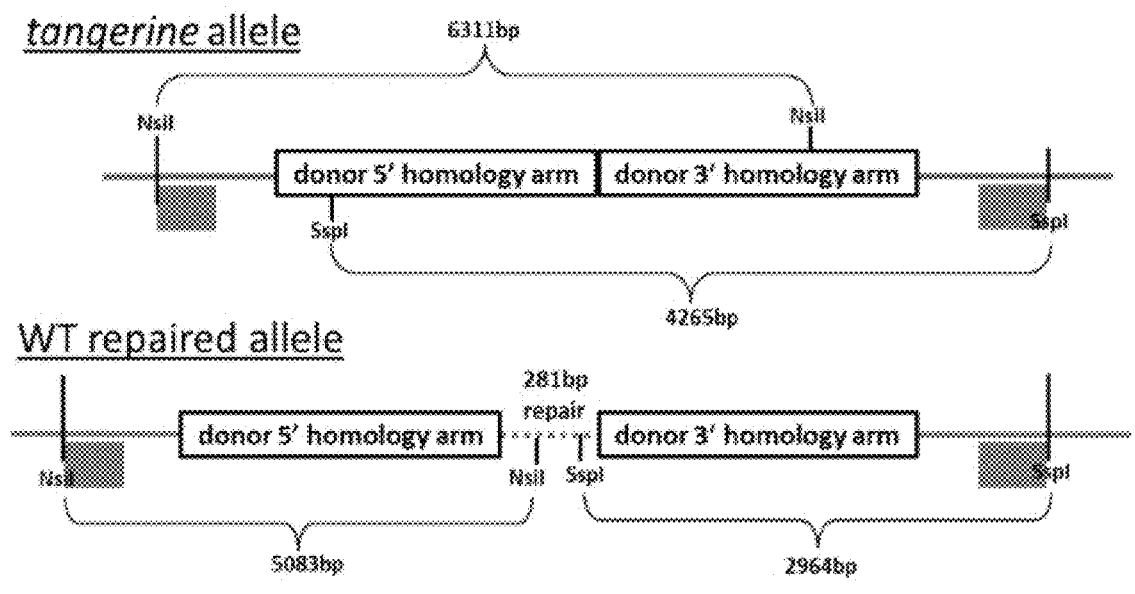
Figure 17B:
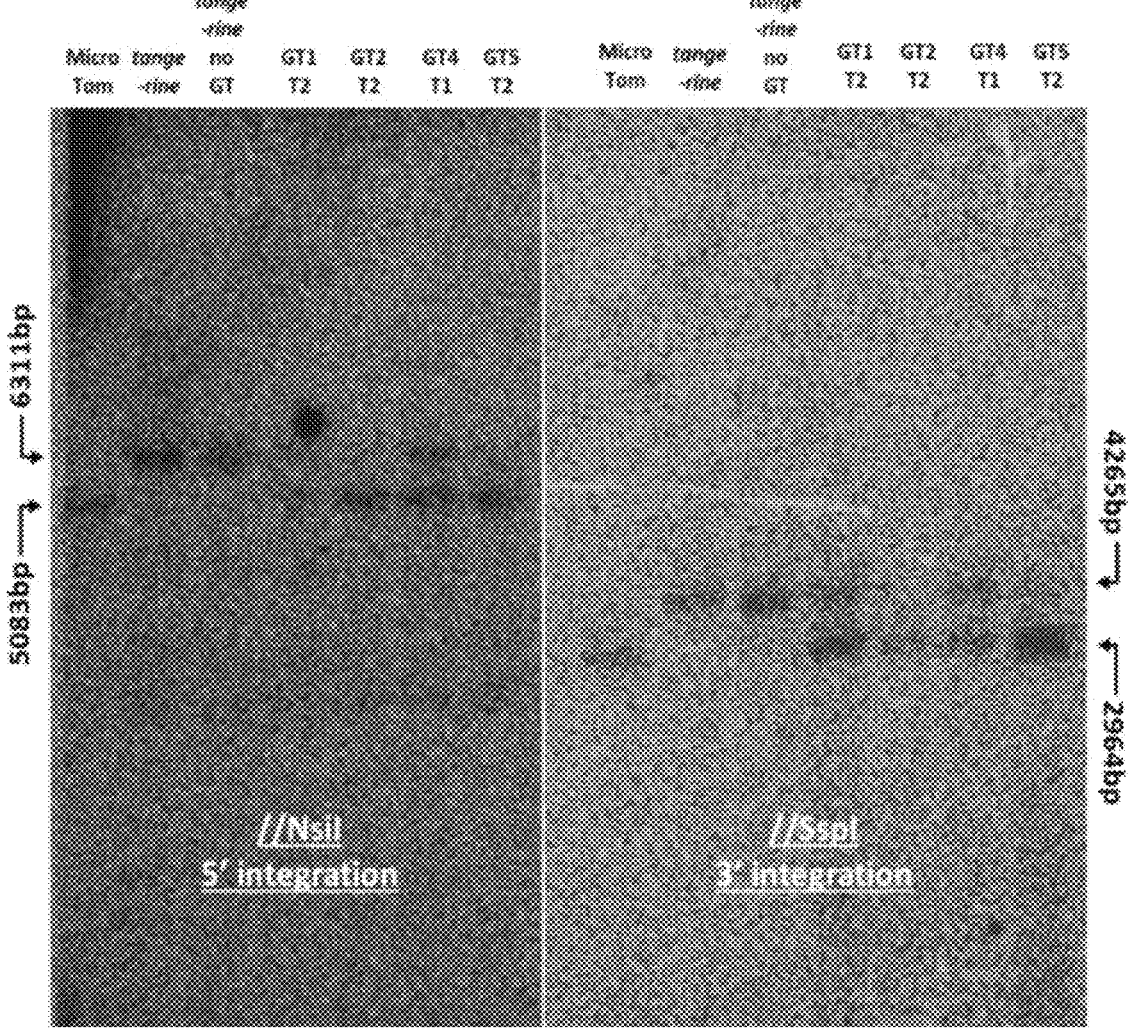

FIGS. 17A and 17B show Southern blot hybridization of 4 $T_0$ plants with gene targeting phenotype. FIG. 17A shows the location of the NsiI and SspI-HF restriction sites and of the probes (gray rectangles) used in the experiment. FIG. 17B shows the Southern blot results.

Figure 18A:
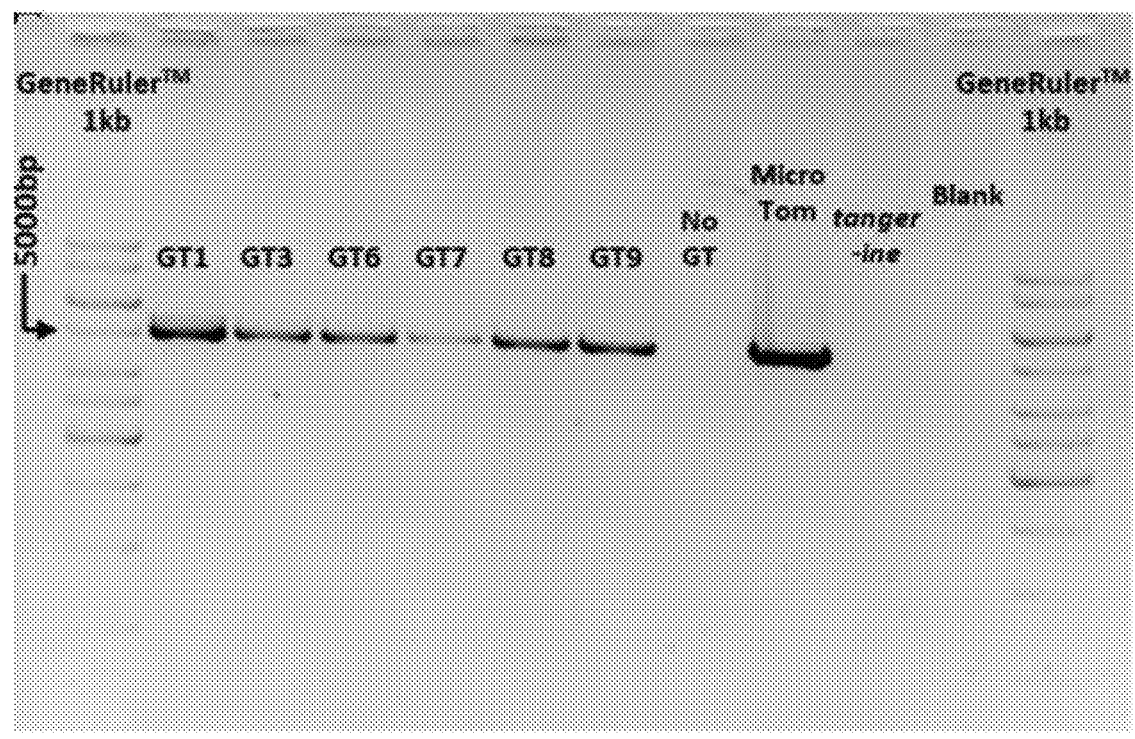
Figure 18B:
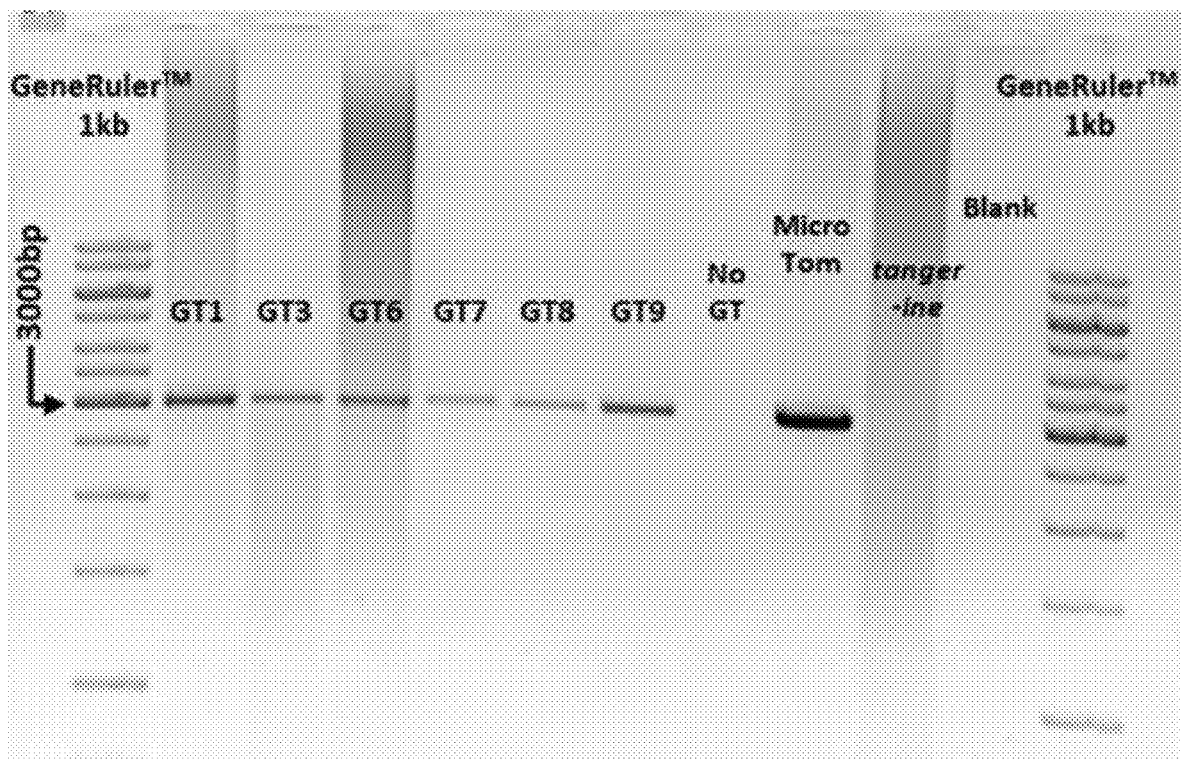

FIGS. 18A and 18B show EtBr-stained agarose gels of PCR amplifications of gene targeting integration sites at 5' junction (FIG. 18A) and 3' junction (FIG. 18B). PCR primers are shown in FIG. 8.

Figure 19:
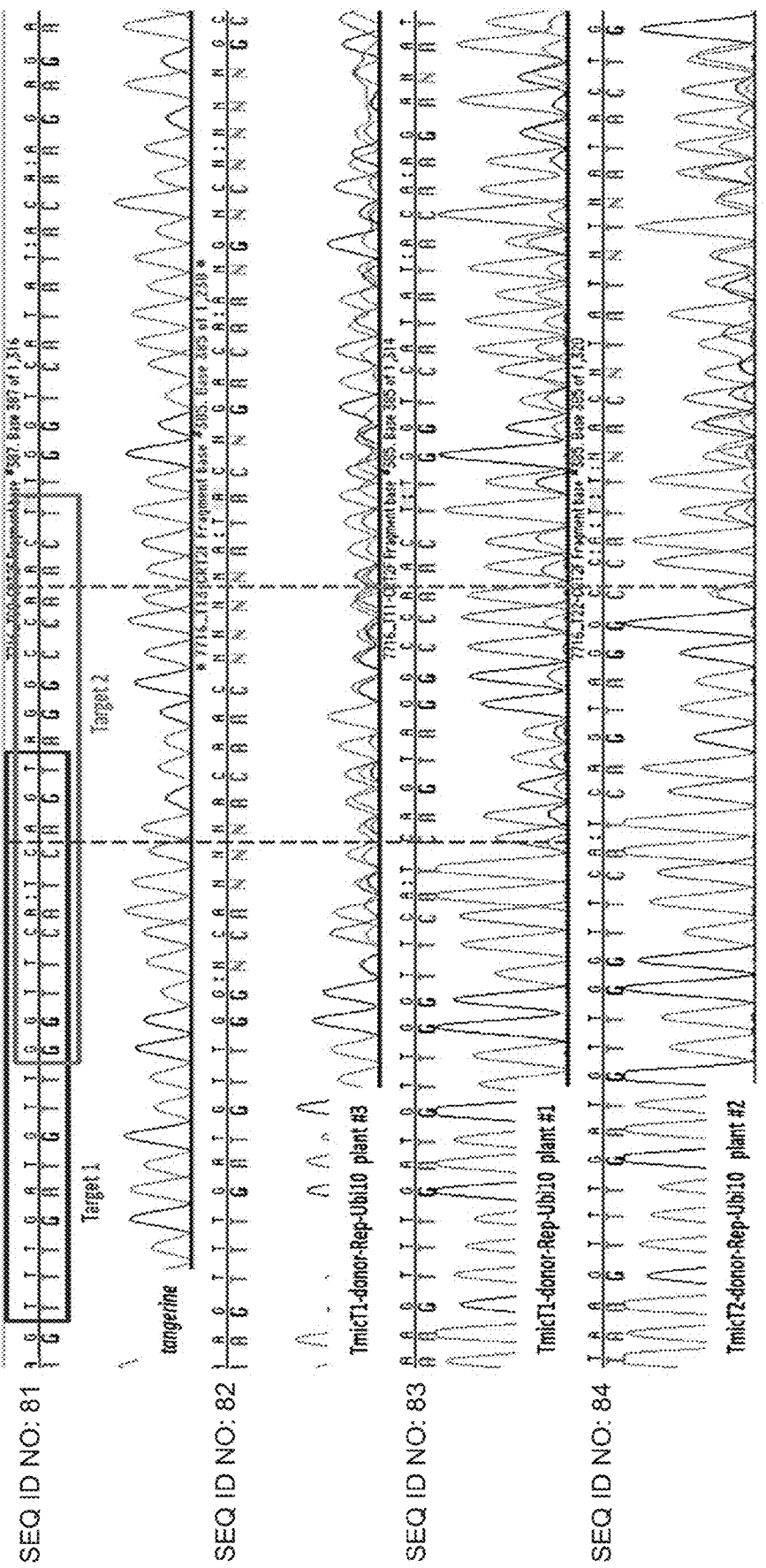

FIG. 19 shows Sanger sequencing of tangerine target sites. Target #1 and target #2 sequences are marked by brown and green boxes, respectively. Dashed lines show Cas9 cleavage site. Upper panel: not transformed tangerine mutant (SEQ ID NO: 81). Two middle panels: TmicT1-donor-Rep-Ubi10 transformed $T_0$ plants #3 (SEQ ID NO: 82) and #1 (SEQ ID NO: 83). Bottom panel: TmicT2-donor-Rep-Ubi10 transformed $T_0$ plant #2 (SEQ ID NO: 84).

Figure 20:
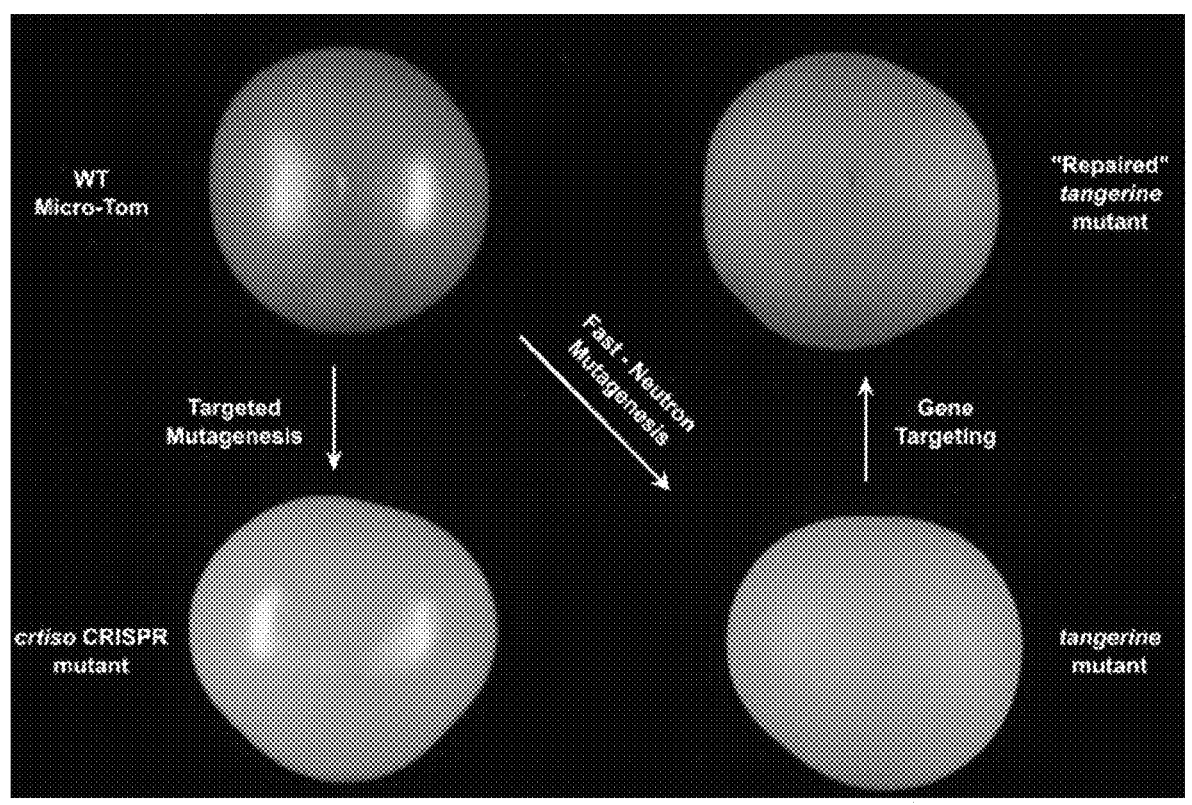

FIG. 20 shows a summary of the phenotypes obtained by gene targeting, gene targeting experiment and random mutagenesis. WT Micro-Tom tomato fruit that was used as the background for the gene targeting experiment shows a red glossy surface. Tangerine mutant fruit used as the background for the gene targeting assay transformations shows a yellow non-glossy (matte) surface. Crtiso CRISPR mutant is the result of gene targeting using the CRISPR/Cas9 system of the crtiso gene where the fruit surface remains glossy, as in the Micro-Tom WT fruit, but the color is yellow. A "repaired" tangerine mutant repaired by gene targeting obtaining a red tomato, with the non-glossy fruit surface.

DETAILED DESCRIPTION

The present subject matter may be understood more readily by reference to the following detailed description which forms a part of this disclosure. It is to be understood that this disclosure is not limited to the specific products, methods, conditions or parameters described and/or shown herein, and that the terminology used herein is for the purpose of describing particular embodiments by way of example only and is not intended to be limiting of the claimed disclosure.

A skilled artisan would appreciate that the singular form "a", "an" and "the" include plural references unless the context clearly dictates otherwise. For example, the term "a compound" or "at least one compound" may include a plurality of compounds, including mixtures thereof.

Throughout this application, various embodiments may be presented in a range format. It should be understood that the description in range format is merely for convenience and brevity and should not be construed as an inflexible limitation on the scope of disclosure herein. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

In some embodiments, the term "about", refers to a deviance of between 0.0001-5% from the indicated number or range of numbers. In some embodiment, the term "about", refers to a deviance of between 1-10% from the indicated number or range of numbers. In some embodiment, the term "about", refers to a deviance of 1%, 2%, 3%, 4%, 5%, 6%, 7%, 8%, 9%, or 10%, from the indicated number or range of numbers. In some embodiments, the term "about", refers to a deviance of up to 25% from the indicated number or range of numbers.

In some embodiments, disclosed herein are methods for gene targeting in a plant cell comprising expressing a nuclease expressed under a ubiquitin regulatory sequence. A skilled artisan would appreciate that said methods allow the generation of genetically modified plants comprising a desirable phenotype.

Methods for Gene Targeting

Disclosed herein is a method for gene targeting in a plant cell, the method comprising: (a) introducing into said plant cell a first nucleic acid comprising a viral replicon comprising a donor nucleic acid sequence, said donor sequence targeted to a plant endogenous DNA sequence; (b) introducing into said plant cell a second nucleic acid comprising a nuclease system, wherein said nuclease system is targeted to said plant endogenous DNA sequence, and wherein at least one component of said nuclease system is expressed under a UBQ10 regulatory sequence; wherein homologous recombination occurs between the donor sequence and the plant endogenous sequence.

A skilled artisan would appreciate that gene targeting comprises a process by which the genetic information of a cell or an organism is changed. Similarly, in some embodiments, gene targeting modifies the expression and/or activity of a gene of interest. In some embodiments, the term "gene targeting" can be used interchangeably with "site-directed mutagenesis", "site-specific mutagenesis", "oligonucleotide-directed mutagenesis", "gene replacement", "gene modification", "knock-in", "homology-directed repair", "homology-dependent repair", "gene targeting", "targeted mutagenesis", having all the same qualities and meanings.

In some embodiments, gene targeting comprises the introduction to a cell of a donor nucleic acid sequence, containing the desired mutation as well as at least one sequence complementary to the template DNA around the mutation site, so it can hybridize with the DNA in the gene of interest leading to homologous recombination. The mutation may be a single base change (a point mutation), multiple base changes, deletions, or insertions. In some embodiments, the donor sequence is then introduced or ectopically expressed into a host cell as a vector. Optionally, mutated cells can be selected by DNA sequencing to check that they contain the desired mutation.

In some embodiments, gene targeting comprises gene editing, gene replacement, or a combination of both.

A skilled artisan would appreciate that, in some embodiments, a viral replicon comprises an autonomously replication region of viral DNA that replicates from a single origin of replication. In some embodiments, nonessential regions of the viral genome are replaced by foreign sequences, in order for these foreign sequences to be expressed in transfected cells. In some embodiments, said foreign sequences comprise a donor nucleic acid sequence or a target gene. In some embodiments, said viral replicon is selected from a group comprising. a geminiviral replicon, a bean yellow dwarf virus (BeYDV) replicon, a cabbage leaf curl virus (CalCuV) replicon, a tomato leaf curl virus (ToLCV) replicon, a wheat dwarf virus (WDV) replicon, a tobacco rattle virus (TRV) replicon, or any combination thereof. In some embodiments, said viral replicon comprises a part of a naturally occurring viral replicon. In some embodiments, said viral replicon comprises essential parts of a naturally occurring viral replicon.

In some embodiments, a geminiviral replicon comprises 2 long intergenic regions (LIR), a short intergenic region (SIR), a replication initiator protein (Rep) or any combination thereof. Said 2 LIRs are present on the T-DNA. Following cleavage by Rep, the replicon comprises only one LIR.

In some embodiments, LIR and SIR are the only cis-elements required for replication of a geminiviral replicon. The LIR comprises a bi-directional promoter and a stem-loop structure that is needed for initiation of rolling-circle replication (RCR). The SIR is the origin of C-strand synthesis and contains transcription termination and polyadenylation signals. Rep is required for replication, and it can be supplied in trans, therefore it needs not be present in the viral replicon.

Methods for transforming a plant are known to those skilled in the art. One skilled in the art would appreciate that the terms "transformation" and "transforming" describe a process by which a foreign DNA, such as a recombinant nucleic acid molecule or an expression vector as described herein, enters and changes a recipient cell into a transformed, genetically altered or transgenic cell. Transformation may be stable, wherein the nucleic acid sequence is integrated into the organism genome and as such represents a stable and inherited trait, or transient, wherein the nucleic acid sequence is expressed by the cell transformed but is not integrated into the genome, and as such represents a transient trait. In some embodiments, a recombinant nucleic acid molecule described herein is stably transformed into the plant cell.

A skilled artisan would appreciate that a donor nucleic acid sequence might comprise any nucleic acid to be integrated into a plant cell. In some embodiments, said donor nucleic acid comprises at least one nucleotide region similar or identical to the plant genome. In some embodiments, said donor sequence is integrated into the cell genome by homologous recombination. In some embodiments, said donor sequence comprises a gene, a part of a gene, a regulatory sequence, or any combination thereof. In some embodiments, said donor nucleic acid sequence comprises a mutated gene, a mutated regulatory sequence, a mutated promoter, a mutated terminator, or any mutated version of a naturally occurring oligonucleotide sequence. In some embodiments, said naturally occurring oligonucleotide comprises a plant endogenous DNA sequence.

A skilled artisan would appreciate that a plant endogenous DNA sequence might comprise any endogenous DNA sequence that an artisan wishes to genetically modify. In some embodiments, said plant endogenous DNA sequence comprises a gene, a part of a gene, a regulatory sequence, or any combination thereof.

In some embodiments, a nuclease system comprises a system used for gene targeting. In some embodiments, a nuclease system is selected from a group comprising: a nickase, a zinc finger nuclease (ZFN) system, a transcription activator-like effector nuclease (TALEN) system, a meganuclease, or a clustered regularly interspaced short palindromic repeats (CRISPR)/CRISPR associated proteins (Cas) nuclease, or any combination thereof.

A skilled artisan would appreciate that a nickase may comprise any enzyme that cuts one strand of a double-stranded DNA at a specific recognition nucleotide sequences, sometimes known as a restriction site. Such enzymes hydrolyse or cut only one strand of the DNA duplex, to produce DNA molecules that are "nicked", rather than cleaved.

A skilled artisan would appreciate that the terms "zinc finger nuclease" or "ZFN" are interchangeable having all the same meanings and qualities, wherein a ZFN encompasses a chimeric protein molecule comprising at least one zinc finger DNA binding domain operatively linked to at least one nuclease capable of double-strand cleaving of DNA. In some embodiments, a ZFN system comprises a ZFN known in the art. In some embodiments, a ZFN system comprises a ZFN newly created to cleave a preselected site.

In some embodiments, a ZFN creates a double-stranded break at a preselected endogenous target site. In some embodiments, a ZFN comprises a DNA-binding domain and a DNA-cleavage domain, wherein the DNA binding domain is comprised of at least one zinc finger and is operatively linked to a DNA-cleavage domain. In another embodiment, a zinc finger DNA—binding domain is at the N-terminus of the chimeric protein molecule and the DNA—cleavage domain is located at the C-terminus of the molecule. In another embodiment, a zinc finger DNA-binding domain is at the C-terminus of the chimeric protein molecule and the DNA—cleavage domain is located at the N-terminus of the molecule. In another embodiment, a zinc finger binding domain encompasses the region in a zinc finger nuclease that is capable of binding to a target locus, for example a preselected endogenous target site as disclosed herein. In another embodiment, a zinc finger DNA-binding domain comprises a protein domain that binds to a preselected endogenous target site on at least one homologous chromosome. In another embodiment, a zinc finger DNA-binding domain comprises a protein domain that binds to a polymorphic allele on at least one homologous chromosome. In another embodiment, a zinc finger DNA-binding domain comprises a protein domain that binds to a preselected endogenous target site on both homologous chromosomes. In another embodiment, a zinc finger DNA-binding domain comprises a protein domain that binds to polymorphic alleles on both homologous chromosomes.

In some embodiments, a TALEN system comprises a TAL effector DNA binding domain and a DNA cleavage domain, wherein said TAL effector DNA binding domain binds within said preselected endogenous target site, thereby targeting the DNA cleavage domain to cleave the DNA within said preselected endogenous target site.

A skilled artisan would appreciate that the terms "transcription activator-like effector nuclease", "TALEN", and "TAL effector nuclease" may be used interchangeably having all the same meanings and qualities, wherein a TALEN encompasses a nuclease capable of recognizing and cleaving its target site, for example a preselected endogenous target site as disclosed herein. In another embodiment, a TALEN comprises a fusion protein comprising a TALE domain and a nucleotide cleavage domain. In another embodiment, a TALE domain comprises a protein domain that binds to a nucleotide in a sequence-specific manner through one or more TALE-repeat modules. A skilled artisan would recognize that TALE-repeat modules comprise a variable number of about 34 amino acid repeats that recognize plant DNA sequences. Further, repeat modules can be rearranged according to a simple cipher to target new DNA sequences. In another embodiment, a TALE domain comprises a protein domain that binds to a preselected endogenous target site on at least one homologous chromosome. In another embodiment, a TALE domain comprises a protein domain that binds to a polymorphic allele on at least one homologous chromosome. In another embodiment, a TALE domain comprises a protein domain that binds to a preselected endogenous target site on both homologous chromosomes. In another embodiment, a TALE domain comprises a protein domain that binds to polymorphic alleles on both homologous chromosomes.

In one embodiment, a TALE domain comprises at least one of the TALE-repeat modules. In another embodiment, a TALE domain comprises from one to thirty TALE-repeat modules. In another embodiment, a TALE domain comprises more than thirty repeat modules. In another embodiment, a TALEN fusion protein comprises an N-terminal domain, one or more of TALE-repeat modules followed by a half-repeat module, a linker, and a nucleotide cleavage domain.

A skilled artisan would appreciate that clustered regularly interspaced short palindromic repeats (CRISPR)/CRISPR associated protein (Cas) system comprises genome engineering tools based on the bacterial CRISPR/Cas prokary-otic adaptive immune system. This RNA-based technology is very specific and allows targeted cleavage of genomic DNA guided by a customizable small noncoding RNA, resulting in gene modifications by both non-homologous end joining (NHEJ) and homology-directed repair (HDR) mechanisms (Belhaj K. et al., 2013. Plant Methods 2013, 9:39). In some embodiments, a CRISPR/Cas system comprises a CRISPR/Cas9 system.

In some embodiments, a CRISPR/Cas system comprises a Cas nuclease and a gRNA molecule, wherein said gRNA molecule binds within said preselected endogenous target site thereby guiding said Cas nuclease to cleave the DNA within said preselected endogenous target site.

A skilled artisan would appreciate that the terms "single-guide RNA", "sgRNA", and "gRNA" are interchangeable having all the same qualities and meanings. An sgRNA may encompass a chimeric RNA molecule which is composed of a targeting sequence (crRNA) and a Cas nuclease recruiting sequence (tracrRNA). In some embodiments, a crRNA is complementary to a genomic preselected target site, wherein the crRNA "targets" the CRISPR associated polypeptide (Cas) nuclease protein to the preselected target site.

In some embodiments, the length of crRNA sequence complementary is 19-22 nucleotides long e.g., 19-22 consecutive nucleotides complementary to the target site. In another embodiment, the length of crRNA sequence complementary to the region of DNA is about 15-30 nucleotides long. In another embodiment, the length of crRNA sequence complementary to the region of DNA is about 15, 16, 17, 18, 19, 20, 21, 22, 23, 24, 25, 26, 27, 28, 29, or 30 nucleotides long. In another embodiment, the length of crRNA sequence complementary to the region of DNA is 20 nucleotides long. In some embodiments, the crRNA is located at the 5' end of the sgRNA molecule. In another embodiment, the crRNA comprises 100% complementation within the preselected target sequence. In another embodiment, the crRNA comprises at least 80% complementation within the preselected target sequence. In another embodiment, the crRNA comprises at least 85% complementation within the preselected target sequence. In another embodiment, the crRNA comprises at least 90% complementation within the preselected target sequence. In another embodiment, the crRNA comprises at least 95% complementation within the preselected target sequence. In another embodiment, the crRNA comprises at least 97% complementation within the preselected target sequence. In another embodiment, the crRNA comprises at least 99% complementation within the preselected target sequence. In another embodiment, a tracrRNA is 100-300 nucleotides long and provides a binding site for the Cas nuclease e.g., a Cas9 protein forming the CRISPR/Cas9 complex.

A skilled artisan would appreciate that a "target sequence" can be any DNA sequence that an artisan wishes to mutate. In some embodiments, the terms "target sequence" and "plant endogenous DNA sequence" are used herein interchangeably, having all the same qualities and meanings.

A skilled artisan would appreciate that a guide RNA may contain nucleotide sequences other than the region complementary or substantially complementary to a region of a target DNA sequence, for example a preselected endogenous target site. In another embodiment, a guide RNA comprises a crRNA or a derivative thereof. In another embodiment, a guide RNA comprises a crRNA: tracrRNA chimera.

In some embodiments, a CRISPR/Cas system comprises a single-guide RNA (sgRNA) and/or a Cas protein known in the art. In some embodiments, a CRISPR/Cas system comprises a single-guide RNA (sgRNA) and/or a Cas protein newly created to cleave at a preselected site.

In another embodiment, a CRISPR/Cas system comprises a Type I CRISPR-Cas system, or a Type II CRISPR-Cas system, or a Type III CRISPR-Cas system, or derivatives thereof. In another embodiment, a CRISPR-Cas system comprises an engineered and/or programmed nuclease system derived from naturally accruing CRISPR-Cas systems. In another embodiment, a CRISPR-Cas system comprises engineered and/or mutated Cas proteins. In another embodiment, a CRISPR-Cas system comprises engineered and/or programmed guide RNA.

In another embodiment, a gRNA molecule comprises a domain that is complementary to and binds to a preselected endogenous target site on at least one homologous chromosome. In another embodiment, a gRNA molecule comprises a domain that is complementary to and binds to a polymorphic allele on at least one homologous chromosome. In another embodiment, a gRNA molecule comprises a domain that is complementary to and binds to a preselected endogenous target site on both homologous chromosomes. In another embodiment, a gRNA molecule comprises a domain that is complementary to and binds to polymorphic alleles on both homologous chromosomes.

Cas enzymes comprise RNA-guided DNA endonuclease able to make double-stranded breaks (DSB) in DNA. The term "Cas enzyme" may be used interchangeably with the terms "CRISPR-associated endonucleases" or "CRISPR-associated polypeptides" having all the same qualities and meanings. In one embodiment, a Cas enzyme is selected from the group comprising Cas1, Cas1B, Cas2, Cas3, Cas4, Cas5, Cas6, Cas7, Cas8, Cas9, Cas10, C2cl, CasX, NgAgo, Cpf1, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4, or homologs thereof, or modified versions thereof. In another embodiment, a Cas enzyme comprises Cas9. In another embodiment, a Cas enzyme comprises Cas1. In another embodiment, a Cas enzyme comprises Cas1B. In another embodiment, a Cas enzyme comprises Cas2. In another embodiment, a Cas enzyme comprises Cas3. In another embodiment, a Cas enzyme comprises Cas4. In another embodiment, a Cas enzyme comprises Cas5. In another embodiment, a Cas enzyme comprises Cas6. In another embodiment, a Cas enzyme comprises Cas7. In another embodiment, a Cas enzyme comprises Cas8. In another embodiment, a Cas enzyme comprises Cas10. In another embodiment, a Cas enzyme comprises Cpf1. In another embodiment, a Cas enzyme comprises Csy1. In another embodiment, a Cas enzyme comprises Csy2. In another embodiment, a Cas enzyme comprises Csy3. In another embodiment, a Cas enzyme comprises Cse1. In another embodiment, a Cas enzyme comprises Cse2. In another embodiment, a Cas enzyme comprises Csc1. In another embodiment, a Cas enzyme comprises Csc2. In another embodiment, a Cas enzyme comprises Csa5. In another embodiment, a Cas enzyme comprises Csn2. In another embodiment, a Cas enzyme comprises Csm2. In another embodiment, a Cas enzyme comprises Csm3. In another embodiment, a Cas enzyme comprises Csm4. In another embodiment, a Cas enzyme comprises Csm5. In another embodiment, a Cas enzyme comprises Csm6. In another embodiment, a Cas enzyme comprises Cmr1. In another embodiment, a Cas enzyme comprises Cmr3. In another embodiment, a Cas enzyme comprises Cmr4. In another embodiment, a Cas enzyme comprises Cmr5. In another embodiment, a Cas enzyme comprises Cmr6. In another embodiment, a Cas enzyme comprises Csb1. In another embodiment, a Cas enzyme comprises Csb2. In another embodiment, a Cas enzyme comprises Csb3. In another embodiment, a Cas enzyme comprises Csx17. In another embodiment, a Cas enzyme comprises Csx14. In another embodiment, a Cas enzyme comprises Csx10. In another embodiment, a Cas enzyme comprises Csx16, CsaX. In another embodiment, a Cas enzyme comprises Csx3. In another embodiment, a Cas enzyme comprises Csx1, Csx15, Csf1. In another embodiment, a Cas enzyme comprises Csf2. In another embodiment, a Cas enzyme comprises Csf3. In another embodiment, a Cas enzyme comprises Csf4. In another embodiment, a Cas enzyme comprises Cpf1. In another embodiment, a Cas enzyme comprises C2cl. In another embodiment, a Cas enzyme comprises CasX. In another embodiment, a Cas enzyme comprises NgAgo. In another embodiment, a Cas enzyme is Cas homologue. In another embodiment, a Cas enzyme is a Cas orthologue. In another embodiment, a Cas enzyme is a modified Cas enzyme. In another embodiment, a Cas enzyme is any CRISPR-associated endonucleases known in the art.

In some embodiment, a nuclease gene of the nuclease system is operably linked to a gene enhancer. In some embodiments, a nuclease gene of the nuclease system is operably linked to an UBQ10 regulatory sequence. In some embodiments, a Cas nuclease gene is operably linked to an UBQ10 regulatory sequence. In some embodiment, a gRNA of the nuclease system is operably linked to a gene enhancer. In some embodiments, a gRNA of the nuclease system is operably linked to an UBQ10 regulatory sequence.

In some embodiment, a nuclease gene and a gRNA are operably linked to a gene enhancer. In some embodiments, a nuclease gene and a gRNA are operably linked to an UBQ10 regulatory sequence. In some embodiments, a Cas nuclease gene and a gRNA are operably linked to an UBQ10 regulatory sequence.

In some embodiments, disclosed herein is a method for gene targeting in a plant cell, wherein no selection marker or reporter gene are used for generating said transgenic plant cell.

In some embodiments, a nuclease system is ectopically expressed in a plant cell by introducing into said plant cell a nucleic acid encoding said nuclease system. In some embodiments, a single expression vector comprises a nucleotide encoding a nuclease system, a viral replicon and a donor sequence.

There are various methods of introducing foreign genes into both monocotyledonous and dicotyledonous plants (See Potrykus 11991. *Annu Rev Plant Physiol Plant Mol Biol* 42, 205-225; Shimamoto K. et al., 1989. *Nature* 338, 274-276). Transformation methods may include, for example, but are not limited to, the use of liposomes, electroporation, chemicals that increase free DNA uptake, injection of the DNA directly into the plant, particle gun bombardment, transformation using viruses and microprojection.

Plant transformation methods are fully described in U.S. Patent Application Publications US 20110209247; US 20110113514; US 20100199371; US 20070079396, US 20080307541; US 20030028913: and US20030196219; and U.S. Pat. Nos. 5,015,580; 5,550,318; 5,538,880; 6,160,208; 6,399,861; 6,403,865; 5,635,055; 5,824,877; 5,591,616; 5,981,840 and 6,384,301, which are incorporated by reference herein in their entirety.

In some embodiments, the transformation can be performed by an *Agrobacterium*-mediated gene transfer. The

*Agrobacterium*-mediated system includes the use of plasmid vectors that contain defined DNA segments which integrate into the plant genomic DNA. Methods of inoculation of the plant tissue vary depending upon the plant species and the *Agrobacterium* delivery system. The transformation can be performed with any suitable tissue explant that provides a good source for initiation of whole-plant differentiation (See Horsch et al., 1988. *Plant Molecular Biology Manual* A5, 1-9, Kluwer Academic Publishers, Dordrecht).

In some embodiments, the transformation can be performed by a viral vector-based gene transfer. In some embodiments, the transformation can be performed with the use of a virus vector to generate, for example, plants expressing a nuclease system, a donor nucleic acid sequence, or a target gene. In some embodiments, the transformation can be performed with the use of a virus vector to generate, for example, plants having an increased rate of mutagenesis. In some embodiments, the transformation can be performed with the use of a virus vector to generate, for example, plants having an increased rate of gene targeting. In some embodiments, the transformation can be performed with the use of a virus vector to generate, for example, plants having an increased rate of targeted gene editing.

In some embodiments, the transformation can be performed by a direct DNA uptake method. There are various methods of direct DNA transfer into plant cells. In electroporation, the protoplasts are briefly exposed to a strong electric field, opening up mini-pores to allow DNA to enter. In microinjection, the DNA is mechanically injected directly into the cells using micropipettes. In microparticle bombardment, the DNA is adsorbed on microprojectiles such as magnesium sulfate crystals or tungsten particles, and the microprojectiles are physically accelerated into cells or plant tissues.

In some embodiments, gene targeting is used for enhancing a beneficial trait or quality in a plant. In some embodiments, gene targeting is used for reducing a detrimental trait or quality in a plant. In some embodiments, gene targeting is used for enabling a plant to adapt to changing environmental conditions.

Expression of a Gene Linked to a UBQ10 Regulatory Sequence

In some embodiments, disclosed herein is a recombinant nucleic acid molecule comprising a first nucleotide sequence encoding a gene of interest, wherein said gene of interest is operably linked to a regulatory sequence of the gene encoding Ubiquitin10 (UBQ10).

A skilled artisan would appreciate that the term "operably linked" may encompass a functional linkage between two nucleic acid sequences. For example, a promoter sequence can be operably linked to a sequence encoding a gene of interest, such that the promoter sequence is able to initiate transcription of the gene of interest. A skilled artisan would appreciate that the terms "operably linked" and "fused" may in some embodiments be used interchangeably herein having the same meanings and qualities.

A skilled artisan would appreciate that a "regulatory sequence" comprises a segment of a nucleic acid molecule capable of increasing or decreasing the expression of genes operably linked to it. Further, the terms "regulatory sequence", "regulatory element", and "regulatory region" are used herein interchangeably having all the same qualities and meanings. In some embodiments, a regulatory sequence is selected from a group comprising: an enhancer, a silencer, a proximal promoter, a core promoter, an operator, a 5' UTR, a 3' UTR, or any combination thereof.

In some embodiments, a regulatory sequence comprises a part of an enhancer, a silencer, a proximal promoter, a core promoter, an operator, a 5' UTR, a 3' UTR, or any combination thereof. In some embodiments, a regulatory sequence comprises a promoter-terminator cassette. In some embodiments a gene of interest can be inserted adjacently to a regulatory sequence. In some embodiments a gene of interest can be inserted within a regulatory sequence. In some embodiments, a regulatory sequence comprises a contiguous chromosomal region. In some embodiments a regulatory sequence comprises a non-continuous chromosomal region.

In some embodiments, a region adjacent to a gene of interest comprises a regulatory sequence that regulates its expression. In some embodiments, the terms "regulatory sequence" and "adjacent region" are used interchangeably having all the same qualities and meanings.

A skilled artisan would appreciate that the term "promoter" or "promoter region" may encompass a nucleic acid control sequence located upstream from the transcriptional start of a gene, and which is involved in recognizing and binding of RNA polymerase and other proteins, thereby directing transcription of an operably linked nucleic acid sequence encoding a target protein.

Plant promoters are not well defined, and it is common to use a region located 1-2 Kb upstream of the start codon of a plant with the hope of including the plant gene promoter region. This upstream region, which includes the 5' UTR, may or may not include all of the promoter. Further, it cannot be ruled out that an enhancer of the gene is located even 5 Kb upstream or elsewhere in the genome. Thus, even though upstream nucleic acid sequence of a gene is known, the exact location of the plant promoter may not be known.

In some embodiments, a promoter region comprises a 5' UTR. In some embodiments, a promoter region comprises a 5' UTR and additional upstream sequences. In some embodiments, a promoter comprises the entire region 1-2 Kb upstream of a start codon. In some embodiments, a promoter comprises the nucleic acid sequence about 1 Kb upstream of a start codon. In some embodiments, a promoter comprises the nucleic acid sequence about 2 Kb upstream of a start codon.

In some embodiments, a promoter region comprising a 5' UTR is needed for the highest level of expression of a target gene. In some embodiments, a promoter region comprising a 5' UTR and additional upstream sequences UTR is needed for the highest level of expression of a target gene. In some embodiments, a promoter comprising the entire region 1-2 Kb upstream of a start codon UTR is needed for the highest level of expression of a target gene. In some embodiments, a promoter comprising the nucleic acid sequence about 1 Kb upstream of a start codon UTR is needed for the highest level of expression of a target gene. In some embodiments, a promoter comprising the nucleic acid sequence about 2 Kb upstream of a start codon UTR is needed for the highest level of expression of a target gene. In some embodiments, a promoter comprising the nucleic acid sequence more than 2 Kb upstream of a start codon UTR is needed for the highest level of expression of a target gene. In some embodiments, a promoter comprising part of the nucleic acid sequence about 2 Kb upstream of a start codon UTR is needed for the highest level of expression of a target gene.

In some embodiments, a "target gene" is a gene or a nucleic acid sequence that an artisan wishes to express in a cell. In some embodiments, a "target gene" and a "gene of interest" are used herein interchangeably having all the same qualities and meanings. In some embodiments, a "target gene" and a "donor sequence" are used herein interchangeably having all the same qualities and meanings.

In some embodiments, a regulatory region comprises regulatory elements, such as 5' leaders and introns for enhancing transcription, 3' untranslated regions (such as polyadenylation signals and sites), and DNA for transit or signal peptides.

In some embodiments, promoters functionally equivalent to UBQ10 promoters can be used. For the identification of functionally equivalent promoters, the promoter strength and/or expression pattern of a candidate promoter may be analyzed, for example, by operably linking the promoter to a reporter gene and assaying the expression level and pattern of the reporter gene in various tissues of the plant. Suitable well-known reporter genes include, for example, but are not limited to, beta-glucuronidase or beta-galactosidase, green fluorescent protein (GFP), red-fluorescent protein (RFP), and luciferase. The promoter activity can be assayed, for example, by measuring the enzymatic activity. The promoter strength and/or expression pattern may then be compared to that of a reference promoter (such as the one used in the methods disclosed herein). Alternatively, promoter strength may be assayed by quantifying mRNA levels or by comparing mRNA levels of the nucleic acid used in the methods disclosed herein, with mRNA levels of housekeeping genes such as 18S rRNA, using methods known in the art, such as Northern blotting with densitometric analysis of autoradiograms, quantitative real-time PCR or RT-PCR (See Heid et al., 1996 *Genome Methods* 6: 986-994).

A skilled artisan would appreciate that the term "terminator" or "terminator region" may encompass a nucleic acid control sequence located downstream from the transcriptional stop of a gene, and which is involved in recognizing and binding of polypeptides that effectively stop transcription of a target protein.

In some embodiments, a terminator region comprises a 3' UTR. In some embodiments, a terminator region comprises a 3' UTR and additional downstream sequences. In some embodiments, a terminator comprises a region about 1 Kb downstream of a stop codon. In some embodiments, a terminator comprises an intron. In some embodiments, a terminator region comprising a 3' UTR is needed for the highest efficiency stop of transcription.

A skilled artisan would appreciate that an enhancer is a short (50-1500 bp) region of DNA that can be bound by proteins to increase the likelihood that transcription of a particular gene will occur. These proteins are sometimes referred to as transcription factors. They can be located up to 1 Mbp (1,000,000 bp) away from the gene, upstream or downstream from the start site. Contrarily, silencers are oligonucleotide sequences capable of binding transcription regulation factors that inhibit the expression of an adjacent gene. These transcriptions factors are generally known as repressors.

UBQ10 Regulatory Elements

The terms "polyubiquitin10 gene", "ubiquitin10 gene", "ubi10", and "UBQ10" are used herein interchangeably having all the same qualities and meanings. The genomic region located ~2 kb upstream the UBQ10 contains a promoter region and the 5' UTR. Notably, this 5' UTR is conserved in plants. It is ~400 to 600 bp long and contains a ~300-500 bp long intron whose 3' end is adjacent to the start codon of this gene. The presence of this intron allows high gene expression in eukaryotes, especially when expressing prokaryotic genes, as exon-exon junctions are known to enhance gene expression in eukaryotes.

In some embodiments, wherein the UBQ10 is from tomato or potato, the 5' UTR is 593 bp long and contains a 494 bp long intron. In some embodiments, wherein the UBQ10 is from *Arabidopsis*, the 5' UTR is 389 bp long with an intron of 304 bp.

In some embodiments, the UBQ10 comprises a plant gene. In some embodiments, the UBQ10 comprises a *Solanaceous* plant gene. In some embodiments, the *Solanaceous* plant is selected from the group comprising a cultivated tomato plant, a wild-tomato plant, a cultivated potato plant, a wild-potato plant, an aubergine plant, a chili pepper plant, and a bell pepper plant. A skilled artisan would appreciate that the *Solanaceous* family comprises a large number species (over 3,000), including but not limited to species of tomatoes, peppers, chilies, aubergine, potatoes, and tobacco plants. In some embodiments, the UBQ10 is selected from any species of *Solanaeceous* plant.

In some embodiments, the UBQ10 comprises an *Arabidopsis* plant gene. In some embodiments, the UBQ10 comprises an *Arabidopsis thaliana* plant gene.

The nucleic acid sequences of UBQ10s are well known in the art and publicly available in genetic sequence databases. In some embodiments, the POLYUBIQUITIN10 nucleic acid gene sequences of tomato, potato, and *Arabidopsis* comprise SEQ ID Nos: 1, 3, and 5, respectively, wherein the encoded amino acid sequences of tomato, potato, and *Arabidopsis* are SEQ ID Nos: 2, 4, and 6, respectively.

The Polyubiquitin 10 protein encoded by the UBQ10 is involved in protein degradation. The Polyubiquitin 10 polypeptide consists of six polypeptide repeats. It is located on the chromosome 7 in tomato (Solyc07g064130) and potato (Sotub07g026130).

In some embodiments, a nucleic acid sequence comprising a tomato UBQ10 comprises the following nucleic acid sequence:

```
                                        (SEQ ID NO: 22)
gtcaactaccccaatttaaattttatttgattaagatatttttatggac ctactttataattaaaaatattttctatttgaaaaggaaggacaaaaat catacaattttggtccaactactcctctcttttttttttttggctttata aaaaaggaaagtgattagtaataaataattaaataatgaaaaaaggagg aaataaaattttcgaattaaaatgtaaaagagaaaaaggagagggagta atcattgtttaactttatctaaagtaccccaattcgattttacatgtat atcaaattatacaaatattttattaaaatatagatattgaataattta ttattcttgaacatgtaaataaaaattatctattatttcaattttata taaactattatttgaaatctcaattatgattttttaatatcactttcta tccatgataatttcagcttaaaaagtttgtcaataattacattaattt tgttgatgaggatgacaagatttcggtcatcaattacatatacacaaat tgaaatagtaagcaacttgattttttttctcataatgataatgacaaag acacgaaaagacaattcaatattcacattgatttattttttatatgataa taattacaataataatattcttataaagaaagagatcaattttgactga tccaaaaatttatttatttttactataccaacgtcactaattatatcta ataatgtaaaacaattcaatcttacttaaatattaatttgaaataaact atttttataacgaaattactaaatttatccaataacaaaaaggtcttaa gaagacataaattctttttttgtaatgctcaaataaatttgagtaaaaa
```

-continued agaatgaaattgagtgatttttttttaatcataagaaaataaataatta atttcaatataataaaacagtaatataatttcataaatggaattcaata cttacctcttagatataaaaaataaatataaaaataaagtgtttctaat aaacccgcaatttaaatTaaaatatttaatattttcaatcaaatttaaat aattatattaaaatatcgtagaaaaagagcaatatataatacaagaaag aagatttaagtacaattatcaactattattatactctaattttgttata tttaatttcttacggttaaggtcatgttcacgataaactcaaaatacgc tgtatgaggacatattttaaattttaaccaataataaaaactaagttatt tttagtatattttttttgtttaacgtgacttaatttttcttttctagagg agcgtgtaagtgtcaacctcattctcctaattttcccaaccacataaaa aaaaaataaaggtagcttttgcgtgttgatttggtacactacacgtcat tattacacgtgtttcgtatgattggttaatccatgaggcggtttcctc tagagtcggccataccatctataaaataaagctttctgcagctcatttt ttcatcttctatctgatttctattataatttctctgaattgccttcaaa tttctctttcaaggttagaattttttctctatttttggttttttgtttgt ttagattctgagtttagttaatcaggtgctgttaaagccctaaattttg agtttttttcggttgtttgatggaaaatacctaacaattgagttttttt catgttgttttgtcggagaatgcctacaattggagttcctttcgttgtt ttgatgagaaagcccctaatttgagtgtttttccgtcgatttgatttta aaggtttatattcgagttttttttcgtcggtttaatgagaaggcctaaaa taggagttttttctggttgatttgactaaaaaagccatggaattttgtgt ttttgatgtcgctttggttctcaaggcctaagatctgagtttctccggt tgttttgatgaaaaagccctaaaattggagtttttatcttgtgttttag gttgtttaatccttataatttgagtttttttcgttgttctgattgttgt ttttatgaattttgcagATGCAGATCTTTGTGAAAACTCTCACCGGAAA

GACTATCACCCTAGAGGTGGAAAGTTCTGATACAATCGACAACGTTAAG

GCTAAGATCCAGGATAAGGAAGGAATTCCCCCGGATCAGCAAAGGCTTA

TCTTCGCTGGAAAGCAGTTGGAGGACGGACGTACTCTAGCTGATTACAA

CATCCAGAAGGAGTCCACCCTCCATTTGGTGCTCCGTCTACGTGGTGGT

ATGCAGATCTTCGTGAAGACTCTCACGGGTAAGACGATTACCCTTGAGG

TCGAAAGCTCAGACACCATTGACAACGTCAAGGCTAAGATCCAGGATAA

GGAAGGCATTCCCCCAGACCAGCAGAGGTTGATCTTTGCACGAAAGCAG

TTGGAAGATGGCCGCACCCTAGCTGACTACAACATCCAGAAGGAGTCCA

CCCTCCATTTGGTGCTCCGTCTCCGTGGTGGTATGCAGATCTTCGTTAA

GACTCTTACCGGAAAGACCATCACTTTCGAGGTGGAAAGCTCCGACACC

ATTGACAACGTGAAGGCTAAGATCCAGGATAAGGAAGGGATCCCCCCAG

ACCAGCAGAGGTTGATCTTCGCTGGAAAGCAGCTCGAGGATGGTCGCAC

CCTGGCTGACTACAACATCCAGAAGGAGTCTACCCTCCATCTTGTCCTC

CGTCTCCGTGGTGGTATGCAGATTTTTGTTAAGACCCTCACCGGAAAGA

CCATCACTTTGGAGGTGGAAAGCTCCGACACGATTGATAATGTTAAGGC

-continued

TAAGATCCAGGACAAGGAGGGAATTCCTTCAGACCAGCAGAGGTTGATT

TTCGCTGGTAAGCAGCTCGAGGACGGCCGCACCCTTGCCGACTACAACA

TCCAGAAGGAGTCGACCCTTCACCTTGTCCTCCGTCTACGTGGTGGTAT

GCAAATCTTTGTGAAGACCCTTACCGGGAAAACCATCACCCTGGAGGTT

GAGAGCTCCGACACCATTGACAATGTCAAGGCCAAGATCCAAGACAAGG

AGGGTATTCCCCCAGACCAGCAGAGGTTGATTTTTTGCTGGCAAGCAGCT

CGAGGATGGCCGCACTTTGGCGGACTATAACATCCAAAAGGAGTCGACC

CTGCACTTGGTGCTTAGGCTGAGGGGAGGAATGCAGATCTTTGTGAAGA

CCTTGACCGGGAAGACCATCACTTTGGAGGTGGAGAGTTCTGACACCAT

CGACAATGTGAAAGCTAAGATTCAGGACAAGGAGGGGATCCCACCAGAC

CAGCAGAGGTTGATTTTCGCTGGTAAGCAGCTTGAGGATGGCCGCACCC

TTGCTGACTACAATATCCAGAAGGAGTCCACCCTGCACCTTGTCCTCCG

TCTCCGTGGTGGTTTTTAAgttgtggttgtctggttgcgtctgttgccc gttgtctgttgcccattgtggtggttgtgtgtttgtatgatggtcgttaag gatcatcaatgtgttttcgcttttttgttccattctgtttctcatttgtg aataataatggtatctttatgaatatgcagtttgtggtttcttttctgA ttgcagttctgagcattttgtttttgcttccgtttactataccacttac agtttgcactaatttagttgatatgcgagccatctgatgtttgatgatt caaatggcgtttatgtaactcgtacccgagtggatggagaagagctcca ttgccggtttgtttcatgggtggcggagggcaactcctgggaaggaaca aaagaaaaaccgtgatacgagttcatgggtgagagctccagcttgatcc cttctctgtcgatcaaatttgaattttttggatcacggcaggctcacaag ataatccaaagtaaaacataatgaatttgtacttctcaatgatcactta ttttttagcaaatcagcaattgtgcatgtcaaatgatttcggtgtaagag aaagagttgatgaatcaaaatatctgtagctggatcaagaatctgaggc agttgtatgtatcaatgatctttccgctacaatgatgttagctatccga gtcaaattgttgtagaattgcatacttcggcatcacattctggatgaca taataaataggaagtcttcagatccctaaaaaaattgagagctaataaca ttagtcctagatgtaactgggtgacaaccaagaaagagacatgcaaata ctacttttgtttgaaggagcatccctggtttgacatattttttctgaat atcaaactttgaaactctacctagtctaatgtctaacgacagatcttac tggtttaactgcagtgatatctactatcttttggaatgttttctccttc agttatacatcaagttccaagatgcaggtgtgcttgattgatgtacatg gctgtgagaagtgcatcctgatgttcagatgatggttcattctaatgtc ttttccttcaatcagtttttctcagtctgacttagcttgtttcatctgca tgtttgaatgttcgtttactcatagtaattgcatttttgtagcagaaca tatcattggtcatggtttcaactgtgcgcgagtcttatgcttattcaaa ctaggaaagcctccgtctagagggtacacgagttgttgctctgtgtgcg tcagtccatagtattaatcttgctagttgtagtatattgtttatgtgga -continued

```
ctcggaattcatcatatgctccttctttgcatcaagtaaggcaaggtaa tgtatagaagctttttaactctttcatggaagctggcctttgccagcat accatccagaagatatcaaccctgcatcttggctgccg
```

The coding region of the UBQ10 of SEQ ID NO: 22 is shown in all capital letters. The ATG start codon for transcription of the POLYUBIQUIN10 gene (SEQ ID NO: 22) is shown in bold (nucleotides 2076-2078 of SEQ ID NO: 22). The TAA stop codon for the stop of transcription of the POLYUBIQUTIN10 gene (SEQ ID NO: 22) is shown in bold (nucleotides 3447-3449 of SEQ ID NO: 22). In one embodiment, the polynucleotide sequence of a tomato UBQ10 comprises a homolog of SEQ ID NO: 22. In one embodiment, the polynucleotide sequence of a tomato UBQ10 is at least 70% homologous to SEQ ID NO: 22. In another embodiment, the polynucleotide sequence of a tomato UBQ10 is at least 80% homologous to SEQ ID NO: 22. In another embodiment, the polynucleotide sequence of a tomato UBQ10 is at least 90% homologous to SEQ ID NO: 22. In another embodiment, the polynucleotide sequence of a tomato UBQ10 is at least 95% homologous to SEQ ID NO: 22. In another embodiment, the polynucleotide sequence of a tomato UBQ10 is at least 98% homologous to SEQ ID NO: 22. In another embodiment, the polynucleotide sequence of a tomato UBQ10 is at least 99% homologous to SEQ ID NO: 22. A skilled artisan would appreciate the homology may be determined using BlastN software of the National Center of Biotechnology Information (NCBI) using default parameters.

In some embodiments, a nucleic acid sequence comprising a potato UBQ10 comprises the following nucleic acid sequence:

```
                                        (SEQ ID NO: 33)
ccaagacaatttcagcttaaaaagtttattaatatttacattagtttt gttgatgaggatgacaagattttggtcatcaattacatatacccaaatt gaatacttagtaagcaacttaatgttttttcataatgataatgacagaca caaaaaaaacccatttattattcacattgattgattttttatatgcacta tagtaataataataatatttcttataaagcaagaggtcaattttttatt ttattataccaacgacactaaattatatttgataatgtaaaacaattca attttacttaaatatcatgaaataaactattttttataaccaaattacta aatttatccaataaaaaaaagtcattaagaagacataaaataaatttga gtaaaaagagtgaagtcgactgactttttttttttatcataagaaaataa attattaactttaacctaataaaacactaatataatttcatggaatcta atacttacctcttagatataagaaaaagcgtttctaatagaccctcaat ttacattaaatattttcaatcaagtttaaataacaaatatcaatatgag gtcaataacagtatcaaaataatatgaaaaaagagcaatacataatata agaaagaagatttaagtgcacttatcaaggtagtattatatcctaattt gctaatatttaaactcttatatttaaggtcatgttcacgataaacttga aatgcgctttattagagcatatattaaaatatataataataataaataccta aaaata aaataaagttatttttagtatatattttttacatgacctacattttttct agtttttttctaaaggagcgtgtaagtgtcaacctcattctcctaatttttt
```

-continued

```
ccccaccacataaaaattaaaaaggaaaggtagcttttgcgtgttgttt tggtacactacacctcattattacacgtgtcctcatatagttggttaac ccgtgaggcggtttcctctagagtcggccatgccatctataaaatgaag ctttctgcacctcaattttttcatcttctatctgatttctattataaattt ctattaattgccttcaaatttctcttttcaaggttagaaatcttctctat ttttttggtttttgtctgtttagattctcgaattagctaatcaggtgctg ttaaagccctaaaatttgagttttttttccgtcgaattgatgctaaagg cttaaaattagagttttttcgtcggtttgactctgaaggcctaaaattt ggggtttttccgggtgatttgatgataaagccctagaatttgagttttttt tatttgtcggtttgatgaaaaaggccttaaatttaatttttttcccggt tgatttgatgaaaaagccctagaatttgtgttttttcgtcggtttgatt ctaaaggcctaaaatttgagtttttccggttgtttttgatgaaaaagccc taaaatttgagtttttttccccgtgtttttagattgtttggttttaattct tgaatcagataatcagggagtgtgaaaagccctaaaatttgagttttttt tcgttgttctgattgttgtttttatgaatttgcagATGCAGATCTTTGT

GAAAACTCTCACCGGAAAGACCATCACCCTAGAGGTGGAAAGTTCTGAT

ACAATCGACAACGTTAAGGCTAAGATTCAGGATAAGGAAGGAATTCCCC

CGGATCAGCAAAGGCTTATCTTCGCCGGAAAGCAGTTGGAGGACGGACG

TACTCTAGCTGATTACAACATCCAGAAGGAGTCTACCCTCCATTTGGTG

CTCCGTCTACGTGGTGGTATGCAGATCTTCGTTAAGACTCTTACGGGTA

AGACGATTACCCTTGAGGTCGAAAGCTCAGACACCATTGACAATGTTAA

GGCTAAGATCCAGGATAAGGAAGGCATTCCCCCAGACCAGCAGAGGTTG

ATCTTTGCAGGGAAACAGTTGGAAGATGGCCGCACCCTAGCTGACTACA

ACATCCAGAAGGAGTCTACCCTACATTTGGTCCTCCGTCTCCGTGGTGG

TATGCAGATCTTCGTTAAGACTCTTACCGGAAAGACCATCACTTTGGAG

GTGGAAAGCTCCGACACCATTGACAACGTGAAGGCTAAGATCCAGGATA

AGGAGGGAATTCCCCCAGACCAGCAGAGGTTGATCTTCGCTGGTAAGCA

ATTGGAGGACGGCCGCACCCTAGCTGACTACAACATCCAGAAGGAGTCT

ACCCTCCATCTTGTCCTCCGTCTCCGTGGTGGTATGCAGATTTTTGTTA

AGACCCTCACCGGGAAGACCATCACTTTGGAGGTTGAAAGCTCCCACAC

CATTGATAATGTCAAGGCTAAGATCCAGGACAAGGAGGGAATTCCCCCA

GACCAGCAGAGGTTGATCTTCGCTGGAAAGCAATTGGAGGATGGCCGCA

CCCTAGCTGACTACAACATCCAGAAGGAGTCCACCCTTCACCTTGTCCT

CCGTCTCCGTGGTGGTATGCAGATTTTTGTTAAGACCCTTACCGGGAAG

ACCATCACCCTGGAGGTTGAGAGCTCCGACACCATTGACAATGTTAAGG

CCAAGATCCAAGACAAGGAGGGTATTCCCCCAGACCAGCAGAGGTTGAT

CTTCGCTGGTAAACAGCTTGAGGATGGCCGCACCCTTGCGGACTACAAC

ATTCAGAAGGAGTCCACCCTTCACTTGGTGCTGAGGCTGAGGGGAGGAA

TGCAGATCTTTGTGAAGACCTTAACCGGGAAGACCATCACCTTGGAGGT

GGAGAGTTCTGACACCATCGACAATGTGAAAGCTAAGATTCAGGACAAG
```

-continued

GAGGGGATCCCACCAGACCAGCAGAGGTTGATCTTTGCTGGTAAGCAGC

TTGAAGATGGACGCACCCTTGCCGACTACAATATCCAGAAGGAGTCCAC

TCTGCACCTTGTCCTCCGTCTCCGTCTGTGGTTTTTAAgttgcctgttg ttggttgtcgtgttgtctggctgtgtctgttgcccattgtggtggttat gtgtttgcattatggtcttaaaggatcatcaatgtgttttcgctttctg ttcccttctgtttctcatttgtgaataataatggcgtctttatgaacat ccaatttctggtttcttttctgatcgcagtttgagtatttgttttttgct tttgcctccgtctattacaccactttgcaattactataatatactaaaa gccttcgatccatcttctgtttgatgattcgaatggtatttatttaact catacccaagtgaagcataaagttagaggagagttcctgttccattgcc tgtttgtatcatgagcaactcatgttaataaacataagaaaaaccatga tgcaatctgtgtagctgatagactttgatgacagacgactcataagtaa caagagataacaaagaggaaacataataaacatgtacgggaagtcctcc aacaatgactataatcacatgtttttgtagattagcaattgtacatgtc aaatgatcttggattaaggaaggagcttgtgaatcaaaacatctgaatt tggacctagagtcttgaggtgatcgtactttggatggagagaccatgaa taagaataaatgaatctggaactgagaactaaatggaagacacactgat ccaacagattaagcttatgacattaatcacagaaggtaactcggtgaca accaagaacggggagctgcaaattctattgtcttaacaacggaccttta ctggtttaactgttatgatgtcttttataggtggcttttgggttgttct tcgctctatccttttatgtaactttcaagaaccaaccaaatgcaggtgt tctagatagatacgtggcatgtgagaagggaccctgaagttcagatg acggt.

The coding region of the UBQ10 of SEQ ID NO: 33 is shown in all capital letters. The ATG start codon for transcription of the POLYUBIQUTIN10 gene (SEQ ID NO: 33) is shown in bold(nucleotides 1604-16060f SEQ ID NO: 33). The TAA stop codon for the stop of transcription of the POLYUBIQUTIN10 gene (SEQ ID NO: 33) is shown in bold (nucleotides 2975-2977 of SEQ ID NO: 33). In one embodiment, the polynucleotide sequence of a potato UBQ10 comprises a homolog of SEQ ID NO: 33. In one embodiment, the polynucleotide sequence of a potato UBQ10 is at least 70% homologous to SEQ ID NO: 33. In another embodiment, the polynucleotide sequence of a potato UBQ10 is at least 80% homologous to SEQ ID NO: 33. In another embodiment, the polynucleotide sequence of a potato UBQ10 is at least 90% t homologous to SEQ ID NO: 33. In another embodiment, the polynucleotide sequence of a potato UBQ10 is at least 95% homologous to SEQ ID NO: 33. In another embodiment, the polynucleotide sequence of a potato UBQ10 is at least 98% homologous to SEQ ID NO: 33. In another embodiment, the polynucleotide sequence of a potato UBQ10 is at least 99% homologous to SEQ ID NO: 33.

In some embodiments, a nucleic acid sequence comprising an *Arabidopsis* UBQ10 comprises the following nucleic acid sequence:

(SEQ ID NO: 40)

ctccacttctacttccagcacgcttcttacttttaccacagctcttgca cctaaccataacaccttccctgtatgatcgcgaagcacccaccctaagc cacattttaatccttctgttggccatgccccatcaaagttgcacttaac ccaagattgtggtggagcttcccatgtttctcgtctgtcccgacggtgt tgtggttggtgctttccttacattctgagcctctttccttctaatccac tcatctgcatcttcttgtgtccttactaatacctcattggttccaaatt ccctccctttaagcaccagctcgtttctgttcttccacagcctcccaag tatccaagggactaaagcctccacattcttcagatcaggatattcttgt ttaagatgttgaactctatggaggtttgtatgaactgatgatctaggac cggataagttcccttcttcatagcgaacttattcaaagaatgttttgtg tatcattcttgttacattgttattaatgaaaaaatattattggtcattg gactgaacacgagtgttaaatatggaccaggccccaaataagatccatt gatatatgaattaaataacaagaatataaatcgagtcaccaaaccacttgc cttttttaacgagacttgttcaccaacttgatacaaaagtcattatcct atgcaaatcaataatcatacaaaaatatccaataacactaaaaaattaa aagaaatggataatttcacaatatgttatacgataaagaagttactttt ccaagaaattcactgattttataagcccacttgcattagatataatggca aaaaaaacaaaaaggaaaagaaataaagcacgaagaattctagaaaat acgaaatacgcttcaatgcagtgggacccacggttcaattattgccaat tttcagctccaccgtatatttaaaaaatataaaacgataatgctaaaaaaa tataaatcgtaacgatcgttaaatctcaacggctggatcttatgacgac cgttagaaattgtggttgtcgacgagtcagtaataaacggcgtcaaagt ggttgcagccggcacacacgagtcgtgtttatcaactcaaagcacaaat acttttcctcaacctaaaaataaggcaattagccaaaaacaactttgcg tgtaaacaacgctcaatacacgtgtcattttattattagctattgcttc accgccttagctttctcgtgacctagtcgtcctcgtcttttcttcttct tcttctataaaacaataacccaaagagctcttcttcttcacaattcagat ttcaatttctcaaaatcttaaaaactttctctcaattctctctaccgtg atcaaggtaaatttctgtgttccttattctctcaaaatcttcgattttg ttttcgttcgatcccaatttcgtatatgttctttggtttagattctgtt aatcttagatcgaagacgattttctgggtttgatcgttagatatcatct taattctcgattagggtttcatagatatcatccgatttgttcaaataat ttgagttttgtcgaataattactcttcgatttgtgatttctatctagat ctggtgttagtttctagtttgtgcgatcgaatttgtcgattaatctgag tttttctgattaacagATGCAGATCTTTGTTAAGACTCTCACCGGAAAG

ACAATCACCCTCGAGGTGGAAAGCTCCGACACCATCGACAACGTTAAGG

CCAAGATCCAGGATAAGGAGGGCATTCCTCCGGATCAGGAGAGGCTTAT

TTTCGCCGGCAAGCAGGTAGAGGATGGGCGTACGTTGGCTGATTACAAT

-continued

ATCCAGAAGGAATCCACCCTCCACTTGGTCCTCAGGCTCCGTGGTGGTA

TGCAGATTTTCGTTAAAACCCTAACGGGAAAGACGATTACTCTTGAGGT

GGAGAGTTCTGACACCATCGACAACGTCAAGGCCAAGATCCAAGACAAA

GAGGGTATTCCTCCGGACCAGCAGAGGCTGATCTTCGCCGGAAAGCAGT

TGGAGGATGGCAGAACTCTTGCTGACTACAATATCCAGAAGGAGTCCAC

CCTTCATCTTGTTCTCAGGCTCCGTGGTGGTATGCAGATTTTCGTTAAG

ACGTTGACTGGGAAAACTATCACTTTGGAGGTGGAGAGTTCTGACACCA

TTGATAACGTGAAAGCCAAGATCCAAGACAAAGAGGGTATTCCTCCGGA

CCAGCAGAGATTGATCTTCGCCGGAAAACAACTTGAAGATGGCAGAACT

TTGGCCGACTACAACATTCAGAAGGAGTCCACACTCCACTTGGTCTTGC

GTCTGCGTGGAGGTATGCAGATCTTCGTGAAGACTCTCACCGGAAAGAC

CATCACTTTGGAGGTGGAGAGTTCTGACACCATTGATAACGTGAAAGCC

AACATCCAGGACAAAGAGGGTATCCCACCGGACCAGCAGAGATTGATCT

TCGCCGGAAAGCAACTTGAAGATGGAAGAACTTTGGCTGACTACAACAT

TCAGAAGGAGTCCACACTTCACTTGGTCTTGCGTCTGCGTGGAGGTATG

CAGATCTTCGTGAAGACTCTCACCGGAAAGACTATCACTTTGGAGGTAG

AGAGCTCTGACACCATTGACAACGTGAAGGCCAAGATCCAGGATAAGGA

AGGAATCCCTCCGGACCAGCAGAGGTTGATCTTTGCCGGAAAACAATTG

GAGGATGGTCGTACTTTGGCGGATTACAACATCCAGAAGGAGTCGACCC

TTCACTTGGTGTTGCGTCTGCGTGGAGGTATGCAGATCTTCGTCAAGAC

TTTGACCGGAAAGACCATCACCCTTGAAGTGGAAAGCTCCGACACCATT

GACAACGTCAAGGCCAAGATCCAGGACAAGGAAGGTATTCCTCCGGACC

AGCAGCGTCTCATCTTCGCTGGAAAGCAGCTTGAGGATGGACGTACTTT

GGCCGACTACAACATCCAGAAGGAGTCTACTCTTCACTTGGTCCTGCGT

CTTCGTGGTGGTTTCTAAatctcgtctctgttatgcttaagaagttcaa tgtttcgtttcatgtaaaactttggtggtttgtgttttggggccttgta taatccctgatgaataagtgttctactatgtttccgttcctgttatctc tttctttctaatgacaagtcgaacttcttctttatcatcgcttcgtttt tattatctgtgcttcttttgtttaatacgcctgcaaagtgactcgactc tgtttagtgcagttctgcgaaacttgtaaatagtccaattgttggcctc tagtaatagatgtagcgaaagtgttgagctgttgggtctaaggatggc ttgaacatgttaatcttttaggttctgagtatgatgaacattcgttgtt gctaagaaatgcctgtaatgtcccacaaatgtagaaaatggttcgtacc tttgtccaagcattgatatgtctgatgagaggaaactgcaagatactga gcttggtttaacgaaggagaggcagtttcttccttccaaagcatttcat ttgacaatgccttgatcatcttaagtagagtttctgttgtggaaagttt gaaactttgaagaaacgactctcaagtaaattgatgatcacagtgaaa gtgtatgttacataagtggatatttcacccttttttccatcaatcaaaac -continued atcatatagtaatccattggtttatacaaacatcaaaatacatttacct ctgaaatgaggaaaaaaatgcaaagagatttttgaaaatttccaacaaa tg.

The coding region of the UBQ10 of a SEQ ID NO: 40 is shown in all capital letters. The ATG start codon for transcription of the POLYUBIQUTIN10 gene (SEQ ID NO: 40) is shown in bold (nucleotides 1683-1685 of SEQ ID NO: 40). The TAA stop codon for the stop of transcription of the POLYUBIQUTIN10 gene (SEQ ID NO: 40) is shown in bold (nucleotides 3054-3056 of SEQ ID NO. 40). In one embodiment, the polynucleotide sequence of an *Arabidopsis* UBQ10 comprises a homolog of SEQ ID NO: 40. In one embodiment, the polynucleotide sequence of an *Arabidopsis* UBQ10 is at least 70% homologous to SEQ ID NO: 40. In another embodiment, the polynucleotide sequence of an *Arabidopsis* UBQ10 is at least 80% homologous to SEQ ID NO: 40. In another embodiment, the polynucleotide sequence of a *Arabidopsis* UBQ10 is at least 90% homologous to SEQ ID NO: 40. In another embodiment, the polynucleotide sequence of an *Arabidopsis* UBQ10 is at least 95% homologous to SEQ ID NO: 40. In another embodiment, the polynucleotide sequence of an *Arabidopsis* UBQ10 is at least 98a homologous to SEQ ID NO: 40. In another embodiment, the polynucleotide sequence of an *Arabidopsis* UBQ10 is at least 99% homologous to SEQ ID NO: 40.

In some embodiments, a nucleic acid sequence comprising an *Arabidopsis* UBQ10 comprises the following nucleic acid sequence:

(SEQ ID NO: 47)

gtcgacgagtcagtaataaacggcgtcaaagtggttgcagccggcacac acgagtcgtgtttatcaactcaaagcacaaatacttttcctcaacctaa aaataaggcaattagccaaaaacaactttgcgtgtaaacaacgctcaat acacgtgtcattttattattagctattgcttcaccgccttagctttctc gtgacctagtcgtcctcgtcttttcttcttcttcttctataaaacaata cccaaagagctcttcttcttcacaattcagatttcaatttctcaaaatc ttaaaaactttctctcaattctctctaccgtgatcaaggtaaatttctg tgttccttattctctcaaaatcttcgattttgtttcgttcgatcccaa tttcgtatatgttctttggtttagattctgttaatcttagatcgaagac gattttctgggtttgatcgttagatatcatcttaattctcgattagggt ttcatagatatcatccgatttgttcaaataatttgagttttgtcgaata attactcttcgatttgtgatttctatctagatctggtgttagtttctag tttgtgcgatcgaatttgtcgattaatctgagttttttctgattaacagA

TGCAGATCTTTGTTAAGACTCTCACCGGAAAGACAATCACCCTCGAGCT

GGAAAGCTCCGACACCATCGACAACGTTAAGGCCAAGATCCAGGATAAG

GAGGGCATTCCTCCGGATCAGCAGAGGCTTATTTTCGCCGGCAAGCAGC

TAGAGGATGGCCGTACGTTGGCTGATTACAATATCCAGAAGGAATCCAC

CCTCCACTTGGTCCTCAGGCTCCGTGGTGGTATGCAGATTTTCGTTAAA

ACCCTAACGGGAAAGACGATTACTCTTGAGGTGGAGAGTTCTGACACCA

-continued

```
TCGACAACGTCAAGGCCAAGATCCAAGACAAAGAGGGTATTCCTCCGGA

CCAGCAGAGGCTGATCTTCGCCGGAAAGCAGTTGGAGGATGGCAGAACT

CTTGCTGACTACAATATCCAGAAGGAGTCCACCCTTCATCTTGTTCTCA

GGCTCCGTGGTGGTATGCAGATTTTCGTTAAGACGTTGACTGGGAAAAC

TATCACTTTGGAGGTGGAGAGTTCTGACACCATTGATAACGTGAAAGCC

AAGATCCAAGACAAAGAGGGTATTCCTCCGGACCAGCAGAGATTGATCT

TCGCCGGAAAACAACTTGAAGATGGCAGAACTTTGGCCGACTACAACAT

TCAGAAGGAGTCCACACTCCACTTGGTCTTGCGTCTGCGTGGAGGTATG

CAGATCTTCGTGAAGACTCTCACCGGAAAGACCATCACTTTGGAGGTGG

AGAGTTCTGACACCATTGATAACGTGAAAGCCAAGATCCAGGACAAAGA

GGGTATCCCACCGGACCAGCAGAGATTGATCTTCGCCGGAAAGCAACTT

GAAGATGGAAGAACTTTGGCTGACTACAACATTCAGAAGGAGTCCCACAC

TTCACTTGGTCTTGCGTCTGCGTGGAGGTATGCAGATCTTCGTGAAGAC

TCTCACCGGAAAGACTATCACTTTGGAGGTAGAGAGCTCTGACACCATT

GACAACGTGAAGGCCAAGATCCAGGATAAGGAAGGAATCCCTCCGGACC

AGCAGAGGTTGATCTTTGCCGGAAAACAATTGGAGGATGGTCGTACTTT

GGCGGATTACAACATCCAGAAGGAGTCGACCCTTCACTTGGTGTTGCGT

CTGCGTGGAGGTATGCAGATCTTCGTCAAGACTTTGACCGGAAAGACCA

TCACCCTTGAACTGGAAAGCTCCGACACCATTGACAACGTCAAGGCCAA

GATCCAGGACAAGGAAGGTATTCCTCCGGACCAGCAGCGTCTCATCTTC

GCTGGAAAGCAGCTTGAGGATGGACGTACTTTGGCCGACTACAACATCC

AGAAGGAGTCTACTCTTCACTTGGTCCTGCGTCTTCGTGGTGGTTTCTA

Aatctcgtctctgttatgcttaagaagttcaatgtttcgtttcatgtaa aactttggtggtttgtgttttggggccttgtataatccctgatgaataa gtgttctactatgtttccgttcctgttatctctttctttctaatgacaa gtcgaacttcttctttatcatcgcttcgtttttattatctgtgcttctt ttgtttaatacgcctgcaaagtgactcgactctgtttagtgcagttctg cgaaacttgtaaatagtccaattgttggcctctagtaatagatgtagcg aaagtgttgagctgttgggttctaaggatggcttgaacatgttaatctt ttaggttctgagtatgatgaacattcgttgttgctaagaaatgcctgta atgtcccacaaatgtagaaaatggttcgtacctttgtccaagcattgat atgtctgatgagaggaaactgcaagatactgagcttggtttaacgaagg agaggcagtttcttccttccaaagcatttcatttgacaatgccttgatc atcttaagtagagtttctgttgtggaaagtttgaaacttttgaagaaacg actctcaagtaaattgatgatcacaagtgaaagtgtatgttacataagt ggatatttcacccttttttccatcaatcaaaacatcatatagtaatccat tggtttatacaaacatcaaaatacatttacctctgaaatgaggaaaaaa atgcaaagagattttgaaaatttccaacaaatg.
```

The coding region of the UBQ10 of SEQ ID NO: 47 is shown in all capital letters. The ATG start codon for transcription of the POLYUBIQUITIN10 gene (SEQ ID NO: 47) is shown in bold (nucleotides 637-639 of SEQ ID NO: 47). The TAA stop codon for the stop of transcription of the POLYUBIQUTIN10 gene (SEQ ID NO: 47) is shown in bold (nucleotides 2008-2010 of SEQ ID NO: 47). In one embodiment, the polynucleotide sequence of an *Arabidopsis* UBQ10 comprises a homolog of SEQ ID NO: 47. In one embodiment, the polynucleotide sequence of an *Arabidopsis* UBQ10 is at least 70% homologous to SEQ ID NO: 47. In another embodiment, the polynucleotide sequence of an *Arabidopsis* UBQ10 is at least 80% homologous to SEQ ID NO: 47. In another embodiment, the polynucleotide sequence of a *Arabidopsis* UBQ10 is at least 90% homologous to SEQ ID NO: 47. In another embodiment, the polynucleotide sequence of an *Arabidopsis* UBQ10 is at least 95% homologous to SEQ ID NO: 47. In another embodiment, the polynucleotide sequence of an *Arabidopsis* UBQ10 is at least 98% homologous to SEQ ID NO: 47. In another embodiment, the polynucleotide sequence of an *Arabidopsis* UBQ10 is at least 99% homologous to SEQ ID NO: 47.

In some embodiments, a nucleic acid sequence comprising a first regulatory region comprises the following nucleic acid sequence:

```
                                        (SEQ ID NO: 44)
gtaaatttctgtgttccttattctctcaaaatcttcgattttgtttttcg ttcgatcccaatttcgtatatgttctttggtttagattctgttaatctt agatcgaagacgattttctgggtttgatcgttagatatcatcttaattc tcgattagggtttcatagatatcatccgatttgttcaaataatttgagt tttgtcgaataattactcttcgatttgtgatttctatctagatctggtg ttagtttctagtttgtgcgatcgaatttgtcgattaatctgagtttttc tgattaacag.
```

In some embodiments, a nucleic acid sequence comprising a first regulatory region comprises the following nucleic acid sequence:

```
                                        (SEQ ID NO: 23)
gtcaactaccccaatttaaattttatttgattaagatattttttatgga cctactttataattaaaaatattttctatttgaaaaggaaggacaaaa atcatacaattttggtccaactactcctctctttttttttttttggcttt ataaaaaggaaagtgattagtaataaataattaaataatgaaaaaag gaggaaataaaattttcgaattaaaatgtaaaagagaaaaaggagagg gagtaatcattgtttaactttatctaaagtaccccaattcgattttac atgtatatcaaattatacaaatattttattaaaatatagatattgaat aattttattattcttgaacatgtaaataaaaattatctattatttcaa tttttatataaactattatttgaaatctcaattatgattttttaatat cactttctatccatgataatttcagcttaaaaagtttgtcaataatt acattaatttgttgatgaggatgacaagatttcggtcatcaattaca tatacacaaattgaaatagtaagcaacttgattttttttctcataatg ataatgacaaagacacgaaaagacaattcaatattcacattgatttat ttttatatgataataattacaataataatattcttataaagaaagaga tcaattttgactgatccaaaaatttatttattttactataccaacgtc actaattatatctaataatgtaaaacaattcaatcttacttaaatatt
```

-continued

```
aatttgaaataaactattttttataacgaaattactaaatttatccaat aacaaaaaggtcttaagaagacataaaattctttttttgtaatgctcaa ataaatttgagtaaaaaagaatgaaattgagtgatttttttttaatca taagaaaataaataattaatttcaatataataaaacagtaatataatt tcataaatggaattcaatacttacctcttagatataaaaaataaatat aaaaataaagtgtttctaataaacccgcaatttaaataaaatatttaa tattttcaatcaaatttaaataattatattaaaatatcgtagaaaaag agcaatatataatacaagaaagaagatttaagtacaattatcaactat tattatactctaattttgttatatttaatttcttacggttaaggtcat gttcacgataaactcaaaatacgctgtatgaggacatattttaaattt taaccaataataaaactaagttattttttagtatatttttttgtttaac gtgacttaattttttcttttctagaggagcgtgtaagtgtcaacctcat tctcctaattttcccaaccacataaaaaaaaaataaaggtagcttttg cgtgttgatttggtacactacacgtcattattacacgtgttttcgtat gattggttaatccatgaggcggtttcctctagagtcggccataccatc tataaaataaagctttctgcagctcatttttttcatcttctatctgatt tctattataatttctctgaattgccttcaaatttctctttcaaggtta gaatttttctctatttttttggtttttgtttgtttagattctgagttta gttaatcaggtgctgttaaagccctaaattttgagttttttttcggttg ttttgatggaaaatacctaacaattgagtttttttcatgttgtttgtc ggagaatgcctacaattggagttcctttcgttgtttttgatgagaaagc ccctaatttgagtgtttttccgtcgatttgattttaaaggtttatatt cgagtttttttcgtcggtttaatgagaaggcctaaaataggagttttt ctggttgatttgactaaaaaagccatggaattttgtgtttttgatgtc gctttggttctcaaggcctaagatctgagtttctccggttgttttgat gaaaaagccctaaaattggagttttttatcttgtgtttttaggttgtttt ctatccttataatttgagtttttttcgttgttctgattgttgtttttat gaattttgcag.
```

In some embodiments, a nucleic acid sequence comprising a first regulatory region comprises the following nucleic acid sequence:

```
                                    (SEQ ID NO: 24)
gtcaactaccccaatttaaattttatttgattaagatattttt atggac ctactttataattaaaaatattttctatttgaaaaggaaggacaaaat catacaattttggtccaactactcctctcttttttttttttggctttata aaaaaggaaagtgattagtaataaataattaaataatgaaaaaaggagg aaataaaattttcgaattaaaatgtaaaagagaaaaaggagagggagta atcattgtttaacttttatctaaagtaccccaattcgattttacatgtat atcaaattatacaaatattttattaaaatatagatattgaataattta ttattcttgaacatgtaaataaaaaattatctattatttcaattttata taaactattatttgaaatctcaattatgattttttaatatcactttcta
```

-continued

```
tccatgataatttcagcttaaaaagtttgtcaataattacattaattt tgttgatgaggatgacaagatttcggtcatcaattacatatacacaaat tgaaatagtaagcaacttgattttttttctcataatgataatgacaaag acacgaaaagacaattcaatattcacattgatttattttttatatgataa taattacaataataatattcttataaagaaagagatcaattttgactga tccaaaatttatttatttttactataccaacgtcactaattatatcta ataatgtaaaacaattcaatcttacttaaatattaatttgaaataaact attttttataacgaaattactaaatttatccaataacaaaaaggtcttaa gaagacataaattctttttttgtaatgctcaaatataaatttgagtaaaaa agaatgaaattgagtgatttttttttttaatcataagaaaataaataatta atttcaatataataaaacagtaatataatttcataaatggaattcaata cttacctcttagatataaaaaataaatataaaaataaagtgtttctaat aaacccgcaatttaaataaaatatttaatattttcaatcaaatttaaat aattatattaaaatatcgtagaaaaagagcaatatataatacaagaaag aagatttaagtacaattatcaactattattatactctaattttgttata tttaatttcttacggttaaggtcatgttcacgataaactcaaaatacgc tgtatgaggacatattttaaattttaaccaataataaaactaagttatt tttagtatatttttttgtttaacgtgacttaattttttcttttctagagg agcgtgtaagtgtcaacctcattctcctaattttcccaaccacataaaa aaaaaataaaggtagcttttgcgtgttgatttggtacactacacgtcat tattacacgtgttttcgtatgattggttaatccatgaggcggtttcctc tagagtcggcca.
```

```
                                    (SEQ ID NO: 25)
taccatctataaaataaagctttctgcagctcatttttttcatcttctat ctgatttctattataatttctagaattgccttcaaatttctctttcaa g.
```

In some embodiments, a nucleic acid sequence comprising a first regulatory region comprises the following nucleic acid sequence:

```
                                    (SEQ ID NO: 26)
gttagaattttttctctattttttttggtttttgtttgtttagattctgagt ttagttaatcaggtgctgttaaagccctaaattttgagttttttttcggt tgttttgatggaaaatacctaacaattgagttattcatgttgattgtcg gagaatgcctacaattggagttcctacgagtatgatgagaaagcccta atttgagtgatttccgtcgatttgattttaaaggtttatattcgagtta tttcgtcggataatgagaaggcctaaaataggagatttctggttgattt gactaaaaaagccatggaattttgtgtttttgatgtcgctttggttctc aaggcctaagatctgagtttctccggttgttttgatgaaaaagccctaa aattggagttttttatcttgtgtttttaggttgtttttaatccttataattt gagtttttttcgttgttctgattgttgtttttatgaattttgcag.
```

US 12,559,765 B2

31

In some embodiments, a nucleic acid sequence comprising a first regulatory region comprises the following nucleic acid sequence:

(SEQ ID NO: 34)
```
ccaagacaatttcagcttaaaaagtttttattaatatttacattagtt
ttgttgatgaggatgacaagattttggtcatcaattacatataccca
aattgaatacttagtaagcaacttaatgttttttcataatgataatga
cagacacaaaaaaaacccatttattattcacattgattgattttttat
atgcactatagtaataataataatatttcttataaagcaagaggtca
attttttattttattataccaacgacactaaattatatttgataatg
taaaacaattcaattttacttaaatatcatgaaataaactattttta
taaccaaattactaaatttatccaataaaaaaaagtcattaagaaga
cataaaataaatttgagtaaaaagagtgaagtcgactgacttttttt
tttatcataagaaaataaattattaactttaacctaataaaacacta
atataatttcatggaatctaatacttacctcttagatataagaaaaa
gcgtttctaatagaccctcaatttacattaaatattttcaatcaagt
ttaaataacaaatatcaatatgaggtcaataacagtatcaaaataat
atgaaaaagagcaatacataatataagaagaagatttaagtgcac
ttatcaaggtagtattatatcctaatttgctaatatttaaactctta
tatttaaggtcatgttcacgataaacttgaaatgcgctttattagag
catatattaaaataaaaaaaatacctaaaataaaataaagttattt
tagtatatattttttacatgacctacatttttctagttttttctaaa
ggagcgtgtaagtgtcaacctcattctcctaattttccccaccacat
aaaaattaaaaaggaaaggtagcttttgcgtgttgtttggtacact
acacctcattattacacgtgtcctcatatagttggttaacccgtgag
gcggtttcctctagagtcggccaTGCCATCTATAAAATGAAGCTTTC
TGCACCTCAATTTTTCATCTTCTATCTGATTTCTATTATAATTTCTA
TTAATTGCCTTCAAATTTCTCTTTCAAGgttagaaatcttctctatt
ttttggtnttgtctgtttagattctcgaattagctaatcaggtgctg
ttaaagccctaaaatttgagttttttttccgtcgaattgatgctaaa
ggcttaaaattagagttttttcgtcggtttgactctgaaggcctaaa
atggggttttccgggtgatttgatgataaagccctagaatttgagt
ttttttatttgtcggtttgatgaaaaaggccttaaatttaatttttt
tcccggttgatttgatgaaaaagccctagaatttgtgttttttcgtc
ggtttgattctaaaggcctaaaatttgagttttttccggttgttttga
tgaaaaagccctaaaatttgagttttttccccgtgtttttagattgtt
tggttttaattcttgaatcagataatcagggagtgtgaaaagcccta
aaatttgagttttttttcgttgttctgattgttgtttttatgaatttg
cag.
```

In some embodiments, a nucleic acid sequence comprising a first regulatory region comprises the following nucleic acid sequence:

(SEQ ID NO: 35)
```
ccaagacaatttcagcttaaaaagtttttattaatatttacatta
gttttgttgatgaggatgacaagattttggtcatcaattacata
tacccaaattgaatacttagtaagcaacttaatgttttttcataa
tgataatgacagacacaaaaaaaacccatttattattcacattg
attgattttttatatgcactatagtaataataataatatttctta
taaagcaagaggtcaattttttattttattataccaacgacact
aaattatatttgataatgtaaaacaattcaattttacttaaaata
tcatgaaataaactattttttataaccaaattactaaatttatcc
aataaaaaaaagtcattaagaagacataaaataaatttgagtaa
aaagagtgaagtcgactgacttttttttttatcataagaaaata
aattattaactttaacctaataaaacactaatataatttcatgg
aatctaatacttacctcttagatataagaaaaagcgtttctaat
agaccctcaatttacattaaatattttcaatcaagtttaaataa
caaatatcaatatgaggtcaataacagtatcaaaataatatgaa
aaaagagcaatacataatataagaagaagatttaagtgcactt
atcaaggtagtattatatcctaatttgctaatatttaaactctt
atatttaaggtcatgttcacgataaacttgaaatgcgctttatt
agagcatatattaaaataaaaaaaatacctaaaataaaataaag
ttattttttagtatatattttttacatgacctacatttttctagt
tttttctaaaggagcgtgtaagtgtcaacctcattctcctaatt
ttccccaccacataaaaattaaaaaggaaaggtagcttttgcgt
gttgtttggtacactacacctcattattacacgtgtcctcata
tagttggttaacccgtgaggcggtttcctctagagtcggcca.
```

In some embodiments, a nucleic acid sequence comprising a first regulatory region comprises the following nucleic acid sequence:

(SEQ ID NO: 36)
```
tgccatctataaaatgaagctttctgcacctcaattttttcatct
tctatctgatttctattataatttctattaattgccttcaaatt
tctctttcaag.
```

In some embodiments, a nucleic acid sequence comprising a first regulatory region comprises the following nucleic acid sequence:

(SEQ ID NO. 37)
```
gttagaaatcttctctattttttggttttttgtctgtttagattctc
gaattagctaatcaggtgctgttaaagccctaaaatttgagttttt
tttccgtcgaattgatgctaaaggcttaaaattagagttttttccg
tcggtttgaactgaaggcctaaaatttggggtttccgggtgattt
gatgataaagccctagaatttgagttttttttatttgtcggtttgat
```

-continued

```
gaaaaaggccttaaatttaatttttttcccggttgatttgatgaaa aagccctagaatttgtgtttttttcgtcggtttgattctaaaggcct aaaatttgagttttttccggttgtttttgatgaaaaagccctaaaatt tgagtttttttcccccgtgtttttagattgtttggttttaattcttgaa tcagataatcagggagtgtgaaaagccctaaaatttgagttttttt cgttgttctgattgttgtttttatgaaattgcag.
```

In some embodiments, a nucleic acid sequence comprising a first regulatory region comprises the following nucleic acid sequence:

```
                                          (SEQ ID NO: 41)
ctccacttctacttccagcacgcttcttacttttaccacagctcttg cacctaaccataacaccttccctgtatgatcgcgaagcacccaccct aagccacattttaatccttctgttggccatgccccatcaaagttgca cttaacccaagattgtggtggagcttcccatgtttctcgtctgtccc gacggtgttgtggttggtgctttccttacattctgagcctctttcct tctaatccactcatctgcatcttcttgtgtccttactaatacctcat tggttccaaattccctcccttttaagcaccagctcgtttctgttcttc cacagcctcccaagtatccaagggactaaagcctccacattcttcag atcaggatattcttgtttaagatgttgaactctatggaggtttgtat gaactgatgatctaggaccggataagttcccttcttcatagcgaact tattcaaagaatgttttgtgtatcattcttgttacattgttattaat gaaaaaatattattggtcattggactgaacacgagtgttaaatatgg accaggccccaaataagatccattgatatatgaattaaataacaaga ataaatcgagtcaccaaaccacttgcctttttttaacgagacttgttc accaacttgatacaaaagtcattatcctatgcaaatcaataatcata caaaaatatccaataacactaaaaaattaaaagaaatggataaatttc acaatatgttatacgataaagaagttacttttccaagaaattcactg attttataagcccacttgcattagataaatggcaaaaaaaacaaaa aggaaaagaaataaagcacgaagaattctagaaaatacgaaatacgc ttcaatgcagtgggacccacggttcaattattgccaattttcagctc caccgtatatttaaaaaataaaacgataatgctaaaaaaatataaat cgtaacgatcgttaaatctcaacggctggatcttatgacgaccgtta gaaattgtggttgtcgacgagtcagtaataaacggcgtcaaagtggt tgcagccggcacacacgagtcgtgtttatcaactcaaagcacaaata cttttcctcaacctaaaaataaggcaattagccaaaaacaactttgc gtgtaaacaacgctcaatacacgtgtcattttattattagctattgc ttcaccgccttagctttctcgtgacctagtcgtcctcgtcttttctt cttcttcttctataaaacaatacccaaagagctcttcttcttcacaa ttcagatttcaatttctcaaaatcttaaaaactttctctcaattctc tctaccgtgatcaaggtaaatttctgtgttccttattctctcaaaat cttcgattttgttttcgttcgatcccaatttcgtatatgttctttgg
```

-continued

```
tttagattctgttaatcttagatcgaagacgattttctgggtttgat cgttagatatcatcttaattctcgattagggtttcatagatatcatc cgatttgttcaaataatttgagttttgtcgaataattactcttcgat ttgtgatttctatctagatctggtgttagtttctagtttgtgcgatc gaatttgtcgattaatctgagttttttctgattaacag.
```

In some embodiments, a nucleic acid sequence comprising a first regulatory region comprises the following nucleic acid sequence:

```
                                          (SEQ ID NO: 42)
ctccacttctacttccagcacgcttcttacttttaccacagctcttg cacctaaccataacaccttccctgtatgatcgcgaagcacccaccct aagccacattttaatccttctgttggccatgccccatcaaagttgca cttaacccaagattgtggtggagcttcccatgtttctcgtctgtccc gacggtgttgtggttggtgctttccttacattctgagcctctttcct tctaatccactcatctgcatcttcttgtgtccttactaatacctcat tggttccaaattccctcccttttaagcaccagctcgtttctgttcttc cacagcctcccaagtatccaagggactaaagcctccacattcttcag atcaggatattcttgtttaagatgttgaactctatggaggtttgtat gaactgatgatctaggaccggataagttcccttcttcatagcgaact tattcaaagaatgttttgtgtatcattcttgttacattgttattaat gaaaaaatattattggtcattggactgaacacgagtgttaaatatgg accaggccccaaataagatccattgatatctgaattaaataacaaga ataaatcgagtcaccaaaccacttgcctttttttaacgagacttgttc accaacttgatacaaaagtcattatcctatgcaaatcaataatcata caaaaatatccaataacactaaaaaattaaaagaaatggataaatttc acaatatgttatacgataaagaagttacttttccaagaaattcactg attttataagcccacttgcattagataaatggcaaaaaaaacaaaa aggaaaagaaataaagcacgaagaattctagaaaatacgaaatacgc ttcaatgcagtgggacccacggttcaattattgccaattttcagctc caccgtatatttaaaaaataaaacgataatgctaaaaaaatataaat cgtaacgatcgttaaatctcaacggctggatcttatgacgaccgtta gaaattgtggttgtcgacgagtcagtaataaacggcgtcaaagtggt tgcagccggcacacacgagtcgtgtttatcaactcaaagcacaaata cttttcctcaacctaaaaataaggcaattagccaaaaacaactttgc gtgtaaacaacgctcaatacacgtgtcattttattattagctattgc ttcaccgccttagctttctcgtgacctagtcgtcctcgtcttttctt cttcttcttctataaaacaatacc.
```

In some embodiments, a nucleic acid sequence comprising a first regulatory region comprises the following nucleic acid sequence:

```
                                        (SEQ ID NO: 43)
caaagagctcttcttcttcacaattcagatttcaatttctcaa aatcttaaaaacatctctcaattctctctaccgtgatcaag.
```

In some embodiments, a nucleic acid sequence comprising a first regulatory region comprises the following nucleic acid sequence:

```
                                        (SEQ ID NO: 48)
gtcgacgagtcagtaataaacggcgtcaaagtggttgcagccggcac acacgagtcgtgtttatcaactcaaagcacaaatacttttcctcaac ctaaaaataaggcaattagccaaaaacaactttgcgtgtaaacaacg ctcaatacacgtgtcattttattattagctattgcttcaccgcctta gctttctcgtgacctagtcgtcctcgtcttttcttcttcttctcta taaaacaatacccaaagagctcttcttcttcacaattcagatttcaa tttctcaaaatcttaaaaactttctctcaattctctctaccgtgatc aaggtaaatttctgtgttccttattctctcaaaatcttcgattttgt tttcgttcgatcccaatttcgtatatgttctttggtttagattctgt taatcttagatcgaagacgattttctgggtttgatcgttagatatca tcttaattctcgattagggtttcatagatatcatccgatttgttcaa ataatttgagttttgtcgaataattactcttcgatttgtgatttcta tctagatctggtgttagtttctagtttgtgcgatcgaatttgtcgat taatctgagtttttctgattaacag.
```

In some embodiments, a nucleic acid sequence comprising a first regulatory region comprises the following nucleic acid sequence:

```
                                        (SEQ ID NO: 49)
gtcgacgagtcagtaataaacggcgtcaaagtggttgcagccggca cacacgagtcgtgtttatcaactcaaagcacaaatacttttcctca acctaaaaataaggcaattagccaaaaacaactttgcgtgtaaaca acgctcaatacacgtgtcattttattattagctattgcttcaccgc cttagctttctcgtgacctagtcgtcctcgtcttttcttcttcttc ttctataaaacaatacc.
```

In some embodiments, a nucleic acid sequence comprising a first regulatory region comprises a homolog of any one of SEQ ID NOs: 23, 24, 25, 26, 34, 35, 36, 37, 41, 41, 43, 44, 48, or 49. In one embodiment, a nucleic acid sequence comprising a first regulatory region is at least 70% homologous to any one of SEQ ID NOs: 23, 24, 25, 26, 34, 35, 36, 37, 41, 41, 43, 44, 48, or 49. In another embodiment, a nucleic acid sequence comprising a first regulatory region is at least 80% homologous to any one of SEQ ID NOs: 23, 24, 25, 26, 34, 35, 36, 37, 41, 41, 43, 44, 48, or 49. In another embodiment, a nucleic acid sequence comprising a first regulatory region is at least 90% homologous to any one of SEQ ID NOs: 23, 24, 25, 26, 34, 35, 36, 37, 41, 41, 43, 44, 48, or 49. In another embodiment, a nucleic acid sequence comprising a first regulatory region is at least 95% homologous to any one of SEQ ID NOs: 23, 24, 25, 26, 34, 35, 36, 37, 41, 41, 43, 44, 48, or 49. In another embodiment, a nucleic acid sequence comprising a first regulatory region is at least 98% homologous to any one of SEQ ID NOs: 23, 24, 25, 26, 34, 35, 36, 37, 41, 41, 43, 44, 48, or 49. In another embodiment, a nucleic acid sequence comprising a first regulatory region is at least 99% homologous to any one of SEQ ID NOs: 23, 24, 25, 26, 34, 35, 36, 37, 41, 41, 43, 44, 48, or 49.

In some embodiments, a nucleic acid sequence comprising a first regulatory region comprises a combination of any one of SEQ ID NOs: 23, 24, 25, 26, 34, 35, 36, 37, 41, 41, 43, 44, 48, or 49.

In some embodiments, an UBQ10 regulatory sequence comprises a *Solanum lycopersicum* UBQ10 regulatory sequence.

Expression of a Target Gene Linked to UBQ10

In some embodiments, disclosed herein is a recombinant nucleic acid molecule comprising: a first nucleic acid sequence of a first regulatory region; and a second nucleic acid sequence of a second regulatory region, wherein said first regulatory region is adjacent to the nucleic acid sequence encoding a UBQ10 extending about 2 Kb upstream but not including the start codon of the UBQ10, and wherein said second regulatory region is adjacent to the nucleic acid sequence encoding a UBQ10 extending about 1 Kb downstream from but not including the stop codon region of UBQ10, and wherein said first and second nucleic acid sequences are fused to a nucleic acid sequence of a target gene.

In some embodiments, a recombinant nucleic acid molecule disclosed herein comprises: a first nucleic acid sequence of a first regulatory region; and a second nucleic acid sequence of a second regulatory region, wherein said first region comprises a nucleic acid sequence adjacent to the nucleic acid sequence encoding a UBQ10 extending about 2 Kb upstream but not including the start codon of the UBQ10, and wherein said second region comprises nucleic acid sequence adjacent to the nucleic acid sequence encoding a UBQ10 extending about 1 Kb downstream from but not including the stop codon region of UBQ10, and wherein said first and second nucleic acid sequences are operably linked to a nucleic acid sequence of a target gene, wherein the first nucleic acid sequence is 5' of the target gene and the second nucleic acid sequence is 3' of the target gene.

In some embodiments, a recombinant nucleic acid molecule disclosed herein comprises: a first nucleic acid sequence of a first regulatory region; and a second nucleic acid sequence of a second regulatory region, wherein said first region comprises a nucleic acid sequence adjacent to the nucleic acid sequence encoding a UBQ10 extending about 2 Kb upstream but not including the start codon of the UBQ10, and wherein said second region comprises nucleic acid sequence adjacent to the nucleic acid sequence encoding a UBQ10 extending about 1 Kb downstream from but not including the stop codon region of UBQ10, and wherein said first and second nucleic acid sequences are operably linked to a nucleic acid sequence of a multiple cloning site (MCS), wherein the first nucleic acid sequence is 5' of the MCS and the second nucleic acid sequence is 3' of the MCS.

A skilled artisan would appreciate that the term "multiple cloning site" (MCS) may be used interchangeable with the term "polylinker region" having all of the same meanings and qualities. The skilled artisan would appreciate that an MCS encompasses a DNA region within a recombinant nucleic acid molecule that contains multiple unique restriction enzyme cut sites. Recombinant nucleic acid molecules may in some embodiments may be comprised in a plasmid or expression vector. Inclusion of MCS is very useful in biotechnology, allowing for foreign DNA to be inserted into the recombinant nucleic acid, for example but not limited to an expression vector. In some embodiments, the foreign DNA comprises a target gene disclosed herein. This enables the expression vector to act as a vector to insert DNA into another cell, for example but not limited to, for use in targeted gene editing.

In some embodiments, a MCS is suitable for cloning a nucleic acid encoding a target gene within the recombinant nucleic acid molecule. In some embodiments, a MCS comprises a short segment of DNA which contains many (up to ~20) restriction sites. Restriction sites within an MCS are typically unique to the plasmid or expression vector within which a recombinant nucleic acid molecule would be comprised, occurring only once within the plasmid or expression vector. The nucleic acid sequences of MCS are well known to one of skilled in the art.

In some embodiments, disclosed herein is a recombinant nucleic acid molecule comprising: a first nucleic acid sequence of a first regulatory region; and a second nucleic acid sequence of a second regulatory region, wherein said first region is adjacent to the nucleic acid sequence encoding a UBQ10 extending about 2 Kb upstream but not including the start codon of the UBQ10, and wherein said second region is adjacent to the nucleic acid sequence encoding a UBQ10 extending about 1 Kb downstream from but not including the stop codon region of UBQ10, and wherein said first and second nucleic acid sequences are fused to a nucleic acid sequence of a target gene.

In some embodiments, disclosed herein is a recombinant nucleic acid molecule comprising: a first nucleic acid sequence of a first regulatory region; and a second nucleic acid sequence of a second regulatory region, wherein said first region comprises a nucleic acid sequence adjacent to the nucleic acid sequence encoding a UBQ10 extending about 2 Kb upstream but not including the start codon of the UBQ10, and wherein said second region comprises nucleic acid sequence adjacent to the nucleic acid sequence encoding a UBQ10 extending about 1 Kb downstream from but not including the stop codon region of UBQ10, and wherein said first and second nucleic acid sequences are operably linked to a nucleic acid sequence of a target gene.

In some embodiments, a first regulatory region comprises the nucleotide sequence directly 5' to the ATG start codon of a POLYUNBIQUITIN10 gene starting from the nucleotide 5' to the ATG. In some embodiments, a first regulatory region comprises a nucleotide sequence upstream of the ATG start codon of a POLYUNBIQUITIN10 gene. In some embodiments, a first regulatory region comprises the about 2 Kb nucleotide sequence upstream of the ATG start codon of a POLYUNBIQUITIN10 gene. In some embodiments, a first regulatory region comprises the about 2 Kb nucleotide sequence directly upstream of the ATG start codon of a POLYUNBIQUITIN10 gene, starting from the nucleotide 5' to the ATG.

The downstream region of the UBQ10 may include a 3' untranslated region (UTR), an intron, or a terminator region, or a combination thereof. A skilled artisan would appreciate that the terms "downstream" and "3 prime (3')" may in some embodiments be used interchangeably herein having all the same qualities and meanings.

In some embodiments, a second nucleic acid sequence of a second regulatory region comprises the following nucleic acid sequence:

(SEQ ID NO: 27)
gttgtggttgtctggttgcgtctgttgcccgttgtctgttgcccatt gtggtggttgtgtttgtatgatggtcgttaaggatcatcaatgtgtt ttcgctttttgttccattctgtttctcatttgtgaataataatggta tctttatgaatatgcagtttgtggtttctttttctgattgcagttctg agcattttgtttttgcttccgtttactataccacttacagtttgcac taatttagttgatatgcgagccatctgatgtttgatgattcaaatgg cgtttatgtaactcgtacccgattcatgggtgagagctccagcttga tcccttctctgtcgatcaaatttgaattttttggatcacggcaggctc acaagataatccaaagtaaaacataatgaatagtacttctcaatgat cacttatttttagcaaatcagcaattgtgcatgtcaaatgatttcgg tgtaagagaaagagttgatgaatcaaaatatctgtagctggatcaag aatctgaggcagttgtatgtatcaatgatctttccgctacaatgatg ttagctatccgagtcaaattgttgtagaattgcatacttcggcatca cattctggatgacataataaataggaagtcttcagatccctaaaaaa ttgagagctaataacattagtcctagatgtaactgggtgacaaccaa gaaagagacatgcaaatactacttttgtttgaaggagcatccctggt ttgacatatttttctgaatatcaaactttgaaactctacctagtct aatgtctaacgacagatcttactggtttaactgcagtgatatctact atcttttggaatgtttctccttcagttatacatcaagttccaagat gcaggtgtgcttgattgatgtacatggctgtgagaagtgcatcctga tgttcagatgatggttcattctaatgtcttttccttcaatcagtttt ctcagtctgacttagcttgtttcatctgcatgtttgaatgttcgttt actcatagtaattgcattttgtagcagaacatatcattggtcatgg tttcaactgtgcgcgagtcttatgcttattcaaactaggaaagcctc cgtctagagggtacacgagttgttgctctgtgtgcgtcagtccatag tattaatcttgctagttgtagtatattgtttatgtggactcggaatt catcatatgctccttctttgcatcaagtaaggcaaggtaatgtatag aagcttttaactctttcatggaagctggcctttgccagcataccat ccagaagatatcaaccctgcatcttggctgccg.

In some embodiments, a second nucleic acid sequence of a second regulatory region comprises the following nucleic acid sequence:

(SEQ ID NO: 28)
ttgcagttctgagcattttgttttttgcttccgtttactataccactt acagtttgcactaatttagttgatatgcgagccatctgatgtttgat gattcaaatggcgtttatgtaactcgtacccgagtggatggagaaga gctccattgccggtttgtttcatgggtggcggagggcaactcctggg aaggaacaaaagaaaaaccgtgatacgagttcatgggtgagagctcc -continued agcttgatcccttctctgtcgatcaaatttgaattttggatcacgg caggctcacaagataatccaaagtaaaacataatgaatagtacttct caatgatcacttattttttagcaaatcagcaattgtgcatgtcaaatg atttcggtgtaagagaaagagttgatgaatcaaaatatctgtagctg gatcaagaatctgaggcagttgtatgtatcaatgatctttccgctac aatgatgttagctatccgagtcaaattgttgtagaattgcatacttc ggcatcacattctggatgacataataaataggaagtcttcagatccc taaaaaattgagagctaataacattagtcctagatgtaactgggtga caaccaagaaagagacatgcaaatactactttgtttgaaggagcat ccctggtttgacatattttttctgaatatcaaactttgaaactctac ctagtctaatgtctaacgacagatcttactggtttaactgcagtgat atctactatcttttggaatgtttctccttcagttatacatcaagtt ccaagatgcaggtgtgcttgattgatgtacatggctgtgagaagtgc atcctgatgttcagatgatggttcattctaatgtctttttccttcaat cagtttctcagtctgacttagcttgtttcatctgcatgtttgaatg ttcgtttactcatagtaattgcatttttgtagcagaacatatcattg gtcatggtttcaactgtgcgcgagtcttatgcttattcaaactagga aagcctccgtctagagggtacacgagttgttgctctgtgtgcgtcag tccatagtattaatcttgctagttgtagtatattgtttatgtggact cggaattcatcatatgctccttctttgcatcaagtaaggcaaggtaa tgtatagaagctttttaactctttcatggaagctggcctttgccagc ataccatccagaagatatcaaccctgcatcttggctgccg.

In some embodiments, a second nucleic acid sequence of a second regulatory region comprises the following nucleic acid sequence:

```
                                    (SEQ ID NO: 29)
gttgtggttgtctggttgcgtctgttgcccgttgtctgttgcccat tgtggtggttgtgtttgtatgatggtcgttaaggatcatcaatgtg ttttcgcttttgttccattctgtttctcatttgtgaataataatg gtatctttatgaatatgcagtttgtggtttcttttctga.
```

In some embodiments, a second nucleic acid sequence of a second regulatory region comprises the following nucleic acid sequence.

```
                                    (SEQ ID NO: 38)
gttgcctgttgttggttgtcgtgttgtctggctgtgtctgttgccc attgtggtggttatgtgtttgcattatggtcttaaaggatcatcaa tgtgttttcgcttctgttcctttctgtttctcatttgtgaataat aatggcgtctttatgaacatccaatttctggtttcttttctgatcg cagtttgagtatttgtttttgcttttgcctccgtctattacaccac tttgcaattactataatatactaaaagccttcgatccatcttctgt ttgatgattcgaatggtatttatttaactcatacccaagtgaagca taaagttagaggagagttcctgttccattgcctgtttgtatcatga
```

-continued gcaactcatgttaataaacataagaaaaaccatgatgcaatctgtg tagctgatagactttgatgacagacgactcataagtaacaagagat aacaaagaggaaacataataaacatgtacgggaagtcctccaacaa tgactataatcacatgtttttgtagattagcaattgtacatgtcaa atgatcttggattaaggaaggagcttgtgaatcaaaacatctgaat ttggacctagagtcttgaggtgatcgtactttggatggagagacca tgaataagaataaatgaatctggaactgagaactaaatggaagaca cactgatccaacagattaagcttatgacattaatcacagaaggtaa ctcggtgacaaccaagaacggggagctgcaaattctattgtcttaa caacggacctttactggtttaactgttatgatgtctttttataggtg gcttttgggttgttcttcgctctatccttttatgtaactttcaaga accaaccaaatgcaggtgttctagatagatatacgtggcatgtgag aagggaccctgaagttcagatgacggt.

In some embodiments, a second nucleic acid sequence of a second regulatory region comprises the following nucleic acid sequence:

```
                                    (SEQ ID NO: 39)
gttgcctgttgttggttgtcgtgttgtctggctgtgtctgttgcccatt gtggtggttatgtgtttgcattatggtcttaaaggatcatcaatgtgtt ttcgctttctgttcctttctgtttctcatttgtgaataataatggcgtc tttatgaacatccaatttctggtttctttt.
```

In some embodiments, a second nucleic acid sequence of a second regulatory region comprises the following nucleic acid sequence:

```
                                    (SEQ ID NO: 45)
atctcgtctctgttatgcttaagaagttcaatgtttcgtttcatgta aaactttggtggtttgtgtttggggccttgtataatccctgatgaa taagtgttctactatgtttccgttcctgttatctctttctttctaat gacaagtcgaacttcttctttatcatcgcttcgttttttattatctgt gcttcttttgtttaatacgcctgcaaagtgactcgactctgtttagt gcagttctgcgaaacttgtaaatagtccaattgttggcctctagtaa tagatgtagcgaaagtgttgagctgttgggttctaaggatggcttga acatgttaatcttttaggttctgagtatgatgaacattcgttgttgc taagaaatgcctgtaatgtcccacaaatgtagaaaatggttcgtacc tttgtccaagcattgatatgtctgatgagaggaaactgcaagatact gagcttggtttaacgaaggagaggcagtttcttccttccaaagcatt tcatttgacaatgccttgatcatcttaagtagagtttctgttgtgga aagtttgaaactttgaagaaacgactctcaagtaaattgatgatcac aagtgaaagtgtatgttacataagtggatatttcacccttttttccat
```

-continued

```
caatcaaaacatcatatagtaatccattggtttatacaaacatcaaa atacatttacctctgaaatgaggaaaaaaatgcaaagagatttttga aaatttccaacaaatg.
```

In some embodiments, a second nucleic acid sequence of a second regulatory region comprises the following nucleic acid sequence:

```
                                          (SEQ ID NO: 46)
atctcgtctctgttatgcttaagaagttcaatgtttcgtttcatgt aaaactttggtggtttgtgttttggggccttgtataatccctgatg aataagtgttctactatgtttccgttcctgttatctctttctttct aatgacaagtcgaacttcttctttatcatcgcttcgttttttattat ctgtgcttcttttgtttaatacgcctgcaaagtgactcgactctgt ttagtgcagttctgcgaaacttgtaaatagtccaattgttggcctc tagtaatagatgtagcgaaagtgttgagctgttgggttctaaggat ggcttgaacatgttaatctttaggttctgagtatgatgaacattc gttgttgc.
```

In some embodiments, a second nucleic acid sequence of a second regulatory region comprises a homolog of any one of SEQ ID NOs: 27, 28, 29, 38, 39, 45, or 46. In one embodiment, a second nucleic acid sequence of a second regulatory region is at least 70% homologous to any one of SEQ ID NOs: 27, 28, 29, 38, 39, 45, or 46. In another embodiment, a second nucleic acid sequence of a second regulatory region is at least 80% homologous to any one of SEQ ID NOs: 27, 28, 29, 38, 39, 45, or 46. In another embodiment, a second nucleic acid sequence of a second regulatory region is at least 90% homologous to any one of SEQ ID NOs: 27, 28, 29, 38, 39, 45, or 46. In another embodiment, a second nucleic acid sequence of a second regulatory region is at least 95% homologous to any one of SEQ ID NOs: 27, 28, 29, 38, 39, 45, or 46. In another embodiment, a second nucleic acid sequence of a second regulatory region is at least 98% homologous to any one of SEQ ID NOs: 27, 28, 29, 38, 39, 45, or 46. In another embodiment, a second nucleic acid sequence of a second regulatory region is at least 99% homologous to any one of SEQ ID NOs: 27, 28, 29, 38, 39, 45, or 46.

In some embodiments, a second nucleic acid sequence of a second regulatory region comprises a combination of any one of SEQ ID NOs: 27, 28, 29, 38, 39, 45, or 46.

In some embodiments, a nucleic acid sequence comprising a second nucleic acid sequence of a second regulatory region comprises a contiguous portion of a chromosome. In some embodiments, a nucleic acid sequence comprising a second nucleic acid sequence of a second regulatory region comprises a non-contiguous portion of a chromosome.

In some embodiments, a second regulatory region comprises the nucleotide sequence directly 3' to the stop codon of a POLYUNBIQUITIN10 gene starting from the nucleotide 3' to the stop codon. In some embodiments, a second regulatory region comprises a nucleotide sequence downstream of the stop codon of a POLYUNBIQUITIN10 gene. In some embodiments, a second regulatory region comprises the about 1 Kb nucleotide sequence downstream of the stop codon of a POLYUNBIQUITIN10 gene. In some embodiments, a second regulatory region comprises the about 1 Kb nucleotide sequence directly downstream of the stop codon of a POLYUNBIQUITIN10 gene, starting from the nucleotide 3' to the stop codon.

In some embodiments, a first nucleic acid sequence of a first regulatory region and a second nucleic acid from a second regulatory region comprises upstream and downstream nucleotide sequences of the same POLYUNBIQUITIN10 gene. In some embodiments, a first nucleic acid sequence of a first regulatory region and a second nucleic acid from a second regulatory region comprises upstream and downstream nucleotide sequences of different POLYUNBIQUITIN10 genes.

In some embodiments, a recombinant nucleic acid molecule comprises a first nucleic acid sequence of a first regulatory region and a second nucleic acid sequence from a second regulatory region of the same POLYUNBIQUITIN10 gene, wherein the first and second nucleic acid sequences are operably linked to a nucleic acid sequence of a target gene, wherein the first nucleic acid sequence is 5' of the target gene and the second nucleic acid sequence is 3' of the target gene. In some embodiments, a recombinant nucleic acid molecule comprises a first nucleic acid sequence of a first regulatory region and a second nucleic acid from a second regulatory region of different POLYUNBIQUITIN10 genes operably linked to a nucleic acid sequence of a target gene wherein the first nucleic acid sequence is operably linked 5' of the target gene and the second nucleic acid sequence is operably linked 3' of the target gene.

In some embodiments, a first nucleic acid sequence of a first regulatory region and a second nucleic acid from a second regulatory region of a POLYUNBIQUITIN10 gene, comprise a promoter-terminator cassette, wherein the first nucleic acid sequence of a first regulatory region comprises a promoter and the second nucleic acid from a second regulatory region comprises a terminator region, and a gene of interest may be inserted between the promoter and terminator regions.

In some embodiments, a recombinant nucleic acid molecule comprises a first nucleic acid sequence of a first regulatory region comprising the nucleic acid sequence of any one of SEQ ID NO: 23, 24, 25, 26, 34, 35, 36, 37, 41, 41, 43, 44, 48, or 49, or a homolog thereof, and a second nucleic acid from a second regulatory region comprising the nuclide acid sequence of any one of SEQ ID NO: 27, 28, 29, 38, 39, 45, or 46, or a homolog thereof wherein the first nucleic acid sequence is operably linked 5' of the target gene and the second nucleic acid sequence is operably linked 3' of the target gene. In some embodiments, a recombinant nucleic acid molecule comprises a first nucleic acid sequence of a first regulatory region comprising the nucleic acid sequence set forth in SEQ ID NO: 23, or a homolog thereof, and a second nucleic acid from a second regulatory region comprising the nuclide acid sequence set forth in SEQ ID NO: 27, or a homolog thereof, wherein SEQ ID NO: 23 is operably linked 5' of the target gene and SEQ ID NO: 27 is operably linked 3' of the target gene.

In some embodiments, a target gene is operably linked to a first nucleic acid sequence of a first regulatory region without any intervening sequences. Examples include but are not limited to, the ATG start codon of a target gene being directly fused to the 3' nucleotide of any one of SEQ ID NO: 23, 24, 25, 26, 34, 35, 36, 37, 41, 41, 43, 44, 48, or 49, or a homolog thereof. In some embodiments, the ATG start codon of a target gene is directly fused to the 3' nucleotide of SEQ ID NO. 23.

In some embodiments, a target gene is operably linked to a first nucleic acid sequence of a first regulatory region, wherein intervening nucleotides are present between the ATG start codon of the target gene and the 3' nucleotide of the first nucleic acid sequence of a first regulatory region. Examples include, but are not limited to, the ATG start codon of a target gene being operably linked to the 3' nucleotide of any one of SEQ ID NO: 23, 24, 25, 26, 34, 35, 36, 37, 41, 41, 43, 44, 48, or 49, or a homolog thereof, wherein intervening nucleotides are present between the ATG start codon of the target gene and the 3' nucleotide of the first nucleic acid sequence of a first regulatory region. In some embodiments, the ATG start codon of a target gene is operably linked to the 3' nucleotide of SEQ ID NO: 23, wherein intervening nucleotides are present between the ATG start codon of the target gene and the 3' nucleotide of SEQ ID NO: 23.

In some embodiments, a target gene is operably linked to a second nucleic acid sequence of a second regulatory region without any intervening sequences. Examples include but are not limited to, the stop codon of a target gene being directly fused to the 5' nucleotide of any one of SEQ ID NO: 27, 28, 29, 38, 39, 45, or 46, or a homolog thereof. In some embodiments, the stop codon of a target gene is directly fused to the 5' nucleotide of SEQ ID NO: 27.

In some embodiments, a target gene is operably linked to a second nucleic acid sequence of a second regulatory region, wherein intervening nucleotides are present between the stop codon of the target gene and the 5' nucleotide of the second nucleic acid sequence of a second regulatory region. Examples include, but are not limited to, the stop codon of a target gene being operably linked to the 5' nucleotide of any one of SEQ ID NO: 27, 28, 29, 38, 39, 45, or 46, or a homolog thereof, wherein intervening nucleotides are present between the stop codon of the target gene and the 5' nucleotide of the second nucleic acid sequence of a second regulatory region. In some embodiments, the stop codon of a target gene is operably linked to the 5' nucleotide of SEQ ID NO: 27, wherein intervening nucleotides are present between the stop codon of the target gene and the 5' nucleotide of SEQ ID NO: 27.

In some embodiments, a stop codon comprises a TAA, TAG, or TGA codon.

In some embodiments, a recombinant nucleic acid molecule disclosed herein comprises: a first nucleic acid sequence of a first regulatory region; and a second nucleic acid sequence of a second regulatory region, wherein said first region comprises a nucleic acid sequence adjacent to the nucleic acid sequence encoding a UBQ10 extending about 2 Kb upstream but not including the start codon of the UBQ10, and wherein said second region comprises nucleic acid sequence adjacent to the nucleic acid sequence encoding a UBQ10 extending about 1 Kb downstream from but not including the stop codon region of UBQ10, and wherein said first and second nucleic acid sequences are operably linked to a nucleic acid sequence of a target gene, wherein the first nucleic acid sequence is 5' of the target gene and the second nucleic acid sequence is 3' of the target gene.

In some embodiments, a recombinant nucleic acid molecule disclosed herein comprises: a first nucleic acid sequence of a first regulatory region; and a second nucleic acid sequence of a second regulatory region, wherein said first region comprises a nucleic acid sequence adjacent to the nucleic acid sequence encoding a UBQ10 extending about 2 Kb upstream but not including the start codon of the UBQ10, and wherein said second region comprises nucleic acid sequence adjacent to the nucleic acid sequence encoding a UBQ10 extending about 1 Kb downstream from but not including the stop codon region of UBQ10, and wherein said first and second nucleic acid sequences are operably linked to a nucleic acid sequence of a multiple cloning site (MCS), wherein the first nucleic acid sequence is 5' of the MCS and the second nucleic acid sequence is 3' of the MCS.

One of skilled in the art is well aware of the genetic elements that need to be present on the vector in order to successfully transform, select and propagate host cells containing the sequence of interest, for example a target gene. The sequence of interest can be operably linked to one or more promoter sequences a vector.

In some embodiments, an expression vector comprises a recombinant nucleic acid molecule as described herein. In certain embodiments, a recombinant nucleic acid molecule described herein forms part of an expression vector comprising all necessary elements for expression of the target gene. In certain embodiments, a recombinant nucleic acid molecule described herein forms part of an expression vector comprising all necessary elements for expression of a target gene that could be inserted in the MCS. In some embodiments, a library comprises a recombinant nucleic acid molecule as described herein.

Constructs and vectors may also include a transit peptide for targeting of a gene to a plant organelle, for example, to a chloroplast, leucoplast or other plastid organelle. The expression cassettes or the construct disclosed herein may be included in a host cell, plant cell, seed, agricultural product or plant.

In some embodiments, disclosed herein is a recombinant nucleic acid molecule comprising a first nucleotide sequence encoding a gene of interest, wherein said gene of interest is operably linked to a regulatory sequence of the genes encoding chlorophyll a/b binding protein (CAB), chlorophyll a/b binding protein 1 (CAB1), or a combination thereof.

Expression of a Nuclease System Operably Linked to a Ubiquitin Promoter

In some embodiments, a target gene comprises any gene to be expressed. In some embodiments, the target gene encodes a nuclease, a nickase, a ZFN system, a TALEN system, a meganuclease, or a CRISPR/Cas nuclease used in targeted gene editing or a homolog thereof.

In some embodiments, the target gene encodes a CRISPR associated protein 9 (CAS9) or a homolog thereof. In some embodiments, the target gene is a wild-type CAS9, or a homolog thereof. In some embodiments, the target gene is a mutant CAS9 or a homolog thereof. Numerous mutations modulating CAS9 function are known in the art. In a one exemplary embodiment, the target gene is CAS9 comprising a mutation in RuvC domain, for example CAS9-D10A. In another exemplary embodiment, the target gene is CAS9 comprising a mutation in HNH domain, for example CAS9-H840A. The nucleic acid and amino acid sequences of wild-type CAS9 and of numerous CAS9 mutants are well known in the art and publicly available in genetic sequence databases.

In some embodiments, a target gene described herein comprise homologs, analogs, or orthologs thereof. In some embodiments, target genes comprise functional fragments, functional variants, or functional derivatives encoding functional fragments, functional variants, or functional derivatives of a nickase, or a CRISPR-associated endonuclease (CAS nuclease), or a DNA endonuclease enzyme used in targeted gene editing.

In some embodiments, target genes are 30%, 40%, 50%, 60%, 70%, 75%, 80%, 85%, 90%, 95%, 98%, 99%, or 100% identical to the sequences of the genes known in the art. In one embodiment, a target gene comprises sequences that are complementary to the sequences of the genes encoding a nickase, or a CRISPR-associated endonuclease (CAS nuclease), or a DNA endonuclease enzyme used in targeted gene editing known in the art. In another embodiment, target genes comprise sequences of the genes encoding a nickase, or a CRISPR-associated endonuclease (CAS nuclease), or a DNA endonuclease enzyme used in targeted gene editing that hybridize, for example, under stringent conditions, to the sequences of the genes known in the art.

In some embodiments, use of a recombinant nucleic acid molecule comprising a UBQ10 regulatory sequence, increases the content of a nuclease, a nickase, a ZFN system, a TALEN system, a meganuclease, or a CRISPR/Cas nuclease used in targeted gene editing used in targeted gene editing by about 15-1000 fold compared with a corresponding nucleic acid molecule not comprising an UBQ10 regulatory sequence. In some embodiments, use of a recombinant nucleic acid molecule comprising a UBQ10 regulatory sequence, increases the content of a nuclease, a nickase, a ZFN system, a TALEN system, a meganuclease, or a CRISPR/Cas nuclease used in targeted gene editing used in targeted gene editing by about 15-750 fold compared with a corresponding nucleic acid molecule not comprising an UBQ10 regulatory sequence. In some embodiments, use of a recombinant nucleic acid molecule comprising a UBQ10 regulatory sequence, increases the content of a nuclease, a nickase, a ZFN system, a TALEN system, a meganuclease, or a CRISPR/Cas nuclease used in targeted gene editing used in targeted gene editing by about 15-500 fold compared with a corresponding nucleic acid molecule not comprising an UBQ10 regulatory sequence.

In some embodiments, use of a recombinant nucleic acid molecule comprising a a UBQ10 regulatory sequence, increases the content of a nuclease, a nickase, a ZFN system, a TALEN system, a meganuclease, or a CRISPR/Cas nuclease used in targeted gene editing used in targeted gene editing by about 15-250 fold compared with a corresponding nucleic acid molecule not comprising an UBQ10 regulatory sequence. In some embodiments, use of a recombinant nucleic acid molecule comprising a UBQ10 regulatory sequence, increases the content of a nuclease, a nickase, a ZFN system, a TALEN system, a meganuclease, or a CRISPR/Cas nuclease used in targeted gene editing used in targeted gene editing by about 50-200 fold compared with a corresponding nucleic acid molecule not comprising an UBQ10 regulatory sequence.

In some embodiments, use of a recombinant nucleic acid molecule comprising a UBQ10 regulatory sequence, increases the content of a nuclease, a nickase, a ZFN system, a TALEN system, a meganuclease, or a CRISPR/Cas nuclease used in targeted gene editing used in targeted gene editing by about 100-250 fold compared with a corresponding nucleic acid molecule not comprising an UBQ10 regulatory sequence. In some embodiments, use of a recombinant nucleic acid molecule comprising a UBQ10 regulatory sequence, increases the content of a nuclease, a nickase, a ZFN system, a TALEN system, a meganuclease, or a CRISPR/Cas nuclease used in targeted gene editing used in targeted gene editing by about 100-400 fold compared with a corresponding nucleic acid molecule not comprising an UBQ10 regulatory sequence.

In some embodiments, use of a recombinant nucleic acid molecule comprising a UBQ10 regulatory sequence, increases the content of a nuclease, a nickase, a ZFN system, a TALEN system, a meganuclease, or a CRISPR/Cas nuclease used in targeted gene editing used in targeted gene editing by about 250-500 fold compared with a corresponding nucleic acid molecule not comprising an UBQ10 regulatory sequence.

In some embodiments, use of a recombinant nucleic acid molecule comprising a UBQ10 regulatory sequence, increases the content of a nuclease, a nickase, a ZFN system, a TALEN system, a meganuclease, or a CRISPR/Cas nuclease used in targeted gene editing used in targeted gene editing by about 250-750 fold compared with a corresponding nucleic acid molecule not comprising an UBQ10 regulatory sequence. In some embodiments, use of a recombinant nucleic acid molecule comprising a UBQ10 regulatory sequence, increases the content of a nuclease, a nickase, a ZFN system, a TALEN system, a meganuclease, or a CRISPR/Cas nuclease used in targeted gene editing by about 100 fold compared with a corresponding nucleic acid molecule not comprising an UBQ10 regulatory sequence.

In some embodiments, use of a recombinant nucleic acid molecule comprising a UBQ10 regulatory sequence, increases the content of a nuclease, a nickase, a ZFN system, a TALEN system, a meganuclease, or a CRISPR/Cas nuclease used in targeted gene editing used in targeted gene editing in at least 200, 300, 400, 500, 600, 700, 800, 900, or 1,000 fold compared with a corresponding nucleic acid molecule not comprising an UBQ10 regulatory sequence.

In some embodiments, use of a recombinant nucleic acid molecule disclosed herein, increases target mutagenesis by 100% compared with a corresponding nucleic acid molecule not comprising an UBQ10 regulatory sequence.

In some embodiments, a target gene comprises a guiding RNA (gRNA). In some embodiments a target gene comprises a gRNA and a nuclease.

Recombinant Nucleic Acid Molecules

Specifically, disclosed herein is a recombinant nucleic acid molecule comprising a first nucleotide sequence encoding a target gene, wherein said target gene is operably linked to a UBQ10 regulatory sequence. In some embodiments, said target gene comprises a nuclease system gene, or a part thereof.

In some embodiments, disclosed herein is a recombinant nucleic acid molecule comprising a first nucleotide sequence encoding a nuclease system, wherein said nuclease system is targeted to a plant endogenous DNA sequence, and wherein at least one component of said nuclease system is operably linked to a UBQ10 regulatory sequence. In some embodiments, the nucleic acid molecule further comprises a second nucleotide sequence encoding a viral replicon comprising a donor nucleic acid sequence targeted to a plant endogenous DNA sequence.

Some of the embodiments of the replicon and its components are detailed above in "Methods of Gene targeting Section" and are incorporated herein by reference. In some embodiments, a replication initiator protein (Rep) of the replicon is operably linked to a promoter. In some embodiments, said promoter is a constitutive promoter. In some embodiments, said promoter is a tissue-specific promoter, which restricts Rep expression to any tissue of interest. In some embodiments, said promoter comprises a CAMV 35S promoter.

In some embodiments, a donor nucleic acid sequence is located between the LIRs. In some embodiments, a nucleic acid encoding a nuclease system is between the LIRs. In some embodiments, a nucleic acid encoding a guiding RNA (gRNA) is between the LIRs. In some embodiments, a donor nucleic acid sequence, a nucleic acid encoding a nuclease system, and a nucleic acid encoding a gRNA are located between the LIRs. In some embodiments, a donor nucleic acid sequence and a nucleic acid encoding a nuclease system are located between the LIRs. In some embodiments, a donor nucleic acid sequence and a nucleic acid encoding a gRNA are located between the LIRs. In some embodiments, a nucleic acid encoding a nuclease system and a nucleic acid encoding a gRNA are located between the LIRs.

In some embodiments, a donor nucleic acid sequence is operably linked to a UBQ10 regulatory sequence. In some embodiments, a nucleic acid encoding a nuclease system is operably linked to a UBQ10 regulatory sequence. In some embodiments, a nucleic acid encoding a gRNA is operably linked to a UBQ10 regulatory sequence.

In some embodiments, a replicon, a donor nucleic acid sequence, a nucleic acid encoding a nuclease system, and a nucleic acid encoding a gRNA are all located in a same recombinant nucleic acid molecule or expression vector. A skilled artisan would appreciate, however, that all these elements should not be necessarily located in a same nucleic acid molecule or expression vector. In some embodiments, a donor nucleic acid sequence is located in a second nucleic acid molecule or expression vector. In some embodiments, a nucleic acid encoding a nuclease system is located in a second nucleic acid molecule or expression vector. In some embodiments, a nucleic acid encoding a gRNA is located in a second recombinant nucleic acid molecule or expression vector. In some embodiments, these elements are located in 3 separate recombinant nucleic acid molecules or expression vector.

In some embodiments, a nucleic acid encoding a selection marker is further included in the expression vector. A number of selection markers are known in the literature, and a skilled artisan would appreciate how to incorporate them in the vectors described here. In some embodiments, a selection marker comprises neomycin phosphotransferase II (NPTII), which confers resistance to kanamycin, neomycin, geneticin (G418), and paromomycin.

A skilled artisan would appreciate that the terms "nucleic acid sequence" and "nucleotide sequence" may be used interchangeably having all the same qualities and meanings. A skilled artisan would appreciate that the terms "expression vector", "expression construct", "recombinant nucleic acid" are, in some embodiments, used interchangeably having all the same qualities and meanings. In one embodiment, a "genomic polynucleotide sequence" refers to a sequence derived (isolated) from a chromosome and thus it represents a contiguous portion of a chromosome.

In one embodiment, a "composite polynucleotide sequence" refers to a sequence, which is comprised of difference nucleotide sequences that represent non-contiguous portions of a chromosome. In one embodiment, a composite sequence can include nucleic acid sequences from multiple sources. In one embodiment, a composite sequence can include nucleic acid sequences from multiple genes. In one embodiment, a composite sequence can include nucleic acid sequences from a single gene, wherein the sequence does not represent a contiguous portion of a chromosome.

In some embodiments, the methods for gene targeting disclosed herein comprise the use of any of the recombinant nucleic acid molecules described in this section.

Genetically Modified Plants

In some embodiments, a genetically modified plant described herein comprises at least one cell comprising a recombinant nucleic acid molecule as disclosed herein.

A genetically modified plant comprising at least one cell comprising a recombinant nucleic acid molecule as disclosed herein, may in some embodiments first be selected based on the expression of the target gene or protein encoded by the target gene. In some embodiments, a genetically modified plant comprising at least one cell comprising a recombinant nucleic acid molecule disclosed herein, may in some embodiments first be selected based on an increased content of a nuclease, a nickase, a ZFN system, a TALEN system, a meganuclease, or a CRISPR/Cas nuclease used in targeted gene editing or a homolog thereof. In some embodiments, a genetically modified plant comprising at least one cell comprising a recombinant nucleic acid molecule disclosed herein, may in some embodiments first be selected based on an increased mutagenesis activity compared with an unmodified plant. In some embodiments, a genetically modified plant comprising at least one cell comprising a recombinant nucleic acid molecule disclosed herein, may in some embodiments first be selected based on an increased gene targeting activity compared with an unmodified plant.

In some embodiments, a genetically modified plant is a *Solanaceous* crop plant. In some embodiments, a Solanaceae crop plant is selected from the group comprising a cultivated tomato plant, a wild-tomato plant, a cultivated potato plant, a wild-potato plant, an aubergine plant, a chili pepper plant, and a bell pepper plant. In some embodiments, the expression of a target gene is increased compared to its expression in a corresponding unmodified plant.

In some embodiments, an expression vector is operably linked to an additional promoter sequence so that the expression of the targeting molecule can be controlled under different conditions. In another embodiment, the targeting gene is operably linked to a constitutive promoter. In another embodiment, the targeting gene is operably linked to an inducible promoter. In another embodiment, the targeting gene is operably linked to a tissue active or specific promoter. In another embodiment, the targeting gene is operably linked to a developmental-stage active or specific promoter. When the targeting gene is linked to a constitutive promoter, changes in expression of a gene will be observed in all tissues and at all times and a broad overview of the effects of the expression of the gene on a plant will be observed. When the targeting gene is linked to a tissue specific promoter or an inducible promoter or developmental-stage promoter, the expression of the targeting gene may be turned on or off in a particular tissue such as seed, roots, flowers, leaves, shoots, fruits or stems, during a particular period in development, such as early, middle or late stages in development, or under particular conditions, such as specific environmental or disease stresses.

A skilled artisan would appreciate that early stages of plant development may encompass the time before flowering, which would encompass the time after moving from the tissue culture to soil (in a laboratory situation). A skilled artisan would appreciate that late stage, also referred to as "an older stage" or "older plant", of plant development may encompass a time after early stage. Plant development may also be described wherein a first stage may encompass seed germination, a second stage may encompass a vegetative growth stage, a third stage may encompass a reproductive stage wherein flowers and fruit are produced.

In some embodiments, a plant may be transformed with more than one expression vector. In some embodiments, an additional expression vector comprises nucleic acid sequence encoding a guide RNA molecule. In some embodiments, an additional expression vector comprises nucleic acid sequence encoding other elements of a targeted gene editing system.

In some embodiments, the genetically modified plant comprises increased gene targeting activity compared to a corresponding unmodified plant.

In some embodiments, a cell comprises a recombinant nucleic acid molecule as described herein. In some embodiments, the cell is a plant cell. In some embodiments, the plant cell is a Solanaceae plant cell. In some embodiments, the plant cell is a Solanaceae crop plant cell. In some embodiments, a Solanaceae crop plant comprises cultivated tomato plant, a wild-tomato plant, a cultivated potato plant, a wild-potato plant, an aubergine plant, a chili pepper plant, and a bell pepper plant. In some embodiments, the cell is an algae cell.

Methods for Generating a Genetically Modified Plant

In some embodiments, disclosed herein is a method for producing a transgenic plant seed, the method comprising: (a) introducing into at least one cell of a plant a first nucleic acid comprising a viral replicon comprising a donor nucleic acid sequence, said donor sequence targeted to a plant endogenous DNA sequence; and (b) introducing into the cell of (a) a nucleic acid comprising a nuclease system, wherein said nuclease system is targeted to said plant endogenous DNA sequence, and wherein at least one component of said nuclease system is expressed under a UBQ10 regulatory sequence; (c) generating a transgenic plant from said at least one cell; and (d) growing said transgenic plant to obtain a seed.

In some embodiments, methods for generating a transgenic plant or alga, comprise transforming a plant or algae cell with a nucleic acid molecule disclosed herein or an expression vector comprising a nucleic acid molecule disclosed herein. The transfer of foreign genes into the genome of a plant or algae is called transformation. Methods for transforming a plant cell with nucleic acids sequences are well known in the art, as are methods of transforming algae.

Transformation of plant or algae species is now a fairly routine technique. As used herein the term "transformation" or "transforming" may encompass in some embodiments, a process by which a foreign DNA, such as a recombinant nucleic acid molecule disclosed herein, or an expression vector comprising a recombinant nucleic acid molecule disclosed herein, enters and changes a recipient cell into a transformed, genetically modified or transgenic cell. Transformation may be stable, wherein the nucleic acid sequence is integrated into the plant genome and as such represents a stable and inherited trait, or transient, wherein the nucleic acid sequence is expressed by the cell transformed but is not integrated into the genome, and as such represents a transient trait. In some embodiments, the recombinant nucleic acid molecule disclosed herein is stably transformed into a plant cell.

A transgenic plant is then grown under conditions suitable for the expression of the target gene. The regeneration, development and cultivation of plants from single plant protoplast transformants or from various transformed explants is well known in the art (See Weissbach and Weissbach, In.: Methods for Plant Molecular Biology, (Eds.), 1988 Academic Press, Inc., San Diego, Calif.). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

Markers or other techniques, known to one of skilled in the art, can be used to determine whether the transgenic molecule is stably integrated into the genome of said plant.

The regenerated plants containing the foreign, exogenous gene that encodes a target gene or a homolog thereof, can then be further propagated as is well known in the art. The particular method of propagation will depend on the starting plant tissue and the particular plant species to be propagated.

In some embodiments, the generated transformed plants are clonally propagated. In some embodiments, the generated transformed plants are propagated by classical breeding techniques. In some embodiments, the regenerated plants are self-pollinated to provide homozygous transgenic plants. Otherwise, pollen obtained from the regenerated plants is crossed to seed-grown plants of agronomically important lines, or pollen from plants of these important lines is used to pollinate regenerated plants. A transgenic plant containing a desired target gene may then be cultivated using methods well known to one of skill in the art.

In some embodiments, transgenic plants can be observed or tested for whether the transgenic molecule is effective in inducing floral fate or its associated phenotypic trait in the transgenic plants.

Throughout this application a plant, plant part, seed or plant cell transformed with, or transformed by, a construct or a nucleic acid is to be understood as meaning a plant, plant part, seed or plant cell that carries said construct or said nucleic acid as a transgene due the result of an introduction of said construct or said nucleic acid by biotechnological means. The plant, plant part, seed or plant cell therefore comprises said recombinant construct or said recombinant nucleic acid. Any plant, plant part, seed or plant cell that no longer contains said recombinant construct or said recombinant nucleic acid after introduction in the past, is termed null-segregant, nullizygote or null control, but is not considered a plant, plant part, seed or plant cell transformed with said construct or with said nucleic acid within the meaning of this application.

In some embodiments, methods disclosed herein are for producing a transgenic seed that can be used to produce a crop of transgenic plants with an enhanced trait resulting from expression of a stably-integrated recombinant DNA construct. In some embodiments, an enhanced trait is selected from the group comprising increased expression of a target gene; increased content of a nuclease, a nickase, a ZFN system, a TALEN system, a meganuclease, or a CRISPR/Cas nuclease used in targeted gene editing or a homolog thereof; increased mutagenesis; increased gene targeting; or any combination thereof.

In some embodiments, provided herein is a method for generating a transgenic plant, the method comprising: transforming a cell of the plant substantially the same genetic background with at least one nucleic acid molecule to obtain a recombinant plant cell; and generating a transgenic plant from said recombinant plant cell, wherein said nucleic acid molecule comprises: (a) donor nucleic acid sequence, said donor sequence targeted to a plant endogenous DNA sequence; and/or (b) a nuclease system, wherein said nuclease system is targeted to said plant endogenous DNA sequence, and wherein at least one component of said nuclease system is expressed under a UBQ10 regulatory sequence.

In some embodiment, the method further comprises steps of determining whether the transgenic molecule is stably integrated into the genome of said plant; and determining whether the transgenic molecule is effective in gene targeting in said transgenic plant. In some embodiments, provided herein is a method for producing a seed of a plant, the method comprising: transforming a cell of the plant of substantially the same genetic background with a nucleic acid molecule to obtain a recombinant plant cell; generating a transgenic plant from said recombinant plant cell; and growing said plant to obtain a seed, thereby producing said seed of said plant, wherein said nucleic acid molecule is the recombinant molecule disclosed herein.

In some embodiments, provided herein is a method for generating a transgenic plant, the method comprising: transforming a cell of the plant with a nucleic acid molecule to obtain a recombinant plant cell; and generating a transgenic plant from said recombinant plant cell, wherein said nucleic acid molecule comprises: (a) donor nucleic acid sequence, said donor sequence targeted to a plant endogenous DNA sequence; and (b) a nuclease system targeted to said plant endogenous DNA sequence, and wherein at least one component of said nuclease system is expressed under a UBQ10 regulatory sequence.

In some embodiment, the method further comprises steps of determining whether the transgenic molecules are stably integrated into the genome of said plant; and determining whether the transgenic molecules are effective in gene targeting in said transgenic plant. In some embodiments, provided herein is a method for producing a seed of a plant, the method comprising: transforming a cell of the plant of not substantially the same genetic background with a nucleic acid molecule to obtain a recombinant plant cell; generating a transgenic plant from said recombinant plant cell; and growing said plant to obtain a seed, thereby producing said seed of said plant, wherein said nucleic acid molecule is the recombinant molecule disclosed herein.

In some embodiments, provided herein is a transgenic plant comprising recombinant nucleic acid molecule comprising: a first nucleic acid sequence of a first regulatory region; and a second nucleic acid sequence of a second regulatory region, wherein said first region comprises a nucleic acid sequence adjacent to the nucleic acid sequence encoding a UBQ10 extending about 2 Kb upstream but not including the start codon of the UBQ10, and wherein said second region comprises nucleic acid sequence adjacent to the nucleic acid sequence encoding a UBQ10 extending about 1 Kb downstream from but not including the stop codon region of UBQ10, and wherein said first and second nucleic acid sequences are operably linked to a nucleic acid sequence of a target gene, wherein the first nucleic acid sequence is 5' of the target gene and the second nucleic acid sequence is 3' of the target gene.

In some embodiments, said target gene comprises: (a) donor nucleic acid sequence, said donor sequence targeted to a plant endogenous DNA sequence; and (b) a nuclease system targeted to said plant endogenous DNA sequence, and wherein at least one component of said nuclease system is expressed under a UBQ10 regulatory sequence.

In some embodiments, provided herein is a transgenic plant comprising recombinant nucleic acid molecule comprising: a first nucleic acid sequence of a first regulatory region; and a second nucleic acid sequence of a second regulatory region, wherein said first region comprises a nucleic acid sequence adjacent to the nucleic acid sequence encoding a UBQ10 extending about 2 Kb upstream but not including the start codon of the UBQ10, and wherein said second region comprises nucleic acid sequence adjacent to the nucleic acid sequence encoding a UBQ10 extending about 1 Kb downstream from but not including the stop codon region of UBQ10, and wherein said first and second nucleic acid sequences are operably linked to a target gene and the second nucleic acid sequence is 3' of said target gene.

The recombinant nucleic acid molecules described herein are not limited to manipulating coding regions. In some embodiments, the recombinant nucleic acid molecules can be used in modifying promoters for activation or repression of genes.

The term "plant" as used herein may relate to any member of Plantae kingdom, including flowering plants, conifers, ferns, clubmosses, hornworts, liverworts, mosses and the green algae. In some embodiments, the plant is a monocot or dicot plant. Examples of monocot plant includes, but are not limited to, corn, wheat, rice, sugar cane, and banana. Examples of dicot plant includes, but are not limited to, soybean, beans, peas, lentils, peanuts, tomatoes, potatoes, cotton, and perennial fruit trees including grapes, apple, and orange.

In some embodiments, methods described are used to increase gene targeting in a plant, wherein the method comprises transforming at least one plant cell of the plant with the recombinant nucleic acid molecule disclosed herein or an expression vector comprising the recombinant nucleic acid molecule, thereby producing a plant with increasing gene targeting, compared to a corresponding non-transformed plant.

In some embodiments, the method for generating a transgenic plant comprises transforming at least one plant cell of the plant with the recombinant nucleic acid molecule disclosed herein or an expression vector comprising the recombinant nucleic acid molecule, thereby producing a plant with increasing gene targeting, compared to a corresponding non-transformed plant.

In some embodiments, disclosed herein is a method for producing a transgenic seed of a plant, the method comprising: transforming at least one cell of the plant with a recombinant molecule described herein, and generating a transgenic plant from said at least one transformed plant cell; and growing said transgenic plant to obtain a seed, thereby producing said seed of said plant, wherein any plant produced from said seed has at least a mutated gene.

In some embodiments, said mutated gene comprises a donor nucleic acid sequence, said donor sequence targeted to a plant endogenous DNA sequence. In some embodiments, said donor nucleic acid sequence is integrated to the plant genome in a region nicked by a nuclease system targeted to said plant endogenous DNA sequence, wherein at least one component of said nuclease system is expressed under a regulatory sequence. In some embodiments, said regulatory sequence is a UBQ10 regulatory sequence.

In some embodiments, a genetically modified algae described herein comprises at least one cell comprising a recombinant nucleic acid molecule as disclosed herein.

There are various methods of introducing foreign genes into algae (See for example, Radakovits et al., Eukaryotic Cell April 2010 vol. 9(4): 486-501; Radakovits et al., Nat Commun. 2012 Feb. 21; 3: 686; Killan et al., PNAS 2011 vol. 108(52):21265-21269; and Newell, Transgenic Plant Journal. April 2007 vol. 1(1):81-98). Algal transformation methods are fully described in U.S. Pat. Nos. 5,661,017 and 7,001,772, and Application Publication US 2008/0194029.

A genetically modified alga comprising at least one cell comprising a recombinant nucleic acid molecule as disclosed herein, may in some embodiments first be selected based on the expression of the target gene or protein encoded by the target gene. In some embodiments, a genetically modified alga comprising at least one cell comprising a recombinant nucleic acid molecule disclosed herein, may in some embodiments first be selected based on an increased content of a nuclease, a nickase, a ZFN system, a TALEN system, a meganuclease, or a CRISPR/Cas nuclease used in targeted gene editing or a homolog thereof. In some embodiments, a genetically modified alga comprising at least one cell comprising a recombinant nucleic acid molecule disclosed herein, may in some embodiments first be selected based on an increased mutagenesis activity compared with an unmodified alga. In some embodiments, a genetically modified alga comprising at least one cell comprising a recombinant nucleic acid molecule disclosed herein, may in some embodiments first be selected based on an increased gene targeting activity compared with an unmodified alga.

In some embodiments, an alga may be transformed with more than one expression vector. In some embodiments, an additional expression vector comprises nucleic acid sequence encoding a guide RNA molecule. In some embodiments, an additional expression vector comprises nucleic acid sequence encoding other elements of a targeted gene editing system.

In some embodiments, the genetically modified alga comprises increased gene targeting activity compared to a corresponding unmodified alga.

The following examples are presented in order to more fully illustrate embodiments disclosed herein. They should in no way be construed, however, as limiting the broad scope disclosed herein.

EXAMPLES

Example 1

Identification of Upstream Region to Promote Gene Expression

Objective: As a first step towards optimizing expression of a gene in plants, for example but not limited to the CAS9 gene, the best upstream regulatory region to promote gene expression was sought.

Methods: In order to identify the best upstream region to promote gene expression, initial studies looked for the genes that display highest expression in all plant tissues. To this end, the tomato transcriptome was analyzed and several candidate genes were identified.

Transient expression assays: The region located ~2 kb upstream the candidate genes was then amplified and fused to the RED FLUORESCENT PROTEIN (RFP)gene, [~2 kb upstream region-RFP-~1 kb downstream region]. The reporter RFP gene was then introduced into *agrobacterium*, and the resulting transformed bacteria were used to inoculate leaves of *Nicotiana benthamiana* (*N. benthamiana*). RFP fluorescence was then measured 7 days post inoculation.

The six candidate genes were CHLOROPHYLL A-B BINDING PROTEIN (Solyc03005760; SlCAB1; SEQ ID NO: 7), CHLOROPHYLL A-B BINDING PROTEIN (Solyc02g071010; SlCAB; SEQ ID NO: 10), GLYCERAL-DEHYDE-3-PHOSPHATE DEHYDROGENASE (Solyc04g009030; SlGAPDH; SEQ ID NO: 13). TYPE 2 METALLOTHIONEIN (Solyc09g010800; SlMETALL; SEQ ID NO: 16), POLYUBIQUITIN10 (Solyc07g064130; SlUBQ10; SEQ ID NO: 22), and RIBULOSE BISPHOS-PHATE CARBOXYLASE SMALL CHAIN (Solyc03g034220; SlRBCS; SEQ ID NO: 30).

The plasmids harboring the RFP gene included ~2 Kb upstream and ~1 Kb downstream regions from the candidate genes. The upstream and downstream regions for each plasmid used are provided in Table 1:

TABLE 1

| Upstream (Promoter) and downstream (Terminator) sequences used in the RFP plasmids | | | | |
|---|---|---|---|---|
| Name | Upstream Gene Source & Sequence | | Downstream Gene Source & Sequence | |
| SlCAB1 | SlCAB1 | SEQ ID NO: 8 | SlTHI4 | SEQ ID NO: 21 |
| SlCAB | SlCAB | SEQ ID NO: 11 | SlTHI4 | SEQ ID NO: 21 |
| SlGAPDH | SlGAPDH | SEQ ID NO: 14 | SlTHI4 | SEQ ID NO: 21 |
| SlMETAL | SlMETAL | SEQ ID NO: 17 | SlTHI4 | SEQ ID NO: 21 |
| SlUBQ10 | SlUBQ10 | SEQ ID NO: 23 | SlUBQ10 | SEQ ID NO: 27 |
| SlRBCS | SlRBCS | SEQ ID NO: 31 | SlTHI4 | SEQ ID NO: 21 |

The cauliflower mosaic virus (CaMV) promoter was used as a control.

Plasmids harboring the RFP gene and including ~2 Kb upstream and ~1 Kb downstream regions from the UBQ10s from other plant species were also constructed. The other plant genes included potato (StUBQ10, Sotub07g26130, SEQ ID NO: 33), and *Arabidopis thaliana* (AtUBQ10 long, AT4G05320, SEQ ID NO: 40; and AtUBQJ short, AT4G05320, SEQ ID NO: 47). The upstream and downstream regions for each plasmid from the UBQ10s from other plant species are provided in Table 2.

TABLE 2

| Upstream (Promoter) and downstream (Terminator) sequences used in the RFP plasmids | | | | |
|---|---|---|---|---|
| Name | Upstream Gene Source & Sequence | | Downstream Gene Source & Sequence | |
| StUBQ10 | StUBQ10 | SEQ ID NO: 34 | StUBQ10 | SEQ ID NO: 38 |
| AtUBQ10 long | AtUBQ10 long | SEQ ID NO: 41 | AtUBQ10 long | SEQ ID NO: 45 |
| AtUBQ10 short | AtUBQ10 short | SEQ ID NO: 48 | AtUBQ10 short | SEQ ID NO: 45 |

Results:

It was observed that the region ~2 kb upstream and ~1 kb downstream of the SlUBQ10 directed RFP expression in the strongest manner (FIG. 1).

Next, it was determined whether the genomic regions adjacent to the POLYUBIQUITIN10 of other plant species were also able to direct gene expression in the strongest manner. To this end, the RIP gene was fused to the ~2 kb upstream and ~1 kb downstream genomic regions of the UBQ10 of potato (*Solanum tuberosum*) and *Arabidopsis* (*Arabidopsis thaliana*). A short (~700 bp; SEQ ID NO: 48) and a long (~1700 bp; SEQ ID NO: 41) genomic region upstream of the *Arabidopsis* UBQ10 were compared. The capacity of these four genomic regions (SlUBQ10, StUBQ10, AtUBQ10 long, AtUBQ10 short) to direct RFP expression was determined in a transient expression assay on *N. benthamiana* leaves.

*Solanum tuberosum Arabidopsis thaliana* It was observed that in all three species, the regions ~2 kb upstream and ~1 kb downstream of the UBQ10 directed RFP expression in the strongest manner (FIG. 2). In addition, RFP expression under the shorter upstream region (SEQ ID NO: 48) of the AtUBQ10 was lower than that of the other genomic regions measured here (FIG. 2).

Conclusion: The regions ~2 kb upstream and ~1 kb downstream of the UBQ10 were found to enhance the expression of sequences adjacent to them. In order to achieve the highest expression of a target gene, for example but not limited to the CAS9 gene, the target can be fused between the regions ~2 kb upstream and ~1 kb downstream of the UBQ10.

Example 2

Use of the Adjacent Regions of the UBQ10 for High-Efficiency Expression of a Pepper Gene in Tomato Plants Objective: To verify that the regions ~2 kb upstream and ~1 kb downstream of the UBQ10 induce high expression of a gene fuse amid them in tomato plants. To provide a plant with stable and high expression levels of the VANILIN SYNTHASE gene of *Capsicum* annum (CaVAN).

Method: The VANILIN SYNTHASE gene of *Capsicum* annum (CaVAN) was fused to the genomic regions located ~2 kb upstream (SEQ ID NO: 23) and 1 kb downstream (SEQ ID NO: 27) the SlUBQ10 of tomato: [~2 kb upstream region-CaVAN-~1 kb downstream region], and this cassette was introduced into tomato plants. This expression cassette was generated using standard molecular biology procedures, and the tomatoes (*Solanum lycopersicum* cv. microtom) were transformed using *Agrobacterium tumefaciens*, as described in the litterature. The CaVAN expression was measured by qPCR in transgenic tomato lines (T1).

Results:

The (SlUBQ10 cassette efficiently enhanced the expression of CaVAN. FIG. 3 shows the relative expression levels of the VANILIN SYNTHASE gene of *Capsicum* annum (CaVAN) observed in 4 transgenic tomato plants containing a cassette consisting of the SlUBQ10 promoter/terminator fused to the CaVAN coding sequence.

Conclusion:

The SlUBQ10 promoter/terminator cassette efficiently enhanced the expression of a non-tomato gene fused into it in tomato plants.

Example 3

Use of the Adjacent Regions of the UBQ10 for High-Efficiency CRISPR-Cas Expression in Tomato Plants The results presented in Example 1 show that the genomic region located ~2 kb upstream and (but not necessarily) ~1 kb downstream the UBQ10, is able to enhance the expression of genes fused into it.

It is desirable obtaining high and stable CAS9 expression in plants. Since plants having high CAS9 expression levels can be efficiently mutagenized. Therefore, in order to obtain high and stable CAS9 expression, the CAS9 gene was fused among the ~2 kb upstream and ~1 kb downstream of the UBQ10 gene.

Objective: To provide a plant with stable and high expression levels of the CAS9 gene, thereby providing means and methods to efficiently mutagenize plants and algae.

Methods: The genomic region located ~2 kb upstream the UBQ10 contains a promoter region and the 5' UTR. Notably, this 5' UTR is conserved in plants. It is ~400 to 600 bp long and contains a ~300-500 bp long intron whose 3' end is adjacent to the start codon of this gene. The presence of this intron allows high gene expression in eukaryotes, especially when expressing prokaryotic genes, as exon-exon junctions are known to enhance gene expression in eukaryotes. Used herein, the tomato promoter region includes at least SEQ ID NO: 24, and the 5' UTR including the intron comprises SEQ ID NO: 25 and SEQ ID NO: 26.

To obtain the highest CAS9 expression, the CAS9 gene was fused to the genomic region located ~2 kb upstream (SEQ ID NO: 23) and 1 kb downstream (SEQ ID NO: 27) the SlUBQ10 of tomato [~2 kb upstream region-CAS9-~1 kb downstream region], and this CAS9 cassette was introduced into tomato plants cv. M82 and cv microtom.

Moreover, in order to define the most suitable expression cassette to direct CAS9 expression, and to obtain the highest mutation rate, the CRISPR-CAS system was used to mutagenize the CRTISO gene (Solyc10g081650, SEQ ID NO: 74). This gene is involved in *carotenoid* biosynthesis and a homozygous or bi-allelic mutation(s) in this gene causes the plants to display an orange color in the young leaves, in the flowers and in the fruit tissues. Furthermore, in an attempt to improve the mutation rate, the BeYDV Replicon was also used, which generate high levels of CAS9 and gRNA copies (Baltes N J et al. (2014) Plant Cell, 26(1):151-63).

Early stage results are those results collected after moving the plant from tissue culture to soil and before the flowering of the plant Late stage results are those results encompassing reproductive growth.

DNA sequence analysis was performed using Illumina sequencing HiSeq 2500 system, high output run, paired-end 125 bp at the G-INCPM.

Results:

The expression level of CAS9 was then determined in the transgenic tomato plants and found to be high (FIGS. 4A and 4B). In this experiment, the mutation rate obtained when the CAS9 gene was overexpressed using the SlPOLYUBIQ-UITIN10 cassette (SlUBQ10 promoter region (SEQ ID NO: 23)/SlUBQ10 terminator region (SEQ ID NO: 27) was compared with the mutation rate when the CAS9 gene was expressed in a *Petroselinum crispum* UBIQUITIN4 (PcU-BIQUITIN4) cassette (See, Fauser, F. et al., The Plant Journal (2014) 79, 348-359).

Several transgenic tomato plants (cv microtom) were produced that harbored a CRISPR-CAS construct designed to target either the CRTISO) gene (Solyc10g081650) or the PSY1 gene (Solyc03g031860). In this experiment, the CAS9 gene was overexpressed either under the control of the PcUBIQUITIN4 cassette, or under the control of the SlPOLYUBIQUITIN10 cassette (SlUBQ10 promoter region (SEQ ID NO: 23)/SlUBQ10 terminator region (SEQ ID NO: 27)), with or without the use of the BeYDV Replicon. Then the phenotype (orange color of the flowers for crtiso, and yellow color of the fruits of psy1) of the plants obtained was monitored as an indication of the indel frequency (Table 3).

TABLE 3

Phenotypic analysis of gene targeting of the CRTISO and PSY1 loci in Micro-Tom Wild Type plants

| Construct | $T_0$ plants that gave fruit | $T_0$ fruit phenotype | | | |
|---|---|---|---|---|---|
| | | Red (WT) | Orange/ Yellow | Chimera | Mutated phenotype/total |
| Rep-crtiso-ubi4 | 22 | 0 | 22 | 0 | 100% |
| Rep-psy1-ubi4 | 32 | 4 | 7 | 21 | 54.7% |
| Rep-crtiso-ubi10 | 2 | 0 | 2 | 0 | 100% |

TABLE 3-continued

Phenotypic analysis of gene targeting of the CRTISO and PSY1 loci in Micro-Tom Wild Type plants

| Construct | T$_0$ plants that gave fruit | T$_0$ fruit phenotype | | | |
| | | Red (WT) | Orange/ Yellow | Chimera | Mutated phenotype/total |
|---|---|---|---|---|---|
| Rep-psy1-ubi10 | 4 | 0 | 2 | 2 | 50% |
| crtiso-ubi4 | 28 | 0 | 26 | 2 | 96.4% |
| psy1-ubi4 | 32 | 7 | 21 | 4 | 71.9% |
| crtiso-ubi10 | 29 | 1 | 28 | 0 | 96.6% |
| psy1-ubi10 | 12 | 4 | 6 | 2 | 58.3% |

High frequencies of mutants were observed in the first generation of transformants, and all samples (of all different constructs) were sent for DNAseq analysis to determine indel frequencies (FIGS. 5A and 5B).

Conclusion: It was determined that the region ~2 kb upstream and ~1 kb downstream of the UBQ10 provides a suitable expression cassette to express foreign genes at high levels in plants. In particular, this cassette was very effective for expressing the CAS9 gene for generating highly efficient gene targeting. Use of the UBQ10 cassette to express the CAS9 gene at an early stage of plant development would be advantageous for the breeder who wishes to mutagenize a given gene in a plant, as it allows the breeder to obtain the desired mutation throughout the plant and in the seeds.

Example 4

General Methods Used in Examples 5-8

Cloning T-DNA Cassettes and *Agrobacterium*-Mediated Transformation

All T-DNA constructs were built using the Golden Braid (GB) cloning system on pCAMBIA binary vectors (Sarrion-Perdigones et al., Methods Mol. Biol. (2014) 1116, 133-151). All geminiviral components on pLSL and pREP plasmids (Baltes et al., Plant Cell (2014) 26, 151-163) and the CRISPR components, Ubiquitin4-2 promoter from *Petroselinum crispum* (PcUbi4-2) on pDE-Cas9 plasmid (Fauser et al., *Plant J.* (2014) 79, 348-359) U6-26:gRNA, synthesized by IDT (integrated DNA Technologies) and Ubiquitin10 from *Solanum lycopersicum* (Solyc07g064130) promoter region (2079 bp upstream to the ATG translation initiation codon (SEQ ID NO: 23)) and terminator region (1443 bp downstream to the TAA stop codon (SEQ ID NO: 27)) were cloned to GB vectors. Sequences of the gRNAs were cloned by BbsI digestion and ligation of primers. The primers used for gRNA ligation are shown in Table 4.

TABLE 4

Primers used for gRNA ligation

| Name | Sequence | SEQ ID NO: |
|---|---|---|
| crtiso_t3_Fw | 5'-*ATTGCGATGCTACCAGCATTCTG* | 50 |
| crtiso_t3_Rv | 5'-*GCTACGATGGTCCTAAGACCAAA* | 51 |
| psy1_t2_Fw | 5'-*ATTGAGCGTATATAATGCTGCTT* | 52 |
| psy1_t2_Rv | 5'-*TCGCATATATTACGACGAACAAA* | 53 |
| Tmic_t1_Fw | 5'-*ATTGTTTGATGTTGGTTCATCAGT* | 54 |

TABLE 4-continued

Primers used for gRNA ligation

| Name | Sequence | SEQ ID NO: |
|---|---|---|
| Tmic_t1_Rv | 5'-*AAACTACAACCAAGTAGTCACAAA* | 55 |
| Tmic_t2_Fw | 5'-*ATTGGTTCATCAGTAGGCCAACT* | 56 |
| Tmic_t2_Rv | 5'-*CAAGTAGTCATCCGGTTGACAAA* | 57 |

Cotyledon transformation was done using *Agrobacterium* strain GV3101 as described in Meissner et al. Plant J. (1997), 12, 1465-1472, with minor changes (no tobacco feeder cells layer and with 1 mg zeatin medium for first selection plates, 0.5 mg zeatin, and the addition of 0.5 mg zeatin-riboside medium for the second selection plates and 0.2 mg zeatin for the third selection plates).

Plant Material and Growth Conditions

The gene targeting cassettes, comprising a CRISPR/Cas9 system, a gRNA, a geminiviral replicon, and a kanamycin resistance gene (FIG. 6), were transformed into wild-type (WT) Micro-Tom tomato (*Lycopersicon esculentum*). Gene targeting cassettes, comprising a CRISPR/Cas9 system, a gRNA, a geminiviral replicon, a donor sequence, and a kanamycin resistance gene (FIG. 7), were transformed into tangerine, a Micro-Tom fast neutron mutant with a 281 bp deletion in the CRTISO gene (Isaacson et al. Plant Cell (2002) 14, 333-42). Control targeted mutagenesis cassettes lacked one of either Rep protein or the entire replicon (FIG. 6). Control gene targeting cassettes lacked one of either Rep protein or Cas9 (FIG. 7). Plants were grown in 1 liter pots in a monitored greenhouse in the Weizmann Institute of Science, Rehovot. The climate growth conditions were of 23° C., 70% humidity during the day and 19° C., 60% humidity during the night.

Isolation of DNA

DNA extraction was done by grinding two to three leaves in liquid nitrogen with an electric drill in a 1.5 ml Eppendorf tube. One volume of 700 μl pre-heated (to 65° C.) extraction buffer (0.8M NaCl, 0.15M Sorbitol, 0.12M Tris-HCl pH=7.5, 22 mM EDTA, 0.8% CTAB, 0.8% sodium lauryl sarcosinate) was added to each tube and incubated for 20 minutes in 65° C. One volume of 800 μl chloroform-octanol (24:1) was added to each tube and centrifuged at 13,000 rpm for 5 minutes. This step was repeated twice. One volume of 1.4 ml pre-cooled (4° C.) storage buffer (80% EtOH, 0.2M NaAcetate) was added to the supernatant in a new 2 ml Eppendorf tube. DNA precipitation was done by centrifugation at 13,000 rpm for 20 minutes in 4° C. The pellet was re-suspended in 50 μl of H$_2$O.

PCR Analysis

Two PCRs were performed using Taq Ready Mix (2x) (Hylabs) to confirm integration of the truncated CRTISO donor DNA to the tangerine locus. Each PCR was done with one primer from the genomic locus and one primer from the donor DNA 281 bp. To assess integration from the 5' end, crtisoUpFw primer was used: 5'-CCTATGATCTAACAT-AATCTTGAAC (SEQ ID NO: 57) corresponding to the genomic locus and DelRv primer: 5'-GTGTGGCGAGGTATCAGAC (SEQ ID NO: 58) corresponding to the 281 bp complementation sequence. For integration from the 3' end, DelFw primer: 5'-CACACCGCTCCATAGTCTG (SEQ ID NO: 59) corresponding to the 281 bp complementation sequence and crtiso4Rv primer: 5'-GTAACACATCTAAGTGTAGGGG (SEQ ID NO: 60) corresponding to the genomic locus were used (FIG. 8).

are underlined). Samples of different constructs were distributed randomly in all libraries. Deep sequencing was done using Illumina sequencing HiSeq 2500 system, high output run, paired-end 125 bp, at the Nancy and Stephen Grand Israel National Center for Personalized Medicine (G-IN-CPM), the Weizmann Institute of Science.

TABLE 5

| Primers used for amplicon amplification | | |
|---|---|---|
| Name | Sequence (5' to 3') | SEQ ID NO: |
| Crtiso HT Fw GACT | NNNNNNGACTCTCTGCATCTATAAAAGACAGC | 63 |
| Crtiso HT Fw TAGC | NNNNNNTAGCCTCTGCATCTATAAAAGACAGC | 64 |
| Crtiso HT Fw CGTA | NNNNNNCGTACTCTGCATCTATAAAAGACAGC | 65 |
| Crtiso HT Rv | NNNNNNTATTTAAGTGAAGAATGGTAAAGG | 66 |
| Psy1 HT Fw ATCG | NNNNNNATCGGTATCGCCCCTGAATCAAAG | 67 |
| Psy1 HT Fw GTAC | NNNNNNGTACGTATCGCCCCTGAATCAAAG | 68 |
| Psy1 HT Fw CGTA | NNNNNNCAGTGTATCGCCCCTGAATCAAAG | 69 |
| Psy1 HT Rv | NNNNNNAGTTCTGCAATTTTATTCCCAG | 70 |

Two PCRs were done to check for heterozygosity of the T$_0$ plants that were positive for gene targeting. One PCR was done using two primers for each side of the deletion/complementation, crtiso2Fw primer: 5'-GCTTTGGGTGA-TAGCAAACC (SEQ ID NO: 61) and crtiso2Rv primer: 5'-GTGGACGGTTTACTGGAAAG (SEQ iD NO: 62). The second PCR was done using one primer upstream to the deletion/complementation, crtiso2Fw (SEQ ID NO: 61), and one primer corresponding to the genomic locus, crtiso4Rv (SEQ ID NO: 60). Long range PCR was done using TaKaRa LA Taq® in order to amplify unique fragments for GT using primers upstream and downstream to the donor and the 281 bp complementation (FIG. 9).

Southern Blot Analysis

Genomic DNA was extracted from Micro-Tom WT plant, from tangerine fast-neutron mutant, and from "TmicT2-donor-Rep-Ubi10" progeny of tangerine background plants with and without the gene targeting phenotype using Mache-rey-Nagel NucleoSpin® Plant H extraction kit. DNA was digested with NsiI and SspI-HF (New England Biolabs®) and fractionated on 0.8% agarose gels, transferred to nylon membranes (Hybond N+, Amersham), and hybridized overnight at 65° C. with 32P-labeled genomic 5' and 3' end probes as described in Results. The hybridization signal was obtained using a BIO-RAD phosphoimager PMI.

DNA Amplification and High-Throughput Sequencing

Genomic DNA extractions from gene targeting T$_0$ plants of all 8 constructs were used to produce amplicons for high-throughput (HT) deep sequencing. 18 cycles PCR on plant samples were done using KAPA HiFi HotStart Ready-Mix (KAPA Biosystems-50 µl reactions according to the manufacturer's protocol). Primers were designed to amplify 274 bp of the CRTISO gene and 272 bp of the PSY1 gene, while the forward primer was 50-60 bp from the CRISPR target site. Primers had 6 degenerated bases (N) at the 5' end (NNNNNN), and the forward primer had a 4 bases barcode to indicate the specific sample in each library (6 samples per library—3 of CRTISO, 3 of PSY)). The barcodes used for crtiso were GACT, TAGC and CGTA, and the barcodes used for PSY1 were ATCG, GTAC and CAGT (Table 5, barcodes Mutations Detection by Sanger Sequencing Various plant DNA samples of the gene targeting experiments were tested for CRISPR activity and NHEJ events by Sanger sequencing. Amplification of the target area was done using REDTaq® ReadyMix™ PCR Reaction Mix (Sigma-Aldrich), standard PCR protocol reaction on genomic DNA. After amplification detection by gel electrophoresis, positive reactions were put in an ExoI-Sap reaction to remove primers and nucleotides. Reaction total 9 µl: 5 µl PCR reaction, 1 µl Exonuclease I (New England BioLabs® Inc), 1 µl shrimp alkaline phosphatase (New England Bio-Labs® Inc), 2 µl DDW. The reaction was put for incubation in 37° C. for 30 minutes, followed by 10 minutes deactivation at 80° C. 10 mM primer were added to the reaction to a volume of 10 µl that was sent for Sanger sequencing at the DNA sequencing unit, Biological Services Department, the Weizmann Institute of Science with Applied Biosystems 3730 DNA Analyzer. PCRs for junction detection of the gene targeting plants were also sent to Sanger sequencing after the Exo-Sap reaction described above. Long range PCR fragments were extracted from gel using RBC HiYield™ Gel/PCR DNA Fragments Extraction Kit and were analyzed as described above. Due to low concentration, amplified 3' junctions were subcloned to pGEM®-T Easy vector before sequencing.

Quantitative PCR

The relative number of replicons was detected by quantitative PCR (qPCR) analysis on various genomic DNA samples. The Fast SYBR® Green master mix (Applied Biosystems) was used for the DNA qPCR reactions, according to the manufacturer protocol, in triplicate (3 technical replicates) 10 µl reactions. PCR amplification was tracked on StepOne™ system (Applied Biosystems). For the gene targeting system, a primer pair that can amplify the CRTISO donor was used (crtiso4Fw primer: 5'-TCTTTCACGCT-GATGTGTGC (SEQ ID NO: 71) and crtiso3Rv primer: 3'-CTCTAGGACCCAACGACAGA (SEQ ID NO: 72)) and for the endogenous control the primer pair crtiso5Fw (5'-GGAGAACGAAGAGGGAAGAAC (SEQ ID NO: 73)) and crtiso4Rv were used (that are not on the CRTISO donor). The amplification efficiencies of all primer pairs were approximately equal (Calibration of primers: crtiso4F-3R slope −3.45, $R^2$ 0.99; crtiso5F-4R slope −3.47, $R^2$ 0.99).

Example 5

Gene Targeting

Objective: To improve targeted mutation rates by using stable and high expression levels of the CAS9 gene. The experiments and results presented here expand those presented in Example 3. Some of the results of Example 3 are included here.

Methods: Two different promoters were tested for constitutive expression of the Cas9 endonuclease, Ubiquitin 4-2 from *Petroselinum crispum* ("Ubi4", as used in Steinert et al. Plant J. (2015) 84, 1295-1305) and Ubiquitin 10 from *Solanum lycopersicum* ("Ubi10"). Two genes were targeted, the *Carotenoid isomerase* (CRTISO) gene (Solyc10g081650), and phytoene synthase 1 (PSY1) gene (Solyc03g031860) from the *carotenoid* biosynthesis pathway, due to their distinct fruit phenotype (Enfissi el al. Plant J. (2016), 89, 774-788). The crtiso mutant has orange fruits, yellowish young leaves and pale petals, while the psy1 mutant has a yellow fruit but other organs are wild type (Isaacson el al., Plant Cell (2002), 14, 333-42). Both are recessive mutations, in which homozygous or bi-allelic mutant result in a non-WT phenotype.

In addition, it was tested whether the amplification of Cas9 and gRNA through geminiviral replicon rolling circle replication (RCR), enhanced the DSB rate as seen through the analysis of non-homologous end-joining (NHEJ) DSB repair events. All constructs used in these experiments are shown in FIG. 6.

Early stage results are results collected after moving the plant from tissue culture to soil and before the flowering of the plant. Late stage results are those results encompassing reproductive growth. DNA sequence analysis was performed using Illumina sequencing HiSeq 2500 system, high output run, paired-end 125 bp at the G-INCPM.

Results: Mutated phenotypes were easy to detect already in the $T_0$ transformed plant. Many plants had all their fruits fully mutated, i.e. orange fruit color phenotype of crtiso or yellow fruits corresponding to the psy1 mutation (FIG. 10A), indicating early mutagenesis events. Some plants had a "chimeric" phenotype, i.e. a mixture of WT (red color) fruits, yellow or orange (tangerine) fruits (depending on the target) and sectored fruits, indicating late somatic mutations. In the case of early mutation events, plants with the CRISPR/Cas9 system targeting the CRTISO gene had late greening of the young leaves phenotype as early as 2 days after moving to the greenhouse (FIG. 10B). A further phenotype of the crtiso mutation was the pale orange petals (FIG. 10C).

Only plants that were positive for transfer DNA (T-DNA) integration and produced fruits were considered in the phenotypic analysis. The phenotype was scored as red, orange or yellow if all the fruits of the $T_0$ plant were red, orange or yellow respectively. $T_0$ plants were considered as chimeras if they bear a mixture of WT (red) or mutant (orange or yellow) or sectored fruits. Remarkably, for the CRTISO target most constructs showed similar and very high frequencies of mutagenesis having close to 100% mutations in both alleles. For the PSY1 target, the frequency of mutagenesis ranged between 70-50%. Despite the presence of the geminiviral replicon, no mutagenesis enhancing effect was observed. Plant phenotypes for each transformant are summarized in Table 3 (see Example 3)

Conclusion: Constructs targeted against crtiso showed very high frequencies of mutagenesis. These frequencies were similar for all tested crtiso constructs. The presence of a geminiviral replicon did not enhance the efficiency of constructs targeted against psy1.

Example 6

Detection of Mutants by Next Generation Sequence

Objective: To determine the frequencies and sequences of the mutation footprints for the CRTISO and PSY1 targets.

Methods: Tissue from true leaves of $T_0$ plants transformed with the eight different constructs shown in FIG. 6 was collected and their DNA was extracted. The region around the CRTISO or PSY1 target was PCR-amplified and sent to deep sequencing using Illumina Hi-Seq for detection of mutations. Overall, results were obtained from 156 plants; 76 plants with gRNA targeting the CRTISO gene and 80 plants with gRNA targeting the PSY1 gene. For negative control, amplicons were obtained from Micro-Tom plants expressing only the Cas9 under Ubi10 promoter (no gRNA). Plants with more than >97% of the Illumina reads different from WT were considered as fully mutated, since minor amount of WT reads might correspond to contaminations or very minor chimerism from the calli. This assumption is supported by the phenotypic data showing plants containing only mutant fruits.

Results: The frequencies and sequence of the various mutation footprints are shown in FIGS. 11A and 11B for the CRTISO and PSY1 targets respectively. Mutation frequencies are higher in plants targeting the CRTISO gene, when most of the plants had only up to 4 different repair footprints per plant. The tomato plants are diploid, therefore a multiplicity of footprints probably suggests that plants are chimeric with different types of mutations being formed during development.

Conversely, the presence of one or two types of footprints, in the absence of the WT sequence, suggests that early events occurred and were clonally inherited in all cells. Plants with bi-allelic mutations were often observed, and plants that were homozygous to a certain type of footprint, for example (−T) and (−AGCAT) mutation events (FIG. 11A, plants Ubi4 #9 and Ubi10 #2, respectively). Fewer mutation events were obtained with thepsyl gRNA, while a (−G) deletion was commonly observed, with one plant that appears to be homozygous for this repair footprint (FIG. 11B, plant rep Ubi4 38). Overall 64 plants out of 76 were fully mutated in the CRTISO gene (84%) compared to 15 plants out of 80 that were fully mutated in the psy1 gene (19%). Across all analyzed plants, 90.4% and 56.4% of the WT alleles were mutated in CRTISO and PSY1 loci respectively. In order to test transmission to the next generation $T_1$ progeny of $T_0$ plants that had lost the WT allele were grown. All $T_1$ progeny had a mutant phenotype. Sequencing of crtiso in two $T_1$ progeny of $T_0$ plant crtiso-Ubi10 #18 which had three mutated alleles (FIG. 11A), gave rise to one plant homozygous for −1 T deletion, and another plant heterozygote for −1 T deletion and a −9 (ACCAGCATT) deletion. These results show efficient mutagenesis rates and transmission to the next generation.

Conclusions: Gene targeting using the CRISPR-Cas9 system was extended to a new locus (CRTISO). Mutation frequencies were very high at the CRTISO locus, altering 90.4% of the WT alleles in $T_0$ plants. Sequence analysis from leaf tissues of $T_0$ plants showed little chimerism, with most plants containing only one or two mutant alleles, suggesting very early CRISPR-Cas9 mutagenesis in the somatic embryo. Mutagenesis frequency was lower for the PSY1 locus. Considering that all components used for PSY1 mutagenesis were similar to those used for CRTISO, the gRNA design or the epigenetic context must be the reason for low mutagenesis at PSY1 locus.

Example 7

Repairing of the Crtiso Allele-Gene Replacement

Objective: To replace a defective endogenous gene with a wildtype sequence, with no selection for homologous recombination during the tissue culture stage.

Methods: A tangerine Micro-Tom mutant with a 281 bp deletion in the crtiso gene, generated using fast-neutron mutagenesis (Meissner et al. Plant J. (1997), 12, 1465-1472) and described by Isaacson et al., Plant Cell (2002), 14, 333-42, was chosen as a target in order to perform a knock-in experiment whereby the deletion in the crtiso gene is replaced by the WT sequence. The system combines induction of a DSB by a CRISPR/Cas9 system in the site of the tangerine deletion, together with delivery of a gemini-viral replicon that carries a 3796 bp donor repair template. Phenotypically, the replacement of the defective tangerine allele by the WT donor sequence was expected to result in a red WT fruit phenotype. A repair in one of the alleles is sufficient for developing red fruits since the tangerine mutation is recessive. FIG. 12 shows the gene targeting strategy used in these experiments. Plants were transformed with a single construct, from those depicted in FIG. 7, containing Cas9 under the expression of the SlUbiquitin10 (Ubi10) promoter, a gRNA (U6-26:tangerine t1 or t2), the Rep protein, a CRTISO gene that contains the WT coding region that is deleted in the tangerine mutant and serves as the donor repair template. The donor repair template is ampli-fied using the geminiviral replicon. A DSB (lightening symbol) is induced in the tangerine mutant deletion allele using the CRISPR/Cas9 system. Recombination in the regions of homology between the donor and the broken target (1778 bp and 1737 bp 5' and 3' regions respectively) results in the replacement of the deletion allele by the WT sequence (red box), leading to a red instead of tangerine fruit color phenotype.

The transfer DNA (T-DNA) constructs used in the gene targeting experiment ("TmicT1-donor-Rep-Ubi10" and "TmicT2-donor-Rep-Ubi10", FIG. 7) harbors both the CRISPR/Cas9 system, with Cas9 expressed under the Ubi10 promoter, the replicon machinery, and two different gRNAs, "T1" and "T2". CRISPR gRNAs were designed to match target sequences only in the tangerine allele. These target sequences become destroyed, or inactivated, upon insertion of the repair donor sequence. T1 targets a sequence adjacent to the CRIPSR mandatory PAM sequence. Therefore, T1 target sequence is destroyed upon repair, since the inserted donor sequence separates PAM from the target sequence. T2 targets a sequence flanking the tangerine deletion site. Therefore, upon repair, T2 target sequence is destroyed since the donor sequence is inserted within it (FIG. 13).

TmicT1-donor-Rep-Ubi10 and TmicT2-donor-Rep-Ubi10 constructs enabled replicon amplification together with DSB induction already in the $T_0$ plant, giving rise to 32 and 36 transformed $T_0$ plants with ripe fruits, respectively. Plants were also transfected with control constructs. Table 6 shows the construct used in the experiments (FIG. 7) and the number of plants with ripe fruits for each of them.

TABLE 6

Phenotypic analysis of gene targeting of the CRTISO and PSY1 loci in Micro-Tom Wild Type plants

| Construct name | # of plants |
|---|---|
| TmicT1-donor-Rep-Ubi10 | 32 |
| TmicT2-donor-Rep-Ubi10 | 36 |
| TmicT1-donor-Rep | 11 |
| TmicT2-donor-Rep | 12 |
| TmicT1-donor-Ubi10 | 13 |
| TmicT2-donor-Ubi10 | 12 |
| TmicT1-donor | 10 |
| TmicT2-donor | 17 |
| Rep-Ubi10 | 7 |
| Rep | 2 |
| Ubi10 | 5 |

While tangerine mutants have late greening of the young leaves phenotype, it is not a reliable marker being very much affected by light growth conditions. Therefore, it was not taken into account when selecting kanamycin-resistant calli for regeneration in the treatment or in the controls.

Results: The presence of replicons in transfected cells was measured by DNA quantitative PCR of plants transfected either with the full cassette constructs including Rep, or with their CRISPR-only controls. Replicon amplification was measured by using primers annealing to both the tangerine locus and the CRTISO donor, the tangerine mutant served as the baseline copy number. Four groups were tested; "TmicT1-donor-Rep-Ubi10" and "TmicT2-donor-Rep-Ubi10" contained all the components for the GT experiment, compared to plants without the replicon "TmicT1-donor-Ubi10" and "TmicT2-donor-Ubi10", which served as nega-tive controls. Each treatment had 3 biological replicates. Results showed up to 90-fold increase in replicon copy number in comparison to the endogenous control (FIG. 14).

Nine (9) out of the 36 tested $T_0$ plants that were trans-formed with "TmicT2-donor-Rep-Ubi10" were found to have only red fruits (25%). $T_1$ progeny of eight of these nine plants were grown, showing Mendelian segregation for the red/orange phenotype, indicating that $T_0$ plants were het-erozygous and showing transmission to the next generation. The ninth plant was highly sterile and a single seed was obtained giving rise to a single $T_1$ plant with orange fruits. 1 out of the 12 tested $T_0$ plant that were transformed with control "Tmic-T2-donor-Ubi10" construct devoid of repli-con activity, gave rise to a chimeric plant with red and orange fruits. The $T_1$ progeny of orange fruits gave rise to orange fruits and the $T_1$ progeny of the red fruits segregated for the red/orange phenotype, indicating that the red fruits from $T_0$ plants were heterozygous. All other experiments and control constructs had only orange fruits.

In order to confirm that the red fruits were the product of "TmicT2-donor-Rep-Ubi10" gene targeting, validation was done by PCR amplification of DNA extracted from leaf tissue of the 9 $T_0$ plants having only red fruits. Primers were designed to amplify the gene target event, but not the tangerine locus. To identify integration at the 5' end of the CRTISO donor, PCR was done using one forward primer from the 5' of the crtiso locus (crtisoUpFw) that does not exist on the donor and a second reverse primer from the WT 281 bp complementation (delRv) that does not exist on tangerine (FIG. 15A). PCR products of 8 GT plants were checked next to Micro-Tom WT as positive control, tanger-ine mutant and no template (blank) as negative controls.

PCR products were separated by electrophoresis in an EtBr-stained agarose gel, showing that the size of the amplified fragments corresponded to the expected 2122 bp length of the repaired sequence 8 GT plants were checked next to Micro-Tom WT as positive control, and tangerine mutant and no template (blank) as negative controls (FIG. 15B). To identify integration at the 3' end, primers delFw (not present on tangerine) and crtiso4Rv (from the 3' of the crtiso locus) were used (FIG. 15A), yielding the expected PCR fragment size of 1971 bp for a GT allele (FIG. 15C). To check if the red-fruit plants are homozygous or heterozygous, the tangerine allele or the WT allele (originated from repaired allele or donor sequence), were PCR amplified with 2 pairs of primers flanking the tangerine deletion. The first pair of primers, crtiso2Fw and crtiso2Rv, amplified either the tangerine allele (668 bp), the WT repaired allele (949 bp), or both (FIG. 9). The second pair of primers, crtiso2Fw and crtiso4Rv, amplified either the tangerine allele (2235 bp), the WT repaired allele (2516 bp), or both (FIG. 9). PCR products were loaded into an EtBr agarose gel and separated by electrophoresis. Electrophoresis revealed 668 bp and 949 bp PCR products amplified with the first pair of primers (FIG. 16A), and 2235 bp and 2516 bp PCR products amplified with the second pair of primers (FIG. 16B), showing $T_0$ plants were heterozygous.

The progeny of 4 $T_0$ plants with gene targeting phenotype was analyzed by Southern blot hybridization. Southern blot was done on genomic DNA digested by NsiI and SspI-HF, to detect 5' and 3' integration respectively. FIG. 17A shows the location of the NsiI and SspI-HF restriction sites and of the probes (red rectangles) used in the Southern blot analysis. Southern blot of Micro-Tom WT DNA (lane 1) showed only the expected WT NsiI 5083 bp/SspI 2964 bp fragment, while tangerine mutant DNA (lane 2) and tangerine mutant that had the T-DNA but did not undergo GT (lane 3) showed the expected NsiI 6311 bp/SspI 3964 bp fragments (FIG. 17B). GT progeny plants (GT1, GT4, GT5, corresponding to lanes 4, 6 and 7 respectively), showed heterozygosity at their CRTISO locus with both tangerine and WT repaired alleles fragments. GT2 progeny plant was homozygous for the WT repaired allele.

PCR fragments were amplified from upstream and downstream of the WT 281 bp complementation region to the CRTISO) locus using TaKaRa LA Taq® (FIGS. 18A and 18B). Sanger sequencing of the amplified fragments were found to have the expected sequence for homologous recombination between the donor sequence and the 5' and 3' junctions of the locus (FIG. 8).

In order to understand absence of repair in transfected plants, Sanger sequencing was performed in $T_0$ plants transfected with the TmicT1-donor-Rep-Ubi10 and TmicT2-donor-Rep-Ubi10 construct still having the tangerine phenotype after transfection. FIG. 19 shows the sequences obtained from a not-transformed tangerine mutant (upper panel), plants #3 and #1 transformed with TmicT1-donor-Rep-Ubi10 (two middle panels), and plant #2 transformed with TmicT2-donor-Rep-Ubi10. Non-homologous end joining (NHEJ) was detected in target region T1 and target region T2. Importantly, NHEJ repair at this site prevent a second DSB and repair by homologous recombination.

Conclusion: A very high rate of gene targeting was achieved in the absence of selection for the targeting event. In addition, gene targeting, namely the replacement of the deleted tangerine allele by the WT sequence, occurred very early in development as inferred from the finding that all the fruits of the GT $T_0$ plants (9 out of 36) were red (WT) and that this phenotype was germinally transmitted. This is consistent with the early timing of CRISPR-Cas9-induced DSB induction. Considering that Cas9 cannot cleave its DNA target again after error-prone DSB break occurs, it is necessary to have a precise coordination of the DSB induction together with the donor amplification to increase the chances of template invasion during the homologous-recombination-mediated repair. Moreover, all steps in the process must be optimal for gene targeting (rather than non-homologous end joining) to take place, such as strong Cas9 expression (here under the tomato Ubi10 promoter), an effective gRNA and coordinated amplification of the geminiviral replicon, in this case all components were cloned in a single construct and were co-expressed.

These experiments are an unexpected advance over earlier reports, showing the feasibility of selection-free and efficient gene targeting. Only selection by Kanamycin resistance at the stage of transformation was used, and plants were grown with no knowledge on their phenotype until flowering (white petals in tangerine versus yellow in WT) and fruit ripening (orange versus red).

Example 8

Repairment of the Crtiso Allele is not Due to Random Contamination

Objective: To validate that plants are repaired by CRISPR/Cas9 and not by seed or pollen contamination.

Methods: The WT Micro-Tom fruit has a glossy and red fruit surface. By contrast, the tangerine mutant has a non-glossy surface and orange color, as a consequence of the several mutations in its background (Meissner et al. (1997) ibid) (FIG. 20). Surfaces of tomatoes were observed in tangerine mutant plants targeted or not with the CRISPR/Cas9 construct.

Results: Glossy red surfaces were observed in WT plants. The glossiness was maintained in CRTISO mutated plants, showing that CRTISO mutations do not affect glossiness. Non-glossy yellow surfaces were observed in tangerine mutants. While tangerine mutants having the CRISPR/Cas9 construct showed a repaired red surface, the non-glossy phenotype was maintained (FIG. 20).

Conclusion: Gene targeting occurred in the tangerine background by the CRISPR/Cas9 construct and could not be due to a contamination, as plants with red non-glossy phenotype did not exist in the mutant collection.

While certain features of methods of gene targeting and gene replacement have been illustrated and described herein, many modifications, substitutions, changes, and equivalents will now occur to those of ordinary skill in the art. It is, therefore, to be understood that the appended claims are intended to cover all such modifications and changes.

The invention claimed is:

1. A method for gene targeting in a plant cell, the method comprising:
    (a) introducing into said plant cell a first nucleic acid comprising a viral replicon comprising a donor nucleic acid sequence, said donor sequence targeted to an endogenous DNA sequence in said plant cell; and
    (b) introducing into said plant cell a second nucleic acid comprising a nuclease system, wherein said nuclease system is targeted to said endogenous DNA sequence, and wherein at least one component of said nuclease system is expressed under the control of a POLYU-BIQUITIN10 (UBQ10) gene regulatory sequence;
    wherein homologous recombination occurs between the donor sequence and said plant endogenous DNA sequence,
    wherein said UBQ10 gene regulatory sequence comprises a recombinant nucleic acid molecule comprising:
    (i) a first regulatory region comprising the sequence of SEQ ID NO:34 or a homolog thereof having at least 95% identity with the sequence of SEQ ID NO:34, and wherein said first regulatory region is 5' of said at least one component of said nuclease system; and
    (ii) a second regulatory region comprising the sequence of SEQ ID NO:38 or a homolog thereof having at least 95% identity with the sequence of SEQ ID NO:38, and wherein said second regulatory region is 3' of said at least one component of said nuclease system;
    wherein said nuclease system is selected from a nickase, a CRISPR/Cas system, or a DNA endonuclease enzyme used in targeted gene editing, and
    wherein said viral replicon is selected from the group consisting of: a geminiviral replicon, a bean yellow dwarf virus (BeYDV) replicon, a cabbage leaf curl virus (CalCuV) replicon, a tomato leaf curl virus (ToLCV) replicon, a wheat dwarf virus (WDV) replicon, or any combination thereof.

2. The method of claim 1, wherein said donor sequence comprises a gene, a mutated gene, a part of a gene, a regulatory sequence, a mutated regulatory sequence, a sequence upstream of a gene, a sequence downstream of a gene, an exon sequence, an intron sequence, or any combination thereof.

3. The method of claim 1, wherein said CRISPR/Cas system comprises a Cas nuclease and a gRNA molecule, wherein said gRNA molecule binds within said plant endogenous DNA sequence.

4. The method of claim 3, wherein said Cas nuclease is selected from the group consisting of Cas1, Cas1B, Cas2, Cas3, Cas4, Cas5, Cas6, Cas7, Cas8, Cas9, Cas10, C2cl, CasX, NgAgo, Cpf1, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4.

5. The method of claim 1, wherein said at least one component of said nuclease system comprises a Cas nuclease.

6. The method of claim 1, wherein a single expression vector comprises said first nucleic acid and said second nucleic acid.

7. The method of claim 1, wherein the homologous recombination between said donor sequence and said plant endogenous DNA sequence comprises gene editing, gene replacement, or a combination of both.

8. A recombinant nucleic acid molecule comprising a first nucleotide sequence encoding a nuclease system and a second nucleotide sequence encoding a viral replicon comprising a donor nucleic acid sequence targeted to endogenous DNA sequence, wherein said nuclease system is targeted to said endogenous DNA sequence in said plant, and wherein at least one component of said nuclease system is operably linked to a UBQ10 gene regulatory sequence, wherein said UBQ10 gene regulatory sequence comprises:

(a) a first regulatory region comprising the sequence of SEQ ID NO:34 or a homolog thereof having at least 95% identity with the sequence of SEQ ID NO:34, and wherein said first regulatory region is 5' of said at least one component of said nuclease system; and (b) a second regulatory region comprising the sequence of SEQ ID NO:38 or a homolog thereof having at least 95% identity with the sequence of SEQ ID NO:38, and wherein said second regulatory region is 3' of said at least one component of said nuclease system;

wherein said nuclease system is selected from a nickase, a CRISPR/Cas system, or a DNA endonuclease enzyme used in targeted gene editing, and wherein said viral replicon is selected from the group consisting of: a geminiviral replicon, a BeYDV replicon, a CalCuV replicon, a ToLCV replicon, a WDV replicon, or any combination thereof.

9. The recombinant nucleic acid of claim 8, wherein said donor sequence comprises a gene, a mutated gene, a part of a gene, a regulatory sequence, a mutated regulatory sequence, a sequence upstream of a gene, a sequence downstream of a gene, an exon sequence, an intron sequence, or any combination thereof.

10. The recombinant nucleic acid of claim 8, wherein said CRISPR/Cas system comprises a Cas nuclease and a gRNA molecule, wherein said gRNA molecule binds within said plant endogenous DNA sequence.

11. The recombinant nucleic acid of claim 10, wherein said Cas nuclease is selected from the group consisting of Cas1, Cas1B, Cas2, Cas3, Cas4, Cas5, Cas6, Cas7, Cas8, Cas9, Cas10, C2cl, CasX, NgAgo, Cpf1, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4.

12. The recombinant nucleic acid of claim 8, wherein at least one component of said nuclease system comprises a Cas nuclease.

13. A method for producing a transgenic plant seed, the method comprising:

(a) introducing into at least one cell of a plant a first nucleic acid comprising a viral replicon comprising a donor nucleic acid sequence, said donor sequence targeted to an endogenous DNA sequence of said plant; and (b) introducing into said at least one cell of a plant (a) a second nucleic acid comprising a nuclease system, wherein said nuclease system is targeted to said endogenous DNA sequence of said plant, and wherein at least one component of said nuclease system is expressed under the control of a UBQ10 gene regulatory sequence;

(c) generating a transgenic plant from said at least one cell of a said plant; and (d) growing said transgenic plant to obtain a seed;

wherein homologous recombination occurs between the donor sequence and said plant endogenous DNA sequence;

thereby producing a transgenic seed of the plant, wherein any plant produced from said seed comprises said donor nucleic acid sequence, wherein said UBQ10 gene regulatory sequence comprises a recombinant nucleic acid molecule comprising:

(i) a first regulatory region comprising the sequence of SEQ ID NO:34 or a homolog thereof having at least 95% identity with the sequence of SEQ ID NO:34, and wherein said first regulatory region is 5' of said at least one component of said nuclease system; and (ii) a second regulatory region comprising the sequence of SEQ ID NO:38 or a homolog thereof having at least 95% identity with the sequence of SEQ ID NO:38, and wherein said second regulatory region is 3' of said at least one component of said nuclease system;

wherein said nuclease system is selected from a nickase, a CRISPR/Cas system, or a DNA endonuclease enzyme used in targeted gene editing, and wherein said viral replicon is selected from the group consisting of: a geminiviral replicon, a BeYDV replicon, a CalCuV replicon, a ToLCV replicon, a WDV replicon, or any combination thereof.

14. The method of claim 13, wherein said donor sequence comprises a gene, a mutated gene, a part of a gene, a regulatory sequence, a mutated regulatory sequence, a sequence upstream of a gene, a sequence downstream of a gene, an exon sequence, an intron sequence, or any combination thereof.

15. The method of claim 13, wherein said CRISPR/Cas system comprises a Cas nuclease and a gRNA molecule, wherein said gRNA molecule binds within said plant endogenous DNA sequence.

16. The method of claim 15, wherein said Cas nuclease is selected from the group consisting of Cas1, Cas1B, Cas2, Cas3, Cas4, Cas5, Cas6, Cas7, Cas8, Cas9, Cas10, C2cl, CasX, NgAgo, Cpf1, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4.

17. The method of claim 13, wherein said at least one component of said nuclease system comprises a Cas nuclease.

18. The method of claim 13, wherein said first nucleic acid and said second nucleic acid are located on a single expression vector.

* * * * *

SEQUENCE LISTING

<160> NUMBER OF SEQ ID NOS: 84

<210> SEQ ID NO 1
<211> LENGTH: 3406
<212> TYPE: DNA
<213> ORGANISM: Solanum lycopersicum

<400> SEQUENCE: 1

```
taccatctat aaaataaagc tttctgcagc tcattttttc atcttctatc tgatttctat      60
tataatttct ctgaattgcc ttcaaatttc tctttcaagg ttagaatttt tctctatttt     120
ttggtttttg tttgtttaga ttctgagttt agttaatcag gtgctgttaa agccctaaat     180
tttgagtttt tttcggttgt tttgatggaa aatacctaac aattgagttt tttcatgttg     240
ttttgtcgga gaatgcctac aattggagtt cctttcgttg ttttgatgag aaagcccta     300 atttgagtgt ttttccgtcg atttgatttt aaaggtttat attcgagttt ttttcgtcgg     360
tttaatgaga aggcctaaaa taggagtttt tctggttgat ttgactaaaa aagccatgga     420
attttgtgtt tttgatgtcg ctttggttct caaggcctaa gatctgagtt tctccggttg     480
ttttgatgaa aaagccctaa aattggagtt tttatcttgt gttttaggtt gttttaatcc     540
ttataatttg agttttttcg ttgttctgat tgttgttttt atgaatttg cagatgcaga     600 tctttgtgaa aactctcacc ggaaagacta tcaccctaga ggtggaaagt tctgatacaa     660
tcgacaacgt taaggctaag atccaggata aggaaggaat tcccccggat cagcaaaggc     720
ttatcttcgc tggaaagcag ttggaggacg gacgtactct agctgattac aacatccaga     780
aggagtccac cctccatttg gtgctccgtc tacgtggtgg tatgcagatc ttcgtgaaga     840
ctctcacggg taagacgatt acccttgagg tcgaaagctc agacaccatt gacaacgtca     900
aggctaagat ccaggataag gaaggcattc ccccagacca gcagaggttg atctttgcag     960
gaaagcagtt ggaagatggc cgcaccctag ctgactacaa catccagaag gagtccaccc    1020
tccatttggt gctccgtctc cgtggtggta tgcagatctt cgttaagact cttaccggaa    1080
agaccatcac tttggaggtg aaagctccg acaccattga caacgtgaag gctaagatcc    1140
aggataagga agggatcccc ccagaccagc agaggttgat cttcgctgga aagcagctcg    1200
aggatggtcg caccctggct gactacaaca tccagaagga gtctaccctc catcttgtcc    1260
tccgtctccg tggtggtatg cagatttttg ttaagaccct caccggaaag accatcactt    1320
tggaggtgga aagctccgac accattgata atgttaaggc taagatccag gacaaggagg    1380
gaattccttc agaccagcag aggttgattt tcgctggtaa gcagctcgag gacggccgca    1440
cccttgccga ctacaacatc cagaaggagt cgacccttca ccttgtcctc cgtctacgtg    1500
gtggtatgca aatctttgtg aagacccta ccgggaaaac catcaccctg gaggttgaga    1560
gctccgacac cattgacaat gtcaaggcca agatccaaga caaggagggt attcccccag    1620
accagcagag gttgattttt gctggcaagc agctcgagga tggccgcact ttggcggact    1680
ataacatcca aaaggagtcg accctgcact tggtgcttag gctgaggggga ggaatgcaga    1740 tctttgtgaa gaccttgacc gggaagacca tcactttgga ggtggagagt tctgacacca    1800
tcgacaatgt gaaagctaag attcaggaca aggagggat cccaccagac cagcagaggt    1860
tgattttcgc tggtaagcag cttgaggatg ccgcaccct tgctgactac aatatccaga    1920
aggagtccac cctgcacctt gtcctccgtc tccgtggtgg tttttaagtt gtggttgtct    1980
ggttgcgtct gttgcccgtt gtctgttgcc cattgtggtg gttgtgtttg tatgatggtc    2040
gttaaggatc atcaatgtgt tttcgctttt tgttccattc tgtttctcat ttgtgaataa    2100
```

-continued

```
taatggtatc tttatgaata tgcagtttgt ggtttctttt ctgattgcag ttctgagcat   2160
tttgtttttg cttccgttta ctataccact tacagtttgc actaatttag ttgatatgcg   2220
agccatctga tgtttgatga ttcaaatggc gtttatgtaa ctcgtacccg agtggatgga   2280
gaagagctcc attgccggtt tgtttcatgg gtggcggagg gcaactcctg ggaaggaaca   2340
aaagaaaaac cgtgatacga gttcatgggt gagagctcca gcttgatccc ttctctgtcg   2400
atcaaatttg aattttttgga tcacggcagg ctcacaagat aatccaaagt aaaacataat   2460
gaatagtact tctcaatgat cacttatttt tagcaaatca gcaattgtgc atgtcaaatg   2520
atttcggtgt aagagaaaga gttgatgaat caaaatatct gtagctggat caagaatctg   2580
aggcagttgt atgtatcaat gatctttccg ctacaatgat gttagctatc cgagtcaaat   2640
tgttgtagaa ttgcatactt cggcatcaca ttctggatga cataataaat aggaagtctt   2700
cagatcccta aaaaattgag agctaataac attagtccta gatgtaactg ggtgacaacc   2760
aagaaagaga catgcaaata ctacttttgt ttgaaggagc atccctggtt tgacatattt   2820
tttctgaata tcaaactttg aaactctacc tagtctaatg tctaacgaca gatcttactg   2880
gtttaactgc agtgatatct actatctttt ggaatgtttt ctccttcagt tatacatcaa   2940
gttccaagat gcaggtgtgc ttgattgatg tacatggctg tgagaagtgc atcctgatgt   3000
tcagatgatg gttcattcta atgtcttttc cttcaatcag ttttctcagt ctgacttagc   3060
ttgtttcatc tgcatgtttg aatgttcgtt tactcatagt aattgcattt ttgtagcaga   3120
acatatcatt ggtcatggtt tcaactgtgc gcgagtctta tgcttattca aactaggaaa   3180
gcctccgtct agagggtaca cgagttgttg ctctgtgtgc gtcagtccat agtattaatc   3240
ttgctagttg tagtatattg tttatgtgga ctcggaattc atcatatgct ccttctttgc   3300
atcaagtaag gcaaggtaat gtatagaagc tttttaactc tttcatggaa gctggccttt   3360
gccagcatac catccagaag atatcaaccc tgcatcttgg ctgccg               3406
```

<210> SEQ ID NO 2
<211> LENGTH: 457
<212> TYPE: PRT
<213> ORGANISM: Solanum lycopersicum

<400> SEQUENCE: 2

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140
```

-continued

```
Leu Val Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
                180                 185                 190

Gln Arg Leu Ile Phe Ala Gly Lys Gln Leu Glu Asp Gly Arg Thr Leu
            195                 200                 205

Ala Asp Tyr Asn Ile Gln Lys Glu Ser Thr Leu His Leu Val Leu Arg
        210                 215                 220

Leu Arg Gly Gly Met Gln Ile Phe Val Lys Thr Leu Thr Gly Lys Thr
225                 230                 235                 240

Ile Thr Leu Glu Val Glu Ser Ser Asp Thr Ile Asp Asn Val Lys Ala
                245                 250                 255

Lys Ile Gln Asp Lys Glu Gly Ile Pro Pro Asp Gln Gln Arg Leu Ile
            260                 265                 270

Phe Ala Gly Lys Gln Leu Glu Asp Gly Arg Thr Leu Ala Asp Tyr Asn
        275                 280                 285

Ile Gln Lys Glu Ser Thr Leu His Leu Val Leu Arg Leu Arg Gly Gly
    290                 295                 300

Met Gln Ile Phe Val Lys Thr Leu Thr Gly Lys Thr Ile Thr Leu Glu
305                 310                 315                 320

Val Glu Ser Ser Asp Thr Ile Asp Asn Val Lys Ala Lys Ile Gln Asp
                325                 330                 335

Lys Glu Gly Ile Pro Pro Asp Gln Gln Arg Leu Ile Phe Ala Gly Lys
            340                 345                 350

Gln Leu Glu Asp Gly Arg Thr Leu Ala Asp Tyr Asn Ile Gln Lys Glu
        355                 360                 365

Ser Thr Leu His Leu Val Leu Arg Leu Arg Gly Gly Met Gln Ile Phe
    370                 375                 380

Val Lys Thr Leu Thr Gly Lys Thr Ile Thr Leu Glu Val Glu Ser Ser
385                 390                 395                 400

Asp Thr Ile Asp Asn Val Lys Ala Lys Ile Gln Asp Lys Glu Gly Ile
                405                 410                 415

Pro Pro Asp Gln Gln Arg Leu Ile Phe Ala Gly Lys Gln Leu Glu Asp
            420                 425                 430

Gly Arg Thr Leu Ala Asp Tyr Asn Ile Gln Lys Glu Ser Thr Leu His
        435                 440                 445

Leu Val Leu Arg Leu Arg Gly Gly Phe
    450                 455
```

```
<210> SEQ ID NO 3
<211> LENGTH: 2914
<212> TYPE: DNA
<213> ORGANISM: Solanum tuberosum

<400> SEQUENCE: 3
tgccatctat aaaatgaagc tttctgcacc tcaatttttc atcttctatc tgatttctat     60
tataatttct attaattgcc ttcaaatttc tctttcaagg ttagaaatct tctctatttt    120
ttggtttttg tctgtttaga ttctcgaatt agctaatcag gtgctgttaa agccctaaaa    180
tttgagtttt ttttccgtcg aattgatgct aaaggcttaa aattagagtt ttttcgtcgg    240
tttgactctg aaggcctaaa atttgggggtt ttccgggtga tttgatgata aagccctaga    300
```

-continued

```
atttgagttt ttttatttgt cggtttgatg aaaaaggcct taaatttaat ttttttcccg    360
gttgatttga tgaaaaagcc ctagaatttg tgtttttttcg tcggtttgat tctaaaggcc    420
taaaatttga gttttttccgg ttgtttttgat gaaaaagccc taaaatttga gttttttccc    480 cgtgtttttag attgtttggt tttaattctt gaatcagata atcagggagt gtgaaaagcc    540
ctaaaatttg agttttttttc gttgttctga ttgttgtttt tatgaatttg cagatgcaga    600
tctttgtgaa aactctcacc ggaaagacca tcaccctaga ggtggaaagt tctgatacaa    660
tcgacaacgt taaggctaag attcaggata aggaaggaat tcccccggat cagcaaaggc    720
ttatcttcgc cggaaagcag ttggaggacg gacgtactct agctgattac aacatccaga    780
aggagtctac cctccatttg gtgctccgtc tacgtggtgg tatgcagatc ttcgttaaga    840
ctcttacggg taagacgatt acccttgagg tcgaaagctc agacaccatt gacaatgtta    900
aggctaagat ccaggataag gaaggcattc ccccagacca gcagaggttg atctttgcag    960
ggaaacagtt ggaagatggc cgcaccctag ctgactacaa catccagaag gagtctaccc   1020
tacatttggt cctccgtctc cgtggtggta tgcagatctt cgttaagact cttaccggaa   1080
agaccatcac tttggaggtg gaaagctccg acaccattga caacgtgaag gctaagatcc   1140
aggataagga gggaattccc ccagaccagc agaggttgat cttcgctggt aagcaattgg   1200
aggacggccg caccctagct gactacaaca tccagaagga gtctaccctc atcttgtcc   1260 tccgtctccg tggtggtatg cagatttttg ttaagaccct caccgggaag accatcactt   1320
tggaggttga aagctccgac accattgata atgtcaaggc taagatccag gacaaggagg   1380
gaattccccc agaccagcag aggttgatct tcgctggaaa gcaattggag gatggccgca   1440
ccctagctga ctacaacatc cagaaggagt ccacccttca ccttgtcctc cgtctccgtg   1500
gtggtatgca gatttttgtt aagacccta ccgggaagac catcaccctg gaggttgaga   1560
gctccgacac cattgacaat gttaaggcca agatccaaga caaggagggt attcccccag   1620
accagcagag gttgatcttc gctggtaaac agcttgagga tggccgcacc cttgcggact   1680
acaacattca gaaggagtcc acccttcact tggtgctgag gctgaggggga ggaatgcaga   1740 tctttgtgaa gaccttaacc gggaagacca tcaccttgga ggtggagagt tctgacacca   1800
tcgacaatgt gaaagctaag attcaggaca aggaggggat cccaccagac cagcagaggt   1860
tgatctttgc tggtaagcag cttgaagatg gacgcaccct tgccgactac aatatccaga   1920
aggagtccac tctgcacctt gtcctccgtc tccgtggtgg tttttaagtt gcctgttgtt   1980
ggttgtcgtg ttgtctggct gtgtctgttg cccattgtgg tggttatgtg tttgcattat   2040
ggtcttaaag gatcatcaat gtgttttcgc tttctgttcc ttttctgtttc tcatttgtga   2100 ataataatgg cgtctttatg aacatccaat ttctggtttc ttttctgatc gcagtttgag   2160
tatttgtttt tgcttttgcc tccgtctatt acaccacttt gcaattacta taatatacta   2220
aaagccttcg atccatcttc tgtttgatga ttcgaatggt atttatttaa ctcatacccca   2280 agtgaagcat aaagttagag gagagttcct gttccattgc ctgtttgtat catgagcaac   2340
tcatgttaat aaacataaga aaaccatga tgcaatctgt gtagctgata gactttgatg   2400
acagacgact cataagtaac aagagataac aaagaggaaa cataataaac atgtacggga   2460
agtcctccaa caatgactat aatcacatgt ttttgtagat tagcaattgt acatgtcaaa   2520
tgatcttgga ttaaggaagg agcttgtgaa tcaaaacatc tgaatttgga cctagagtct   2580
tgaggtgatc gtactttgga tggagagacc atgaataaga ataaatgaat ctggaactga   2640
gaactaaatg gaagacacac tgatccaaca gattaagctt atgacattaa tcacagaagg   2700
```

```
taactcggtg acaaccaaga acggggagct gcaaattcta ttgtcttaac aacggacctt   2760
tactggttta actgttatga tgtctttat aggtggcttt tgggttgttc ttcgctctat   2820 cctttttatgt aactttcaag aaccaaccaa atgcaggtgt tctagataga tatacgtggc   2880
atgtgagaag ggaccctgaa gttcagatga cggt                              2914
```

```
<210> SEQ ID NO 4
<211> LENGTH: 457
<212> TYPE: PRT
<213> ORGANISM: Solanum tuberosum

<400> SEQUENCE: 4

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ala Asp Tyr Asn Ile Gln Lys Glu
        50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
                100                 105                 110

Pro Pro Asp Gln Gln Arg Leu Ile Phe Ala Gly Lys Gln Leu Glu Asp
            115                 120                 125

Gly Arg Thr Leu Ala Asp Tyr Asn Ile Gln Lys Glu Ser Thr Leu His
        130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
                180                 185                 190

Gln Arg Leu Ile Phe Ala Gly Lys Gln Leu Glu Asp Gly Arg Thr Leu
            195                 200                 205

Ala Asp Tyr Asn Ile Gln Lys Glu Ser Thr Leu His Leu Val Leu Arg
        210                 215                 220

Leu Arg Gly Gly Met Gln Ile Phe Val Lys Thr Leu Thr Gly Lys Thr
225                 230                 235                 240

Ile Thr Leu Glu Val Glu Ser Ser Asp Thr Ile Asp Asn Val Lys Ala
                245                 250                 255

Lys Ile Gln Asp Lys Glu Gly Ile Pro Pro Asp Gln Gln Arg Leu Ile
                260                 265                 270

Phe Ala Gly Lys Gln Leu Glu Asp Gly Arg Thr Leu Ala Asp Tyr Asn
            275                 280                 285

Ile Gln Lys Glu Ser Thr Leu His Leu Val Leu Arg Leu Arg Gly Gly
        290                 295                 300

Met Gln Ile Phe Val Lys Thr Leu Thr Gly Lys Thr Ile Thr Leu Glu
305                 310                 315                 320

Val Glu Ser Ser Asp Thr Ile Asp Asn Val Lys Ala Lys Ile Gln Asp
                325                 330                 335
```

-continued

```
Lys Glu Gly Ile Pro Pro Asp Gln Gln Arg Leu Ile Phe Ala Gly Lys
        340                 345                 350

Gln Leu Glu Asp Gly Arg Thr Leu Ala Asp Tyr Asn Ile Gln Lys Glu
        355                 360                 365

Ser Thr Leu His Leu Val Leu Arg Leu Arg Gly Gly Met Gln Ile Phe
        370                 375                 380

Val Lys Thr Leu Thr Gly Lys Thr Ile Thr Leu Glu Val Glu Ser Ser
385                 390                 395                 400

Asp Thr Ile Asp Asn Val Lys Ala Lys Ile Gln Asp Lys Glu Gly Ile
                405                 410                 415

Pro Pro Asp Gln Gln Arg Leu Ile Phe Ala Gly Lys Gln Leu Glu Asp
        420                 425                 430

Gly Arg Thr Leu Ala Asp Tyr Asn Ile Gln Lys Glu Ser Thr Leu His
        435                 440                 445

Leu Val Leu Arg Leu Arg Gly Gly Phe
    450                 455
```

```
<210> SEQ ID NO 5
<211> LENGTH: 2531
<212> TYPE: DNA
<213> ORGANISM: Arabidopsis thaliana

<400> SEQUENCE: 5
caaagagctc ttcttcttca caattcagat ttcaatttct caaaatctta aaaactttct        60
ctcaattctc tctaccgtga tcaaggtaaa tttctgtgtt ccttattctc tcaaaatctt       120
cgattttgtt ttcgttcgat cccaatttcg tatatgttct ttggtttaga ttctgttaat       180
cttagatcga agacgatttt ctgggtttga tcgttagata tcatcttaat tctcgattag       240
ggtttcatag atatcatccg atttgttcaa ataatttgag ttttgtcgaa taattactct       300
tcgatttgtg atttctatct agatctggtg ttagtttcta gtttgtgcga tcgaatttgt       360
cgattaatct gagttttct gattaacaga tgcagatctt tgttaagact ctcaccggaa        420
agacaatcac cctcgaggtg gaaagctccg acaccatcga caacgttaag gccaagatcc       480
aggataagga gggcattcct ccggatcagc agaggcttat tttcgccggc aagcagctag       540
aggatggccg tacgttggct gattacaata tccagaagga atccaccctc acttggtcc        600 tcaggctccg tggtggtatg cagattttcg ttaaaccct aacgggaaag acgattactc        660
ttgaggtgga gagttctgac accatcgaca cgtcaaggc caagatccaa gacaaagagg        720
gtattcctcc ggaccagcag aggctgatct tcgccggaaa gcagttggag gatggcagaa       780
ctcttgctga ctacaatatc cagaaggagt ccaccccttca tcttgttctc aggctccgtg      840
gtggtatgca gattttcgtt aagacgttga ctgggaaaac tatcactttg gaggtggaga       900
gttctgacac cattgataac gtgaaagcca gatccaaga caaagagggt attcctccgg        960
accagcagag attgatcttc gccggaaaac aacttgaaga tggcagaact ttggccgact      1020
acaacattca gaaggagtcc acactccact tggtcttgcg tctgcgtgga ggtatgcaga     1080
tcttcgtgaa gactctcacc ggaaagacca tcacttgga ggtggagagt tctgacacca     1140
ttgataacgt gaaagccaag atccaggaca aagagggtat cccaccggac agcagagat      1200 tgatcttcgc cggaaagcaa cttgaagatg aagaactt ggctgactac aacattcaga       1260
aggagtccac acttcacttg gtcttgcgtc tgcgtggagg tatgcagatc ttcgtgaaga     1320
ctctcaccgg aaagactatc actttggagg tagagagctc tgacaccatt gacaacgtga     1380
```

-continued

```
aggccaagat ccaggataag gaaggaatcc ctccggacca gcagaggttg atctttgccg    1440
gaaaacaatt ggaggatggt cgtactttgg cggattacaa catccagaag gagtcgaccc    1500
ttcacttggt gttgcgtctg cgtggaggta tgcagatctt cgtcaagact ttgaccggaa    1560
agaccatcac ccttgaagtg gaaagctccg acaccattga caacgtcaag gccaagatcc    1620
aggacaagga aggtattcct ccggaccagc agcgtctcat cttcgctgga aagcagcttg    1680
aggatggacg tactttggcc gactacaaca tccagaagga gtctactctt cacttggtcc    1740
tgcgtcttcg tggtggtttc taaatctcgt ctctgttatg cttaagaagt tcaatgtttc    1800
gtttcatgta aaactttggt ggtttgtgtt ttggggcctt gtataatccc tgatgaataa    1860
gtgttctact atgtttccgt tcctgttatc tctttctttc taatgacaag tcgaacttct    1920
tctttatcat cgcttcgttt ttattatctg tgcttctttt gtttaatacg cctgcaaagt    1980
gactcgactc tgtttagtgc agttctgcga aacttgtaaa tagtccaatt gttggcctct    2040
agtaatagat gtagcgaaag tgttgagctg ttgggttcta aggatggctt gaacatgtta    2100 atctttagg ttctgagtat gatgaacatt cgttgttgct aagaaatgcc tgtaatgtcc       2160
cacaaatgta gaaatggtt cgtacctttg tccaagcatt gatatgtctg atgagaggaa      2220
actgcaagat actgagcttg gtttaacgaa ggagaggcag tttcttcctt ccaaagcatt     2280
tcatttgaca atgccttgat catcttaagt agagtttctg ttgtggaaag tttgaaactt     2340
tgaagaaacg actctcaagt aaattgatga tcacaagtga aagtgtatgt tacataagtg     2400
gatatttcac cctttttcca tcaatcaaaa catcatatag taatccattg gtttatacaa     2460
acatcaaaat acatttacct ctgaaatgag gaaaaaaatg caaagagatt tttgaaaatt     2520
tccaacaaat g                                                          2531
```

```
<210> SEQ ID NO 6
<211> LENGTH: 457
<212> TYPE: PRT
<213> ORGANISM: Arabidopsis thaliana

<400> SEQUENCE: 6

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
```

-continued

```
                      165                 170                 175
Asn Val Lys Ala Lys Ile Gln Asp Lys Glu Gly Ile Pro Pro Asp Gln
                180                 185                 190

Gln Arg Leu Ile Phe Ala Gly Lys Gln Leu Glu Asp Gly Arg Thr Leu
            195                 200                 205

Ala Asp Tyr Asn Ile Gln Lys Glu Ser Thr Leu His Leu Val Leu Arg
        210                 215                 220

Leu Arg Gly Gly Met Gln Ile Phe Val Lys Thr Leu Thr Gly Lys Thr
    225                 230                 235                 240

Ile Thr Leu Glu Val Glu Ser Ser Asp Thr Ile Asp Asn Val Lys Ala
                245                 250                 255

Lys Ile Gln Asp Lys Glu Gly Ile Pro Pro Asp Gln Gln Arg Leu Ile
                260                 265                 270

Phe Ala Gly Lys Gln Leu Glu Asp Gly Arg Thr Leu Ala Asp Tyr Asn
            275                 280                 285

Ile Gln Lys Glu Ser Thr Leu His Leu Val Leu Arg Leu Arg Gly Gly
        290                 295                 300

Met Gln Ile Phe Val Lys Thr Leu Thr Gly Lys Thr Ile Thr Leu Glu
    305                 310                 315                 320

Val Glu Ser Ser Asp Thr Ile Asp Asn Val Lys Ala Lys Ile Gln Asp
                325                 330                 335

Lys Glu Gly Ile Pro Pro Asp Gln Gln Arg Leu Ile Phe Ala Gly Lys
            340                 345                 350

Gln Leu Glu Asp Gly Arg Thr Leu Ala Asp Tyr Asn Ile Gln Lys Glu
            355                 360                 365

Ser Thr Leu His Leu Val Leu Arg Leu Arg Gly Gly Met Gln Ile Phe
        370                 375                 380

Val Lys Thr Leu Thr Gly Lys Thr Ile Thr Leu Glu Val Glu Ser Ser
    385                 390                 395                 400

Asp Thr Ile Asp Asn Val Lys Ala Lys Ile Gln Asp Lys Glu Gly Ile
                405                 410                 415

Pro Pro Asp Gln Gln Arg Leu Ile Phe Ala Gly Lys Gln Leu Glu Asp
            420                 425                 430

Gly Arg Thr Leu Ala Asp Tyr Asn Ile Gln Lys Glu Ser Thr Leu His
            435                 440                 445

Leu Val Leu Arg Leu Arg Gly Gly Phe
    450                 455
```

```
<210> SEQ ID NO 7
<211> LENGTH: 3578
<212> TYPE: DNA
<213> ORGANISM: Solanum lycopersicum

<400> SEQUENCE: 7
ctctatgttt ggattctttg ttcaagccat tgttactgga aagggaccat tggagaacct      60
tgctgatcac cttgcagacc cagtaaacaa caacgcctgg tcctacgcca caaactttgt     120
ccccggaaaa taaaaatctt aaaacattct caagtttctg atcatttgtt gaccatgtaa     180
agttgtaatt tgtgagttaa cttgaacaat agaattgatt tttcttacat cttattcctg     240
ttatggtata gtcttgaatt tcattttcca atggcatgaa tgagatgctg caagtttcat     300
atcaaagggg aaaaacaggt gactgttcaa aaaaaattat acatttggta tgtggtaaaa     360
gcttaaaagt tgaatataga gaccagtaga ggaacttatg gaatgattca gttctcaaga     420
agcaatactc ttaacttagt gccgacagta gcatgatgat tcctttattt ttaagttgag     480
```

-continued

```
aagtgagatg aattaagagg acatacgttt atttcactac tacgtacgca gtgacatttc    540
aatgataagg gaaaactaat gtatatgttt tgtcttcaga atcagcaagt actctctctg    600 tttcaatttta atccgtctta ctttcatttt ttacaatacc ttgcttcaac ttttcactta    660
acatgtttaa gaccacaaga ttaaataacg ttttggtaca ttatacatat ctttgtttta    720
agatcataag attcaaaaat attctttact ttcttaaatt ccgtaacaag tcaaaattag    780
acaaacaaaa taaaacggag tgagtgatat tgacgagttt ccagatcatt aatagactga    840
tatgtcgtta atttaattag catctttaac ttgaacaaaa tcataaactt cttgtataat    900
cttccttcct tacatatgtc tttagagtaa aagcatctgt gtgacagctt atataacaga    960
ggcagatatc cttccaaaca tggtacattt tgatcagaat ttacagccaa aaggacacat    1020
agtaagcaga agatattcat gacactatgg aaaagaaaat taagttctat gtattgacat    1080
tgtcaaaaat acttgcacaa tcatatcact tattacagtg gctcgcagag gtagccttca    1140
gcatatcagt ttgacagaac caaatagctt tggcttaaac catgtatatg tgttaacata    1200
ttcattaaat atgtatacag aatttactaa tacttgaggt cattgtccta gattctagaa    1260
ctcataaagt tcaaatcttg attagtcttt cctttttaag taattacaag ttgtgataaa    1320
caccagtaac aatataacga gtataatctc ataactaagg tctggcgagg gtaacgtgtt    1380
aggcagacct taccctacat taagtgacat atagcgctgt tagataaaat ctggagaaat    1440
tttcaatgga taatgataag agatatcata ttgtaagttc aacaaatcac agaatagagt    1500
tcaagccttg tagccaatta aaggtggaca acattagttg ggtccccact gtaaacatcc    1560
tgtaaaattg ttggactaga gattgccaag tagcattact tgctgtatat gggatcttga    1620
tacccaatga gatcataaat atagatatca ctagataagg actctttccc tcttaatccc    1680
tatatatgct gaataattcc cttgtaactt caactcatca cagcaaactt caaaagttta    1740
ccatcaaaca cttactttttc tcttgatata aacacaatgg cagctgctac aatggctctt    1800 tcttccccctt cttttgctgg acaggcggtg aaactctcac cctctgcctc agaaatctct    1860
ggaaatggaa ggatcactat gagaaaggct gttgccaagt ctgccccatc tagcagccca    1920
tggtatggcc ctgaccgtgt taagtacttg ggcccattct ctggtgaatc cccaagctac    1980
ttgaccggtg aattccctgg tgactatgga tgggacactg ctggactttc agcagaccct    2040
gagacctttg ccaagaaccg tgaactcgag gtgatccact gtagatgggc tatgcttggt    2100
gctcttggat gtgtctttcc tgagctcttg gcccgcaacg gtgtaaagtt tggtgaggct    2160
gtgtggttca aggccggatc ccagatcttc agcgagggtg gacttgacta cttgggcaac    2220
ccaagcttgg ttcatgcaca aagcatcttg gccatttggg cttgccaagt gtgttgatg    2280 ggagctgttg aaggttaccg tattgctggt ggacctcttg gtgaggttgt cgacccactc    2340
tacccaggtg gaagcttcga cccattaggc cttgctgaag acccagaggc atttgctgag    2400
ctcaaggtaa aggagatcaa gaacggtaga cttgctatgt tctctatgtt tggattcttt    2460
gttcaagcca ttgttaccgg aaaaggtcca ttggagaacc ttgctgatca ccttgcagac    2520
ccagtaaaca acaacgcctg ggccttcgcc acaaactttg ttcccggaaa gtgaatacca    2580
taaaatgatt tttaaatttt catgtaaagt tgttgtgaat gagttgacaa tataatggat    2640
ttttctattc caatgatttt tagtcctgaa ttttcatctt ctaaacccac aatacgaatc    2700
aaacaataaa actttcattc caaaaacaaa agaaacagaa tagagaataa agccctaacg    2760
aacactttca acgatatggt aattaaaaaa ccacagtaaa ggtgtttata gcttaaactt    2820
```

-continued

```
caatttgtag aacatagcag atttattagg tgcatcgtct atgctatgtt tgagctattg    2880
acacacatat actgacaata acaacaaaca gatagtatat tgtttgcttg aatgttaatg    2940
ttataaatta cattaatttc caggtcgaaa atctctgcag atttttaattt tccattatca   3000 cgtacagtgg tgtatagtga tcattatgac taatgtctct tcatgaccat gagattaact    3060
aacaaaagtc tattcatgga tctatgttaa aagaagaaaa aacgatggtg ggtactggcg    3120
ctagttgctt ggattctttg aaaatgtcaa caagtgtgtt tggaattatc agcataaaca    3180
tgaaggtcaa aacttaaaag ttgaattacc attttagcct tatactaaat taaaatatta    3240
taaattaatt aattaattaa atattaaata tgcttaaatt gttaattaag ttgatcactt    3300
attgttaaaa taatgtagga gaatgaatag ttgtaaaaat aattaattat aaagttatta    3360
cgaaaacgta ttagagaaat tttttcatttc tctatctgat cagttttagg tgtaattttg    3420
tcataatgtg tattaatacc acacctccac tatctcatca ttaatattca caccttcata    3480
atctttccac actctcaaga agttgatggc acttcttgga tcacttaatt tgtaatgttt    3540
ttccatcaaa cacttacttt tctcttgata taaacaca                           3578
```

```
<210> SEQ ID NO 8
<211> LENGTH: 1776
<212> TYPE: DNA
<213> ORGANISM: Solanum lycopersicum

<400> SEQUENCE: 8
ctctatgttt ggattctttg ttcaagccat tgttactgga aagggaccat tggagaacct     60
tgctgatcac cttgcagacc cagtaaacaa caacgcctgg tcctacgcca caaactttgt    120
ccccggaaaa taaaaatctt aaaacattct caagtttctg atcatttgtt gaccatgtaa    180
agttgtaatt tgtgagttaa cttgaacaat agaattgatt tttcttacat cttattcctg    240
ttatggtata gtcttgaatt tcattttcca atggcatgaa tgagatgctg caagtttcat    300
atcaaagggg aaaaacaggt gactgttcaa aaaaaattat acatttggta tgtggtaaaa    360
gcttaaaagt tgaatataga accagtagaa ggaacttatg gaatgattca gttctcaaga    420
agcaatactc ttaacttagt gccgacagta gcatgatgat tcctttattt ttaagttgag    480
aagtgagatg aattaagagg acatacgttt atttcactac tacgtacgca gtgacatttc    540
aatgataagg gaaaactaat gtatatgttt tgtcttcaga atcagcaagt actctctctg    600
tttcaattta atccgtctta ctttcatttt ttacaatacc ttgcttcaac ttttcactta    660
acatgtttaa gaccacaaga ttaaataacg ttttggtaca ttatacatat ctttgtttta    720
agatcataag attcaaaaat attctttact ttcttaaatt ccgtaacaag tcaaaattag    780
acaaacaaaa taaaacggag tgagtgatat tgacgagttt ccagatcatt aatagactga    840
tatgtcgtta atttaattag catctttaac ttgaacaaaa tcataaactt cttgtataat    900
cttccttcct tacatatgtc tttagagtaa aagcatctgt gtgacagctt atataacaga    960
ggcagatatc cttccaaaca tggtacattt tgatcagaat ttacagccaa aaggacacat   1020
agtaagcaga agatattcat gacactatgg aaaagaaaat taagttctat gtattgacat   1080
tgtcaaaaat acttgcacaa tcatatcact tattacagtg gctcgcagag gtagccttca   1140
gcatatcagt ttgacagaac caaatagctt tggcttaaac catgtatatg tgttaacata   1200
ttcattaaat atgtatacag aatttactaa tacttgaggt cattgtccta gattctagaa   1260
ctcataaagt tcaaatcttg attagtcttt ccttttttaag taattacaag ttgtgataaa   1320
caccagtaac aatataacga gtataatctc ataactaagg tctggcgagg gtaacgtgtt   1380
```

```
aggcagacct taccctacat taagtgacat atagcgctgt tagataaaat ctggagaaat      1440
tttcaatgga taatgataag agatatcata ttgtaagttc aacaaatcac agaatagagt      1500
tcaagccttg tagccaatta aaggtggaca acattagttg ggtccccact gtaaacatcc      1560
tgtaaaattg ttggactaga gattgccaag tagcattact tgctgtatat gggatcttga      1620
tacccaatga gatcataaat atagatatca ctagataagg actctttccc tcttaatccc      1680
tatatatgct gaataattcc cttgtaactt caactcatca cagcaaactt caaaagttta      1740
ccatcaaaca cttacttttc tcttgatata aacaca                                1776

<210> SEQ ID NO 9
<211> LENGTH: 968
<212> TYPE: DNA
<213> ORGANISM: Solanum lycopersicum

<400> SEQUENCE: 9
ataccataaa atgatttta aattttcatg taaagttgtt gtgaatgagt tgacaatata        60
atggattttt ctattccaat gattttagt cctgaatttt catcttctaa acccacaata       120
cgaatcaaac aataaaactt tcattccaaa aacaaaagaa acagaataga gaataaagcc       180
ctaacgaaca ctttcaacga tatggtaatt aaaaaaccac agtaaaggtg tttatagctt       240
aaacttcaat ttgtagaaca tagcagattt attaggtgca tcgtctatgc tatgtttgag       300
ctattgacac acatatactg acaataacaa caaacagata gtatattgtt tgcttgaatg       360
ttaatgttat aaattacatt aatttccagg tcgaaaatct ctgcagattt taattttcca       420
ttatcacgta cagtggtgta tagtgatcat tatgactaat gtctcttcat gaccatgaga       480
ttaactaaca aaagtctatt catggatcta tgttaaaaga agaaaaaacg atggtgggta       540
ctggcgctag ttgcttggat tctttgaaaa tgtcaacaag tgtgtttgga attatcagca       600
taaacatgaa ggtcaaaact aaaagttga attaccattt tagccttata ctaaattaaa       660
atattataaa ttaattaatt aattaaatat taaatatgct taaattgtta attaagttga       720
tcacttattg ttaaaataat gtaggagaat gaatagttgt aaaaataatt aattataaag       780
ttattacgaa aacgtattag agaaatttt catttctcta tctgatcagt tttaggtgta       840
attttgtcat aatgtgtatt aataccacac ctccactatc tcatcattaa tattcacacc       900
ttcataatct ttccacactc tcaagaagtt gatggcactt cttggatcac ttaatttgta       960
atgttttt                                                              968

<210> SEQ ID NO 10
<211> LENGTH: 3311
<212> TYPE: DNA
<213> ORGANISM: Solanum lycopersicum

<400> SEQUENCE: 10
atgttactaa agttatgctt gtgagtatca taaatgttag gacgatcaat actctaatag        60
tcaatttgaa aaacatgaga ataataagaa aactaaacgt tttgtaattg ttttctttca       120
tggagttaaa ttaagaggaa actttagtat actataaagc catatactaa gcggatagaa       180
tagtgaaatt tcacggagta tattgttgtt tatacaagaa tattgtgcga aacattatgg       240
atatgtacta ttctgctaat ttagcaacat gaatgaaata tacatctacg tatagagtat       300
atgttatgca tagtataatt gtaatatatg tatatttggt ataaaatata cacttttgta       360
catattatat gatagctgtt taatagttgt ttcactatta tttttcttgg aatatcgaac       420
```

-continued

```
actgaacagt tagaaaattt tatcatttta tgcatattaa aaacctctat tctaagtgta      480
ctcttatatt gttaataatc aaatcatttt aagaaattaa gttgtatata ttgttactat      540
tataaagaat tttttataca ataaggtcat ttaaagatat ttacaagtaa acatttttag      600
aataatatgg aatttgtagt ttaagtttac atgctacaaa agcataatat aatatccact      660
tgaccaaaaa cataaaaata actcatggcc atgcaatagt tcagacactt gtgtgtaaaa      720
taggaccact aatttgtatg agtggcaaat tgacaatgat atttcaattt ataatacata      780
tgtataggtt cttcatgaag ctgcatttaa ctaaaggaaa tttcttgatt attatatctc      840
atttcaaatt agtaaggttc ttaatgaatt aaattaaaaa agattggtta atattttgca      900
tccttcattt tcatgaaaaa ctcatagaga agttcaagtc atatttaagt atatgtaata      960
tgtccataaa aaaatcaaca aagatagagc ttgaataaac cctctccgac ccgagacaaa     1020
attatacaaa gaaaagaaaa tgcaatacta gaatgtaaca cataaactgg taccgatttt     1080
tgaatttata acttcacatt ttctagagtt caacaattta tatatcacga aaaagttact     1140
tttaattact ttaaccacac catattcaac ccctttcat ctggttagct ttggaaaatt      1200
tataagtttt acttttcttg cattaattgt tcagttctta gagaaatact tttggatgaa     1260
aaatatctag actaaagaat cttacttgac agcatagagg acaagtttgc aatattcata     1320
gccacatatt tgttggaccc cattagtaaa aatatcttga aaatattgat gggttataaa     1380
atgccaagtg cctaataaaa tcttgaaaac caatgaaatt gtagatagag atatgataag     1440
ataagaacca accatattcc ctcttataaa tagtgttatt aatcacaaaa ttgaaacata     1500
acaacaacca tcaaaacaca attcatttct ttttatttat taaaattaaa ccatggctgc     1560
ttctacaatg gctctttcct cctctacctt cgccggaaag acggtgaaac tcgcaccatc     1620
ttcttctgaa atcagtggaa atgggagaat tacaatgagg aagactgctg ccaagcccaa     1680
gccagcttcc tctggtagcc catggtatgg tcctgaccgt gttaagtact tgggcccatt     1740
ctctggtgaa tcaccaagct atttgactgg tgagttccct ggtgattacg gatgggacac     1800
tgctgggctt tcagctgacc ctgaaacatt cgctaagaac cgtgagttgg aggttattca     1860
ttgcagatgg gccatgcttg gtgctcttgg atgtgttttc cccgagcttt ggcacgtaa      1920 cggtgttaag tttggtgaag ctgtatggtt caaagctgga tctcaaattt tcagcgaggg     1980
cggacttgac tacttgggaa accctagttt ggttcatgca caaagcattt gggctatttg     2040
ggcttgccaa gttgtgttga tgggagccgt tgagggttac cgtattgctg gtgggcctct     2100
tggtgaggtt gttgatccac tttaccctgg tggtagcttt gacccattgg gccttgctga     2160
agacccagag gcttttgctg agctcaaggt gaaggagatc aagaatggta gacttgctat     2220
gttctccatg tttggattct ttgttcaagc tattgtcacc ggaaagggtc cgttggagaa     2280
ccttgccgac cacattgctg acccagttaa caacaacgcc tgggcttttg ccacaaactt     2340
tgttcccgga aagtgagtgc aacaaactct tctccaatta gtgtgagatt atgagttttt     2400
agctttgtga gagatgaatc tgtagaaggg gtcagttttt taaagcattc tgggttatgg     2460
gttcagtaca agattattgt aaattggttt ggattaatta atgaatcttt tcatcttgca     2520
caagcaattt ttaatatcat atttacaatt tttcatctta aaagttatat acatcgatat     2580
aagaacgcat cataagtaga attcaaccta tgatgacagg tatatcaagt tgtttttccc     2640
ttaaaaaact tataacttct aacgagacga attcaaaatt taaaatgttc gatcagtaag     2700
ttctttaaca ctaatactca tggtccatat aaattttaaa gatatatcta ctttgtaatc     2760
agttcagata aacctgtagc gaagaagtga aagacgttac tgttattaac aaatttggta     2820
```

-continued

```
agtagtatat gcacaaaatt agtataacca cattgaacta accaatattt caaaacattt      2880
atgttatgga gactagacat gaaagtagaa aagtgggatt ataatgcaat agattactat      2940
tgggaaaaaa acactagcaa ctatagatta aaaacgacga aaaggggggt taaccgtgtt      3000
aaacaagagc taaaagaaaa aacacagacg agacgactag agcactgtgt taactcagac      3060
attacctacg ttacatttaa atctgagata aacacgtaaa gtacagagtc atggcacagg      3120
gcagcaccca gtcaagtttc ttcagggatc gtgaacgagg gttatttcaa cagagagagc      3180
tggaaaggcc actttcacac tcattacaag accccaaaaa aagaaagaac agaaaaacaa      3240
gggaggcagt aagatttagt agccgttttg ccataactgt tgttgagact gctttggctg      3300
gccttgtgaa c                                                          3311

<210> SEQ ID NO 11
<211> LENGTH: 1552
<212> TYPE: DNA
<213> ORGANISM: Solanum lycopersicum

<400> SEQUENCE: 11
atgttactaa agttatgctt gtgagtatca taaatgttag gacgatcaat actctaatag        60
tcaatttgaa aaacatgaga ataataagaa aactaaacgt tttgtaattg ttttctttca       120
tggagttaaa ttaagaggaa actttagtat actataaagc catatactaa gcggatagaa       180
tagtgaaatt tcacggagta tattgttgtt tatacaagaa tattgtgcga aacattatgg       240
atatgtacta ttctgctaat ttagcaacat gaatgaaata tacatctacg tatagagtat       300
atgttatgca tagtataatt gtaatatatg tatatttggt ataaaatata cacttttgta       360
catattatat gatagctgtt taatagttgt ttcactatta tttttcttgg aatatcgaac       420
actgaacagt tagaaaattt tatcatttta tgcatattaa aaacctctat tctaagtgta       480
ctcttatatt gttaataatc aaatcatttt aagaaattaa gttgtatata ttgttactat       540
tataaagaat ttttttataca ataaggtcat ttaaagatat ttacaagtaa acatttttag      600
aataatatgg aatttgtagt ttaagtttac atgctacaaa agcataatat aatatccact       660
tgaccaaaaa cataaaaata actcatggcc atgcaatagt tcagacactt gtgtgtaaaa       720
taggaccact aatttgtatg agtggcaaat tgacaatgat atttcaattt ataacacata       780
tgtataggtt cttcatgaag ctgcatttaa ctaaaggaaa tttcttgatt attatatctc       840
atttcaaatt agtaaggttc ttaatgaatt aaattaaaaa agattggtta atattttgca       900
tccttcattt tcatgaaaaa ctcatagaga agttcaagtc atatttaagt atatgtaata       960
tgtccataaa aaaatcaaca aagatagagc ttgaataaac cctctccgac ccgagacaaa      1020
attatacaaa gaaaagaaaa tgcaatacta gaatgtaaca cataaactgg taccgatttt      1080
tgaatttata acttcacatt ttctagagtt caacaattta tatatcacga aaaagttact      1140
tttaattact ttaaccacac catattcaac cccttttcat ctggttagct ttggaaaatt      1200
tataagtttt actttttctt g cattaattgt tcagttctta gagaaatact tttggatgaa     1260
aaatatctag actaaagaat cttacttgac agcatagagg acaagtttgc aatattcata      1320
gccacatatt tgttggaccc cattagtaaa aatatcttga aaatattgat gggttataaa      1380
atgccaagtg cctaataaaa tcttgaaaac caatgaaatt gtagatagag atatgataag      1440
ataagaacca accatattcc ctcttataaa tagtgttatt aatcacaaaa ttgaaacata      1500
acaacaacca tcaaaacaca attcatttct ttttatttat taaaattaaa cc              1552
```

-continued

<210> SEQ ID NO 12
<211> LENGTH: 955
<212> TYPE: DNA
<213> ORGANISM: Solanum lycopersicum

<400> SEQUENCE: 12

```
gtgcaacaaa ctcttctcca attagtgtga gattatgagt ttttagcttt gtgagagatg       60
aatctgtaga aggggtcagt tttttaaagc attctgggtt atgggttcag tacaagatta      120
ttgtaaattg gtttggatta attaatgaat cttttcatct tgcacaagca attttttaata     180 tcatatttac aatttttcat cttaaaagtt atatacatcg atataagaac gcatcataag      240
tagaattcaa cctatgatga caggtatatc aagttgtttt tcccttaaaa aacttataac      300
ttctaacgag acgaattcaa aatttaaaat gttcgatcag taagttcttt aacactaata      360
ctcatggtcc atataaattt taaagatata tctactttgt aatcagttca gataaacctg      420
tagcgaagaa gtgaaagacg ttactgttat taacaaattt ggtaagtagt atatgcacaa      480
aattagtata accacattga actaaccaat atttcaaaac atttatgtta tggagactag      540
acatgaaagt agaaagtgg gattataatg caatagatta ctattgggaa aaaaacacta       600
gcaactatag attaaaaacg acgaaaaggg gggttaaccg tgttaaacaa gagctaaaag      660
aaaaaacaca gacgagacga ctagagcact gtgttaactc agacattacc tacgttacat      720
ttaaatctga gataaacacg taaagtacag agtcatggca cagggcagca cccagtcaag      780
tttcttcagg gatcgtgaac gagggttatt tcaacagaga gagctggaaa ggccactttc      840
acactcatta caagacccca aaaaaagaaa gaacagaaaa acaagggagg cagtaagatt      900
tagtagccgt tttgccataa ctgttgttga gactgctttg gctggccttg tgaac           955
```

<210> SEQ ID NO 13
<211> LENGTH: 5698
<212> TYPE: DNA
<213> ORGANISM: Solanum lycopersicum

<400> SEQUENCE: 13

```
atgtaaaaag attgatcaga ataaatatta ttgagaagat taaactatgt caaccaataa       60
aataaagaaa ttttatatat taaaatatga atgaaaatgt aaaaagaagt tgggagatga      120
aagaaaaaga aatttaatga gtgaaataaa ttttagagtt cctacacaga agaattgtag      180
aaaatagtaa attaaagttt ttcttagaaa agttaaattt atacaacaaa attatgaaaa      240
catgagaaga cacatggaaa attgaaaagt caaatattat taaaataaat ataaaaaaga      300
tagagatgaa atttaacttt aagaaataca gacatctact ttaatttctt gtcattaaaa      360
aataattaat cattcgtatt tttttaaaat ttgtgtgaga aatttgaaag gtcaaaatct      420
tgaaatgaga ataagaagat tatatatata tatgaaaatt ataaaagttt taatttagta      480
gaggagcaaa atgataattc aacttttcac tttggagctt tccacttata ataatatatg      540
attctaagtc taacttacga agatgaaagt acaaaaaaaa aaagtataat tatttacact      600
tcaatcaaat aataacaatt taatgtgatc aagcaaataa gatataatac ttatatttta      660
tatagaaaaa taaaacattt ttgttcctac caaaatacac cactatttca aaatctaaag      720
gataagggta tatatcatat aaaggaagaa atatttttga agccacaaat ttgcaaaggt      780
gttgatgatt ctttcaatgt aatttaaaat ccttataaag atcattggaa ttaaatgaaa      840
aaaaaaacat ttttataatg aggtagggag aagacagaaa tttcataggc acatcttaac      900
taaattatag ttctattacc gcccaaactc attttatgca taatattgta tacctttag       960
```

```
cttatgtaat atatcctgtg actctacata gttgaagcgc gtgagaaata tttaggtgtc    1020
acgtaagcca aaaagataaa taaaattgca gaaaaaataa ttcagacgaa taatatgacc    1080
ttaatttagt taagacgtgt ctctgagatt tgaatcatag tctagagagg tacttctacc    1140
gatgaggtat aaagaaaaag atggatatgg acaaggggatt tctagttttt ggctggacca    1200
atggcaggga gtcttaggga caaggtggca attttcttat ggatagcaaa taactgccat    1260
gtcatcaatt tacacataat aatgtttaat agaagaaaag aataatcaaa ttgccaataa    1320
gaacaaaact ctttgaaaaa atttaattag aaattttcct ttcttgatca ttaaaagtgt    1380
aagttaccta tacataatta gaatgttttc ttgcttttgc taaataaaca taaaataata    1440
tttcaaaata tattataacg aaacttgttt tttctacctc cattatgaca tacttgatat    1500
attctcgcta gttgtttgcc tttgttttta gtattatcaa ctttactagt aaaattatta    1560
ctcgttttta ctatctctcg tggacaaccg atgtttatgt gttacataaa cttttgaggt    1620
gtttagatga tcattttgta agttgaagtg ttcgactaac agaatgaaga taagttgagg    1680
tgtctgaata tgcatactca aagttaaaat gtgtacttag catttaaaga caagttgagc    1740
gtctgtttat gtattatgcc taacaaaaat cgaaacatat gatgcaaaaa aaaacaaaaa    1800
atctagcaca tcaagtaaaa aaaaaattaa aatggaacat acaagtagac aaatctcaac    1860
catacaatga gtgagaggct atctatctat ctatcatcca taatctcatc cattttcttc    1920
cctccattca ttcattcata aacttccaca atttttcttc atcaacacat aaactgtact    1980
gctgttgctg taattctctt aaagaacaat ggctgctctc tcagtagcca acacttctct    2040
taaggtacct cattcactcg tcctgcattc catcttatta ttaattgatc ctgacttgtt    2100
cgggactgag acgtacgtag ttatgaatat gtttgttgtt ttcttaaaac tgatggacag    2160
gttaacaaca aaggattctc tgaattctct ggtttgagaa cctcatcagc tgttccattt    2220
gggaggaaaa ctaatgatga tttgttctct gttgctggct tacaaacctc tgctgtgagt    2280
attattatac aactactact attattgcat cataagatag tttaagttct gtgcaccgac    2340
gatgtaaaac atttatacgc tatcaggtca tagcctttaa ttagtattga tagtgtaaaa    2400
aatctaacat tgtcggtgta tacaacttga atccttacaa agtttaagga aaaaagaata    2460
tgtatccttc atgtcttgtt gtgatcaaga tgtgctctaa attttttttc gggggaaaaa    2520
agacagatat accccgaat aatcgtaaat ggtatgcaga tacactccgt catacttttg    2580
agacattagt gccctacta tccaaaaact agagcatata tgaccttcac tctaacggaa    2640 gactaaaatag ggacacgtgg cgcaatctta tatgttgata aatgtcggat cgatggataa    2700
gattgtgaca tgtgtatgtc tgttaatata aagggtatat atgctctagt ttttgaacag    2760
taggggcaac aatgttccaa aagtatgacg gagggtactt gcataccact tacgatagtt    2820
caagggtata tttgtccttt ttccttttct ttcccttgta tgttctacct tttctatgtt    2880
gaaagcagcc tccatacaaa gatctttatg caaattcatc aatttgataa gttttaagga    2940
agatcaaaca ctataaaatg aatgataaca ttgtataaac atctaaattg tatttccttc    3000
ctatgttatg ttgctcggac tgtccaaaat tgttgttgca cccatgtcgg gttctcccaa    3060
aatgtactac ttttggagta tccgacatgc acttgtcagc attttttgac gagtctgagt    3120
aacatagctt ccaacgatgt ttcttgtggt aattggattt aatgaaatgt agattggagg    3180
aaggaagaac aagaggatag taactgaggc aaagttgaaa gtggctatca atggatttgg    3240
aagaattgga aggaacttct tgaggtgctg gcatggtaga aaagactcac ctcttgatgt    3300
```

-continued

```
cattgccatc aatgacactg gtggtgtcaa gcaagcctct caccttctca aatatgactc   3360
cacccttggc atctttgatg ctgacgtcaa gccggttggc actgatggca tctctgtcga   3420
tggaaaagtc atccaagtcg tctccaaccg tgaccctgtg aacctcccat gggggtatgt   3480
tctttcatac taacatataa caaaacagat ttaagttgta tatgtttaca cgtagtgtaa   3540
ctaatttaca ttatacgttt gcagattcag gaaactcata ttattagttg tctaaacaga   3600
aacagtcgtt ctaagtttta atagccatga attatagact taagggtaac aaccaaacct   3660
aaactatcac attttttgcga gtttcatacg tcagctatcc attgttctac ttagtactta   3720
catacctaaa ctgacacatt tttgcgagct tcatacctca actattactt gcttcatatt   3780
aaaaaatacc ttgatgttga gttggcctac atgcctgttg ttgattgaga acaaatatat   3840
ggccaacttg agagatagtt taggtacaaa aagagaacaa tggatagttg agatatgaaa   3900
ctcgcgagga agtgatagtt taagtgttta attatcatta actctgaatt aaaacatgat   3960
taatttagct catgtagtgt ctaacatata gtactagctt gagataccta gtaaacatct   4020
aaactattgt tcaaaatgtg ttctgtaatt tgttcagaga acttggagtt gacttagtca   4080
tagaaggtac cggagttttt gtagacagag aaggtgccgg taaacacatc caggccggag   4140
ccaagaaggt gctcatcacc gcccccggaa aaggtgacat ccctacttat gttgttggtg   4200
tcaatgctga actttacagc catgatgaac ctatcatcag caatgcctct tgtaccacca   4260
actgccttgc tcctttcgtc aaggttcttg accagaaatt tggtaataca tcttgatcta   4320
gtcatacacg agcatatact gttagtatat ataacttaaa ctcatcaata aattatcttt   4380
ccttatcata ggaattatca agggaacaat gacaactact cactcttaca ccggtgacca   4440
aaggcttctt gatgcaagcc acagggatct tagacgtgca cgagctgcag cactgaacat   4500
agttccaacc tcaactggtg ctgctaaggc tgtggctctt gttctcccaa gcctcaaggg   4560
gaaactcaac ggcattgccc tccgtgttcc cacccctaac gtctcggttg tggaccttgt   4620
tgtgcaagtc accaagaaga catttgctga ggaagtgaat gctgcattca gagaggccgc   4680
tgataaggaa ctcaatggca ttctatctgt ctgtgatgaa ccactcgtgt cagttgactt   4740
ccggtgcagt gacgtgtcat caactgttga ttcttcactc accatggtca tgggagatga   4800
catggttaag gttattgctt ggtatgacaa tgaatggggt tactcacaga gggttgttga   4860
tcttgctgac attgttgcaa accagtggaa atgaaacatg aaaataaaat aaagcagtac   4920
tactaaatag tggcttaatt tatatttttt taaccttgct tgtagattct tattcctttt   4980
tgaaaattgt aatgagaact ataacaattt tccaccttgt gaaatctcaa ttcaataaaa   5040
gtcccctttc ttgtctttat acagtccgct tctgtatatg ttgcaaagga gctctttgaa   5100
gacttattcc agataggtag aatgtaccaa aatgttcttc aatctcgtgc atgtcatgtg   5160
gaaagtttaa attagagagt tgtcaaaaca agaaagagac tttcatttgc tgaaacggac   5220
tacaaaaaga aagtaggaca agtaaattga aacggagggg agtacaagat attctgtagt   5280
tcaacatcat gtaattggtg ataggttgct cgaactcttc aacaacatgc aaggtgtgtg   5340
tcggatcctc caaaagttta tgtatgtttg aaggatctga cacatgagcg acaacatttt   5400
tggaggattc gagtaacata gattaggtga tgaatggact aaatactgaa gcaaaaactt   5460
attatactca taggtaacta cattttttgga ggattcgagt aacatagatt aatgtgctcc   5520
agaagttttt tgtgattcca aaagagcttc cttgatagag tacaattggg aaacagtttc   5580
agtgatgttc attctttcag ctccagaata tgcagaacaa gcaaccccga ctcgaagaac   5640
agaaacaaga aactccttat tctgatagat atttgtgctt ttaccttgct catcttct     5698
```

```
<210> SEQ ID NO 14
<211> LENGTH: 2008
<212> TYPE: DNA
<213> ORGANISM: Solanum lycopersicum

<400> SEQUENCE: 14
atgtaaaaag attgatcaga ataaatatta ttgagaagat taaactatgt caaccaataa      60
aataaagaaa ttttatatat taaaatatga atgaaaatgt aaaaagaagt tgggagatga     120
aagaaaaaga aatttaatga gtgaaataaa ttttagagtt cctacacaga agaattgtag     180
aaaatagtaa attaaagttt ttcttagaaa agttaaattt atacaacaaa attatgaaaa     240
catgagaaga cacatggaaa attgaaaagt caaatattat taaaataaat ataaaaaaga     300
tagagatgaa atttaacttt aagaaataca gacatctact ttaatttctt gtcattaaaa     360
aataattaat cattcgtatt tttttaaaat ttgtgtgaga aatttgaaag gtcaaaatct     420
tgaaatgaga ataagaagat tatatatata tatgaaaatt ataaaagttt taatttagta     480
gaggagcaaa atgataattc aacttttcac tttggagctt tccacttata ataatatatg     540
attctaagtc taacttacga agatgaaagt acaaaaaaaa aaagtataat tatttacact     600
tcaatcaaat aataacaatt taatgtgatc aagcaaataa gatataatac ttatatttta     660
tatagaaaaa taaaacattt ttgttcctac caaaatacac cactatttca aaatctaaag     720
gataagggta tatatcatat aaaggaagaa atattttttga agccacaaat ttgcaaaggt     780
gttgatgatt ctttcaatgt aatttaaaat ccttataaag atcattggaa ttaaatgaaa     840
aaaaaaacat ttttataatg aggtagggag aagacagaaa tttcataggc acatcttaac     900
taaattatag ttctattacc gcccaaactc attttatgca taatattgta taccttttag     960
cttatgtaat atatcctgtg actctacata gttgaagcgc gtgagaaata tttaggtgtc    1020
acgtaagcca aaaagataaa taaaattgca gaaaaaataa ttcagacgaa taatatgacc    1080
ttaatttagt taagacgtgt ctctgagatt tgaatcatag tctagagagg tacttctacc    1140
gatgaggtat aaagaaaaag atggatatgg acaagggatt tctagttttt ggctggacca    1200
atggcaggga gtcttaggga caaggtggca attttcttat ggatagcaaa taactgccat    1260
gtcatcaatt tacacataat aatgtttaat agaagaaaag aataatcaaa ttgccaataa    1320
gaacaaaact ctttgaaaaa atttaattag aaatttttcct ttcttgatca ttaaaagtgt    1380
aagttaccta tacataatta gaatgtttttc ttgcttttgc taaataaaca taaaataata    1440
tttcaaaata tattataacg aaacttgttt tttctacctc cattatgaca tacttgatat    1500
attctcgcta gttgtttgcc tttgttttta gtattatcaa ctttactagt aaaattatta    1560
ctcgttttta ctatctctcg tggacaaccg atgtttatgt gttacataaa cttttgaggt    1620
gtttagatga tcattttgta agttgaagtg ttcgactaac agaatgaaga taagttgagg    1680
tgtctgaata tgcatactca aagttaaaat gtgtacttag catttaaaga caagttgagc    1740
gtctgtttat gtattatgcc taacaaaaat cgaaacatat gatgcaaaaa aaaacaaaaa    1800
atctagcaca tcaagtaaaa aaaaaattaa aatggaacat acaagtagac aaatctcaac    1860
catacaatga gtgagaggct atctatctat ctatcatcca taatctcatc cattttcttc    1920
cctccattca ttcattcata aacttccaca atttttcttc atcaacacat aaactgtact    1980
gctgttgctg taattctctt aaagaaca                                       2008

<210> SEQ ID NO 15
```

```
<211> LENGTH: 804
<212> TYPE: DNA
<213> ORGANISM: Solanum lycopersicum

<400> SEQUENCE: 15
aacatgaaaa taaaataaag cagtactact aaatagtggc ttaatttata ttttttttaac       60 cttgcttgta gattcttatt ccttttttgaa aattgtaatg agaactataa caattttcca     120
ccttgtgaaa tctcaattca ataaaagtcc cctttcttgt ctttatacag tccgcttctg     180
tatatgttgc aaaggagctc tttgaagact tattccagat aggtagaatg taccaaaatg     240
ttcttcaatc tcgtgcatgt catgtggaaa gtttaaatta gagagttgtc aaaacaagaa     300
agagactttc atttgctgaa acggactaca aaaagaaagt aggacaagta aattgaaacg     360
gaggggagta caagatattc tgtagttcaa catcatgtaa ttggtgatag gttgctcgaa     420
ctcttcaaca acatgcaagg tgtgtgtcgg atcctccaaa agtttatgta tgtttgaagg     480
atctgacaca tgagcgacaa cattttttgga ggattcgagt aacatagatt aggtgatgaa     540
tggactaaat actgaagcaa aaacttatta tactcatagg taactacatt tttgaggat     600 tcgagtaaca tagattaatg tgctccagaa gttttttgtg attccaaaag agcttccttg     660
atagagtaca attgggaaac agtttcagtg atgttcattc tttcagctcc agaatatgca     720
gaacaagcaa ccccgactcg aagaacagaa acaagaaact ccttattctg atagatattt     780 gtgctttttac cttgctcatc ttct                                          804

<210> SEQ ID NO 16
<211> LENGTH: 4578
<212> TYPE: DNA
<213> ORGANISM: Solanum lycopersicum

<400> SEQUENCE: 16
gcgccgtctc gctcgggagg tcactaagtt aaggctagaa actagaaagg tataaatgtt      60
cccaaaaaaa tgatataaaa tagtggttag atatgacgtg atatattgta atttaataga     120
agaatataaa ggtgaatatt aaagtagaca gttaataaat ttaatgttcg tattaagatt     180
attattattc ttttaatatc ttactttttg attttattaa tatttgaaca aacttcatat     240
cgatcaagta actattagta tttgcgtttc atacaaaagt tatataacta gtttctctaa     300
cccaaagtca ctaaatttttg agatacaaac aaaaaagtca caaagtcaaa acatatcata     360
tctacaaagt atcattattt ttagcggaaa atacattatt tctgacatac tactttgtat     420
acataacgaa taatgacata actatgtcat taattaattg aatgtgtcaa agtacaaatt     480
catctagaaa tactttttatc ttggatgtgt aataatatga agttattata tcaagctact     540
tatacaaaga ggaagattga acaagcatga catctcacaca tttcttaatc attttatcgt     600
atataattaa acacatttca ttaacaaaat aatcatttaa ttcttcattt tctattaaaa     660
ttagaactta tttaattatc ttacaatatt ttttatcaat actcttcaat gatcatctta     720
ttcattaaac acaacttaat taatcatatt aaacataaac ttgtgtagtc aattatgaac     780
atacttgtgt agatttttggg ccacaaatta ttggtatcta ccaagttcta gagaaaaaat     840
aatacgtgaa aaaatatttc tcgaaacgta aacattaact attttttatgc taaaagtact     900 atattgaatt attatttttg tttcctatgt aacataaata tttaaatttt atcatcactt     960
tttgaaaaat aattttaatt tttacatgtt aaattattta aataaatatc atattatttg    1020
agataaataa aaagaataaa cattaacaac ttaaaccaag gtacgtgcat gcccacaatt    1080
tgttccaaca gaaaatgtta tttccttggg tagataagaa gtcactatca atttggtcga    1140
```

-continued

```
ttaattcaga aatttatcga gaaattcgta gttgttactt tttttatagca tattaagtaa    1200 cttatttttg tataagaatt tacaaatcac attaataata tatatcgtat taaataaatt    1260
gaacctgatg aattcaatta aaatgacata acagattaaa ttgaacccta atctttcttg    1320
atatcgagtg tgtttggtat gaaggaacca gaaagtgttt tccaattttc tcatgtttgg    1380
ttgggacaaa aattttgaaa aaagtttttc gaatcaactc attttcctca aaattaagaa    1440
aaatgatttc ctttaaaaaa ttaaggaaaa cattttttcca aactctcctc aaatttaaaa   1500
ttacattttt attttaggaa aaacaacaat ctttttaaaa aaatttaatt ctaaattatt    1560
tttttagccg atccctgacc accacccaaa cgcacctatc atctcatatg ctacatcagc    1620
tcgatcacaa tatacttcat ttgtttcgat ttatgtgaca cttttcgttt ttcaagagtc    1680
aaataattaa agtttgaccg aaaacatacg cgcgaaattt tctatttttt aaaataaaat    1740
ttatacaact atataaaaag tactataggt cacaataact gttaattcaa aataaataaa    1800
aataaatata aaaaatttac aatcaaagat aaaatcattt aaatcttgaa aagtgtcaaa    1860
atataaagtt atttagtttg ttataaacat tcgatataga taaataagtc gcggtcgata    1920
gagaatgtaa atatgtctag aacatacgta cgaatggtaa ttgtgattat agaaaacgac    1980
gaatacgtgg atgaaattag gatcatgtat ggaccgactt acaaggataa catattccca    2040
tacgatcacg acacgtgtac ggttaatatc atccatgtac cttcgtttca ctataaatag    2100
acactcatgc ttcttccctc aatcactcat ttctacacca atcaaaaaaa aaaaatcaca    2160
tttgatttct caattcttgt ttcagaccaa tcaatcaatg tcgtgctgtg gaggaaactg    2220
tggctgtgga tctagctgca agtgcggcaa cggctgtgga gggtaaaccc ctaattttttt   2280 ttttcgattt ctcgtcttgc gttcgatatc tgaatgagtg tgcgctttgt aaaggtctat    2340
tttatgggag ataacaactc tacaaaagat tttttttgtt ttgtttttata ttagcttgaa   2400 tttgagaatt ctggttaaga gtttttttttt tgtggtggga tccatgcatg gatgtgtttt   2460
tcttgtgaag gattgagttt tttttttttga gatttgttgg ctgatccctt gattttttatt  2520 tgtttttatct tcttttttatc aaaactttac actactaaat ttttgatccc atgcatggat  2580
tgatgcaaaa tggaattttg atggggaatt gtgggatcac aataatagtt ttgtgttggg    2640 caattttttgt gctaatttttg agggattggt gacaagcaag ggttggatct agaaccaaag   2700
gagcggttat attagtgacc taagacaaaa atcaggattt taaacatgaa ttataataac    2760
atttatataa taataatatt tatataattg atttcttttta gatttcaaat atcaattatt   2820
tttattttaa attatttttt attagataca gtacatcaaa tatgttctaa taatttcttt    2880
atttttatga aaagtttatt tattttttta taaatagtat tcaatatttg ttaaaaaata   2940
ataacttata atttatcatt attaaaagtg aaagtcctta aatttgggac ataaagggca    3000
cttctttttt aacattatgg aatcaccctg ctacgatctc tgaaaatggc gaaagaacaa    3060
actcgaaagc caattatccc gatcatttgg ttatcgagtg ctctgggtta atttgatata    3120
aatacctttt aattttttata tttctatata tatatatata tgaggagtat aaggagtttg   3180
atgggtctaa tttccttatc attgagctgt caatccgtta gtttcacgag ttattactta    3240
ataatattag tgtttgaacc cacaaactcc caccaagctc cgcccttaat tgagctttct    3300
cttgtttgat gttgttgagg gtatgtttca tattttttttt tttttaaattt ggtgtggagt  3360 tgcaagatgt acccagacat gagctacacc gaaagcagca caaccactga gactttggtg    3420
cttggggtgg gacctgagaa gacaagcttc ggcgccatgg agatgggtga atcccctgtt    3480
```

-continued

```
gctgagaatg gctgcaaatg tggatctgac tgcaagtgca acccttgcac ttgttctaag   3540
tgaacgaaaa tatagttgaa acagagcaga gatcatggtg ttagccttct atggctgaag   3600
aaaaatagtt gaaaaaatgt gtgtgtctag tgttttagtg tgtctgtctg ttgaaaacag   3660
ggaaaaaaat gtgttctttt ttccctgtaa taagaaatat agtaatggag tctttatgtg   3720
taagtaacca gtaaatggt ttgtgtaaac atgaatatct ctgcatctgt taattttaac   3780
atataagttt ggatatgtgt tgtggtttca actaattcaa gtacttcctt gataatgttt   3840
tcctgtttct aggctgcaaa actatagtaa atctttagg ttttggtaaa acctaattcc   3900
attgggtgtg gttggagagc atatagtttt tgcgaatatg taaatttcta tcggggaaaa   3960
gggaagatcc gcttgataga ggagtttttca ttcatcagca tagactaaaa gtgctcttcg   4020
agctgagtcg agtttgattc cattctccat ttttcttttg tgactttgct taccatatcc   4080
atgttggacc aatgtataat aaacacaaag atagccacaa ttgtatcaaa tttcacaata   4140
ggaaaaagct atctaacaaa aataataccc aagagatata aagtataata atgctgaaat   4200
attttatggt tggaattagt acaatacaag ccgtttgagt agaaaggaag gtaaatttct   4260
tgtccagttc tagcctgagc ttagtattat aaggtgatta acacaagccc tcaaatccaa   4320
ctactcataa ataatatcac aaagataaat taaaattcta gccagaaaca caatctttct   4380
tatacatgat cctacaaaca acaagatgtt gcagagaagt ttttcattcc aatactcctc   4440
ttgcagccca cctgaataag ttatgtacct agagacaaat actctgagaa tactgcatat   4500
actacagaca cgagaagaag gaataaaatg gaaatgcaga tcatagcgtt gaattacctg   4560
ttttgatgtc aatccaat                                                  4578

<210> SEQ ID NO 17
<211> LENGTH: 2197
<212> TYPE: DNA
<213> ORGANISM: Solanum lycopersicum

<400> SEQUENCE: 17
gcgccgtctc gctcgggagg tcactaagtt aaggctagaa actagaaagg tataaatgtt    60
cccaaaaaaa tgatataaaa tagtggttag atatgacgtg atatattgta atttaataga   120
agaatataaa ggtgaatatt aaagtagaca gttaataaat ttaatgttcg tattaagatt   180
attattattc ttttaatatc ttacttttttg attttattaa tatttgaaca aacttcatat   240
cgatcaagta actattagta tttgcgtttc atacaaaagt tatataacta gtttctctaa   300
cccaaagtca ctaaattttg agatacaaac aaaaaagtca caaagtcaaa acatatcata   360
tctacaaagt atcattattt ttagcggaaa atacattatt tctgacatac tactttgtat   420
acataacgaa taatgacata actatgtcat taattaattg aatgtgtcaa agtacaaatt   480
catctagaaa tacttttatc ttggatgtgt aataatatga agttattata tcaagctact   540
tatacaaaga ggaagattga acaagcatga catctcacaca tttcttaatc attttatcgt   600
atataattaa acacatttca ttaacaaaat aatcatttaa ttcttcattt tctattaaaa   660
ttagaactta tttaattatc ttacaatatt ttttatcaat actcttcaat gatcatctta   720
ttcattaaac acaacttaat taatcatatt aaacataaac ttgtgtagtc aattatgaac   780
atacttgtgt agattttggg ccacaaatta ttggtatcta ccaagttcta gagaaaaaat   840
aatacgtgaa aaaaatattc tcgaaacgta aacattaact attttatgc taaaagtact   900 atattgaatt attattttttg tttcctatgt aacataaata tttaaatttt atcatcactt   960
tttgaaaaat aatttttaatt tttacatgtt aaattattta aataaatatc atattatttg  1020
```

```
agataaataa aaagaataaa cattaacaac ttaaaccaag gtacgtgcat gcccacaatt      1080
tgttccaaca gaaaatgtta tttccttggg tagataagaa gtcactatca atttggtcga      1140
ttaattcaga aatttatcga gaaattcgta gttgttactt ttttatagca tattaagtaa      1200 cttattttg tataagaatt tacaaatcac attaataata tatatcgtat taaataaatt       1260
gaacctgatg aattcaatta aaatgacata acagattaaa ttgaacccta atctttcttg      1320
atatcgagtg tgtttggtat gaaggaacca gaaagtgttt tccaatttc tcatgtttgg       1380 ttgggacaaa aattttgaaa aaagtttttc gaatcaactc attttcctca aaattaagaa      1440
aaatgatttc ctttaaaaaa ttaaggaaaa cattttccca aactctcctc aaatttaaaa      1500
ttacattttt attttaggaa aaacaacaat cttttaaaa aaatttaatt ctaaattatt       1560
tttttagccg atccctgacc accacccaaa cgcacctatc atctcatatg ctacatcagc      1620
tcgatcacaa tatacttcat ttgtttcgat ttatgtgaca cttttcgttt ttcaagagtc      1680
aaataattaa agtttgaccg aaaacatacg cgcgaaattt tctattttt aaaataaaat       1740 ttatacaact atataaaaag tactataggt cacaataact gttaattcaa aataaataaa      1800
aataaatata aaaaatttac aatcaaagat aaaatcattt aaatcttgaa aagtgtcaaa      1860
atataaagtt atttagtttg ttataaacat tcgatataga taaataagtc gcggtcgata      1920
gagaatgtaa atatgtctag aacatacgta cgaatggtaa ttgtgattat agaaaacgac      1980
gaatacgtgg atgaaattag gatcatgtat ggaccgactt acaaggataa catattccca      2040
tacgatcacg acacgtgtac ggttaatatc atccatgtac cttcgtttca ctataaatag      2100
acactcatgc ttcttccctc aatcactcat ttctacacca atcaaaaaaa aaaaatcaca      2160
tttgatttct caattcttgt ttcagaccaa tcaatca                              2197
```

```
<210> SEQ ID NO 18
<211> LENGTH: 1035
<212> TYPE: DNA
<213> ORGANISM: Solanum lycopersicum

<400> SEQUENCE: 18
acgaaaatat agttgaaaca gagcagagat catggtgtta gccttctatg gctgaagaaa        60
aatagttgaa aaaatgtgtg tgtctagtgt tttagtgtgt ctgtctgttg aaaacaggga       120
aaaaaatgtg ttcttttttc cctgtaataa gaaatatagt aatggagtct ttatgtgtaa       180
gtaaccagta aaatggtttg tgtaaacatg aatatctctg catctgttaa ttttaacata       240
taagtttgga tatgtgttgt ggtttcaact aattcaagta cttccttgat aatgttttcc       300
tgtttctagg ctgcaaaact atagtaaatc ttttaggttt tggtaaaacc taattccatt       360
gggtgtggtt ggagagcata tagttttttgc gaatatgtaa atttctatcg gggaaaaggg      420
aagatccgct tgatagagga gttttcattc atcagcatag actaaaagtg ctcttcgagc       480
tgagtcgagt ttgattccat tctccatttt tcttttgtga ctttgcttac catatccatg      540
ttggaccaat gtataataaa cacaaagata gccacaattg tatcaaattt cacaatagga      600
aaaagctatc taacaaaaat aatacccaag agatataaag tataataatg ctgaaatatt      660
ttatggttgg aattagtaca atacaagccg tttgagtaga aaggaaggta aatttcttgt       720
ccagttctag cctgagctta gtattataag gtgattaaca caagccctca aatccaacta      780
ctcataaata atatcacaaa gataaattaa aattctagcc agaaacacaa tctttcttat      840
acatgatcct acaaacaaca agatgttgca gagaagtttt tcattccaat actcctcttg      900
```

| cagcccacct gaataagtta tgtacctaga gacaaatact ctgagaatac tgcatatact | 960 |
| acagacacga gaagaaggaa taaaatggaa atgcagatca tagcgttgaa ttacctgttt | 1020 |
| tgatgtcaat ccaat | 1035 |

<210> SEQ ID NO 19
<211> LENGTH: 3723
<212> TYPE: DNA
<213> ORGANISM: Solanum lycopersicum

<400> SEQUENCE: 19

| tatttctacg tccacgtaga cacatataaa ccttcaaaat aaattattga atagtgtaag | 60 |
| ggtaaaagat catatacaaa attttgtatc gttatatcat tttttatcaa agtttgaata | 120 |
| tatttcagac attttctcat aatcaaagta tatatatata tatttgataa ttcatttacg | 180 |
| taatatgtac atgagaacac acacatagaa gacagataaa taaaatttga atttatttcg | 240 |
| acgaacaatc atgtcttcca actttgcatg tgcacgagta gatacctaaa ttcatataaa | 300 |
| attcacaagt agacgcacat aatatatatg acataataca gataagatat catgtagaaa | 360 |
| gaacgtgtca atttgtttaa tttaatataa agttaagcgt ctacttatga ctaatatttc | 420 |
| gtcaatttt agtaaaatag atattttatt gatatataat ataatataat ttaataacta | 480 |
| aataaaatat cgctataaat tttaaggtcg gagtagtgca tgctttacaa gtgttactta | 540 |
| cactgtaaca ttgccagata ttttttctcat cactcagctc tacacttgtc actcccctat | 600 |
| atatatcctt cttcttcccc ttccatttcc acactcaaaa ctcaaaacac aatcttctcc | 660 |
| gccctaaatc ccagttctca attcttctcc atcaatggct tccaccttag cttcctctgt | 720 |
| tatttccaag actaatttca ttgacacaca caaatcatcc ttctatggcg ttccaatttc | 780 |
| atcacaaact cgattgaaaa tcgttaaatc gactccacaa aacatgtctg tttccatgtc | 840 |
| tgctgatgct tctcctcctt acgatctcgg aagtttcagt tttaatccga ttaaggaatc | 900 |
| gattgttgct cgcgaaatga ctcggaggta tatgacggat atgattactt atgctgatac | 960 |
| tgatgttgtc attgttggtg ctggatctgc tggtttatct tgtgcttatg aactcagcaa | 1020 |
| gaaccctaat gttcaggtat aacttctttt ttttttttaa attattaata ccgagttctt | 1080 |
| atagcgtttt tgaattaaca tacaataaaa attgggttta tcgttgatac tagacttta | 1140 |
| tctgcaattc gaattcgatc tagatttgat atatgataaa tcaaggctca ggtgacttgt | 1200 |
| tctggcctcg attgtatccc tctcttgcaa attcacgtga tactgattga cttgacatca | 1260 |
| cgaattttga attttatcgg ctcaaaagaa aacacaggtt tcctgttaaa agtattttac | 1320 |
| aactttactt ttactcataa atcatgtgat acttttgtcc ttagcctaat ttgctagtat | 1380 |
| taatttgagt ggggcaattc acacgtaaca caccattcgc gatcacaatg aactcatttg | 1440 |
| atgttctgat agctataatt ttggtagatt acaatatcta tgttcttcaa tttgttgttt | 1500 |
| atgtgaattt actttatatg tataggtggc tattcttgag caatctgtga gccctggtgg | 1560 |
| aggtgcttgg ctaggtggac aactcttctc tgctatggtt gtgcgtaagc cagcacatct | 1620 |
| tttcttgaac gagctaggca ttgactacga cgagcaagac aactacgtgg tcatcaaaca | 1680 |
| cgctgccttg ttcacctcaa ccatcatgag caagcttttg gccaggccaa atgtgaagct | 1740 |
| cttcaatgct gttgcaacag aggaccttat cgtgaagaac ggaagagtcg gtggtgttgt | 1800 |
| cactaactgg tctttggttt cccagaacca cgacacacaa tcctgcatgg accctaatgt | 1860 |
| tatggaggct aagattgtgg tcagctcttg tggccacgac ggccccatgg cgccaccgg | 1920 |
| tgttaagagg ctcaggagca ttggcatgat caacagtgtc cctggaatga aagctttgga | 1980 |

```
catgaacgct gctgaggacg cgattgttag acttaccaga gaggtcgtac ctggtatgat    2040
tgtcacagga atggaagttg ctgaaattga tggagcacca cgaatggtta gtatgaaata    2100
cttgaactcc tatattgtat aaactcataa ttagaagtta gaaaagcaac aaacaattca    2160
actaattgga gatgttatac attgtacagg gtccaacttt tggagctatg atgatatcag    2220
gacagaaggc agctcacctc gccctacgag cgttgggatt gcccaacgcc cttgatggaa    2280
ctgcagaaac aagcgtcctc ccggagctta tgttggctgc agctgatgaa gctgaaattg    2340
ctgatgcttg aatgtaatta tagttttcta agcaaggatt atgagaaata ttagtttttc    2400
ctagataagt gagtatggtt gtggtggtga tgataaattg gtaaggggat gatgaataag    2460
agtcttcaag atgaaagtca ttgtgttaac tttggctatt ttattttgat ttatttctat    2520
ttcgaaactt ttatggaaga aagtagattt tagttttggt cgttccttga ataatctttt    2580
aggccttttg ggctttgtac ttgatatggt ttgggcctca ttggagaagc catatgaatg    2640
aacattgtga ttgggctaag atgtttttgc actaatggcc ttttgaggat ttacatccaa    2700
ttactttcaa atgcaaaatt tagttgattt gatttcgatg gagtttgtgg agggtaaaga    2760
gtacgaagac tttatcacta ctttgtggag atagaaaagc tattttttgag agactttcag    2820 ctcaaaatac ttaaatcacg atggttaaga gctaattaca ttattttttct attctatttt    2880 aaataacgaa aactccttga aatttataaa ttttcgattc attttttagac ttttggatat    2940 atcatcggac ttttcgatgc attagtagat attcgaatac atatgtgatg gatgtatcaa    3000
agaggggaaa gacatctgga tacatgacta gacttccgga tatgtcaaca aacatctgga    3060
acatagataa ggaatgtatc agagaggaca gaaatatatt cgagagggga tatgaatgta    3120
tcaacaaaag gagagtgatg tatcaggaga tatttgattt ttttttaaata ataaaaaatt    3180 gcagaaatta tatcaaaata aaatgtttat ttagatcatt tttctaatat ttattggtag    3240
aagttgcaca ttgaagaact ggaaaagata tttaagaaat tgaaatcgaa gataatttat    3300
catcatgaat aatgatgttg aatgaaatga aaaatgataa tagagttgtt attgggatat    3360
aatggtatag ccttagtact cgaaagtttt aaatatacat aataagagaa aaaacataaa    3420
gtgattcttg atattatttt atattttaaa aaagacattt taatttgggg cgtgctatta    3480
acctctaaat aatttcaaat atatattatt acatcatttc gatcaatttc agattttaaa    3540
tacaaatacg atcacacccc aatcattgcg tgtcacatgg taattaaatt tgaaatacta    3600
tttatttcat gttaagtttt tctttatttt tctctcttac cttttttgact tatttaactt    3660 tactagttta attttaattt cattttaaat actatttcat ctcccatcct aacctcaccc    3720
tac                                                                    3723
```

<210> SEQ ID NO 20
<211> LENGTH: 694
<212> TYPE: DNA
<213> ORGANISM: Solanum lycopersicum

<400> SEQUENCE: 20

```
tatttctacg tccacgtaga cacatataaa ccttcaaaat aaattattga atagtgtaag      60
ggtaaaagat catatacaaa attttgtatc gttatatcat tttttatcaa agtttgaata     120
tatttcagac attttctcat aatcaaagta tatatatata tatttgataa ttcatttacg     180
taatatgtac atgagaacac acacatagaa gacagataaa taaaatttga atttatttcg     240
acgaacaatc atgtcttcca actttgcatg tgcacgagta gatacctaaa ttcatataaa     300
```

-continued

```
attcacaagt agacgcacat aatatatatg acataataca gataagatat catgtagaaa      360
gaacgtgtca atttgtttaa tttaatataa agttaagcgt ctacttatga ctaatatttc      420
gtcaaatttt agtaaaatag atattttatt gatatataat ataatataat ttaataacta      480
aataaaatat cgctataaat tttaaggtcg gagtagtgca tgctttacaa gtgttactta      540
cactgtaaca ttgccagata ttttttctcat cactcagctc tacacttgtc actcccctat      600
atatatcctt cttcttcccc ttccatttcc acactcaaaa ctcaaaacac aatcttctcc      660
gccctaaatc ccagttctca attcttctcc atca                                  694
```

```
<210> SEQ ID NO 21
<211> LENGTH: 1372
<212> TYPE: DNA
<213> ORGANISM: Solanum lycopersicum

<400> SEQUENCE: 21
atgtaattat agttttctaa gcaaggatta tgagaaatat tagtttttcc tagataagtg       60
agtatggttg tggtggtgat gataaattgg taagggdatg atgaataaga gtcttcaaga      120
tgaaagtcat tgtgttaact ttggctattt tattttgatt tatttctatt tcgaaacttt      180
tatggaagaa agtagatttt agttttggtc gttccttgaa taatctttta ggccttttgg      240
gctttgtact tgatatggtt tgggcctcat tggagaagcc atatgaatga acattgtgat      300
tgggctaaga tgttttttgca ctaatggcct tttgaggatt tacatccaat tactttcaaa      360
tgcaaaattt agttgatttg atttcgatgg agtttgtgga gggtaaagag tacgaagact      420
ttatcactac tttgtggaga tagaaaagct atttttgaga gactttcagc tcaaaatact      480
taaatcacga tggttaagag ctaattacat tattttttcta ttctatttta aataacgaaa      540
actccttgaa atttataaat tttcgattca ttttttagact tttggatata tcatcggact      600
tttcgatgca ttagtagata ttcgaataca tatgtgatgg atgtatcaaa gaggggaaag      660
acatctggat acatgactag acttccggat atgtcaacaa acatctggaa catagataag      720
gaatgtatca gagaggacag aaatatattc gagaggggat atgaatgtat caacaaaagg      780
agagtgatgt atcaggagat atttgatttt tttaaataa taaaaaattg cagaaattat      840
atcaaaataa aatgtttatt tagatcattt ttctaatatt tattggtaga agttgcacat      900
tgaagaactg gaaagatat ttaagaaatt gaaatcgaag ataatttatc atcatgaata      960
atgatgttga atgaaatgaa aaatgataat agagttgtta ttgggatata atggtatagc     1020
cttagtactc gaaagtttta aatatacata ataagagaaa aaacataaag tgattcttga     1080
tattatttta tattttaaaa aagacatttt aatttggggc gtgctattaa cctctaaata     1140
atttcaaata tatattatta catcatttcg atcaatttca gatttaaat acaaatacga     1200 tcacacccca atcattgcgt gtcacatggt aattaaattt gaaatactat ttatttcatg     1260
ttaagttttt ctttattttt ctctcttacc tttttgactt atttaacttt actagtttaa     1320
ttttaatttc attttaaata ctatttcatc tcccatccta acctcaccct ac            1372
```

```
<210> SEQ ID NO 22
<211> LENGTH: 4888
<212> TYPE: DNA
<213> ORGANISM: Solanum lycopersicum

<400> SEQUENCE: 22
gtcaactacc ccaatttaaa ttttatttga ttaagatatt tttatggacc tactttataa       60
ttaaaaatat tttctatttg aaaaggaagg acaaaaatca tacaattttg gtccaactac      120
```

-continued

```
tcctctcttt ttttttttgg ctttataaaa aaggaaagtg attagtaata aataattaaa    180
taatgaaaaa aggaggaaat aaaatttttcg aattaaaatg taaaagagaa aaaggagagg   240
gagtaatcat tgtttaactt tatctaaagt accccaattc gattttacat gtatatcaaa    300
ttatacaaat attttattaa aatatagata ttgaataatt ttattattct tgaacatgta    360
aataaaaatt atctattatt tcaattttta tataaactat tatttgaaat ctcaattatg    420
attttttaat atcactttct atccatgata atttcagctt aaaaagtttt gtcaataatt    480
acattaattt tgttgatgag gatgacaaga tttcggtcat caattacata tacacaaatt    540
gaaatagtaa gcaacttgat tttttttctc ataatgataa tgacaaagac acgaaaagac    600
aattcaatat tcacattgat ttattttttat atgataataa ttacaataat aatattctta    660
taaagaaaga gatcaatttt gactgatcca aaaatttatt tatttttact ataccaacgt    720
cactaattat atctaataat gtaaaacaat tcaatcttac ttaaatatta atttgaaata    780
aactattttt ataacgaaat tactaaattt atccaataac aaaaaggtct taagaagaca    840
taaattcttt ttttgtaatg ctcaaataaa tttgagtaaa aaagaatgaa attgagtgat    900
ttttttttaa tcataagaaa ataaataatt aatttcaata taataaaaca gtaatataat    960
ttcataaatg gaattcaata cttacctctt agatataaaa aataaatata aaaataaagt   1020
gtttctaata aacccgcaat ttaaataaaa tatttaatat tttcaatcaa atttaaataa   1080
ttatattaaa atatcgtaga aaaagagcaa tatataatac aagaaagaag atttaagtac   1140
aattatcaac tattattata ctctaatttt gttatattta atttcttacg gttaaggtca   1200
tgttcacgat aaactcaaaa tacgctgtat gaggacatat tttaaattttt aaccaataat   1260 aaaactaagt tattttttagt atatttttttt gtttaacgtg acttaatttt tctttttctag   1320 aggagcgtgt aagtgtcaac ctcattctcc taattttccc aaccacataa aaaaaaaata   1380
aaggtagctt ttgcgtgttg atttggtaca ctacacgtca ttattacacg tgttttcgta   1440
tgattggtta atccatgagg cggtttcctc tagagtcggc cataccatct ataaaataaa   1500
gctttctgca gctcatttttt tcatcttcta tctgatttct attataattt ctctgaattg   1560
ccttcaaatt tctctttcaa ggttagaatt ttttctctatt ttttggtttt tgtttgttta   1620
gattctgagt ttagttaatc aggtgctgtt aaagccctaa attttgagtt tttttcggtt   1680
gttttgatgg aaaatacccta acaattgagt tttttcatgt tgtttttgtcg gagaatgcct   1740 acaattggag ttcctttcgt tgtttttgatg agaaagcccc taatttgagt gttttttccgt   1800 cgatttgatt ttaaaggttt atattcgagt ttttttcgtc ggtttaatga gaaggcctaa   1860
aataggagtt tttctggttg atttgactaa aaaagccatg gaattttgtg tttttgatgt   1920
cgctttggtt ctcaaggcct aagatctgag tttctccggt tgtttttgatg aaaaagccct   1980 aaaattggag ttttttatctt gtgttttagg ttgttttaat ccttataatt tgagtttttt   2040
cgttgttctg attgttgttt ttatgaattt tgcagatgca gatctttgtg aaaactctca   2100
ccggaaagac tatcacccta gaggtggaaa gttctgatac aatcgacaac gttaaggcta   2160
agatccagga taaggaagga attcccccgg atcagcaaag gcttatcttc gctggaaagc   2220
agttggagga cggacgtact ctagctgatt acaacatcca gaaggagtcc accctccatt   2280
tggtgctccg tctacgtggt ggtatgcaga tcttcgtgaa gactctcacg ggtaagacga   2340
ttacccttga ggtcgaaagc tcagacacca ttgacaacgt caaggctaag atccaggata   2400
aggaaggcat tcccccagac cagcagaggt tgatctttgc aggaaagcag ttggaagatg   2460
```

-continued

```
gccgcaccct agctgactac aacatccaga aggagtccac cctccatttg gtgctccgtc     2520
tccgtggtgg tatgcagatc ttcgttaaga ctcttaccgg aaagaccatc actttggagg     2580
tggaaagctc cgacaccatt gacaacgtga aggctaagat ccaggataag gaagggatcc     2640
ccccagacca gcagaggttg atcttcgctg gaaagcagct cgaggatggt cgcaccctgg     2700
ctgactacaa catccagaag gagtctaccc tccatcttgt cctccgtctc cgtggtggta     2760
tgcagatttt tgttaagacc ctcaccggaa agaccatcac tttggaggtg gaaagctccg     2820
acaccattga taatgttaag gctaagatcc aggacaagga gggaattcct tcagaccagc     2880
agaggttgat tttcgctggt aagcagctcg aggacggccg caccctcgcc gactacaaca     2940
tccagaagga gtcgacccct caccttgtcc tccgtctacg tggtggtatg caaatctttg     3000
tgaagaccct taccgggaaa accatcaccc tggaggttga gagctccgac accattgaca     3060
atgtcaaggc caagatccaa gacaaggagg gtattccccc agaccagcag aggttgattt     3120
ttgctggcaa gcagctcgag gatggccgca ctttggcgga ctataacatc caaaaggagt     3180
cgaccctgca cttggtgctt aggctgaggg gaggaatgca gatctttgtg aagaccttga     3240
ccgggaagac catcactttg gaggtggaga gttctgacac catcgacaat gtgaaagcta     3300
agattcagga caaggagggg atcccaccag accagcagag gttgattttc gctggtaagc     3360
agcttgagga tggccgcacc cttgctgact acaatatcca gaaggagtcc accctgcacc     3420
ttgtcctccg tctccgtggt ggttttaag ttgtggttgt ctggttgcgt ctgttgcccg     3480
ttgtctgttg cccattgtgg tggttgtgtt tgtatgatgg tcgttaagga tcatcaatgt     3540
gttttcgctt tttgttccat tctgtttctc atttgtgaat aataatggta tctttatgaa     3600
tatgcagttt gtggtttctt ttctgattgc agttctgagc attttgtttt tgcttccgtt     3660
tactatacca cttacagttt gcactaattt agttgatatg cgagccatct gatgtttgat     3720
gattcaaatg gcgtttatgt aactcgtacc cgagtggatg gagaagagct ccattgccgg     3780
tttgtttcat gggtggcgga gggcaactcc tgggaaggaa caaagaaaaa accgtgatac     3840
gagttcatgg gtgagagctc cagcttgatc ccttctctgt cgatcaaatt tgaattttg     3900 gatcacggca ggctcacaag ataatccaaa gtaaaacata atgaatagta cttctcaatg     3960
atcacttatt tttagcaaat cagcaattgt gcatgtcaaa tgatttcggt gtaagagaaa     4020
gagttgatga atcaaaatat ctgtagctgg atcaagaatc tgaggcagtt gtatgtatca     4080
atgatctttc cgctacaatg atgttagcta tccgagtcaa attgttgtag aattgcatac     4140
ttcggcatca cattctggat gacataataa ataggaagtc ttcagatccc taaaaaattg     4200
agagctaata acattagtcc tagatgtaac tgggtgacaa ccaagaaaga gacatgcaaa     4260
tactactttt gtttgaagga gcatccctgg tttgacatat tttttctgaa tatcaaactt     4320
tgaaactcta cctagtctaa tgtctaacga cagatcttac tggtttaact gcagtgatat     4380
ctactatctt ttggaatgtt ttctccttca gttatacatc aagttccaag atgcaggtgt     4440
gcttgattga tgtacatggc tgtgagaagt gcatcctgat gttcagatga tggttcattc     4500
taatgtcttt tccttcaatc agttttctca gtctgactta gcttgtttca tctgcatgtt     4560
tgaatgttcg tttactcata gtaattgcat ttttgtagca gaacatatca ttggtcatgg     4620
tttcaactgt gcgcgagtct tatgcttatt caaactagga aagcctccgt ctagagggta     4680
cacgagttgt tgctctgtgt gcgtcagtcc atagtattaa tcttgctagt tgtagtatat     4740
tgtttatgtg gactcggaat tcatcatatg ctccttcttt gcatcaagta aggcaaggta     4800
atgtatagaa gctttttaac tctttcatgg aagctggcct ttgccagcat accatccaga     4860
```

-continued

```
agatatcaac cctgcatctt ggctgccg                                      4888

<210> SEQ ID NO 23
<211> LENGTH: 2075
<212> TYPE: DNA
<213> ORGANISM: Solanum lycopersicum

<400> SEQUENCE: 23
gtcaactacc ccaatttaaa ttttatttga ttaagatatt tttatggacc tactttataa    60
ttaaaaatat tttctatttg aaaaggaagg acaaaaatca tacaattttg gtccaactac   120
tcctctcttt tttttttttgg ctttataaaa aaggaaagtg attagtaata aataattaaa   180
taatgaaaaa aggaggaaat aaaattttcg aattaaaatg taaaagagaa aaaggagagg   240
gagtaatcat tgtttaactt tatctaaagt accccaattc gattttacat gtatatcaaa   300
ttatacaaat attttattaa aatatagata ttgaataatt ttattattct tgaacatgta   360
aataaaaatt atctattatt tcaattttta tataaactat tatttgaaat ctcaattatg   420
attttttaat atcactttct atccatgata atttcagctt aaaaagtttt gtcaataatt   480
acattaattt tgttgatgag gatgacaaga tttcggtcat caattacata tacacaaatt   540
gaaatagtaa gcaacttgat ttttttttctc ataatgataa tgacaaagac acgaaaagac   600
aattcaatat tcacattgat ttattttttat atgataataa ttacaataat aatattctta   660
taaagaaaga gatcaatttt gactgatcca aaaatttatt tattttttact ataccaacgt   720 cactaattat atctaataat gtaaaacaat tcaatcttac ttaaatatta atttgaaata   780
aactattttt ataacgaaat tactaaattt atccaataac aaaaaggtct taagaagaca   840 taaattctttt tttttgtaatg ctcaaataaa tttgagtaaa aaagaatgaa attgagtgat   900 tttttttttaa tcataagaaa ataaataatt aatttcaata taataaaaca gtaatataat   960
ttcataaatg gaattcaata cttacctctt agatataaaa aataaatata aaaataaagt  1020
gtttctaata aacccgcaat ttaaataaaa tatttaatat tttcaatcaa atttaaataa  1080
ttatattaaa atatcgtaga aaaagagcaa tatataatac aagaaagaag atttaagtac  1140
aattatcaac tattattata ctctaatttt gttatattta atttcttacg gttaaggtca  1200
tgttcacgat aaactcaaaa tacgctgtat gaggacatat tttaaatttt aaccaataat  1260
aaaactaagt tatttttagt atatttttttt gtttaacgtg acttaatttt tcttttctag  1320
aggagcgtgt aagtgtcaac ctcattctcc taattttccc aaccacataa aaaaaaaata  1380
aaggtagctt ttgcgtgttg atttggtaca ctacacgtca ttattacacg tgttttcgta  1440
tgattggtta atccatgagg cggtttcctc tagagtcggc cataccatct ataaaataaa  1500 gcttctgca gctcattttt tcatcttcta tctgatttct attataattt ctctgaattg  1560
ccttcaaatt tctctttcaa ggttagaatt tttctctatt ttttggtttt tgtttgtttta  1620 gattctgagt ttagttaatc aggtgctgtt aaagccctaa attttgagtt tttttcggtt  1680
gttttgatgg aaaatacct acaattgagt tttttcatgt tgttttgtcg gagaatgcct  1740
acaattggag ttcctttcgt tgtttttgatg agaaagcccc taatttgagt gtttttttccgt  1800 cgatttgatt ttaaaggttt atattcgagt ttttttcgtc ggtttaatga gaaggcctaa  1860
aataggagtt tttctggttg atttgactaa aaaagccatg gaattttgtg tttttgatgt  1920
cgctttggtt ctcaaggcct aagatctgag tttctccggt tgtttttgatg aaaaagccct  1980 aaaattggag ttttttatctt gtgttttagg ttgtttttaat ccttataatt tgagttttttt  2040
```

-continued

```
cgttgttctg attgttgttt ttatgaattt tgcag                               2075

<210> SEQ ID NO 24
<211> LENGTH: 1482
<212> TYPE: DNA
<213> ORGANISM: Solanum lycopersicum

<400> SEQUENCE: 24
gtcaactacc ccaatttaaa ttttatttga ttaagatatt tttatggacc tactttataa     60
ttaaaaatat tttctatttg aaaaggaagg acaaaaatca tacaattttg gtccaactac    120
tcctctcttt ttttttttgg ctttataaaa aaggaaagtg attagtaata aataattaaa    180
taatgaaaaa aggaggaaat aaaattttcg aattaaaatg taaaagagaa aaaggagagg    240
gagtaatcat tgtttaactt tatctaaagt accccaattc gattttacat gtatatcaaa    300
ttatacaaat attttattaa aatatagata ttgaataatt ttattattct tgaacatgta    360
aataaaaatt atctattatt tcaattttta tataaactat tatttgaaat ctcaattatg    420 atttttttaat atcactttct atccatgata atttcagctt aaaaagtttt gtcaataatt    480
acattaattt tgttgatgag gatgacaaga tttcggtcat caattacata tacacaaatt    540
gaaatagtaa gcaacttgat tttttttctc ataatgataa tgacaaagac acgaaaagac    600
aattcaatat tcacattgat ttatttttat atgataataa ttacaataat aatattctta    660
taaagaaaga gatcaatttt gactgatcca aaaatttatt tatttttact ataccaacgt    720
cactaattat atctaataat gtaaaacaat tcaatcttac ttaaatatta atttgaaata    780
aactattttt ataacgaaat tactaaattt atccaataac aaaaaggtct taagaagaca    840
taaattcttt ttttgtaatg ctcaaataaa tttgagtaaa aaagaatgaa attgagtgat    900
ttttttttaa tcataagaaa ataaataatt aatttcaata taataaaaca gtaatataat    960
ttcataaatg gaattcaata cttacctctt agatataaaa aataaatata aaaataaagt   1020
gtttctaata aacccgcaat ttaaataaaa tatttaatat tttcaatcaa atttaaataa   1080
ttatattaaa atatcgtaga aaaagagcaa tatataatac aagaaagaag atttaagtac   1140
aattatcaac tattattata ctctaatttt gttatattta atttcttacg gttaaggtca   1200
tgttcacgat aaactcaaaa tacgctgtat gaggacatat tttaaatttt aaccaataat   1260
aaaactaagt tattttttagt atattttttt gtttaacgtg acttaatttt tctttttctag   1320 aggagcgtgt aagtgtcaac ctcattctcc taattttccc aaccacataa aaaaaaaata   1380
aaggtagctt ttgcgtgttg atttggtaca ctacacgtca ttattacacg tgttttcgta   1440
tgattggtta atccatgagg cggtttcctc tagagtcggc ca                      1482

<210> SEQ ID NO 25
<211> LENGTH: 99
<212> TYPE: DNA
<213> ORGANISM: Solanum lycopersicum

<400> SEQUENCE: 25
taccatctat aaaataaagc tttctgcagc tcattttttc atcttctatc tgatttctat     60
tataatttct ctgaattgcc ttcaaatttc tctttcaag                            99

<210> SEQ ID NO 26
<211> LENGTH: 494
<212> TYPE: DNA
<213> ORGANISM: Solanum lycopersicum

<400> SEQUENCE: 26
```

-continued

```
gttagaattt ttctctattt tttggttttt gtttgtttag attctgagtt tagttaatca      60
ggtgctgtta aagccctaaa ttttgagttt ttttcggttg ttttgatgga aaatacctaa     120
caattgagtt ttttcatgtt gttttgtcgg agaatgccta caattggagt tcctttcgtt     180
gttttgatga gaaagcccct aatttgagtg tttttccgtc gatttgattt taaaggttta     240
tattcgagtt ttttcgtcg gtttaatgag aaggcctaaa ataggagttt ttctggttga     300
tttgactaaa aaagccatgg aattttgtgt ttttgatgtc gctttggttc tcaaggccta     360
agatctgagt ttctccggtt gttttgatga aaaagcccta aaattggagt tttatcttg     420 tgttttaggt tgtttaatc cttataattt gagtttttc gttgttctga ttgttgtttt     480
tatgaatttt gcag                                                      494
```

<210> SEQ ID NO 27
<211> LENGTH: 1439
<212> TYPE: DNA
<213> ORGANISM: Solanum lycopersicum

<400> SEQUENCE: 27

```
gttgtggttg tctggttgcg tctgttgccc gttgtctgtt gcccattgtg gtggttgtgt      60
ttgtatgatg gtcgttaagg atcatcaatg tgttttcgct ttttgttcca ttctgtttct     120
catttgtgaa taataatggt atctttatga atatgcagtt tgtggtttct tttctgattg     180
cagttctgag cattttgttt ttgcttccgt ttactatacc acttacagtt tgcactaatt     240
tagttgatat gcgagccatc tgatgtttga tgattcaaat ggcgtttatg taactcgtac     300
ccgagtggat ggagaagagc tccattgccg gtttgtttca tgggtggcgg agggcaactc     360
ctgggaagga acaaaagaaa aaccgtgata cgagttcatg ggtgagagct ccagcttgat     420
cccttctctg tcgatcaaat ttgaatttt ggatcacggc aggctcacaa gataatccaa     480
agtaaaacat aatgaatagt acttctcaat gatcacttat tttagcaaa tcagcaattg     540 tgcatgtcaa atgatttcgg tgtaagagaa agagttgatg aatcaaaata tctgtagctg     600
gatcaagaat ctgaggcagt tgtatgtatc aatgatcttt ccgctacaat gatgttagct     660
atccgagtca aattgttgta gaattgcata cttcggcatc acattctgga tgacataata     720
aataggaagt cttcagatcc ctaaaaaatt gagagctaat aacattagtc ctagatgtaa     780
ctgggtgaca accaagaaag agacatgcaa atactacttt tgtttgaagg agcatccctg     840
gtttgacata ttttttctga atatcaaact ttgaaactct acctagtcta atgtctaacg     900
acagatctta ctggtttaac tgcagtgata tctactatct tttggaatgt tttctccttc     960
agttatacat caagttccaa gatgcaggtg tgcttgattg atgtacatgg ctgtgagaag    1020
tgcatcctga tgttcagatg atggttcatt ctaatgtctt ttccttcaat cagtttctc    1080 agtctgactt agcttgtttc atctgcatgt ttgaatgttc gtttactcat agtaattgca    1140
tttttgtagc agaacatatc attggtcatg gtttcaactg tgcgcgagtc ttatgcttat    1200
tcaaactagg aaagcctccg tctagagggt acacgagttg ttgctctgtg tgcgtcagtc    1260
catagtatta atcttgctag ttgtagtata ttgtttatgt ggactcggaa ttcatcatat    1320
gctccttctt tgcatcaagt aaggcaaggt aatgtataga agctttttaa ctctttcatg    1380
gaagctggcc tttgccagca taccatccag aagatatcaa ccctgcatct tggctgccg    1439
```

<210> SEQ ID NO 28
<211> LENGTH: 1262
<212> TYPE: DNA

<213> ORGANISM: Solanum lycopersicum

<400> SEQUENCE: 28

```
ttgcagttct gagcattttg tttttgcttc cgtttactat accacttaca gtttgcacta       60
atttagttga tatgcgagcc atctgatgtt tgatgattca aatggcgttt atgtaactcg      120
tacccgagtg gatggagaag agctccattg ccggtttgtt tcatgggtgg cggagggcaa      180
ctcctgggaa ggaacaaaag aaaaaccgtg atacgagttc atgggtgaga gctccagctt      240
gatcccttct ctgtcgatca aatttgaatt tttggatcac ggcaggctca caagataatc      300
caaagtaaaa cataatgaat agtacttctc aatgatcact tattttttagc aaatcagcaa      360 ttgtgcatgt caaatgattt cggtgtaaga gaaagagttg atgaatcaaa atatctgtag      420
ctggatcaag aatctgaggc agttgtatgt atcaatgatc tttccgctac aatgatgtta      480
gctatccgag tcaaattgtt gtagaattgc atacttcggc atcacattct ggatgacata      540
ataaatagga agtcttcaga tccctaaaaa attgagagct aataacatta gtcctagatg      600
taactgggtg acaaccaaga aagagacatg caaatactac ttttgtttga aggagcatcc      660
ctggtttgac atattttttc tgaatatcaa actttgaaac tctacctagt ctaatgtcta      720
acgacagatc ttactggttt aactgcagtg atatctacta tcttttggaa tgttttctcc      780
ttcagttata catcaagttc caagatgcag gtgtgcttga ttgatgtaca tggctgtgag      840
aagtgcatcc tgatgttcag atgatggttc attctaatgt cttttccttc aatcagtttt      900
ctcagtctga cttagcttgt ttcatctgca tgtttgaatg ttcgtttact catagtaatt      960 gcattttgt agcagaacat atcattggtc atggtttcaa ctgtgcgcga gtcttatgct     1020
tattcaaact aggaaagcct ccgtctagag ggtacacgag ttgttgctct gtgtgcgtca     1080
gtccatagta ttaatcttgc tagttgtagt atattgttta tgtggactcg gaattcatca     1140
tatgctcctt ctttgcatca agtaaggcaa ggtaatgtat agaagctttt taactctttc     1200
atggaagctg gcctttgcca gcataccatc cagaagatat caaccctgca tcttggctgc     1260
cg                                                                   1262
```

<210> SEQ ID NO 29
<211> LENGTH: 177
<212> TYPE: DNA
<213> ORGANISM: Solanum lycopersicum

<400> SEQUENCE: 29

```
gttgtggttg tctggttgcg tctgttgccc gttgtctgtt gcccattgtg gtggttgtgt       60
ttgtatgatg gtcgttaagg atcatcaatg tgttttcgct ttttgttcca ttctgtttct      120
catttgtgaa taataatggt atctttatga atatgcagtt tgtggtttct tttctga        177
```

<210> SEQ ID NO 30
<211> LENGTH: 4774
<212> TYPE: DNA
<213> ORGANISM: Solanum lycopersicum

<400> SEQUENCE: 30

```
tgaatctact gctaataatg attttgattt gtatttcaat caggcatgag aaaagattag       60
gcatgaagaa ggacaacttc aacctccaat attagtatgg tggaagaatc gtgaaaatca      120
atttccgacc attactagga ttgtttgaga tatgctagcg attcaagcat catcggtcgc      180
ttcggataag cctttaggct cggggtgtga cagatcatga taaggctttg catattgttc      240
cccacgtcat tgtcgagggt ccaattaata tttgagaaaa aaatgcccaa aatcgcatca      300
```

-continued

```
tcaaaaattc attgactagc tcacacaaaa caaactcttg ttgattatcc cctaaatgct      360
aaaaaagggc gtggatcatg atgaggttat atgtattgtt ccctcaagtc attacggaga      420
gtcatgtaag ggttttgaat aaaaaagtgt ctgaaaacca taacatcaga aaatttattg      480
attaacaaac atgaaaaact gaaaaaatca cctaattttt attgagcggc ccttaaatgc      540
taaaagaatt acatgaatca tagtgaagct atacatattg ttctctcaag ttattacgga      600
tggttccatc aaagtttttt ttttttttaaa tggttgaaaa tcatatcacc attaaaactc      660
attgaccaca cacgaaaaac taaaaaaaaa tcgcctaata cctaatgagt gaccactaaa      720
tgctaaaaaa tggcatgatc atggtaagac tatatgttct gttccccaag tcattatgga      780
ggatcatgta aaagttttag aaaaaaagta ctcaaaaatc acattactaa atattacatt      840
gactaacata catgaaaaaa ctgagaaaca tatttaattc agttgccctg aattgctaat      900
cctatacact tcctacactt gtaacgaacc ttaacacaca tgaacaaata ggacattact      960
tggttcaaag ttgatactct tacggcgaaa ggtgtggatc tttagcatag aattcatggg     1020
gcattacaat taattagtaa tactaatttt aataacacta aatcatatta gtctctatag     1080
gtataatata taactctgga gtcactatct gtatttggga tcaacagtta caaaggtacg     1140
agtaaagtct ctgatccgac aaacaatccg tatatcctac cttcccgaaa tttcatgtat     1200
aaaattatac taaaatatta tttttcttgt attatccgat tgaaaattat gcgaattcaa     1260
cataaaactc taaaaaaaga aaataatgaa aattacaact taaaagagtg tctaagttgg     1320
aatcatggta ttacataaag ttgaggacaa tataagcaag caaacaagta ctctagctat     1380
caatttactt tggactacta tatgataaat atttcaaccc ccctcctccc ccaccaaaaa     1440
aaaattaaaa taacaagttg aaggactcaa aaaaaaaaaa aaaaaaaaac tcaaaaccaa     1500
cctcaatcat acattcatat cctcttccta cccccatctt ggatgagata agattaacga     1560
ggtgcttaca cgtgtcacct ctattgtggt gacttaaaaa aaattccaac ctttcatatg     1620
tagatattaa gtaattgtat aatgttatca agaaccacat aacatatcaa aaaccttatc     1680
atttcattat ataaaaggat agtggacatc aaaaggttca tattgaacca aaaaaagaga     1740
gaagaagcaa tatggcttcc tctgtcattt cttcagcagc tgttgccaca cgcagcaatg     1800
ttacacaagc tagcatggtt gcacctttca ctggtctcaa atcttcagcc actttccctg     1860
ttacaaagaa gcaaaacctt gacatcactt ccattgctag caatggtgga agagttagct     1920
gcatgcaggt aactcactca tcggttttcc gaaattgata ttttcttagt atgttgtaac     1980
atgtaatctg tcttatttct cgattcaatt atctaagggt tatatgtatg ttagctactc     2040
tctctggctt aatttatgtg acggtagtac tattttatt tagttagtat aaaaaagagt     2100
gatttacttt gtttcagttt gtttgtttaa tcttaattta acataacttt taagaaaatt     2160
aaaaagtctt ttgaatttgt agttttaaat taaagttacg tagaatgtat taaaatatcc     2220
tacattttgt gatttcaaac atgttaactg tcacgtgaaa aattagaatt agataaattat     2280 caaaaaaaaa aaaagagact ttagaagagt aatataaaca aattgaaaca tgagtatatg     2340
tagttactga cctctgatct agtttatgcc attattattt ttctttttaa gtctgtttta     2400
aaagaatgac atatttttat atttaatagc agtattgatt taagtttgaa aaaaatttct     2460
attttatctt taatgagatg atttataatt acataagtat ttatattatc ttagaccata     2520
aactacgaaa atctctgttt attcttaaaa ttccatttac cattaagtac ctccacataa     2580
gaattaaaaa aagagagtat ctttcaaatt atctgataat tcatagaagt taaaagatcc     2640
```

-continued

```
aattgcttaa cttatctttg attatattaa acacatgaaa agtgtatcct acgtataatc     2700
tctacgttca aaattaaaga caaatttaag atctagaatt gatgaactca aaatatctct     2760
atcttattat tattatgtat atatacaact taattttttcg aaatgttgat gaatgtatgt    2820
taaatccttt acaatagtgc atttttagat aattcgataa gagtgtaaca atattttcag     2880
aaagtcgata actttttttt cttttttttt tttggatatg tgtataggtg tggccaccaa     2940
ttaacatgaa gaagtacgag acactctcat accttcctga tttgtctgac gagcaattgc     3000
ttagtgaaat tgagtacctt ttgaaaaatg gatgggttcc ttgcttggaa tttgagactg     3060
aggtcaatat catatttact tttgtttat cgaaaaatga tatattttta tatttagata      3120
cgatttatat ttaacacttc aatgtttttt ttatgtgtag cacggatttg tctaccgtga     3180
gaacaacaag tcaccaggat actatgatgg aaggtcagta gcggattcat aagttaaaga     3240
attcattcat actttttttt agttaaatcg taggtatagg tacgagaatc atgaaaatta     3300
atataaatat catgtttcga actcgtttat taaaaaaaaa aaactcataa aacatactat     3360
gaacatcact agtctgtata aaaagggaaa aaaagaaga taaatatacc cttagaatat       3420
cataagtggt atgcagatat cttcggtcat agtttttggga cattggtact tctgccgtcc    3480
aaaaactaga acgttgatat atatgttgta gttttttggac cgcagaagca tcaatgtccc    3540
aaaaatatga tgaaaaatat ctgtatacta tttacgatag ttcggatata tttgtcccttt    3600 ttttctaagt ttttataaag ttaaaaagtt aaaattttga atccgcaggt actggaccat     3660
gtggaagttg cctatgtttg ggtgcactga tgcaacccaa gtgttggctg aggttcaaga     3720
ggctaaaaag gcatacccac aagcatgggt cagaatcatt ggattcgaca atgtgcgtca     3780
agtgcagtgt atcagtttca ttgcctacaa gccagaaggc tactaagttt catattagga     3840
acaaaattgt ctttagggac actttgtttt taaatgctac ttaggtcttt tttctttttt     3900
gtcttaattc caacaaactc tttgtgtctt gtactattcg gtttatgttt tggatttatg     3960
agtacctaat tatatgataa tgatttggtg ctttgtttgt aaattttgat tcttgtggtt     4020
tatatgactt tttgtgtttt ataacatctt caatcctaaa tgcaaattgg agtagaggta     4080
ggagattagg tggagaaccg aatacaaatc aataaaataa aagttcagat ggtcaatcaa     4140
aagtgacgca aaatatgatc aatgaagtag ttgagagccg tgaagtatat gtttaaatct     4200
caacctagac aaaaacactc aatgattctt cctatttgtc ataactttgg ttgacaaacc     4260
tagtacttat tattgatagg aggtgacagt gaaattagtc gaggtacttg aatcaagaca     4320
ccagagtcct taagaaagaa tgttggggag aaaaacaaaa cttacatcaa tattttctat     4380
tccaaaattt cacatatata cattatacaa tactactagt ttaatttcaa attatcaaaa     4440
atttgggcca ccaaaaacaa tggattgcat ttacatatgc aaccaaacaa aattatcaca     4500
cacctctcaa cccaccttat tttcactgtg caaaagagag acatctttgc acagtaatat     4560
taaagcaaaa accaaaactt tagcctaaat tctccaaaaa attgttctta ttttctagtt     4620
gaatattcta tatacagagt tcattgtcga tattccttta tacaccgttc agtaaggaag     4680
atttatgcca tagcagccat ttgagagttt aggcagtcaa agccctcgac tctatttggt     4740
gagtgaggtt tcccgagtct tgcccttgca cacc                                 4774
```

<210> SEQ ID NO 31
<211> LENGTH: 1751
<212> TYPE: DNA
<213> ORGANISM: Solanum lycopersicum

<400> SEQUENCE: 31

```
tgaatctact gctaataatg attttgattt gtatttcaat caggcatgag aaaagattag       60
gcatgaagaa ggacaacttc aacctccaat attagtatgg tggaagaatc gtgaaaatca      120
atttccgacc attactagga ttgtttgaga tatgctagcg attcaagcat catcggtcgc      180
ttcggataag cctttaggct cggggtgtga cagatcatga taaggctttg catattgttc      240
cccacgtcat tgtcgagggt ccaattaata tttgagaaaa aaatgcccaa aatcgcatca      300
tcaaaaattc attgactagc tcacacaaaa caaactcttg ttgattatcc cctaaatgct      360
aaaaaagggc gtggatcatg atgaggttat atgtattgtt ccctcaagtc attacggaga      420
gtcatgtaag ggttttgaat aaaaaagtgt ctgaaaacca taacatcaga aaatttattg      480
attaacaaac atgaaaaact gaaaaaatca cctaattttt attgagcggc ccttaaatgc      540
taaaagaatt acatgaatca tagtgaagct atacatattg ttctctcaag ttattacgga      600
tggttccatc aaagtttttt ttttttttaaa tggttgaaaa tcatatcacc attaaaactc      660
attgaccaca cacgaaaaac taaaaaaaaa tcgcctaata cctaatgagt gaccactaaa      720
tgctaaaaaa tggcatgatc atggtaagac tatatgttct gttccccaag tcattatgga      780
ggatcatgta aaagtttttag aaaaaaagta ctcaaaaatc acattactaa atattacatt      840
gactaacata catgaaaaaa ctgagaaaca tatttaattc agttgccctg aattgctaat      900
cctatacact tcctcacttt gtaacgaacc ttaacacaca tgaacaaata ggacattact      960
tggttcaaag ttgatactct tacggcgaaa ggtgtggatc tttagcatag aattcatggg     1020
gcattacaat taattagtaa tactaatttt aataacacta aatcatatta gtctctatag     1080
gtataatata taactctgga gtcactatct gtatttggga tcaacagtta caaaggtacg     1140
agtaaagtct ctgatccgac aaacaatccg tatatcctac cttcccgaaa tttcatgtat     1200
aaaattatac taaaatatta ttttttcttgt attatccgat tgaaaattat gcgaattcaa     1260
cataaaactc taaaaaaaga aaataatgaa aattacaact taaaagagtg tctaagttgg     1320
aatcatggta ttacataaag ttgaggacaa tataagcaag caaacaagta ctctagctat     1380
caatttactt tggactacta tatgataaat atttcaaccc ccctcctccc ccaccaaaaa     1440
aaaattaaaa taacaagttg aaggactcaa aaaaaaaaaa aaaaaaaaac tcaaaaccaa     1500
cctcaatcat acattcatat cctcttccta ccccccatctt ggatgagata agattaacga     1560
ggtgcttaca cgtgtcacct ctattgtggt gacttaaaaa aaattccaac ctttcatatg     1620
tagatattaa gtaattgtat aatgttatca agaaccacat aacatatcaa aaaccttatc     1680
atttcattat ataaaaggat agtggacatc aaaaggttca tattgaacca aaaaaagaga     1740
gaagaagcaa t                                                        1751
```

```
<210> SEQ ID NO 32
<211> LENGTH: 948
<212> TYPE: DNA
<213> ORGANISM: Solanum lycopersicum

<400> SEQUENCE: 32
gtttcatatt aggaacaaaa ttgtctttag ggacactttg tttttaaatg ctacttaggt       60
cttttttctt ttttgtctta attccaacaa actctttgtg tcttgtacta ttcggtttat      120
gttttggatt tatgagtacc taattatatg ataatgattt ggtgctttgt ttgtaaattt      180
tgattcttgt ggtttatatg acttttttgt ttttataaca tcttcaatcc taaatgcaaa      240
ttggagtaga ggtaggagat taggtggaga accgaataca aatcaataaa ataaaagttc      300
```

-continued

```
agatggtcaa tcaaaagtga cgcaaaatat gatcaatgaa gtagttgaga gccgtgaagt      360
atatgtttaa atctcaacct agacaaaaac actcaatgat tcttcctatt tgtcataact      420
ttggttgaca aacctagtac ttattattga taggaggtga cagtgaaatt agtcgaggta      480
cttgaatcaa gacaccagag tccttaagaa agaatgttgg ggagaaaaac aaaacttaca      540
tcaatatttt ctattccaaa atttcacata tatacattat acaatactac tagtttaatt      600
tcaaattatc aaaaatttgg gccaccaaaa acaatggatt gcatttacat atgcaaccaa      660
acaaaattat cacacacctc tcaacccacc ttattttcac tgtgcaaaag agagacatct      720
ttgcacagta atattaaagc aaaaaccaaa actttagcct aaattctcca aaaaattgtt      780
cttattttct agttgaatat tctatataca gagttcattg tcgatattcc tttatacacc      840
gttcagtaag gaagatttat gccatagcag ccatttgaga gtttaggcag tcaaagccct      900
cgactctatt tggtgagtga ggtttcccga gtcttgccct tgcacacc               948
```

```
<210> SEQ ID NO 33
<211> LENGTH: 3924
<212> TYPE: DNA
<213> ORGANISM: Solanum tuberosum

<400> SEQUENCE: 33
```

```
ccaagacaat ttcagcttaa aaagttttat taatatttac attagttttg ttgatgagga       60
tgacaagatt ttggtcatca attacatata cccaaattga atacttagta agcaacttaa      120
tgtttttcat aatgataatg acagacacaa aaaaaaccca tttattattc acattgattg      180
atttttatat gcactatagt aataataata atatttctta taaagcaaga ggtcaatttt      240
ttattttatt ataccaacga cactaaatta tatttgataa tgtaaaacaa ttcaatttta      300
cttaaatatc atgaaataaa ctattttat aaccaaatta ctaaatttat ccaataaaaa      360
aaagtcatta agaagacata aaataaattt gagtaaaaag agtgaagtcg actgacttt       420 ttttttatca taagaaaata aattattaac tttaacctaa taaaacacta atataatttc      480
atggaatcta atacttacct cttagatata agaaaaagcg tttctaatag accctcaatt      540
tacattaaat attttcaatc aagtttaaat aacaaatatc aatatgaggt caataacagt      600
atcaaaataa tatgaaaaaa gagcaataca taatataaga aagaagattt aagtgcactt      660
atcaaggtag tattatatcc taatttgcta atatttaaac tcttatattt aaggtcatgt      720
tcacgataaa cttgaaatgc gctttattag agcatatatt aaaataaaaa aaatacctaa      780
aataaaataa agttattttt agtatatatt ttttacatga cctacatttt tctagttttt      840
tctaaaggag cgtgtaagtg tcaacctcat tctcctaatt ttccccacca cataaaaatt      900
aaaaaggaaa ggtagctttt gcgtgttgtt ttggtacact acacctcatt attacacgtg      960
tcctcatata gttggttaac ccgtgaggcg gtttcctcta gagtcggcca tgccatctat     1020
aaaatgaagc tttctgcacc tcaatttttc atcttctatc tgatttctat tataatttct     1080
attaattgcc ttcaaatttc tctttcaagg ttagaaatct tctctatttt ttggtttttg     1140
tctgtttaga ttctcgaatt agctaatcag gtgctgttaa agccctaaaa tttgagtttt     1200
ttttccgtcg aattgatgct aaaggcttaa aattagagtt ttttcgtcgg tttgactctg     1260
aaggcctaaa atttggggtt ttccgggtga tttgatgata aagccctaga atttgagttt     1320
ttttatttgt cggtttgatg aaaaaggcct taaatttaat tttttttcccg gttgatttga     1380 tgaaaaagcc ctagaatttg tgttttttcg tcggtttgat tctaaaggcc taaaatttga     1440 gttttttccgg ttgtttttgat gaaaaagccc taaaatttga gttttttccc cgtgttttag    1500
```

-continued

```
attgtttggt tttaattctt gaatcagata atcagggagt gtgaaaagcc ctaaaatttg    1560
agtttttttc gttgttctga ttgttgtttt tatgaatttg cagatgcaga tctttgtgaa    1620
aactctcacc ggaaagacca tcaccctaga ggtggaaagt tctgatacaa tcgacaacgt    1680
taaggctaag attcaggata aggaaggaat tcccccggat cagcaaaggc ttatcttcgc    1740
cggaaagcag ttggaggacg gacgtactct agctgattac aacatccaga aggagtctac    1800
cctccatttg gtgctccgtc tacgtggtgg tatgcagatc ttcgttaaga ctcttacggg    1860
taagacgatt acccttgagg tcgaaagctc agacaccatt gacaatgtta aggctaagat    1920
ccaggataag gaaggcattc ccccagacca gcagaggttg atctttgcag ggaaacagtt    1980
ggaagatggc cgcacccta g ctgactacaa catccagaag gagtctaccc tacatttggt    2040
cctccgtctc cgtggtggta tgcagatctt cgttaagact cttaccggaa agaccatcac    2100
tttggaggtg gaaagctccg acaccattga caacgtgaag gctaagatcc aggataagga    2160
gggaattccc ccagaccagc agaggttgat cttcgctggt aagcaattgg aggacggccg    2220
caccctagct gactacaaca tccagaagga gtctaccctc catcttgtcc tccgtctccg    2280
tggtggtatg cagattttttg ttaagaccct caccgggaag accatcactt ggaggttga    2340 aagctccgac accattgata atgtcaaggc taagatccag gacaaggagg gaattccccc    2400
agaccagcag aggttgatct tcgctggaaa gcaattggag gatggccgca ccctagctga    2460
ctacaacatc cagaaggagt ccaccttca ccttgtcctc cgtctccgtg gtggtatgca    2520 gattttttgtt aagacccta c cgggaagac catcaccctg gaggttgaga gctccgacac    2580
cattgacaat gttaaggcca agatccaaga caaggagggt attcccccag accagcagag    2640
gttgatcttc gctggtaaac agcttgagga tggccgcacc cttgcggact acaacattca    2700
gaaggagtcc accccttcact tggtgctgag gctgaggggga ggaatgcaga tctttgtgaa    2760
gaccttaacc gggaagacca tcaccttgga ggtggagagt tctgacacca tcgacaatgt    2820
gaaagctaag attcaggaca aggaggggat cccaccagac cagcagaggt tgatctttgc    2880
tggtaagcag cttgaagatg gacgcaccct tgccgactac aatatccaga aggagtccac    2940
tctgcacctt gtcctccgtc tccgtggtgg tttttaagtt gcctgttgtt ggttgtcgtg    3000
ttgtctggct gtgtctgttg cccattgtgg tggttatgtg tttgcattat ggtcttaaag    3060
gatcatcaat gtgtttttcgc tttctgttcc tttctgtttc tcatttgtga ataataatgg    3120
cgtctttatg aacatccaat ttctggtttc ttttctgatc gcagtttgag tatttgtttt    3180
tgcttttgcc tccgtctatt acaccacttt gcaattacta taatatacta aaagccttcg    3240
atccatcttc gtttgatga ttcgaatggt atttatttaa ctcatacca agtgaagcat    3300 aaagttagag gagagttcct gttccattgc ctgtttgtat catgagcaac tcatgttaat    3360
aaacataaga aaaaccatga tgcaatctgt gtagctgata gactttgatg acagacgact    3420
cataagtaac aagagataac aaagaggaaa cataataaac atgtacggga agtcctccaa    3480
caatgactat aatcacatgt ttttgtagat tagcaattgt acatgtcaaa tgatcttgga    3540
ttaaggaagg agcttgtgaa tcaaaacatc tgaatttgga cctagagtct tgaggtgatc    3600
gtactttgga tggagagacc atgaataaga ataaatgaat ctggaactga gaactaaatg    3660
gaagacacac tgatccaaca gattaagctt atgacattaa tcacagaagg taactcggtg    3720
acaaccaaga acggggagct gcaaattcta ttgtcttaac aacggacctt tactggttta    3780
actgttatga tgtctttat aggtggcttt tgggttgttc ttcgctctat cctttt atgt    3840
```

-continued

```
aactttcaag aaccaaccaa atgcaggtgt tctagataga tatacgtggc atgtgagaag       3900
ggaccctgaa gttcagatga cggt                                             3924

<210> SEQ ID NO 34
<211> LENGTH: 1603
<212> TYPE: DNA
<213> ORGANISM: Solanum tuberosum

<400> SEQUENCE: 34
ccaagacaat ttcagcttaa aaagtttat taatatttac attagttttg ttgatgagga          60
tgacaagatt ttggtcatca attacatata cccaaattga atacttagta agcaacttaa         120 tgttttcat aatgataatg acagacacaa aaaaaaccca tttattattc acattgattg          180
atttttatat gcactatagt aataataata atatttctta taaagcaaga ggtcaatttt         240
ttattttatt ataccaacga cactaaatta tatttgataa tgtaaaacaa ttcaatttta         300
cttaaatatc atgaaataaa ctattttat aaccaaatta ctaaatttat ccaataaaaa         360
aaagtcatta agaagacata aaataaattt gagtaaaaag agtgaagtcg actgactttt         420
ttttttatca taagaaaata aattattaac tttaacctaa taaaacacta atataatttc         480
atggaatcta atacttacct cttagatata agaaaaagcg tttctaatag accctcaatt         540
tacattaaat attttcaatc aagtttaaat aacaaatatc aatatgaggt caataacagt         600
atcaaaataa tatgaaaaaa gagcaataca taatataaga aagaagattt aagtgcactt         660
atcaaggtag tattatatcc taatttgcta atatttaaac tcttatattt aaggtcatgt         720
tcacgataaa cttgaaatgc gctttattag agcatatatt aaaataaaaa aaatacctaa         780
aataaaataa agttattttt agtatatatt ttttacatga cctacatttt tctagttttt         840
tctaaaggag cgtgtaagtg tcaacctcat tctcctaatt ttccccacca cataaaaatt         900
aaaaaggaaa ggtagctttt gcgtgttgtt ttggtacact acacctcatt attacacgtg         960
tcctcatata gttggttaac ccgtgaggcg gtttcctcta gagtcggcca tgccatctat       1020
aaaatgaagc tttctgcacc tcaatttttc atcttctatc tgatttctat tataatttct       1080
attaattgcc ttcaaatttc tctttcaagg ttagaaatct tctctatttt ttggtttttg       1140
tctgtttaga ttctcgaatt agctaatcag gtgctgttaa agccctaaaa tttgagtttt       1200
ttttccgtcg aattgatgct aaaggcttaa aattagagtt ttttcgtcgg tttgactctg       1260
aaggcctaaa atttggggtt ttccgggtga tttgatgata aagccctaga atttgagttt       1320
ttttatttgt cggtttgatg aaaaaggcct taaatttaat tttttttcccg gttgatttga     1380 tgaaaaagcc ctagaatttg tgttttttcg tcggtttgat tctaaaggcc taaaatttga       1440 gttttttccgg ttgttttgat gaaaaagccc taaaatttga gttttttccc cgtgtttttag     1500 attgtttggt tttaattctt gaatcagata atcagggagt gtgaaaagcc ctaaaatttg       1560
agtttttttc gttgttctga ttgttgtttt tatgaatttg cag                        1603

<210> SEQ ID NO 35
<211> LENGTH: 1010
<212> TYPE: DNA
<213> ORGANISM: Solanum tuberosum

<400> SEQUENCE: 35
ccaagacaat ttcagcttaa aaagttttat taatatttac attagttttg ttgatgagga         60
tgacaagatt ttggtcatca attacatata cccaaattga atacttagta agcaacttaa        120 tgttttcat aatgataatg acagacacaa aaaaaaccca tttattattc acattgattg         180
```

-continued

```
attttttatat gcactatagt aataataata atatttctta taaagcaaga ggtcaatttt      240 ttatttttatt ataccaacga cactaaatta tatttgataa tgtaaaacaa ttcaatttta      300
cttaaatatc atgaaataaa ctattttttat aaccaaatta ctaaatttat ccaataaaaa      360
aaagtcatta agaagacata aaataaattt gagtaaaaag agtgaagtcg actgactttt      420
ttttttatca taagaaaata aattattaac tttaacctaa taaaacacta atataatttc      480
atggaatcta atacttacct cttagatata agaaaaagcg tttctaatag accctcaatt      540
tacattaaat attttcaatc aagtttaaat aacaaatatc aatatgaggt caataacagt      600
atcaaaataa tatgaaaaaa gagcaataca taatataaga aagaagattt aagtgcactt      660
atcaaggtag tattatatcc taatttgcta atatttaaac tcttatattt aaggtcatgt      720
tcacgataaa cttgaaatgc gctttattag agcatatatt aaaataaaaa aaatacctaa      780
aataaaataa agttatttttt agtatatatt ttttacatga cctacatttt tctagttttt      840
tctaaaggag cgtgtaagtg tcaacctcat tctcctaatt ttccccacca cataaaaatt      900
aaaaaggaaa ggtagctttt gcgtgttgtt ttggtacact acacctcatt attacacgtg      960
tcctcatata gttggttaac ccgtgaggcg gtttcctcta gagtcggcca              1010
```

<210> SEQ ID NO 36
<211> LENGTH: 99
<212> TYPE: DNA
<213> ORGANISM: Solanum tuberosum

<400> SEQUENCE: 36

```
tgccatctat aaaatgaagc tttctgcacc tcaatttttc atcttctatc tgatttctat       60
tataatttct attaattgcc ttcaaatttc tctttcaag                              99
```

<210> SEQ ID NO 37
<211> LENGTH: 494
<212> TYPE: DNA
<213> ORGANISM: Solanum tuberosum

<400> SEQUENCE: 37

```
gttagaaatc ttctctattt tttggttttt gtctgtttag attctcgaat tagctaatca       60
ggtgctgtta aagccctaaa atttgagttt tttttccgtc gaattgatgc taaaggctta      120
aaattagagt tttttcgtcg gtttgactct gaaggcctaa aatttggggt tttccgggtg      180
atttgatgat aaagccctag aatttgagtt tttttatttg tcggtttgat gaaaaaggcc      240
ttaaatttaa tttttttttccc ggttgatttg atgaaaaagc cctagaattt gtgtttttttc      300 gtcggtttga ttctaaaggc ctaaaatttg agttttttccg gttgttttga tgaaaaagcc      360
ctaaaatttg agtttttttcc ccgtgtttta gattgttttgg ttttaattct tgaatcagat      420
aatcagggag tgtgaaaagc cctaaaattt gagttttttt cgttgttctg attgttgttt      480
ttatgaattt gcag                                                        494
```

<210> SEQ ID NO 38
<211> LENGTH: 947
<212> TYPE: DNA
<213> ORGANISM: Solanum tuberosum

<400> SEQUENCE: 38

```
gttgcctgtt gttggttgtc gtgttgtctg gctgtgtctg ttgcccattg tggtggttat       60
gtgtttgcat tatggtctta aaggatcatc aatgtgtttt cgctttctgt tcctttctgt      120
```

```
ttctcatttg tgaataataa tggcgtctttt atgaacatcc aatttctggt ttcttttctg      180
atcgcagttt gagtatttgt ttttgctttt gcctccgtct attacaccac tttgcaatta      240
ctataatata ctaaaagcct tcgatccatc ttctgtttga tgattcgaat ggtatttatt      300
taactcatac ccaagtgaag cataaagtta gaggagagtt cctgttccat tgcctgtttg      360
tatcatgagc aactcatgtt aataaacata agaaaaacca tgatgcaatc tgtgtagctg      420
atagactttg atgacagacg actcataagt aacaagagat aacaaagagg aaacataata      480
aacatgtacg ggaagtcctc caacaatgac tataatcaca tgtttttgta gattagcaat      540
tgtacatgtc aaatgatctt ggattaagga aggagcttgt gaatcaaaac atctgaattt      600
ggacctagag tcttgaggtg atcgtacttt ggatggagag accatgaata agaataaatg      660
aatctggaac tgagaactaa atggaagaca cactgatcca acagattaag cttatgacat      720
taatcacaga aggtaactcg gtgacaacca agaacgggga gctgcaaatt ctattgtctt      780
aacaacggac ctttactggt ttaactgtta tgatgtctttt tataggtggc ttttgggttg      840
ttcttcgctc tatcctttta tgtaactttc aagaaccaac caaatgcagg tgttctagat      900
agatatacgt ggcatgtgag aagggaccct gaagttcaga tgacggt                    947
```

```
<210> SEQ ID NO 39
<211> LENGTH: 177
<212> TYPE: DNA
<213> ORGANISM: Solanum tuberosum

<400> SEQUENCE: 39
gttgcctgtt gttggttgtc gtgttgtctg gctgtgtctg ttgcccattg tggtggttat       60
gtgtttgcat tatggtctta aaggatcatc aatgtgtttt cgctttctgt tcctttctgt      120
ttctcatttg tgaataataa tggcgtctttt atgaacatcc aatttctggt ttctttt        177
```

```
<210> SEQ ID NO 40
<211> LENGTH: 3824
<212> TYPE: DNA
<213> ORGANISM: Arabidopsis thaliana

<400> SEQUENCE: 40
ctccacttct acttccagca cgcttcttac ttttaccaca gctcttgcac ctaaccataa       60
caccttccct gtatgatcgc gaagcaccca ccctaagcca cattttaatc cttctgttgg      120
ccatgcccca tcaaagttgc acttaaccca agattgtggt ggagcttccc atgtttctcg      180
tctgtcccga cggtgttgtg gttggtgctt ccttacatt ctgagcctct ttccttctaa       240
tccactcatc tgcatcttct tgtgtcctta ctaataccctc attggttcca aattccctcc     300
ctttaagcac cagctcgttt ctgttcttcc acagcctccc aagtatccaa gggactaaag      360
cctccacatt cttcagatca ggatattctt gtttaagatg ttgaactcta tggaggtttg      420
tatgaactga tgatctagga ccggataagt tcccttcttc atagcgaact tattcaaaga      480 atgtttttgtg tatcattctt gttacattgt tattaatgaa aaaatattat tggtcattgg     540
actgaacacg agtgttaaat atggaccagg ccccaaataa gatccattga tatatgaatt      600
aaataacaag aataaatcga gtcaccaaac cacttgcctt tttttaacgag acttgttcac     660 caacttgata caaaagtcat tatcctatgc aaatcaataa tcatacaaaa atatccaata      720
acactaaaaa attaaaagaa atggataatt tcacaatatg ttatacgata aagaagttac      780
ttttccaaga aattcactga ttttataagc ccacttgcat tagataaatg gcaaaaaaaa      840
acaaaaagga aaagaaataa agcacgaaga attctagaaa atacgaaata cgcttcaatg      900
```

```
cagtgggacc cacggttcaa ttattgccaa ttttcagctc caccgtatat ttaaaaaata      960
aaacgataat gctaaaaaaa tataaatcgt aacgatcgtt aaatctcaac ggctggatct     1020
tatgacgacc gttagaaatt gtggttgtcg acgagtcagt aataaacggc gtcaaagtgg     1080
ttgcagccgg cacacacgag tcgtgtttat caactcaaag cacaaatact tttcctcaac     1140
ctaaaaataa ggcaattagc caaaaacaac tttgcgtgta aacaacgctc aatacacgtg     1200
tcattttatt attagctatt gcttcaccgc cttagctttc tcgtgaccta gtcgtcctcg     1260
tcttttcttc ttcttcttct ataaaacaat acccaaagag ctcttcttct tcacaattca     1320
gatttcaatt tctcaaaatc ttaaaaactt tctctcaatt ctctctaccg tgatcaaggt     1380
aaatttctgt gttccttatt ctctcaaaat cttcgatttt gttttcgttc gatcccaatt     1440
tcgtatatgt tctttggttt agattctgtt aatcttagat cgaagacgat tttctgggtt     1500
tgatcgttag atatcatctt aattctcgat tagggtttca tagatatcat ccgatttgtt     1560
caaataattt gagttttgtc gaataattac tcttcgattt gtgatttcta tctagatctg     1620
gtgttagttt ctagtttgtg cgatcgaatt tgtcgattaa tctgagtttt tctgattaac     1680
agatgcagat ctttgttaag actctcaccg gaaagacaat caccctcgag gtggaaagct     1740
ccgacaccat cgacaacgtt aaggccaaga tccaggataa ggagggcatt cctccggatc     1800
agcagaggct tattttcgcc ggcaagcagc tagaggatgg ccgtacgttg gctgattaca     1860
atatccagaa ggaatccacc ctccacttgg tcctcaggct ccgtggtggt atgcagattt     1920
tcgttaaaac cctaacggga aagacgatta ctcttgaggt ggagagttct gacaccatcg     1980
acaacgtcaa ggccaagatc caagacaaag agggtattcc tccggaccag cagaggctga     2040
tcttcgccgg aaagcagttg gaggatggca gaactcttgc tgactacaat atccagaagg     2100
agtccaccct tcatcttgtt ctcaggctcc gtggtggtat gcagattttc gttaagacgt     2160
tgactgggaa aactatcact ttggaggtgg agagttctga caccattgat aacgtgaaag     2220
ccaagatcca agacaaagag ggtattcctc cggaccagca gagattgatc ttcgccggaa     2280
aacaacttga agatggcaga actttggccg actacaacat tcagaaggag tccacactcc     2340
acttggtctt gcgtctgcgt ggaggtatgc agatcttcgt gaagactctc accggaaaga     2400
ccatcacttt ggaggtggag agttctgaca ccattgataa cgtgaaagcc aagatccagg     2460
acaaagaggg tatcccaccg gaccagcaga gattgatctt cgccggaaag caacttgaag     2520
atggaagaac tttggctgac tacaacattc agaaggagtc cacacttcac ttggtcttgc     2580
gtctgcgtgg aggtatgcag atcttcgtga agactctcac cggaaagact atcactttgg     2640
aggtagagag ctctgacacc attgacaacg tgaaggccaa gatccaggat aaggaaggaa     2700
tccctccgga ccagcagagg ttgatctttg ccggaaaaca attggaggat ggtcgtactt     2760
tggcggatta caacatccag aaggagtcga cccttcactt ggtgttgcgt ctgcgtggag     2820
gtatgcagat cttcgtcaag actttgaccg gaaagaccat cacccttgaa gtggaaagct     2880
ccgacaccat tgacaacgtc aaggccaaga tccaggacaa ggaaggtatt cctccggacc     2940
agcagcgtct catcttcgct ggaaagcagc ttgaggatgg acgtactttg ccgactaca     3000 acatccagaa ggagtctact cttcacttgg tcctgcgtct tcgtggtggt ttctaaatct     3060
cgtctctgtt atgcttaaga agttcaatgt ttcgtttcat gtaaaacttt ggtggtttgt     3120
gttttggggc cttgtataat ccctgatgaa taagtgttct actatgtttc cgttcctgtt     3180
atctctttct ttctaatgac aagtcgaact tcttctttat catcgcttcg tttttattat     3240
```

-continued

```
ctgtgcttct tttgtttaat acgcctgcaa agtgactcga ctctgtttag tgcagttctg        3300
cgaaacttgt aaatagtcca attgttggcc tctagtaata gatgtagcga aagtgttgag        3360
ctgttgggtt ctaaggatgg cttgaacatg ttaatctttt aggttctgag tatgatgaac        3420
attcgttgtt gctaagaaat gcctgtaatg tcccacaaat gtagaaaatg gttcgtacct        3480
ttgtccaagc attgatatgt ctgatgagag gaaactgcaa gatactgagc ttggtttaac        3540
gaaggagagg cagtttcttc cttccaaagc atttcatttg acaatgcctt gatcatctta        3600
agtagagttt ctgttgtgga aagtttgaaa cttttgaagaa acgactctca agtaaattga        3660
tgatcacaag tgaaagtgta tgttacataa gtggatattt cacccttttt ccatcaatca        3720
aaacatcata tagtaatcca ttggtttata caaacatcaa aatacattta cctctgaaat        3780
gaggaaaaaa atgcaaagag atttttgaaa atttccaaca aatg                        3824
```

<210> SEQ ID NO 41
<211> LENGTH: 1682
<212> TYPE: DNA
<213> ORGANISM: Arabidopsis thaliana

<400> SEQUENCE: 41

```
ctccacttct acttccagca cgcttcttac ttttaccaca gctcttgcac ctaaccataa          60
caccttccct gtatgatcgc gaagcaccca ccctaagcca cattttaatc cttctgttgg         120
ccatgcccca tcaaagttgc acttaaccca agattgtggt ggagcttccc atgtttctcg         180
tctgtcccga cggtgttgtg gttggtgctt tccttacatt ctgagcctct ttccttctaa        240
tccactcatc tgcatcttct tgtgtcctta ctaatacctc attggttcca aattccctcc        300
ctttaagcac cagctcgttt ctgttcttcc acagcctccc aagtatccaa gggactaaag        360
cctccacatt cttcagatca ggatattctt gtttaagatg ttgaactcta tggaggtttg        420
tatgaactga tgatctagga ccggataagt tcccttcttc atagcgaact tattcaaaga        480 atgtttgtg tatcattctt gttacattgt tattaatgaa aaaatattat tggtcattgg         540
actgaacacg agtgttaaat atggaccagg ccccaaataa gatccattga tatatgaatt        600
aaataacaag aataaatcga gtcaccaaac cacttgcctt ttttaacgag acttgttcac        660
caacttgata caaaagtcat tatcctatgc aaatcaataa tcatacaaaa atatccaata        720
acactaaaaa attaaaagaa atggataatt tcacaatatg ttatacgata aagaagttac        780
ttttccaaga aattcactga ttttataagc ccacttgcat tagataaatg gcaaaaaaaa        840
acaaaaagga aaagaaataa agcacgaaga attctagaaa atacgaaata cgcttcaatg        900
cagtgggacc cacggttcaa ttattgccaa ttttcagctc caccgtatat ttaaaaaata        960
aaacgataat gctaaaaaaa tataaatcgt aacgatcgtt aaatctcaac ggctggatct       1020
tatgacgacc gttagaaatt gtggttgtcg acgagtcagt aataaacggc gtcaaagtgg       1080
ttgcagccgg cacacacgag tcgtgtttat caactcaaag cacaaatact tttcctcaac       1140
ctaaaaataa ggcaattagc caaaaacaac tttgcgtgta acaacgctc aatacacgtg        1200 tcattttatt attagctatt gcttcaccgc cttagctttc tcgtgaccta gtcgtcctcg       1260
tcttttcttc ttcttcttct ataaaacaat acccaaagag ctcttcttct tcacaattca       1320
gatttcaatt tctcaaaatc ttaaaaactt tctctcaatt ctctctaccg tgatcaaggt       1380
aaatttctgt gttccttatt ctctcaaaat cttcgatttt gttttcgttc gatcccaatt       1440
tcgtatatgt tctttggttt agattctgtt aatcttagat cgaagacgat tttctgggtt       1500
tgatcgttag atatcatctt aattctcgat tagggtttca tagatatcat ccgatttgtt       1560
```

-continued

```
caaataattt gagttttgtc gaataattac tcttcgattt gtgatttcta tctagatctg      1620
gtgttagttt ctagtttgtg cgatcgaatt tgtcgattaa tctgagtttt tctgattaac      1680
ag                                                                     1682

<210> SEQ ID NO 42
<211> LENGTH: 1293
<212> TYPE: DNA
<213> ORGANISM: Arabidopsis thaliana

<400> SEQUENCE: 42
ctccacttct acttccagca cgcttcttac ttttaccaca gctcttgcac ctaaccataa        60
caccttccct gtatgatcgc gaagcaccca ccctaagcca cattttaatc cttctgttgg       120
ccatgcccca tcaaagttgc acttaaccca agattgtggt ggagcttccc atgtttctcg       180
tctgtcccga cggtgttgtg gttggtgctt tccttacatt ctgagcctct ttccttctaa       240
tccactcatc tgcatcttct tgtgtcctta ctaataccte attggttcca aattccctcc       300
ctttaagcac cagctcgttt ctgttcttcc acagcctccc aagtatccaa gggactaaag       360
cctccacatt cttcagatca ggatattctt gtttaagatg ttgaactcta tggaggtttg       420
tatgaactga tgatctagga ccggataagt tcccttcttc atagcgaact tattcaaaga       480
atgttttgtg tatcattctt gttacattgt tattaatgaa aaaatattat tggtcattgg       540
actgaacacg agtgttaaat atggaccagg ccccaaataa gatccattga tatatgaatt       600
aaataacaag aataaatcga gtcaccaaac cacttgcctt ttttaacgag acttgttcac       660
caacttgata caaaagtcat tatcctatgc aaatcaataa tcatacaaaa atatccaata       720
acactaaaaa attaaaagaa atggataatt tcacaatatg ttatacgata aagaagttac       780
ttttccaaga aattcactga tttttataagc ccacttgcat tagataaatg gcaaaaaaaa      840
acaaaaagga aaagaaataa agcacgaaga attctagaaa atacgaaata cgcttcaatg       900
cagtgggacc cacggttcaa ttattgccaa ttttcagctc caccgtatat ttaaaaaata       960
aaacgataat gctaaaaaaa tataaatcgt aacgatcgtt aaatctcaac ggctggatct      1020
tatgacgacc gttagaaatt gtggttgtcg acgagtcagt aataaacggc gtcaaagtgg      1080
ttgcagccgg cacacacgag tcgtgtttat caactcaaag cacaaatact tttcctcaac      1140
ctaaaaataa ggcaattagc caaaaacaac tttgcgtgta acaacgctc aatacacgtg       1200 tcattttatt attagctatt gcttcaccgc cttagctttc tcgtgaccta gtcgtcctcg      1260
tcttttcttc ttcttcttct ataaaacaat acc                                  1293

<210> SEQ ID NO 43
<211> LENGTH: 85
<212> TYPE: DNA
<213> ORGANISM: Arabidopsis thaliana

<400> SEQUENCE: 43
caaagagctc ttcttcttca caattcagat ttcaatttct caaaatctta aaaactttct        60
ctcaattctc tctaccgtga tcaag                                             85

<210> SEQ ID NO 44
<211> LENGTH: 304
<212> TYPE: DNA
<213> ORGANISM: Arabidopsis thaliana

<400> SEQUENCE: 44
```

-continued

```
gtaaatttct gtgttcctta ttctctcaaa atcttcgatt ttgttttcgt tcgatcccaa        60
tttcgtatat gttctttggt ttagattctg ttaatcttag atcgaagacg attttctggg       120
tttgatcgtt agatatcatc ttaattctcg attagggttt catagatatc atccgatttg       180
ttcaaataat ttgagttttg tcgaataatt actcttcgat ttgtgatttc tatctagatc       240
tggtgttagt ttctagtttg tgcgatcgaa tttgtcgatt aatctgagtt tttctgatta       300
acag                                                                    304

<210> SEQ ID NO 45
<211> LENGTH: 768
<212> TYPE: DNA
<213> ORGANISM: Arabidopsis thaliana

<400> SEQUENCE: 45
atctcgtctc tgttatgctt aagaagttca atgtttcgtt tcatgtaaaa ctttggtggt        60
ttgtgttttg gggccttgta taatccctga tgaataagtg ttctactatg tttccgttcc       120
tgttatctct ttctttctaa tgacaagtcg aacttcttct ttatcatcgc ttcgttttta       180
ttatctgtgc ttcttttgtt taatacgcct gcaaagtgac tcgactctgt ttagtgcagt       240
tctgcgaaac ttgtaaatag tccaattgtt ggcctctagt aatagatgta gcgaaagtgt       300
tgagctgttg ggttctaagg atggcttgaa catgttaatc ttttaggttc tgagtatgat       360
gaacattcgt tgttgctaag aaatgcctgt aatgtcccac aaatgtagaa aatggttcgt       420
acctttgtcc aagcattgat atgtctgatg agaggaaact gcaagatact gagcttggtt       480
taacgaagga gaggcagttt cttccttcca aagcatttca tttgacaatg ccttgatcat       540
cttaagtaga gtttctgttg tggaaagttt gaaactttga agaaacgact ctcaagtaaa       600
ttgatgatca caagtgaaag tgtatgttac ataagtggat atttcaccct ttttccatca       660
atcaaaacat catatagtaa tccattggtt tatacaaaca tcaaaataca tttacctctg       720
aaatgaggaa aaaaatgcaa agagattttt gaaaatttcc aacaaatg                    768

<210> SEQ ID NO 46
<211> LENGTH: 376
<212> TYPE: DNA
<213> ORGANISM: Arabidopsis thaliana

<400> SEQUENCE: 46
atctcgtctc tgttatgctt aagaagttca atgtttcgtt tcatgtaaaa ctttggtggt        60
ttgtgttttg gggccttgta taatccctga tgaataagtg ttctactatg tttccgttcc       120
tgttatctct ttctttctaa tgacaagtcg aacttcttct ttatcatcgc ttcgttttta       180
ttatctgtgc ttcttttgtt taatacgcct gcaaagtgac tcgactctgt ttagtgcagt       240
tctgcgaaac ttgtaaatag tccaattgtt ggcctctagt aatagatgta gcgaaagtgt       300
tgagctgttg ggttctaagg atggcttgaa catgttaatc ttttaggttc tgagtatgat       360
gaacattcgt tgttgc                                                       376

<210> SEQ ID NO 47
<211> LENGTH: 2778
<212> TYPE: DNA
<213> ORGANISM: Arabidopsis thaliana

<400> SEQUENCE: 47
gtcgacgagt cagtaataaa cggcgtcaaa gtggttgcag ccggcacaca cgagtcgtgt        60
ttatcaactc aaagcacaaa tacttttcct caacctaaaa ataaggcaat tagccaaaaa       120
```

-continued

```
caactttgcg tgtaaacaac gctcaataca cgtgtcattt tattattagc tattgcttca      180
ccgccttagc tttctcgtga cctagtcgtc ctcgtctttt cttcttcttc ttctataaaa      240
caatacccaa agagctcttc ttcttcacaa ttcagatttc aatttctcaa aatcttaaaa      300
actttctctc aattctctct accgtgatca aggtaaattt ctgtgttcct tattctctca      360
aaatcttcga ttttgttttc gttcgatccc aatttcgtat atgttctttg gtttagattc      420
tgttaatctt agatcgaaga cgattttctg ggtttgatcg ttagatatca tcttaattct      480
cgattagggt ttcatagata tcatccgatt tgttcaaata atttgagttt tgtcgaataa      540
ttactcttcg atttgtgatt tctatctaga tctggtgtta gtttctagtt tgtgcgatcg      600
aatttgtcga ttaatctgag tttttctgat taacagatgc agatctttgt taagactctc      660
accggaaaga caatcaccct cgaggtggaa agctccgaca ccatcgacaa cgttaaggcc      720
aagatccagg ataaggaggg cattcctccg gatcagcaga ggcttatttt cgccggcaag      780
cagctagagg atggccgtac gttggctgat tacaatatcc agaaggaatc caccctccac      840
ttggtcctca ggctccgtgg tggtatgcag attttcgtta aaaccctaac gggaaagacg      900
attactcttg aggtggagag ttctgacacc atcgacaacg tcaaggccaa gatccaagac      960
aaagagggta ttcctccgga ccagcagagg ctgatcttcg ccggaaagca gttggaggat     1020
ggcagaactc ttgctgacta caatatccag aaggagtcca cccttcatct tgttctcagg     1080
ctccgtggtg gtatgcagat tttcgttaag acgttgactg ggaaaactat cactttggag     1140
gtggagagtt ctgacaccat tgataacgtg aaagccaaga tccaagacaa agagggtatt     1200
cctccggacc agcagagatt gatcttcgcc ggaaaacaac ttgaagatgg cagaactttg     1260
gccgactaca acattcagaa ggagtccaca ctccacttgg tcttgcgtct gcgtggaggt     1320
atgcagatct tcgtgaagac tctcaccgga aagaccatca ctttggaggt ggagagttct     1380
gacaccattg ataacgtgaa agccaagatc caggacaaag agggtatccc accggaccag     1440
cagagattga tcttcgccgg aaagcaactt gaagatggaa gaactttggc tgactacaac     1500
attcagaagg agtccacact tcacttggtc ttgcgtctgc gtggaggtat gcagatcttc     1560
gtgaagactc tcaccggaaa gactatcact ttggaggtag agagctctga caccattgac     1620
aacgtgaagg ccaagatcca ggataaggaa ggaatccctc cggaccagca gaggttgatc     1680
tttgccggaa acaattgga ggatggtcgt actttggcgg attacaacat ccagaaggag     1740
tcgacccttc acttggtgtt gcgtctgcgt ggaggtatgc agatcttcgt caagactttg     1800
accgaaaaga ccatcaccct tgaagtggaa agctccgaca ccattgacaa cgtcaaggcc     1860
aagatccagg acaaggaagg tattcctccg gaccagcagc gtctcatctt cgctggaaag     1920
cagcttgagg atggacgtac tttggccgac tacaacatcc agaaggagtc tactcttcac     1980
ttggtcctgc gtcttcgtgg tggtttctaa atctcgtctc tgttatgctt aagaagttca     2040
atgtttcgtt tcatgtaaaa ctttggtggt ttgtgttttg gggccttgta taatccctga     2100
tgaataagtg ttctactatg tttccgttcc tgttatctct ttctttctaa tgacaagtcg     2160
aacttcttct ttatcatcgc ttcgttttta ttatctgtgc ttcttttgtt taatacgcct     2220
gcaaagtgac tcgactctgt ttagtgcagt tctgcgaaac ttgtaaatag tccaattgtt     2280
ggcctctagt aatagatgta gcgaaagtgt tgagctgttg ggttctaagg atggcttgaa     2340
catgttaatc ttttaggttc tgagtatgat gaacattcgt tgttgctaag aaatgcctgt     2400
aatgtcccac aaatgtagaa aatggttcgt acctttgtcc aagcattgat atgtctgatg     2460
```

-continued

```
agaggaaact gcaagatact gagcttggtt taacgaagga gaggcagttt cttccttcca     2520
aagcatttca tttgacaatg ccttgatcat cttaagtaga gtttctgttg tggaaagttt     2580
gaaactttga agaaacgact ctcaagtaaa ttgatgatca caagtgaaag tgtatgttac     2640
ataagtggat atttcaccct ttttccatca atcaaaacat catatagtaa tccattggtt     2700
tatacaaaca tcaaaataca tttacctctg aaatgaggaa aaaaatgcaa agagattttt     2760
gaaaatttcc aacaaatg                                                   2778

<210> SEQ ID NO 48
<211> LENGTH: 636
<212> TYPE: DNA
<213> ORGANISM: Arabidopsis thaliana

<400> SEQUENCE: 48
gtcgacgagt cagtaataaa cggcgtcaaa gtggttgcag ccggcacaca cgagtcgtgt       60
ttatcaactc aaagcacaaa tacttttcct caacctaaaa ataaggcaat tagccaaaaa      120
caactttgcg tgtaaacaac gctcaataca cgtgtcattt tattattagc tattgcttca      180
ccgccttagc tttctcgtga cctagtcgtc ctcgtctttt cttcttcttc ttctataaaa      240
caatacccaa agagctcttc ttcttcacaa ttcagatttc aatttctcaa aatcttaaaa      300
actttctctc aattctctct accgtgatca aggtaaattt ctgtgttcct tattctctca      360
aaatcttcga ttttgttttc gttcgatccc aatttcgtat atgttctttg gtttagattc      420
tgttaatctt agatcgaaga cgattttctg ggtttgatcg ttagatatca tcttaattct      480
cgattagggt ttcatagata tcatccgatt tgttcaaata atttgagttt tgtcgaataa      540
ttactcttcg atttgtgatt tctatctaga tctggtgtta gtttctagtt tgtgcgatcg      600
aatttgtcga ttaatctgag tttttctgat taacag                               636

<210> SEQ ID NO 49
<211> LENGTH: 247
<212> TYPE: DNA
<213> ORGANISM: Arabidopsis thaliana

<400> SEQUENCE: 49
gtcgacgagt cagtaataaa cggcgtcaaa gtggttgcag ccggcacaca cgagtcgtgt       60
ttatcaactc aaagcacaaa tacttttcct caacctaaaa ataaggcaat tagccaaaaa      120
caactttgcg tgtaaacaac gctcaataca cgtgtcattt tattattagc tattgcttca      180
ccgccttagc tttctcgtga cctagtcgtc ctcgtctttt cttcttcttc ttctataaaa      240
caatacc                                                              247

<210> SEQ ID NO 50
<211> LENGTH: 23
<212> TYPE: DNA
<213> ORGANISM: Artificial Sequence
<220> FEATURE:
<223> OTHER INFORMATION: crtiso_t3_Fw

<400> SEQUENCE: 50
attgcgatgc taccagcatt ctg                                              23

<210> SEQ ID NO 51
<211> LENGTH: 23
<212> TYPE: DNA
<213> ORGANISM: Artificial Sequence
<220> FEATURE:
<223> OTHER INFORMATION: crtiso_t3_Rv
```

-continued

<400> SEQUENCE: 51
gctacgatgg tcctaagacc aaa                                                                                    23

<210> SEQ ID NO 52
<211> LENGTH: 23
<212> TYPE: DNA
<213> ORGANISM: Artificial Sequence
<220> FEATURE:
<223> OTHER INFORMATION: psy1_t2_Fw

<400> SEQUENCE: 52
attgagcgta tataatgctg ctt                                                                                    23

<210> SEQ ID NO 53
<211> LENGTH: 23
<212> TYPE: DNA
<213> ORGANISM: Artificial Sequence
<220> FEATURE:
<223> OTHER INFORMATION: psy1_t2_Rv

<400> SEQUENCE: 53
tcgcatatat tacgacgaac aaa                                                                                    23

<210> SEQ ID NO 54
<211> LENGTH: 24
<212> TYPE: DNA
<213> ORGANISM: Artificial Sequence
<220> FEATURE:
<223> OTHER INFORMATION: Tmic_t1_Fw

<400> SEQUENCE: 54
attgtttgat gttggttcat cagt                                                                                   24

<210> SEQ ID NO 55
<211> LENGTH: 24
<212> TYPE: DNA
<213> ORGANISM: Artificial Sequence
<220> FEATURE:
<223> OTHER INFORMATION: Tmic_t1_Rv

<400> SEQUENCE: 55
aaactacaac caagtagtca caaa                                                                                   24

<210> SEQ ID NO 56
<211> LENGTH: 23
<212> TYPE: DNA
<213> ORGANISM: Artificial Sequence
<220> FEATURE:
<223> OTHER INFORMATION: Tmic_t2_Fw

<400> SEQUENCE: 56
attggttcat cagtaggcca act                                                                                    23

<210> SEQ ID NO 57
<211> LENGTH: 23
<212> TYPE: DNA
<213> ORGANISM: Artificial Sequence
<220> FEATURE:
<223> OTHER INFORMATION: crtisoUpFw primer

<400> SEQUENCE: 57
caagtagtca tccggttgac aaa                                                                                    23

<210> SEQ ID NO 58

-continued

```
<211> LENGTH: 19
<212> TYPE: DNA
<213> ORGANISM: Artificial Sequence
<220> FEATURE:
<223> OTHER INFORMATION: DelRv primer

<400> SEQUENCE: 58
gtgtggcgag gtatcagac                                                    19

<210> SEQ ID NO 59
<211> LENGTH: 19
<212> TYPE: DNA
<213> ORGANISM: Artificial Sequence
<220> FEATURE:
<223> OTHER INFORMATION: DelFw primer

<400> SEQUENCE: 59
cacaccgctc catagtctg                                                    19

<210> SEQ ID NO 60
<211> LENGTH: 22
<212> TYPE: DNA
<213> ORGANISM: Artificial Sequence
<220> FEATURE:
<223> OTHER INFORMATION: crtiso4Rv

<400> SEQUENCE: 60
gtaacacatc taagtgtagg gg                                                 22

<210> SEQ ID NO 61
<211> LENGTH: 20
<212> TYPE: DNA
<213> ORGANISM: Artificial Sequence
<220> FEATURE:
<223> OTHER INFORMATION: crtiso2Fw

<400> SEQUENCE: 61
gctttgggtg atagcaaacc                                                    20

<210> SEQ ID NO 62
<211> LENGTH: 20
<212> TYPE: DNA
<213> ORGANISM: Artificial Sequence
<220> FEATURE:
<223> OTHER INFORMATION: crtiso2Rv

<400> SEQUENCE: 62
gtggacggtt tactggaaag                                                    20

<210> SEQ ID NO 63
<211> LENGTH: 32
<212> TYPE: DNA
<213> ORGANISM: Artificial Sequence
<220> FEATURE:
<223> OTHER INFORMATION: Crtiso HT Fw GACT
<220> FEATURE:
<221> NAME/KEY: misc_feature
<222> LOCATION: (1)..(6)
<223> OTHER INFORMATION: n is a, c, g, or t

<400> SEQUENCE: 63
nnnnnngact ctctgcatct ataaaagaca gc                                      32

<210> SEQ ID NO 64
<211> LENGTH: 32
<212> TYPE: DNA
<213> ORGANISM: Artificial Sequence
```

```
<220> FEATURE:
<223> OTHER INFORMATION: Crtiso HT Fw TAGC
<220> FEATURE:
<221> NAME/KEY: misc_feature
<222> LOCATION: (1)..(6)
<223> OTHER INFORMATION: n is a, c, g, or t

<400> SEQUENCE: 64
nnnnnntagc ctctgcatct ataaaagaca gc                                    32

<210> SEQ ID NO 65
<211> LENGTH: 32
<212> TYPE: DNA
<213> ORGANISM: Artificial Sequence
<220> FEATURE:
<223> OTHER INFORMATION: Crtiso HT Fw CGTA
<220> FEATURE:
<221> NAME/KEY: misc_feature
<222> LOCATION: (1)..(6)
<223> OTHER INFORMATION: n is a, c, g, or t

<400> SEQUENCE: 65
nnnnnncgta ctctgcatct ataaaagaca gc                                    32

<210> SEQ ID NO 66
<211> LENGTH: 30
<212> TYPE: DNA
<213> ORGANISM: Artificial Sequence
<220> FEATURE:
<223> OTHER INFORMATION: Crtiso HT Rv
<220> FEATURE:
<221> NAME/KEY: misc_feature
<222> LOCATION: (1)..(6)
<223> OTHER INFORMATION: n is a, c, g, or t

<400> SEQUENCE: 66
nnnnnntatt taagtgaaga atggtaaagg                                       30

<210> SEQ ID NO 67
<211> LENGTH: 30
<212> TYPE: DNA
<213> ORGANISM: Artificial Sequence
<220> FEATURE:
<223> OTHER INFORMATION: Psy1 HT Fw ATCG
<220> FEATURE:
<221> NAME/KEY: misc_feature
<222> LOCATION: (1)..(6)
<223> OTHER INFORMATION: n is a, c, g, or t

<400> SEQUENCE: 67
nnnnnnatcg gtatcgcccc tgaatcaaag                                       30

<210> SEQ ID NO 68
<211> LENGTH: 30
<212> TYPE: DNA
<213> ORGANISM: Artificial Sequence
<220> FEATURE:
<223> OTHER INFORMATION: Psy1 HT Fw GTAC
<220> FEATURE:
<221> NAME/KEY: misc_feature
<222> LOCATION: (1)..(6)
<223> OTHER INFORMATION: n is a, c, g, or t

<400> SEQUENCE: 68
nnnnnngtac gtatcgcccc tgaatcaaag                                       30

<210> SEQ ID NO 69
<211> LENGTH: 30
<212> TYPE: DNA
```

<210> ORGANISM: Artificial Sequence
<220> FEATURE:
<223> OTHER INFORMATION: Psy1 HT Fw CGTA
<220> FEATURE:
<221> NAME/KEY: misc_feature
<222> LOCATION: (1)..(6)
<223> OTHER INFORMATION: n is a, c, g, or t

<400> SEQUENCE: 69
nnnnnncagt gtatcgcccc tgaatcaaag                                    30

<210> SEQ ID NO 70
<211> LENGTH: 28
<212> TYPE: DNA
<213> ORGANISM: Artificial Sequence
<220> FEATURE:
<223> OTHER INFORMATION: Psy1 HT Rv
<220> FEATURE:
<221> NAME/KEY: misc_feature
<222> LOCATION: (1)..(6)
<223> OTHER INFORMATION: n is a, c, g, or t

<400> SEQUENCE: 70
nnnnnnagtt ctgcaatttt attcccag                                      28

<210> SEQ ID NO 71
<211> LENGTH: 20
<212> TYPE: DNA
<213> ORGANISM: Artificial Sequence
<220> FEATURE:
<223> OTHER INFORMATION: crtiso4Fw primer

<400> SEQUENCE: 71
tctttcacgc tgatgtgtgc                                               20

<210> SEQ ID NO 72
<211> LENGTH: 20
<212> TYPE: DNA
<213> ORGANISM: Artificial Sequence
<220> FEATURE:
<223> OTHER INFORMATION: crtiso3Rv

<400> SEQUENCE: 72
ctctaggacc caacgacaga                                               20

<210> SEQ ID NO 73
<211> LENGTH: 21
<212> TYPE: DNA
<213> ORGANISM: Artificial Sequence
<220> FEATURE:
<223> OTHER INFORMATION: crtiso5Fw

<400> SEQUENCE: 73
ggagaacgaa gagggaagaa c                                             21

<210> SEQ ID NO 74
<211> LENGTH: 4549
<212> TYPE: DNA
<213> ORGANISM: Solanum lycopersicum

<400> SEQUENCE: 74
atgtgtacct tgagttttat gtatcctaat tcacttcttg atggtacctg caagactgta   60
gctttgggtg atagcaaacc aagatacaat aaacagagaa gttcttgttt tgaccctttg   120
ataattggaa attgtactga tcagcagcag ctttgtggct tgagttgggg ggtggacaag   180
gctaagggaa gaagaggggg tactgtttcc aatttgaaag cagttgtaga tgtagacaaa   240

-continued

```
agagtggaga gctatggcag tagtgatgta gaaggaaatg agagtggcag ctatgatgcc    300
attgttatag gttcaggaat aggtggattg gtggcagcga cgcagctggc ggttaaggga    360
gctaaggttt tagttctgga gaagtatgtt attcctggtg gaagctctgg cttttacgag    420
agggatggtt ataagtttga tgttggttca tcagtgatgt ttggattcag tgataaggtt    480
agttgtctaa atacttgctt tctgttattt aggacataac acagaatact tgctttattt    540
agacagaaag caagtattta gacaagtaca ctaaatatca cgaatcgatc aacaagtaca    600
caacacacac cgctccatag tctgaaagtg tggaagtgat tatgttttca ttcaagaatg    660
catccaaata ttacgtataa tgactacatc tttaacaatt ttttttaatc aagtatggtt    720
ttcattgata ataacaaggc caacttggtc atatacaaga gatataccaa aaaggtcatt    780
aacatagttt atactggcca tggtgtatgc tttttactat tgtatatggt ctgcagtgct    840
tccacgtgat tggactactg ttgttcctgg ttagatttaa actaatgtct cacatctttt    900
gacagggaaa cctcaattta attactcaag cattggcagc agtaggacgt aaattagaag    960
ttatacctga cccaacaact gtacatttcc acctgccaaa tgacctttct gttcgtatac   1020
accgagagta tgatgacttc attgaagagc ttgtgagtaa atttccacat gaaaaggaag   1080
ggattatcaa attttacagt gaatgctgga aggtttgtct tcattaaggt gtctgcaggt   1140
ttggcttaaa ttttggactc cttgatttag actcaaatca tatgatgaat atggatgcac   1200
agatctttaa ttctctgaat tcattggaac tgaagtcttt ggaggaaccc atctaccttt   1260
ttggccagtt cttttaagaag ccccttgaat gcttgactct tggtaagttt ttccttgctt   1320
taacttcaaa tatagtattc cttgaattcg cacatatcca ttggttggac taattcagta   1380
ataagtcccc aatcatggag tcacttttta tccccaaggg cttagttcaa gtagcaaagt   1440
ttgtgggact tgtgactttg gtcaccggtt tgagccctgt ggcatgcgaa caaagctagt   1500
tatttaagtg aagaatggta aaggggaggg gccattatcc ccgagttttg agcactattg   1560
atggtcctga gtgtttgccc tcggtcatca aaaaaattta aggagtcatc tttcacgctg   1620
atgtgtgcag cgcgcgacgt gcttaattat cctaccgtag aatcttaatt tatgccatca   1680
ttattcatta cagcctacta tttgccccag aatgctggta gcatcgctcg gaagtatata   1740
agagatcctg ggttgctgtc ttttatagat gcagaggtga ggcgaataat ctgtgttact   1800
tattatcagc tccaatgatt tctttacctc ttaaagaatt caactccatt gtctcttttg   1860
cagtgcttta tcgtgagtac agttaatgca ttacaaacac caatgatcaa tgcaagcatg   1920
gtaattctgc atattaacct taggccgtgt tgtgtttcgt gatattcagt tccacttcct   1980
cgtgagtttt ctttctgcag gttctatgtg acagacattt tggcggaatc aactaccccg   2040
ttggtggagt tggcgagatc gccaaatcct tagcaaaagg cttggatgat cacggaagtc   2100
agatacttta tagggcaaat gttacaagta tcattttgga caatggcaaa gctgtgagtt   2160
ttctgtcgta agactattta acttttctta tgattgatta ttcccatcat aaaatgcaaa   2220
agctgtagtc tggtgtttgt gttagaaagt tgtagccgac actcttttga tgttcaagga   2280
ctcatgcttc acacactcat aactgtggta aaatcttctt cccatgtgat acgcctttgg   2340
tgtccctaaa tgcatgccgt tttaaaattt aaggttacat tagcatgtca gagtgttaaa   2400
acattataag aaaagaattg gctagtaagt atatagaaaa agaagaaaag aatgaggaga   2460
acgaagaggg aagaacaaat tacttctgtt aaaatgtcat gcatttgtta tagttgattg   2520
taattgatat agtgtactat tttgcttatc acaacattgt gtagattcac atccccttta   2580
```

-continued

```
attgtatttc agttacatcc ctgaagttat tctactgatg tagggtctgt acttttactg        2640
ttctacatac atgaataaat tgtacctaac aatataatga cattgtatgt tgccatgtca        2700
taatggtgtc ttgtgtagca tcttcaatgt tgtctttgcc agtatctgcg caagttcatt        2760
ttctctaatt cttcttttc tttaggtggg agtgaagctt tctgacggga ggaagtttta        2820
tgctaaaacc atagtatcga atgctaccag atgggatact tttggttagt ttacaaggaa        2880
tccagcaaaa cttatatgtt ttcttaagat tctttcgtct tagggccagt actgtggtat        2940
tcttgcacat atttgattct cttaaatct cgtcatctca tgtcaagtgt cttacatctg         3000
taggaaagct tttaaaagct gagaatctgc caaaagaaga agaaaatttc cagaaagctt        3060
atgtaaaagc accttctttt ctttctattc atatgggagt taaagcagat gtactcccac        3120
cagacacaga ttgtcaccat tttgtcctcg aggtactacg gcagttcaat tgatttgcta        3180 tttattttt catacttgat gttcccattc atgattcctt gattttacag gatgattgga        3240
caaatttgga gaaaccatat ggaagtatat tcttgagtat tccaacagtt cttgattcct        3300
cattggcccc agaaggacac catattcttc acattttac aacatcgagc attgaagatt         3360
gggaggtaaa ttcagtacac tccttgagtg ttgttggtag taacctcttc cacatctatg        3420
tctctttttc cttttttatgg aaattaaagt atggcccttt atccttacta gggactctct        3480
ccgaaagact atgaagcgaa gaaagaggtt gttgctgaaa ggattataag cagacttgaa        3540
aaaacactct tcccagggct taagtcatct attctctta aggaggttaa gttcgtgatt         3600
ttatgaactc aatagttgtt cataatgagc aatattatct gtcttcaata gcaaatccac        3660
atgctcttat gcttgctgaa atagtttgg ccgtggagtt acaccatcta tgtttacaat         3720
tgaattcttg taggtgggaa ctccaaagac ccacagacga taccttgctc gtgatagtgg        3780
tacctatgga ccaatgccac gcggaacacc taagggactc ctgggaatgc ctttcaatac        3840
cactgtgagt taatcatcct ttacgtatgt agttgctttt attgttctgc tggtacaaac        3900
agaataaact gttccgtaat gtttctgagc ttacaggcta tagatggtct atattgtgtt        3960
ggcgatagtt gcttcccagg acaaggtgtt atagctgtag cctttcagg agtaatgtgc         4020 gctcatcgtg ttgcagctga cttaggtaaa catgatagtc caaatagttc attttctgag        4080
cttgaaaatc ctaataacat ttgtgcaata tctatttaca catcataagc tcgaccaaat        4140
atttataatg tggccttcaa aaatgaaaat gaatgagtat ttacaacgtc gagcatcaat        4200 agcccttaa atttgctagt aaatttcatt tagacactct aactataaca tattacaatt        4260
gagcacgtga acacatgata aagcgcctgt tatataagat aagtcaacca cacaaaatat        4320
gtgacctcct ccttcaacta tacacatcag ctttaattgg aacaagggag aggtttatgg        4380
cttagtcaag ggttgtcgat gtgttccgcc ttaatttgaa gtccatataa gtaactgtct        4440
gtttggtttg acatcttctc tttttttctgt cacagggttt gaaaaaaaat cagatgtgct        4500
ggacagtgct cttcttagac tacttggttg gttaaggaca ctagcatga                    4549
```

<210> SEQ ID NO 75
<211> LENGTH: 3994
<212> TYPE: DNA
<213> ORGANISM: Solanum lycopersicum

<400> SEQUENCE: 75

```
gatttcacta tattgtaata ttaacttgag gtcactatag gagctcaaaa acttctaatt         60
ttgaatcaat gtctggttat actttttttg tcataactgt atctcaaatg tggtgtttgg        120
tttatctcat tttgcagaag tcaagaaaca ggttactcct gtttgagtga ggaaaagttg        180
```

-continued

```
gtttgcctgt ctgtggtctt tttataatct ttttctacag aagagaaagt gggtaatttt    240
gtttgagagt ggaaatattc tctagtggga atctactagg agtaatttat tttctataaa    300
ctaagtaaag tttggaaggt gacaaaaaga aagacaaaaa tcttggaatt gtttttagaca   360 accaaggttt tcttgctcag aatgtctgtt gccttgttat gggttgtttc tccttgtgac    420
gtctcaaatg ggacaagttt catggaatca gtccgggagg gaaaccgttt ttttgattca    480
tcgaggcata ggaatttggt gtccaatgag agaatcaata gaggtggtgg aaagcaaact    540
aataatggac ggaaattttc tgtacggtct gctattttgg ctactccatc tggagaacgg    600
acgatgacat cggaacagat ggtctatgat gtggttttga ggcaggcagc cttggtgaag    660
aggcaactga gatctaccaa tgagttagaa gtgaagccgg atataccatt tccgggggaat   720 ttgggcttgt tgagtgaagc atatgatagg tgtggtgaag tatgtgcaga gtatgcaaag    780
acgtttaact taggttagct tcttcaatct attcattcgt ttaccaaata ttatttggta    840
agcactaatt atgaatatat atatgttcat gttattgatg aagacaaaat ttgatctttg    900
tttgtttatt caggaactat gctaatgact cccgagagaa gaagggctat ctgggcaata    960
tatggtgagg tttctagcca tttaataaca gttacgcgca caaacacata tgattaatcg   1020
gggacgagaa aaaagaaat gaagtttgag ttttgagggt catatgtaat aggtaaatcc    1080
gagcttgact agcttgagat gtttattgtc atatcatgct caatactaac caaaacactg   1140
aaaaagaact tgattatatt tacatactaa tattttcatt tgcgttgctg ttcacatttt   1200
tacctatgga actggttttt gtgatttgtt atacttcata ttcgatgtta ataaaatata   1260
tcattcctcc cttttctcc acttcaagct ttactgtagt gttgaaaggg gaaactcctt    1320
ttaatgattg catatataaa cgaacttctt gagttgaata gtttctcatt atgatctgtt   1380
taaacagtat ggtgcagaag aacagatgaa cttgttgatg gcccaaacgc atcatatatt   1440
accccggcag ccttagatag gtgggaaaat aggctagaag atgttttcaa tgggcggcca   1500
tttgacatgc tcgatggtgc tttgtccgat acagtttcta actttccagt tgatattcag   1560
gttagtctac caattctatg gtctttatat ttgttcaatt tgcgtttgat gtcacttttg   1620
ctgagggctt ttctaatagc ttacttcagc ctagcggaaa tgtttgtagt tgaatctcta   1680
gttctgtctc ctatatctgt ttctctcgtc ctagatacta cacatacttc atttctgttt   1740
taacatttta ttcgtctttt ggtgttgttt tgtatgtgaa tcatatattt ggaacagaat   1800
cattattagt tcacatgatt tcatttgctt tcttcaatag cgtaattgtc taaccttcca   1860
atatatgttg cagccattca gagatatgat tgaaggaatg cgtatggact tgagaaaatc   1920
gagatacaaa aacttcgacg aactatacct ttattgttat tatgttgctg gtacggttgg   1980
gttgatgagt gttccaatta tgggtatcgc ccctgaatca aaggcaacaa cagagagcgt   2040
atataatgct gctttggctc tggggatcgc aaatcaatta actaacatac tcagagatgt   2100
tggagaagag taagtacaaa gctgtgtttt acgcacataa ttttttttgc taatatttac   2160
atatcaaaat ataggaaaat gagctcttcg gttatccggt ttatattttt tttatgtcaa   2220
cataatagta taaagtaatt agtatcagtc gttctgggaa taaaattgca gaactcaatt   2280
tagccgtgtt gtgaaatcct gcttgttttg agagcttaaa gctcattagt tagtcgttag   2340
agacgaagaa attcttcgtt gtccatcttt attccacctt aaagttgtga tattttcatt   2400
attggtacat ttggcaaaaa cacctgaaca aatttatgac ggatgccttt tgaaagtcac   2460
tatacctgtc tagtcggcgt ttatcacatt tctttgacat attgaacttt gaaacatgat   2520
```

-continued

```
atcagctcta gacagtgacg agccatgatc aatttctttc ctttattctt tctttggaag   2580
tgccgtattt aggcttccgt tgttcttata tattgctttc cctgcagtgc cagaagagga   2640
agagtctact tgcctcaaga tgaattagca caggcaggtc tatccgatga agatatattt   2700
gctggaaggg tgaccgataa atggagaatc tttatgaaga aacaaataca tagggcaaga   2760
aagttctttg atgaggcaga gaaaggcgtg acagaattga gctcagctag tagattccct   2820
gtaagcattc gtaaactctt tagtttttatg aaatgattct tttttcgcgt tattagatga   2880
atatggttgc ttgtgttgag tatttctagg tcgatgaagt tgagacaagg gttttttaagt   2940 tttaacgact tttacggggt gccatgttat ctgctaccta atcttaggta gttgaccgga   3000
agggctagaa ttttaacctc atgttcaccc taccaaccaa gaaatgaacc tcgcatagag   3060
ctcgtagtta tgaatatttg ctttggcatg acattgtgcg gatcatgaaa tgtcttagat   3120
tatatggaaa aatcattcta ttacatcgaa tagatacatt agatctaaga agcacgccgt   3180
gttgtaaatg agaaattcta tagctcagat ctttagtttt ctctgaacga cctacaaacc   3240
aacggataac cttgtattga gcttgtcgtt ctcagtattt gcactaacat tacgtcgtgt   3300
ggatcctgaa atggcttgga ttgctattat tctggatatg gcaaaaccat tttattagta   3360
ctagatatcg aataactaca tttgacccta caagtaccct gggttggagt tacaatatcc   3420
catacctcgt atctttagtg ttctcttatt tatcaccttt gtctactatt ctggcaaaat   3480
aacctcactc gttactcggt gttttccagg tatgggcatc tttggtcttg taccgcaaaa   3540
tactagatga gattgaagcc aatgactaca acaacttcac aaagagagca tatgtgagca   3600
aatcaaagaa gttgattgca ttacctattg catatgcaaa atctcttgtg cctcctacaa   3660
aaactgcctc tcttcaaaga taaagcatga aatgaagata tatatatata tatatatagc   3720
aatatacatt agaagaaaaa aaggaagaag aaatgttgtt gtattgatat aaatgtatat   3780
cataaatatt aggttgtagt aacattcaat ataattatct cttgtagttg ttgtatcttc   3840
actttatctc aactcctttg agagaacttt ccgtagttat ctgctttgca cttggttact   3900
cagaatttta ctgtgggcat gataattgat ataccaaatt cagttttgat tctatcgaaa   3960
aatttgttat tacattttttt tgggggaaa ggaa                               3994
```

<210> SEQ ID NO 76
<211> LENGTH: 25
<212> TYPE: DNA
<213> ORGANISM: Artificial Sequence
<220> FEATURE:
<223> OTHER INFORMATION: crtisoUpFw

<400> SEQUENCE: 76

```
cctatgatct aacataatct tgaac                                         25
```

<210> SEQ ID NO 77
<211> LENGTH: 20
<212> TYPE: DNA
<213> ORGANISM: Artificial Sequence
<220> FEATURE:
<223> OTHER INFORMATION: locus 5' donor junction

<400> SEQUENCE: 77

```
aaaatgtaaa gagggagcaa                                               20
```

<210> SEQ ID NO 78
<211> LENGTH: 20
<212> TYPE: DNA
<213> ORGANISM: Artificial Sequence

```
<220> FEATURE:
<223> OTHER INFORMATION: donor -repair junction

<400> SEQUENCE: 78
tccaaacatc actgatgaac                                              20

<210> SEQ ID NO 79
<211> LENGTH: 20
<212> TYPE: DNA
<213> ORGANISM: Artificial Sequence
<220> FEATURE:
<223> OTHER INFORMATION: repair - donor junction

<400> SEQUENCE: 79
gataataaca aggccaactt                                              20

<210> SEQ ID NO 80
<211> LENGTH: 20
<212> TYPE: DNA
<213> ORGANISM: Artificial Sequence
<220> FEATURE:
<223> OTHER INFORMATION: 3' donor - locus junction

<400> SEQUENCE: 80
aagagggaag aacaaattac                                              20

<210> SEQ ID NO 81
<211> LENGTH: 48
<212> TYPE: DNA
<213> ORGANISM: Artificial Sequence
<220> FEATURE:
<223> OTHER INFORMATION: TANGERINE

<400> SEQUENCE: 81
agtttgatgt tggttcatca gtaggccaac ttggtcatat acaagaga              48

<210> SEQ ID NO 82
<211> LENGTH: 49
<212> TYPE: DNA
<213> ORGANISM: Artificial Sequence
<220> FEATURE:
<223> OTHER INFORMATION: TmicT1-donor-Rep-Ubi10 plant #3
<220> FEATURE:
<221> NAME/KEY: misc_feature
<222> LOCATION: (15)..(15)
<223> OTHER INFORMATION: n is a, c, g, t or u
<220> FEATURE:
<221> NAME/KEY: misc_feature
<222> LOCATION: (18)..(20)
<223> OTHER INFORMATION: n is a, c, g, t or u
<220> FEATURE:
<221> NAME/KEY: misc_feature
<222> LOCATION: (26)..(29)
<223> OTHER INFORMATION: n is a, c, g, t or u
<220> FEATURE:
<221> NAME/KEY: misc_feature
<222> LOCATION: (34)..(34)
<223> OTHER INFORMATION: n is a, c, g, t or u
<220> FEATURE:
<221> NAME/KEY: misc_feature
<222> LOCATION: (40)..(40)
<223> OTHER INFORMATION: n is a, c, g, t or u
<220> FEATURE:
<221> NAME/KEY: misc_feature
<222> LOCATION: (42)..(42)
<223> OTHER INFORMATION: n is a, c, g, t or u
<220> FEATURE:
<221> NAME/KEY: misc_feature
<222> LOCATION: (44)..(47)
<223> OTHER INFORMATION: n is a, c, g, t or u
```

-continued

```
<400> SEQUENCE: 82
aagtttgatg ttggncannn acaacnnnna tacngacaan gncnnnngc                     49

<210> SEQ ID NO 83
<211> LENGTH: 50
<212> TYPE: DNA
<213> ORGANISM: Artificial Sequence
<220> FEATURE:
<223> OTHER INFORMATION: TmicT1-donor-Rep-Ubi10 plant #1
<220> FEATURE:
<221> NAME/KEY: misc_feature
<222> LOCATION: (48)..(48)
<223> OTHER INFORMATION: n is a, c, g, t or u

<400> SEQUENCE: 83
aagtttgatg ttggttcatc agtaggccaa cttggtcata tacaaganat                    50

<210> SEQ ID NO 84
<211> LENGTH: 48
<212> TYPE: DNA
<213> ORGANISM: Artificial Sequence
<220> FEATURE:
<223> OTHER INFORMATION: TmicT2-donor-Rep-Ubi10 plant #2
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: misc_feature
<222> LOCATION: (36)..(36)
<223> OTHER INFORMATION: n is a, c, g, t or u
<220> FEATURE:
<221> NAME/KEY: misc_feature
<222> LOCATION: (40)..(40)
<223> OTHER INFORMATION: n is a, c, g, t or u
<220> FEATURE:
<221> NAME/KEY: misc_feature
<222> LOCATION: (42)..(42)
<223> OTHER INFORMATION: n is a, c, g, t or u

<400> SEQUENCE: 84
taagtttgat gttggttcat cagtaggcca ttnacntatn tnatactg                      48
```